US010000537B2

(12) United States Patent
Klaassen et al.

(10) Patent No.: US 10,000,537 B2
(45) Date of Patent: Jun. 19, 2018

(54) POLYPEPTIDES WITH PERMEASE ACTIVITY

(71) Applicant: DSM IP ASSETS B.V., Heerlen (NL)

(72) Inventors: Paul Klaassen, Echt (NL); Paulus Petrus De Waal, Echt (NL); Rene Marcel De Jong, Echt (NL); Arnold Jacob Mattieu Driessen, Groningen (NL); Jeroen Gerben Nijland, Groningen (NL); Hyun Yong Shin, Groningen (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days. days.

(21) Appl. No.: 14/895,742

(22) PCT Filed: Jun. 4, 2014

(86) PCT No.: PCT/EP2014/061632
§ 371 (c)(1),
(2) Date: Dec. 3, 2015

(87) PCT Pub. No.: WO2014/195376
PCT Pub. Date: Dec. 11, 2014

(65) Prior Publication Data
US 2016/0122400 A1 May 5, 2016

(30) Foreign Application Priority Data

| Jun. 5, 2013 | (EP) | 13170644 |
| Jun. 5, 2013 | (EP) | 13170646 |
| Jun. 5, 2013 | (EP) | 13170648 |
| Dec. 18, 2013 | (EP) | 13197988 |
| Mar. 19, 2014 | (EP) | 14160772 |
| Apr. 10, 2014 | (EP) | 14164270 |

(51) Int. Cl.
| C12P 21/06 | (2006.01) |
| C12P 19/34 | (2006.01) |
| C12N 15/00 | (2006.01) |
| C12N 1/00 | (2006.01) |
| C07H 21/04 | (2006.01) |
| C07K 1/00 | (2006.01) |
| C07K 14/395 | (2006.01) |
| C12P 19/02 | (2006.01) |

(52) U.S. Cl.
CPC ............ C07K 14/395 (2013.01); C12P 19/02 (2013.01)

(58) Field of Classification Search
CPC .............................. C12P 19/02; C07K 14/395
USPC ......... 435/69.1, 91.1, 320.1, 254.21, 254.11; 536/23.1, 23.2; 530/350
See application file for complete search history.

(56) References Cited

U.S. PATENT DOCUMENTS

| 9,034,608 B2 * | 5/2015 | Wisselink | ............ C07K 14/395 |
| | | | 435/139 |
| 9,260,708 B2 * | 2/2016 | Anthony | ............... C12N 9/1205 |

FOREIGN PATENT DOCUMENTS

| WO | 2009109630 A1 | 9/2009 |
| WO | 2011041426 A1 | 4/2011 |
| WO | 2012049173 A1 | 4/2012 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212- 223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Guo et al., Protein tolerance to random amino acid change. PNAS., 2004, vol. 101 (25): 9205-9210.*
International Search Report from corresponding PCT/EP2014/061632, dated Feb. 6, 2015.
Nelissen et al., "Classification of all putative permeases and other membrane plurispanners of the major facilitator superfamily encoded by the complete genome of Saccharamyces cerevisiae", 1997, FEMS Microbiology Reviews, vol. 21, Nr. 2, pp. 113-134, XP002714218.

(Continued)

*Primary Examiner* — Ganapathirama Raghu
(74) *Attorney, Agent, or Firm* — McBee Moore Woodward & Vanik IP, LLC; Susan McBee; Chester Moore

(57) ABSTRACT

The invention relates to a polypeptide having one or more substitution at a position corresponding to position 339 or 376 of SEQ ID NO: 59, wherein the polypeptide is a member of the Major Facilitator Superfamily (MFS). In an embodiment, the substitution is at position corresponding to 376 and wherein the amino acid at that position is replaced by an amino acid that has a van der Waals volume of 80 to 138 Å$^3$ and a side chain hydrophobicity of 10 to 100 $\Delta t_R$.

30 Claims, 36 Drawing Sheets

(56) References Cited

OTHER PUBLICATIONS

Becker et al., "A Modified *Saccaromyces cerevisiae* Strain That Consumes L-Arabinose and Produces Ethanol", Applied and Environmental Microbiology, Jul. 2003, pp. 4144-4150.

Hamacher et al., "Characterization of the xylose-transporting properties of yeast hexose transporters and their influence on xylose utilization", Microbiology, 2002, vol. 148, pp. 2783-2788.

Kasahara et al., "Three Aromatic Amino Acid Residues Critical for Galactose Transport in Yeast Galt Transporter", The Journal of Biological Chemistry, vol. 275, No. 6, Issue of Feb. 11, 2000, pp. 4422-4428.

Kasahara et al., "Identification of a key residue determining substrate affinity in the human glucose transporter GLUT1", Elsevier, Biochima et Biophysica Acta, 1788, 2009, pp. 1051-1055.

Kasahara et al., "Identification of a Key Residue Determining Substrate Affinity in the Yeast Glucose Transporter Hxt7", A Two-Dimensional Comprehensive Study, The Journal of Biological Chemistry, vol. 285, No. 34, pp. 26263-26268, Aug. 20, 2010.

Kuyper et al., "Metabolic engineering of a xylose-isomerase-expressing *Saccaromyces cerevisiae* strain for rapid anaerobic xylose fermentation", Elsevier, FEMS Yeast Research 5, 2005, pp. 399-409.

Luttik et al., "The *Saccharomyces cerevisiae* ICL2 Gene Enclodes a Mitochondrial 2-Methylisocitrate Lyase Involved in Propionyl-Coenzyme A Metabolism", Journal of Bacteriology, vol. 182, No. 24, Dec. 2000, pp. 7007-7013.

Young et al., "Functional Survey for Heterologous Sugar Transport Proteins, Using *Saccharomyces cerevisiae* as a Host", Applied and Environmental Microbiology, May 2011, vol. 77, No. 10, pp. 3311-3319.

Schiestl et al., "High efficiency transformation of intact yeast cells using single stranded nucleic acids as a carrier", Current Genetics, Springer-Verlag, 1989, vol. 16, pp. 339-346.

Wieczorke et al., "Concurrent knock-out of at least 20 transporter genes is required to block uptake of hexoses in *Saccharomyces cerevisiae*", Duesseldorf, Germany, FEBS Letters 464, 1999, pp. 123-128.

Sambrook et al., "Molecular Cloning: A Laboratory Manual." Second Edition. Cold Spring Harbor Laboratory Press, 1989.

* cited by examiner

FIG. 10B

| | 570 | 580 | 590 | 600 | 610 | 620 |
|---|---|---|---|---|---|---|
| SEQ ID NO:150 | HKCITSEEIQEIWEEGVLPWKSEGWIPSSRRGNNYDLEDLQHDDKPWYKAMLE | | | | | --- |
| SEQ ID NO:151 | HKCITSEEVNDMYAEGVLPWKSASWVPVSKRGADYNADDLMHDDQPFYKSLFSRK | | | | | --- |
| SEQ ID NO:152 | HKCITLEEVNEMYVEGVKPWKSGSWISKEKRVSEE | | | | | --- |
| SEQ ID NO:153 | HKCITLEEVNDMYAEGVLPWKSASWVPTSQRGANYDADALMHDDQPFYKKMFGKK | | | | | --- |
| SEQ ID NO:154 | HKCITLEEVNTLWEEGVLPWKSPSWFHQTR---EVLTTTLMI | | | | | --- |
| SEQ ID NO:155 | HKCITLEEVNTLWEEGVLPWKSPSWVPPNKRGTDYNADDLMHDGSTHFTRRCSEKSRSVN | | | | | |
| SEQ ID NO:156 | HKCITLEEVNEMYEENVLPWKSTKWIPPSRRTTDYDLDATRNDPRPFYKRMFTKEK | | | | | --- |
| SEQ ID NO:157 | HKCITLEEVNTMWEEGVLPWKSASWVPPSRRGANYDAEEMTHDDKPLYKRMFSTK | | | | | --- |
| SEQ ID NO:158 | HKCITLEEVDEMWMDGVLPWKSESWVPASRRDGDYDNEKLQHDEKPFYKRMF | | | | | --- |
| SEQ ID NO:159 | HKCITLEEVNTMWLEGVPAWKSASWVPPERRTADYDADAIDHDNRPIYKRFSS | | | | | --- |
| SEQ ID NO:160 | HKCITLEEVNEMYEERIKPWKSGGWIPSSRRTPQPTSSTPLVIVDSK | | | | | --- |
| SEQ ID NO:161 | HKCITLEEVNTMWLEGVPAWKSASWVPPERRTADYDADAIDHDNRPIYKRFSS | | | | | --- |
| SEQ ID NO:162 | HKCITLEEVNTMWLEGVPAWKSASWVPPERRTADYDADAIDHDNRPIYKRFSS | | | | | --- |
| SEQ ID NO:163 | HICISLEEIQLLYEEGIKPWKSASWVPPSRRGISSEESKTEKKDWKKFLKFSKNSD | | | | | --- |
| SEQ ID NO:164 | HIRKKNEQEINKIFEPE | | | | | --- |
| SEQ ID NO:165 | HICISLEEIQLLYEEGIKPWKSASWVPPSRRGASSRETEAKKKSWKEVLKFPKSFN | | | | | --- |
| SEQ ID NO:166 | HICISLEETQLLYEEGIKPWKSASWVPPSRRGASSRETEAKKKSWKEVLKFPKSFN | | | | | --- |
| SEQ ID NO:167 | HICISLEEIQLLYEEGIKPWKSASWVPPSRRGIPSEESKTEKKDWKKFLKFSKGSD | | | | | --- |

FIG. 10C

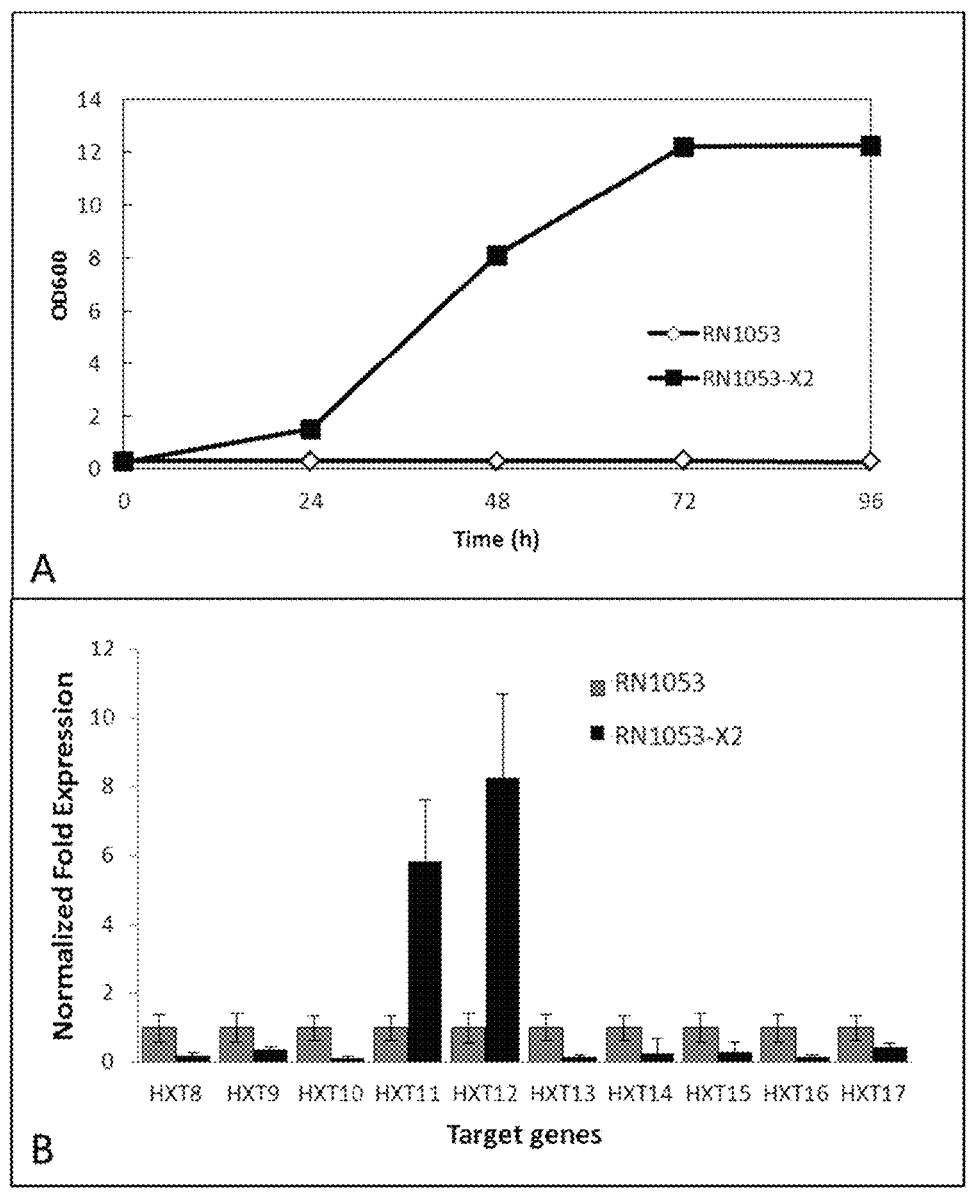
Fig. 12 (A-B)

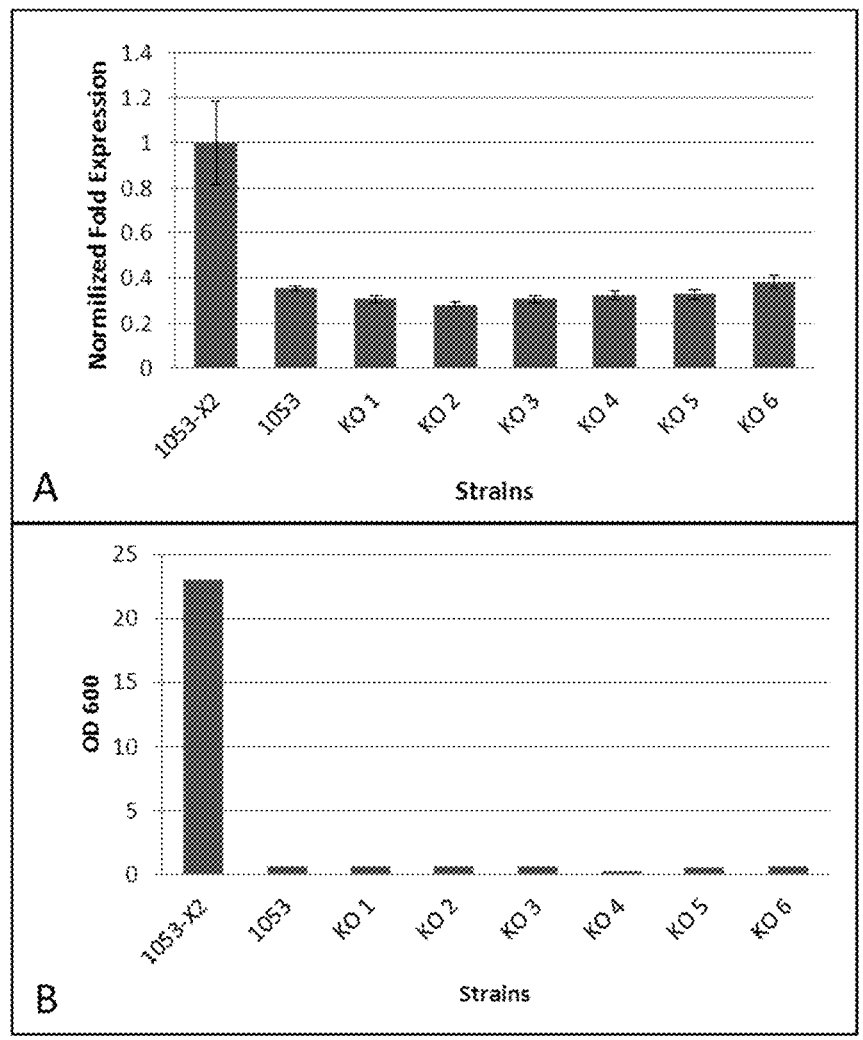
Fig. 13 (A-B)

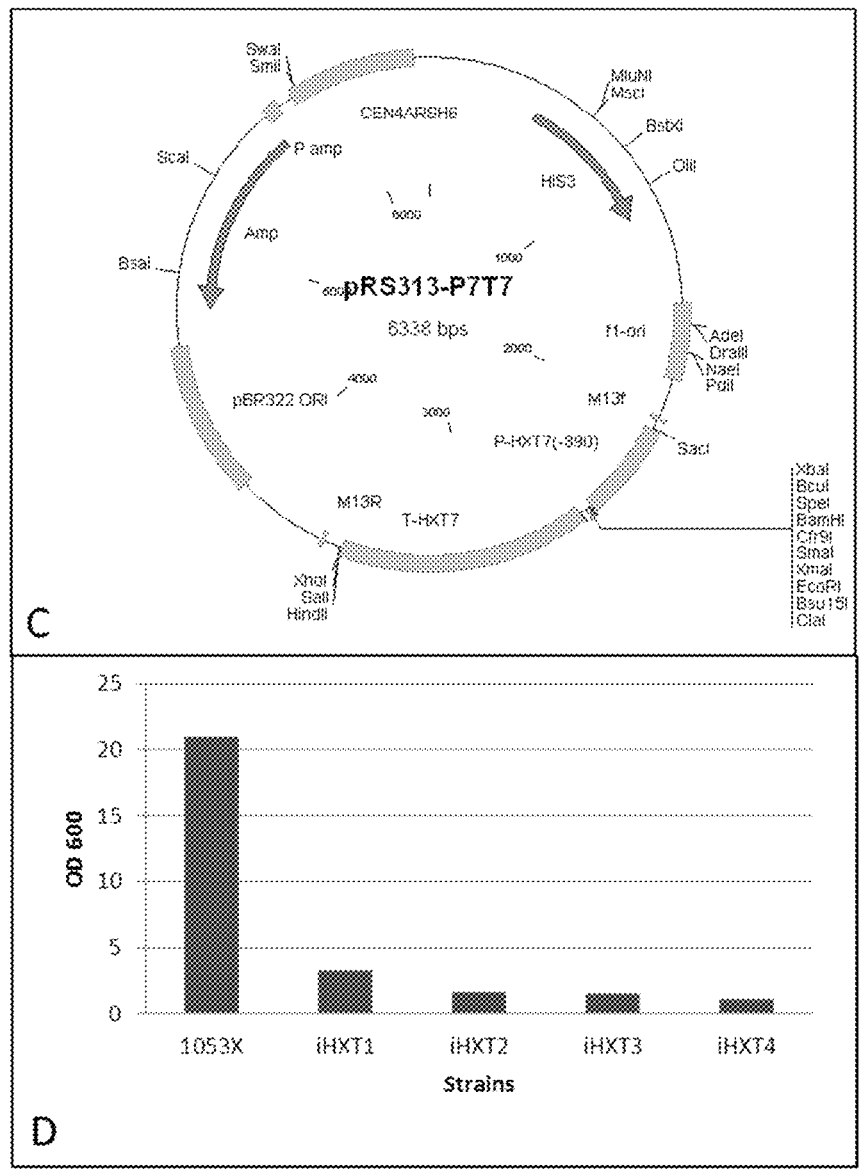
Fig. 13 (C-D)

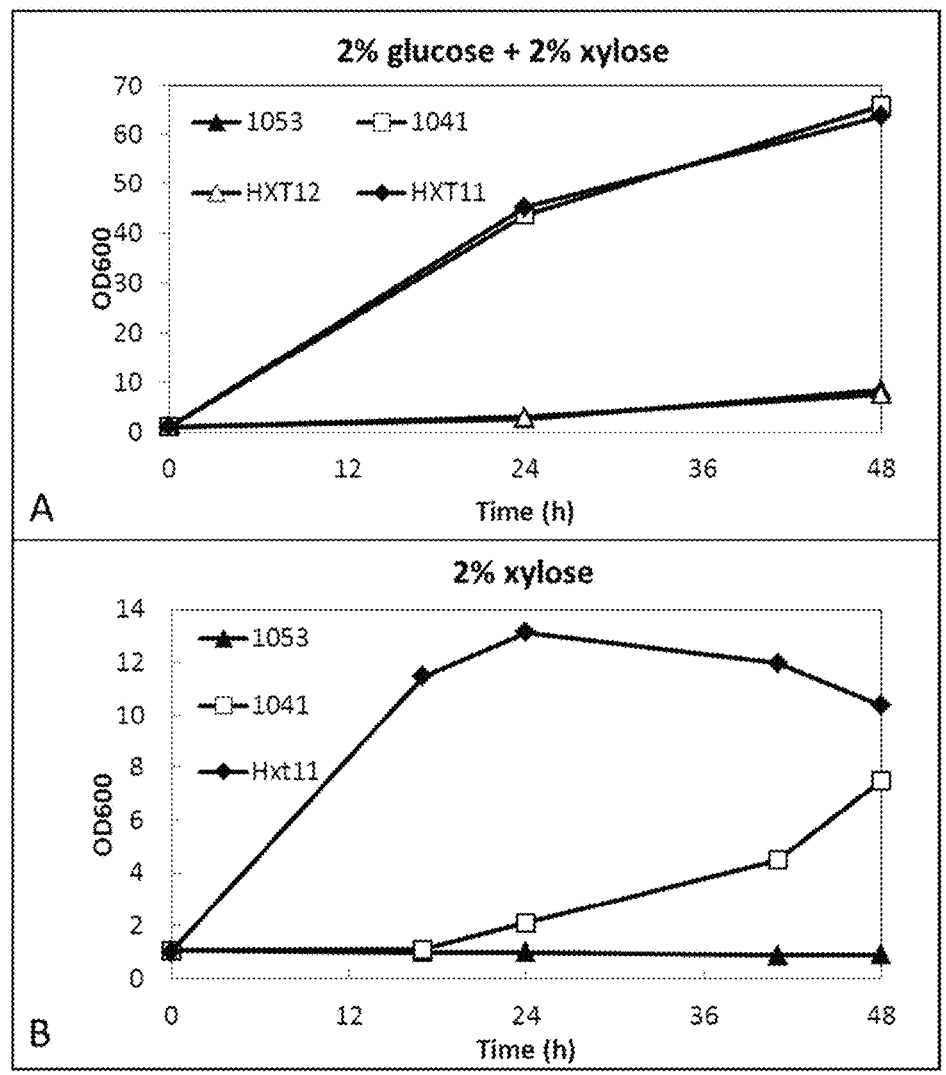
Fig. 14 (A-B)

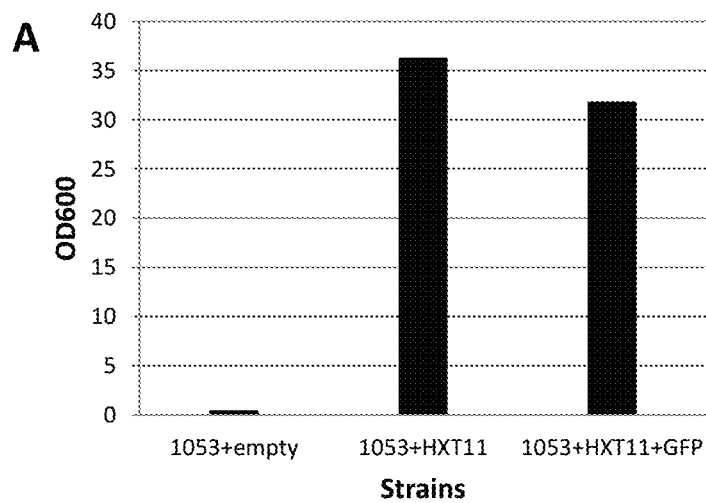
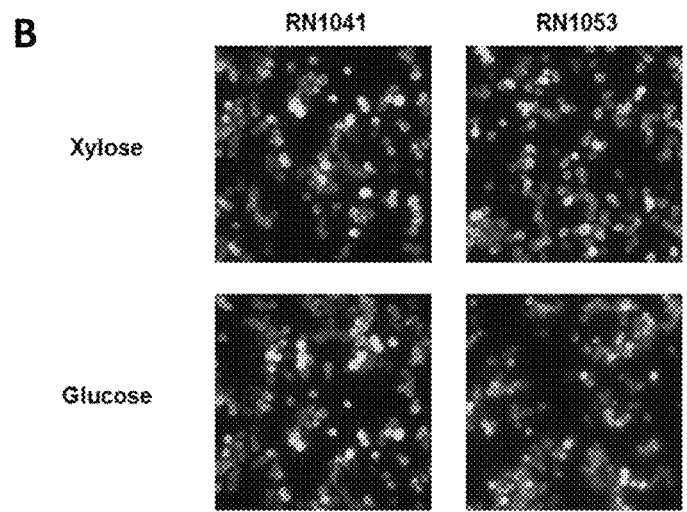
Fig. 16 (A-B)

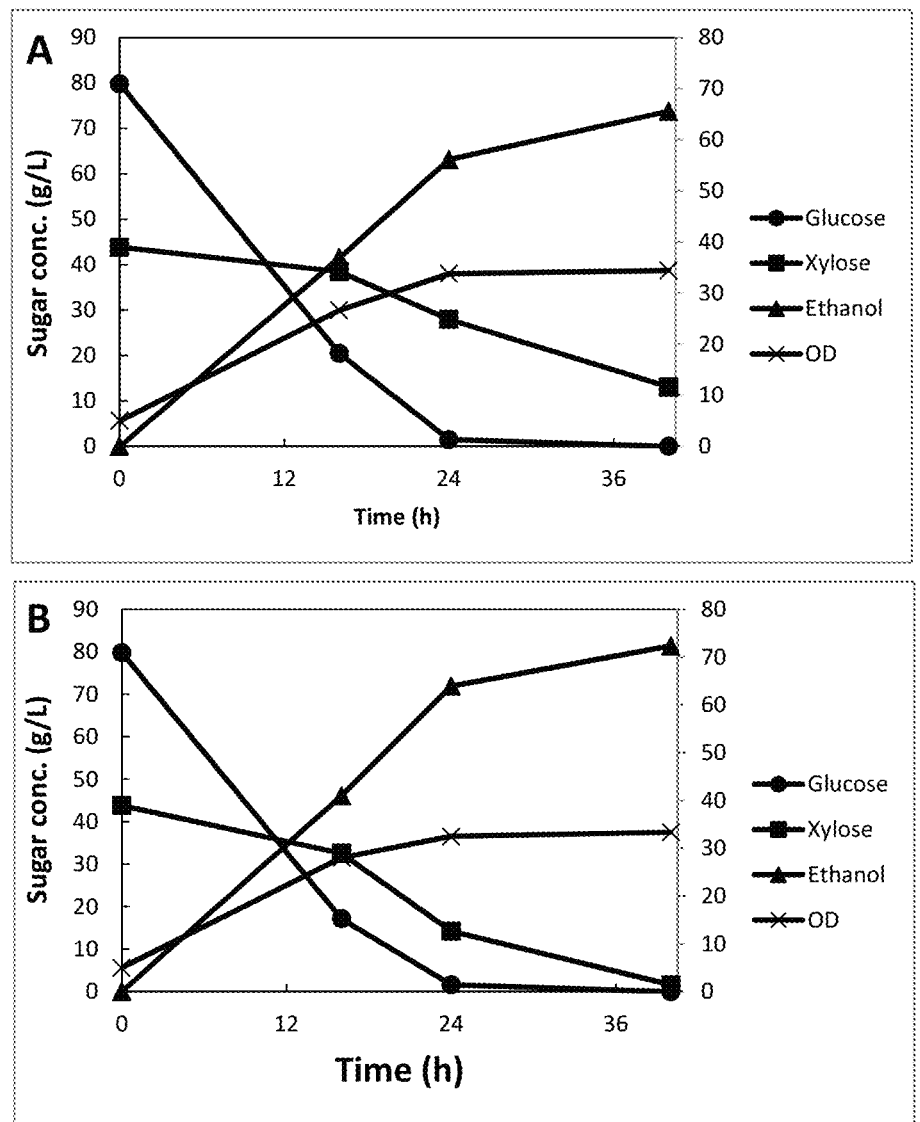
Figure 17 (A-B)

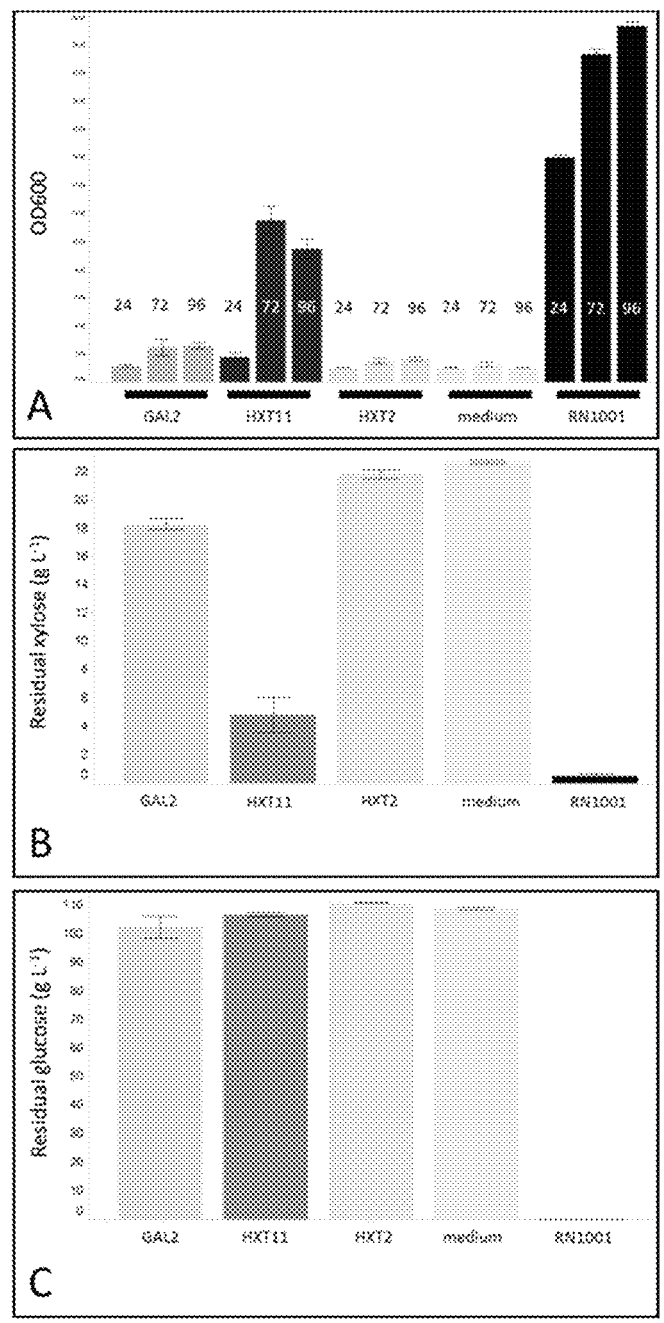
Fig. 18 (A-C)

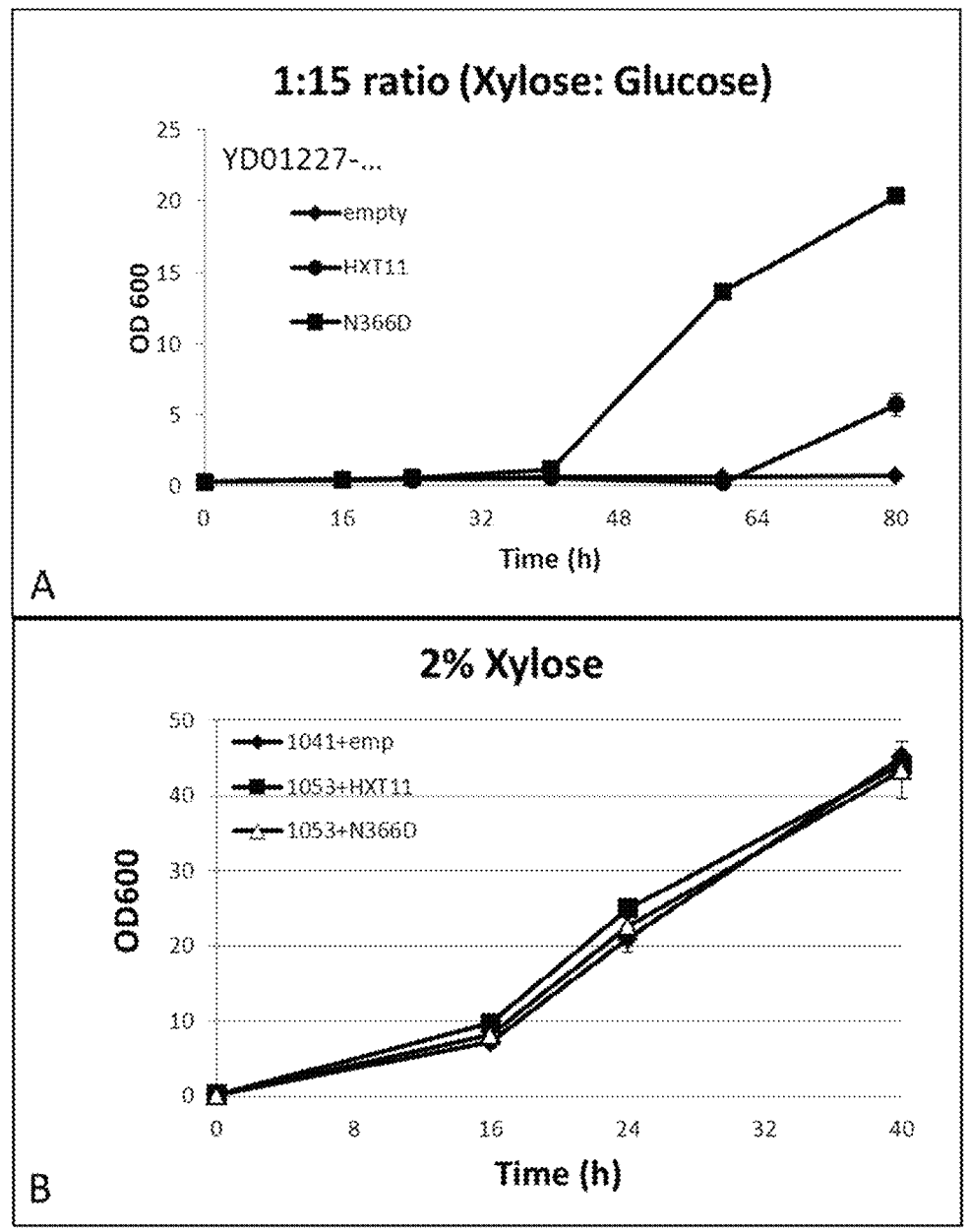
Fig. 19 (A-B)

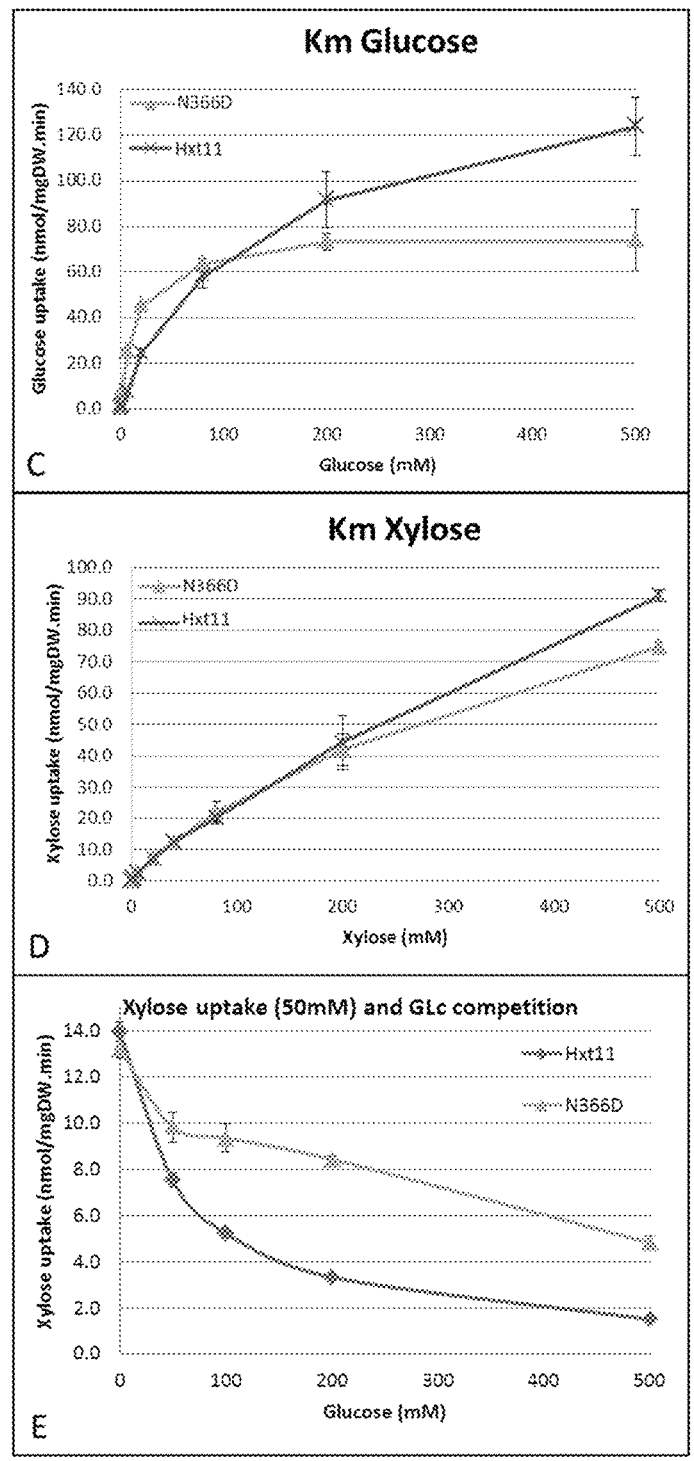
Fig. 19 (C-E)

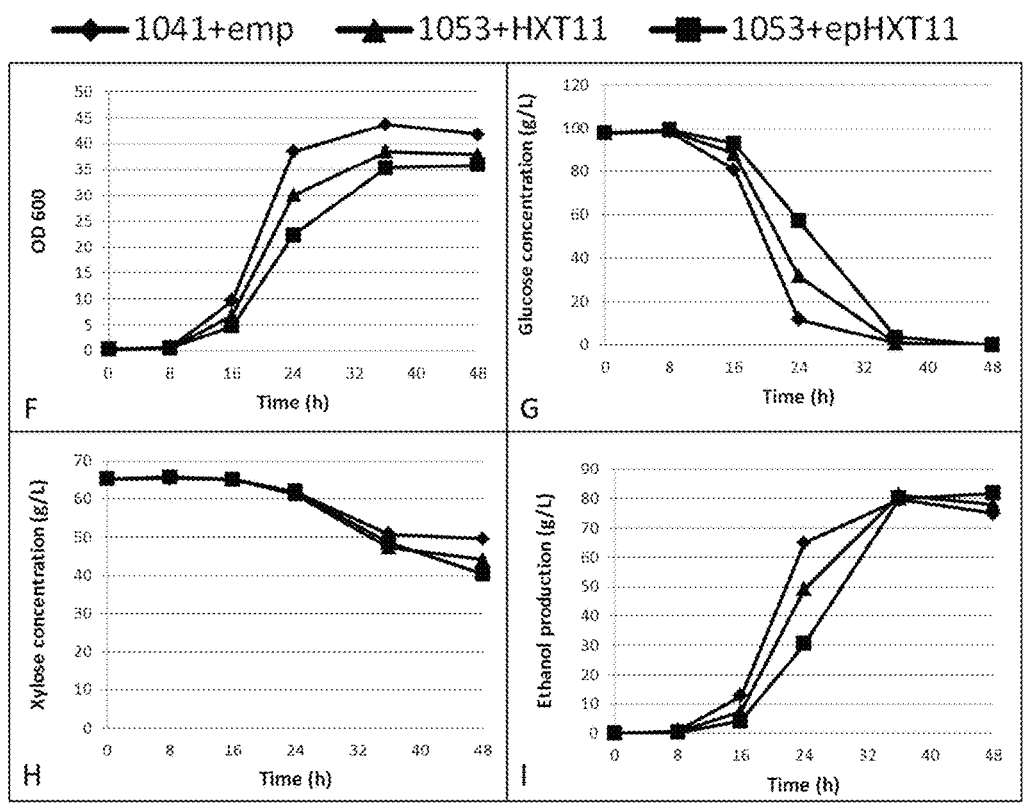
Fig. 19 (C-F)

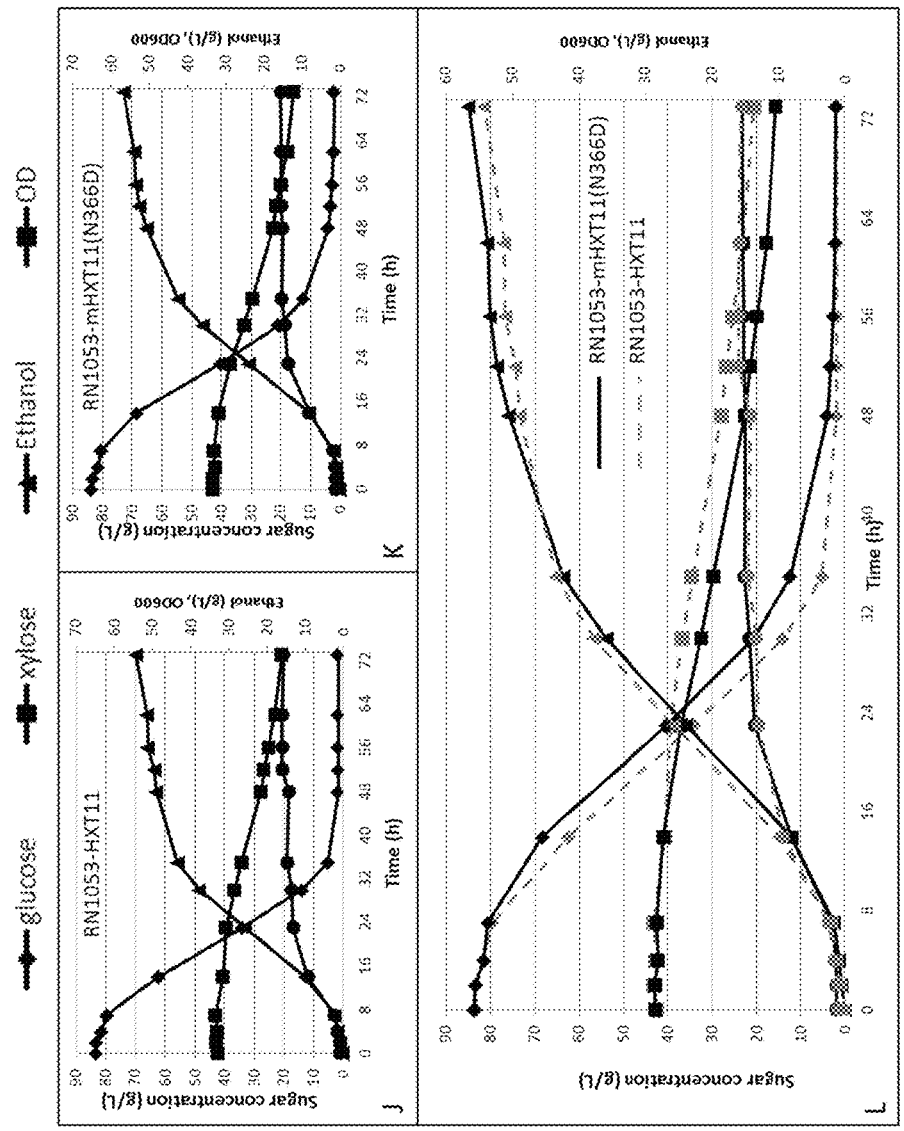
Fig. 19 (J-L)

Fig. 21 (A-C)

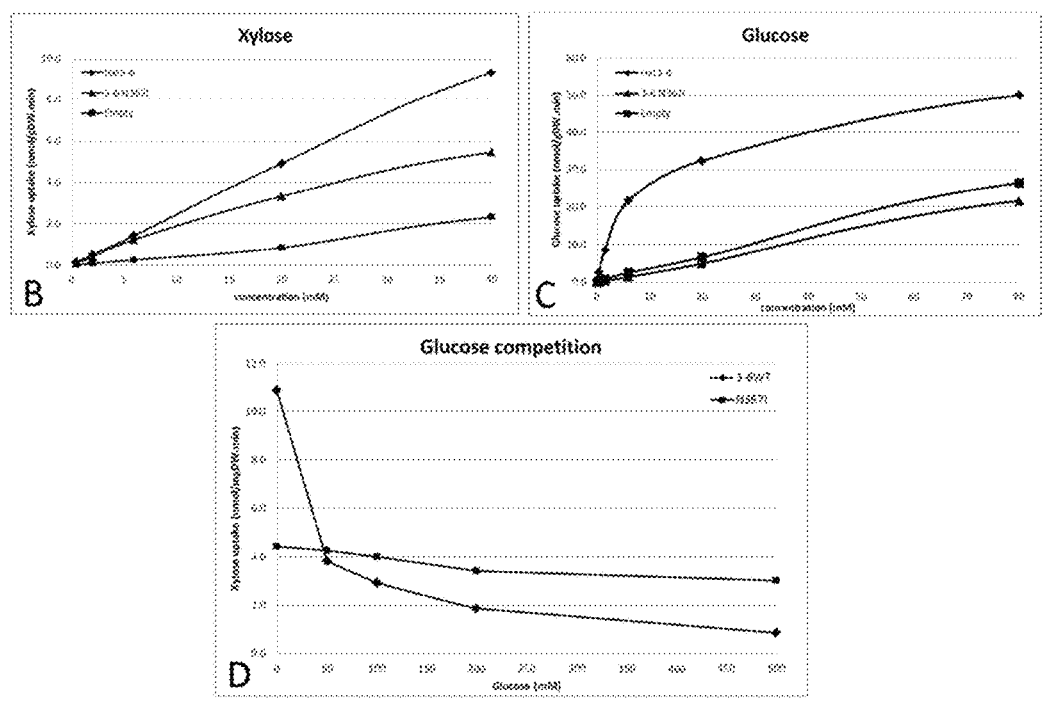
Fig. 22 (B-D)

POLYPEPTIDES WITH PERMEASE ACTIVITY

CROSS REFERENCE TO RELATED APPLICATIONS

This application is a § 371 National Stage Application of PCT/EP2014/061632, filed 4 Jun. 2014, which claims priority to EP 13170644.2, filed 5 Jun. 2013, EP 13170646.7, filed 5 Jun. 2013, EP 13170648.3, filed 5 Jun. 2013, EP 13197988.2, filed 18 Dec. 2013, EP 14160772.1, filed 19 Mar. 2014 and EP 14164270.2, filed 10 Apr. 2014.

BACKGROUND

Field of the Invention

The invention is directed to novel polypeptides and to recombinant organisms expressing the polypeptides. In an embodiment, the present invention relates to novel permease polypeptides with altered sugar specificity and/or sugar transport activity.

Description of Related Art

The plasma membrane of yeast cells and other eukaryotes is a complex bio-membrane, consisting of two layers of phospholipids, with a plethora of proteins embedded in it. Many molecules may cross the plasma membrane by diffusion and osmosis or with the aid of specific transport systems.

Transport systems allow the uptake of nutrients and ions, export of products of metabolism and undesired or harmful substances. Different mechanisms exist. Primary active transporters drive solute accumulation or extrusion by using for instance ATP hydrolysis. Secondary carriers, belonging to the Major Facilitator Superfamily (MFS) transporters, facilitate the transport of one or more molecular species across the membrane in response to chemi-osmotic gradients. In the yeast *Saccharomyces cerevisiae*, 186 MFS proteins have been identified (Nelissen, 1997) in strain S288c.

An example of such a carrier is the Hxt1 protein, involved in hexose transport in *Saccharomyces cerevisiae*.

Permeases are membrane transport proteins, a class of multipass transmembrane proteins that facilitate the diffusion of a specific molecule, herein specifically one or more sugar, in or out of the cell by passive transport. In contrast, active transporters couple molecule transmembrane transport with an energy source such as ATP or a favorable ion gradient.

The terms permease, facilitator, transporter or transport protein or related terms are all describing proteins with multiple membrane spanning domains that exhibit a function in transporting molecules across a membrane. This transport can be brought about by different mechanisms: uniport (transport of one molecule), symport (simultaneous co-transport of two different molecules in the same direction), antiport (simultaneous transport of two molecules in opposite directions) and facilitated diffusion.

The family of sugar transporters in yeast consists of 30-40 members (34 members in strain S288c (Nelissen, 1997)). The sugar transporters can be divided in five clusters: hexose permeases (HXT-genes, GAL2), disaccharide permeases, myo-inositol permeases, sugar receptors and a final cluster of transporters of which the substrate is unknown.

Lignocellulosic biomass, an attractive alternative feedstock for the production of liquid transportation fuels, consists of several different sugars. The hexose fraction of lignocellulose, mainly glucose, can in principle be readily fermented by non-recombinant versions of the yeast *S. cerevisiae*. However, this organism is not able to metabolize the pentose sugars, such as xylose and arabinose, into ethanol.

Methods of creating microorganisms that are able to metabolize pentose sugars are known in the art. For instance, in WO/2009/109630 the construction of expression cassettes and the transformation of *S. cerevisiae* cells into pentose fermenting cells by expressing xylose isomerase are illustrated.

Native pentose-utilizing organisms exist but are lacking well-developed genetic tools and/or low product tolerances, which limit their suitability as hosts for lignocellulosic conversion processes.

As a consequence, efforts have focused on the introduction of pentose conversion pathways in the yeast *S. cerevisiae*, which is still the organism of choice in the ethanol industry, in order to enable pentose fermentation.

Despite the vast amount of progress achieved in the past years, the transport of pentose sugars is still considered to be (one of) the rate-limiting step in pentose metabolism.

Pentose transport in *S. cerevisiae* is mediated by the different members of the hexose transporter (Hxt) family. Hxt4, Hxt5, Hxt7 and Gal2 have been described as the main xylose transporters in *S. cerevisiae* (Hamacher et al, 2002), and Gal2 is also known to mediate arabinose transport (Becker et al, 2003). However, the affinity for the respective pentose sugars is approximately 10 to 100 times lower than for the respective hexose sugars. The lack of a dedicated xylose or arabinose transporter in recombinant yeast cells thus limits the capacity for co-utilization of hexoses and pentoses in sugar mixtures, and prohibits a high pentose catabolic flux. As a consequence, conversion of biomass sugars may be considered bi-phasic: in the first phase, a relatively fast conversion of hexoses (glucose) takes place, while in the second phase, which starts when the hexoses have been exhausted from the medium, pentose fermentation commences, but at a far lower rate as compared to the rate of hexose conversion.

It is therefore a long-felt desire to express pentose-specific sugar transporters, i.e. no glucose interference (pentose specificity) and high affinity to pentose, in an otherwise unchanged transporter landscape, in order to maintain the ability to convert hexoses at approximately the same level.

One way of solving this problem is to screen for heterologous sugar (pentose) transporters which are pentose specific and have a (moderately) high affinity for pentose. However, such efforts have been with limited success so far. Only a few have been shown to be able to facilitate pentose transport upon expression in *S. cerevisiae*, but all favour glucose above xylose (Young et al, 2011, and references therein), as is the case with the *S. cerevisiae* Hxt-proteins, as indicated above.

Another approach is to re-engineer hexose transporters to pentose transporters. For instance, the works by Kasahara et al (2000; 2009; 2010) indicate which residues in several sugar transporters play a key role in the determination of the substrate affinity to the natural substrate.

Mutant hexose transporters that are able to transport pentose sugars more efficiently are known in the art. For instance, in WO/2012/049173, the isolation of mutant hexose transporter genes from cultures of pentose-fermenting *S. cerevisiae* cells is described.

In *Saccharomyces cerevisiae*, the permease GAL2 transports galactose across the cell membrane. It is also known as a transporter of glucose across the membrane.

SUMMARY

An object of the invention is to provide novel permease polypeptides with altered, in particular improved, sugar specificity. Another object of the invention is to provide recombinant strains expressing the permease polypeptide that have improved uptake of the molecule that the permease transports across the cell membrane. Another object is to provide a permease polypeptide that has a improved capacity for transport of C5 sugars, in particular xylose compared to a parent polypeptide. Another object is to provide a permease polypeptide that has reduced transport activity for C6 sugar, in particular glucose, compared to a parent polypeptide. Another object is to provide a method to identify mutations in other related permease polypeptides that have a beneficial effect on the improved capacity for transport of xylose or reduced transport activity for glucose.

One or more of these objects are attained according to the invention. According to the present invention, there is provided a polypeptide having one or more substitution at a position corresponding to position 339 or 376 of SEQ ID NO: 59, wherein the polypeptide is a member of the Major Facilitator Superfamily (MFS). In an embodiment, the substitution is at position corresponding to 376 and wherein the amino acid at that position is replaced by an amino acid that has a van der Waals volume of 80 to 138 Å$^3$ and a side chain hydrophobicity of 10 to 100 $\Delta t_R$. In an embodiment tha amino ccid has at position 376 have a van der Waals volume of 85 to 138 Å$^3$ and a side chain hydrophobicity of 10 to 100 $\Delta t_R$.

The values for van der Waals volume (Å$^3$) for amino acids are herein used as described in: www.proteinsandproteomics.org/content/free/tables_1/t able08.pdf. The corresponding literature is N. J. Darby, Thomas E. Creighton, Protein Structure (1993) Oxford University Press. The values for side chain hydrophobicity ($\Delta t_R$) of amino acids are herein used as described in onlinelibrary.wiley.com/doi/10.1002/psc.310010507/pdf. The reference corresponding to this is Monera, O. D. et al, Journal of Peptide Science 1995; 1(5):319-329.

A polypeptide according to the invention having one or more of these mutations has an advantageous sugar consumption and/or fermentation product production. This will be described in more detail below and will be illustrated by examples 1-5 below.

BRIEF DESCRIPTION OF THE DRAWINGS

FIG. 12 shows (A) Growth curve of evolved strain RN1053-X2 and wild-type strain RN1053 on Verduyn-urea-his supplemented with 2% xylose. Growth curves were expressed as units of optical density (OD) measured at 600 nm wavelength (OD600) over time (h) (B) Expression level of HXT8-HXT17 in the strain RN1053-X2. Expression level relative to ACT1 levels in each sample, was expressed as Normalised Fold Expression Level; expression levels were normalized against RN1053 mRNA levels of the specific HXT gene (RN1053 expression level set to 1).

FIG. 13 (A-B) shows. (A) HXT11 Expression level and (B) Growth of HXT11 knockout strains (KO1 to -6) compared to RN1053-X2-empty (1053-X2) and RN1053-empty. Growth was expressed as units of optical density (OD) measured at 600 nm wavelength (OD600).

FIG. 13 (C-D) shows (C) Plasmid map of pRS313-P7T7, (D) Growth of RN1053-X2 transformed with empty vector control (1053-X), and of four transformants after introduction of pRS313-P7T7-inverse HXT11 (iHXT1 to −4) on Verduyn-urea supplemented with 2% xylose. Growth was expressed as units of optical density (OD) measured at 600 nm wavelength (OD600)

FIG. 14 shows growth profiles of RN1053-HXT11 (Hxt11, closed diamonds), RN1053-HXT12 (Hxt12, open triangles), RN1053-empty vector control (1053; triangles), RN1041-empty vector control (1041; open squares) on Verduyn-urea supplemented with (A) mixture of glucose and xylose (2% each) or (B) 2% xylose. Growth curves were expressed as units of optical density (OD) measured at 600 nm wavelength (OD600) over time (h).

FIG. 16 shows (A) Growth of RN1053 expressing chimeric Hxt11p-GFP protein on 2% xylose at 16 h (initial cell density was OD 0.5). (B) Fluorescence microscopy of RN1053-HXT11 and RN1041-HXT11 grown on Verduyn-urea supplemented with glucose or xylose.

FIG. 17 shows fermentation profiles of sugar consumption and ethanol production of (A) RN1041-empty plasmid and (B) RN1053-HXT11 on Verduyn-urea supplemented with 80 g l$^{-1}$ glucose and 40 g l$^{-1}$ xylose.

FIG. 18 shows growth profiles (OD600)(A), residual xylose (B) and glucose (C) concentrations (g l$^{-1}$) after 96 hours GTAC-screen with YD01227-GAL2 (n=3), YD01227-HXT2 (n=3), YD01227-HXT11 (n=3) transformants. Medium and RN1001 samples were added as controls.

FIG. 19 (A-B). shows growth profiles of shake flask cultures of (A) YD01227-empty, YD01227-HXT11 and YD01227-mHXT11(N366D) transformants (n=2) on Verduyn-urea supplemented with 15% glucose and 1% xylose and, (B) of RN1053-transformants on Verduyn-urea with 2% xylose (n=3).

FIG. 19 (C-E) shows $^{14}$C-radiolabeled sugar uptake profiles by RN1053-HXT11 and RN1053-mHXT11(N366D). (A)$^{14}$C-glucose uptake, and $^{14}$C-xylose uptake in the absence (D) and presence (E) of increasing unlabeled glucose (0-500 mM) concentrations. Sugar uptake was expressed as nmol mg dry weight (DW) of yeast per minute (min).

FIG. 19 (C-F) shows fermentation profiles of RN1041-empty (closed diamonds; 1041+empty), RN1053-HXT11 (closed triangles; 1053+HXT11), RN1053-mHXT11 (N366D) (closed squares; 1053+epHXT11) on Verduyn-urea+100 g l$^{-1}$ glucose and 60 g l$^{-1}$ xylose. (C) Growth curves (expressed by OD600 measurements) over time (h). Constituents measured in the fermentation broth over time (h) such as (D) glucose, (E) xylose and (F) ethanol.

FIG. 19 (J-L) shows fermentation profiles on Verduyn-urea supplemented with 80 g l$^{-1}$ glucose and 40 g l$^{-1}$ xylose of strain RN1053-HXT11 (J and L-grey dashed line) and RN1053-mHXT11(N366D) (K and L-black line). (L) Combined figure of both fermentation profiles illustrated in (J) and (K).

FIG. 22 (B-D) Uptake experiments with Xylose (B) and Glucose (C). Uptake was measured in nmol/mg·DW·min in RN1053-Hxt3-6 (diamonds), RN1053-N367I (triangles) and 1053-emp (squares). (D) Uptake of 50 mM $^{14}$C Xylose in the presence of 0, 50, 100, 200 and 500 mM Glucose in the RN1053-Hxt3-6 (diamonds) and RN1053-N367I strain (squares).

BRIEF DESCRIPTION OF THE SEQUENCE LISTING

Figure 1:
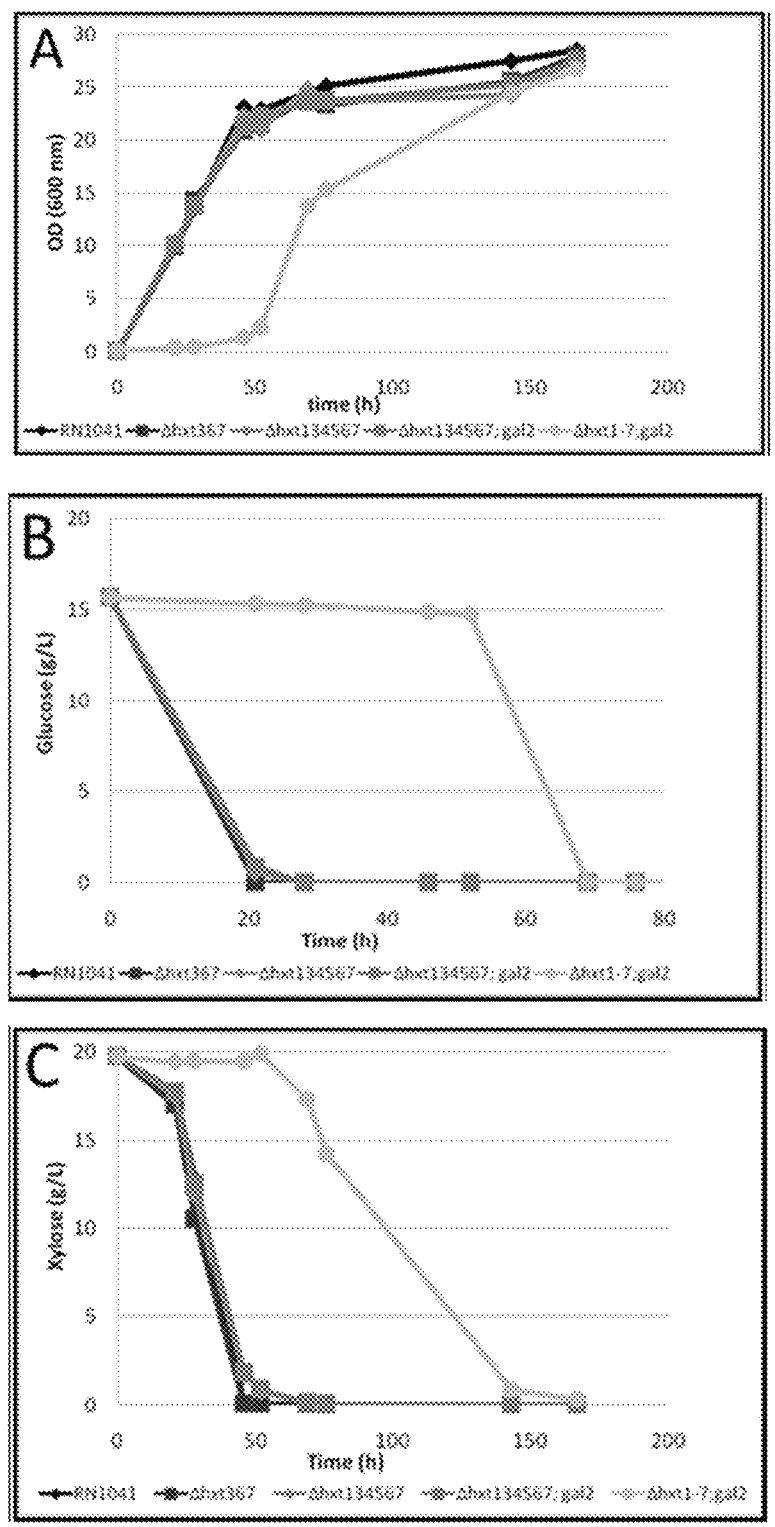
FIG. 1 shows results of aerobic shake flask cultures hexose transporter mutants on Verduyn-urea+15 g l$^{-1}$ glucose+20 g l$^{-1}$ xylose. (A) Optical density measurements at 600 nm wavelength, (B) glucose concentrations (g l$^{-1}$), (C) xylose concentrations during the culture period.

SEQ ID NO: 1: primer 5034-kanf
SEQ ID NO: 2: primer 5035-kanr
SEQ ID NO: 3: primer 5116-If2
SEQ ID NO: 4: primer 5118-Ir2
SEQ ID NO: 5: primer 5115-If1
SEQ ID NO: 6: primer 5117-Ir1
SEQ ID NO: 7: pRN201; TOPO-BLUNT-loxP-kanMX-loxP
SEQ ID NO: 8: pRN251; TOPO-BLUNT-loxP-hphMX-loxP
SEQ ID NO: 9. pRN365; TOPO-BLUNT-loxP-natMX-loxP
SEQ ID NO: 10: primer 115-natf
SEQ ID NO: 11: primer 116-natr
SEQ ID NO: 12: pRN447; TOPO-BLUNT-loxP-zeoMX-loxP
SEQ ID NO: 13: primer 28-H3f
SEQ ID NO: 14: primer 29-H3r
SEQ ID NO: 15: pRN247 (TOPO-BLUNT-HIS3:loxPkanMXloxP)
SEQ ID NO: 16: primer 201-Hx2uf
SEQ ID NO: 17: primer 202-Hx2ur
SEQ ID NO: 18: primer 203-Hx2df
SEQ ID NO: 19: primer 204-Hx2dr
SEQ ID NO: 20: primer 205-Hx3uf
SEQ ID NO: 21: primer 206-Hx3ur
SEQ ID NO: 22: primer 210-Hx4df
SEQ ID NO: 23: primer 211-Hx4dr
SEQ ID NO: 24: primer 212-Hx5uf
SEQ ID NO: 25: primer 213-Hx5ur
SEQ ID NO: 26: primer 229-Hx7df
SEQ ID NO: 27: primer 230-Hx7dr
SEQ ID NO: 28: primer 243-Gal2ufn
SEQ ID NO: 29: primer 244-Gal2urn
SEQ ID NO: 30: primer 233-Ga2df
SEQ ID NO: 31: primer 234-Ga2dr
SEQ ID NO: 32: pRN485; TOPO-BLUNT-GAL2:loxPzeoMXloxP
SEQ ID NO: 33: pRN566; TOPO-BLUNT-HXT367:loxP-hphMX-loxP
SEQ ID NO: 34: pRN569: TOPO-BLUNT-HXT514:loxP-natMX-loxP
SEQ ID NO: 35: pRN635; TOPO-BLUNT-HXT2:loxP-kanMX-loxP
SEQ ID NO: 36: primer 281-Hx3inr2
SEQ ID NO: 37: primer 323-Hx7inr1
SEQ ID NO: 38: primer Hx4inr2
SEQ ID NO: 39: primer Hx5inf
SEQ ID NO: 40: primer 324-Ga2inf1
SEQ ID NO: 41: primer 325-Ga2inr1
SEQ ID NO 42: primer 289-Hx2inf
SEQ ID NO: 43: primer 290-Hx2inr
SEQ ID NO: 44: primer 838-Glk1-psuc227f
SEQ ID NO: 45: primer 834-Hxk2-psuc227f
SEQ ID NO: 46: primer 645-pSUC227r
SEQ ID NO: 47: primer 839-Glk1-psuc225r
SEQ ID NO: 48: primer 835-Hxk2-psuc225r
SEQ ID NO: 49: primer 646-pSUC225f
SEQ ID NO: 50: primer 846-Hxk1_loxP_f
SEQ ID NO: 51: primer 847-Hxk1_loxP_r
SEQ ID NO: 52: primer 848-Gal1_loxP_f
SEQ ID NO: 53: primer 849-Gal1_loxP_r
SEQ ID NO: 54: pRN774; TOPO-BLUNT-loxP-hphMX-loxP (loxP sites in opposite orientation)
SEQ ID NO: 55: pRN775; TOPO-BLUNT-loxP-natMX-loxP (loxP sites in opposite orientation)
SEQ ID NO: 56: WT-GAL2 DNA sequence
SEQ ID NO: 57 pRN993; XbaI site (TCTAGA) and BssHII site (GCGCGC).
SEQ ID NO: 58: pDB1250; WT-GAL2 expression vector for screening; XbaI site (TCTAGA) and BssHII site (GCGCGC).
SEQ ID NO: 59: WT Gal2p amino acid sequence
SEQ ID NO: 60: pRN187 (pSH65-derived CRE recombinase expression vector)
SEQ ID NO: 61: pRN486 (TOPO-BLUNT-his3::loxP-natMX-loxP)
SEQ ID NO: 62: Primer ActinF (Real time PCR)
SEQ ID NO: 63: Primer ActinR (Real time PCR)
SEQ ID NO: 64: Primer HXT1F (Real time PCR)
SEQ ID NO: 65: Primer HXT1R (Real time PCR)
SEQ ID NO: 66: Primer HXT2F (Real time PCR)
SEQ ID NO: 67: Primer HXT2R (Real time PCR)
SEQ ID NO: 68: Primer HXT3F (Real time PCR)
SEQ ID NO: 69: Primer HXT3R (Real time PCR)
SEQ ID NO: 70: Primer HXT4F (Real time PCR)
SEQ ID NO: 71: Primer HXT4R (Real time PCR)
SEQ ID NO: 72: Primer HXT5F (Real time PCR)
SEQ ID NO: 73: Primer HXT5R (Real time PCR)
SEQ ID NO: 74: Primer HXT7F (Real time PCR)
SEQ ID NO: 75: Primer HXT7R (Real time PCR)
SEQ ID NO: 76: Primer HXT8F ((Real time PCR)
SEQ ID NO: 77: Primer HXT8R (Real time PCR)
SEQ ID NO: 78: Primer HXT9F (Real time PCR)
SEQ ID NO: 79: Primer HXT9R (Real time PCR)
SEQ ID NO: 80: Primer HXT10F (Real time PCR)
SEQ ID NO: 81: Primer HXT10R (Real time PCR)
SEQ ID NO: 82: Primer HXT11F (Real time PCR)
SEQ ID NO: 83: Primer HXT11R (Real time PCR)
SEQ ID NO: 84: Primer HXT12F (Real time PCR)
SEQ ID NO: 85: Primer HXT12R (Real time PCR)
SEQ ID NO: 86: Primer HXT13F (Real time PCR)
SEQ ID NO: 87: Primer HXT13R (Real time PCR)
SEQ ID NO: 88: Primer HXT14F (Real time PCR)
SEQ ID NO: 89: Primer HXT14R (Real time PCR)
SEQ ID NO: 90: Primer HXT15F (Real time PCR)
SEQ ID NO: 91: Primer HXT15R (Real time PCR)
SEQ ID NO: 92: Primer HXT16F (Real time PCR)
SEQ ID NO: 93: Primer HXT16R (Real time PCR)
SEQ ID NO: 94: Primer HXT17F (Real time PCR)
SEQ ID NO: 95: Primer HXT17R (Real time PCR)
SEQ ID NO: 96: Primer GAL2F (Real time PCR)
SEQ ID NO: 97: Primer GAL2R (Real time PCR)
SEQ ID NO: 98: Primer KOP11* for KO HXT11
SEQ ID NO: 99: Primer KOT11* for KO HXT11
SEQ ID NO: 100: Primer iHXT11F (Inverse HXT11)
SEQ ID NO: 101: Primer iHXT11R (Inverse HXT11)
SEQ ID NO: 102: Primer HXT11F (Cloning)
SEQ ID NO: 103: Primer HXT12F (Cloning)
SEQ ID NO: 104: Primer HXT11/12R (Cloning)
SEQ ID NO: 105: Primer HXT1 XbaI (Cloning)
SEQ ID NO: 106: Primer R HXT1 Cfr9i (Cloning)
SEQ ID NO: 107: Primer F HXT2 XbaI (Cloning)
SEQ ID NO: 108: Primer R HXT2 Cfr9i (Cloning)
SEQ ID NO: 109: Primer F HXT3 XbaI (Cloning)
SEQ ID NO: 110: Primer R HXT6 Cfr9i (Cloning)
SEQ ID NO: 111: Primer F HXT4 XbaI (Cloning)
SEQ ID NO: 112: Primer R HXT4RN Cfr9I (Cloning)
SEQ ID NO: 113: Primer F HXT5 XbaI (Cloning)
SEQ ID NO: 114: Primer R HXT5 Cfr9i (Cloning)
SEQ ID NO: 115: Primer F HXT7 XbaI (Cloning)
SEQ ID NO: 116: Primer R HXT7 Cfr9I (Cloning)
SEQ ID NO: 117: Plasmid pRS313-P7T7

SEQ ID NO: 118: Plasmid pRS313-P7t7-HXT11+GFP
SEQ ID NO: 119: DNA sequence of HXT11 ORF *Saccharomyces cerevisiae*
SEQ ID NO: 120: DNA sequence of HXT2 ORF *Saccharomyces cerevisiae*
SEQ ID NO: 121: DNA sequence of GAL2 ORF *Saccharomyces cerevisiae*
SEQ ID NO: 122: DNA sequence of HXT3-6 ORF *Saccharomyces cerevisiae*
SEQ ID NO: 123: Hxt11p amino acid sequence *Saccharomyces cerevisiae*
SEQ ID NO: 124: Hxt2p amino acid sequence *Saccharomyces cerevisiae*
SEQ ID NO: 125: Gal2p amino acid sequence *Saccharomyces cerevisiae*
SEQ ID NO: 126: Hxt3-6 amino acid sequence *Saccharomyces cerevisiae*
SEQ ID NO: 127: F HXT36 Bcui
SEQ ID NO: 128: R HXT36 367NNN
SEQ ID NO: 129: F HXT36 367NNN
SEQ ID NO: 130: R HXT36 BamHi
SEQ ID NO: 131: R HXT36 BamHI-stop
SEQ ID NO: 132: F GFP BamHI
SEQ ID NO: 133: R GFP ClaI
SEQ ID NO: 134: F HXT11 XbaI
SEQ ID NO: 135: R HXT11 BamHI
SEQ ID NO: 136: F HXT11 366NNN
SEQ ID NO: 137: R HXT11 366NNN
SEQ ID NO: 138: F HXT11 N366F
SEQ ID NO: 139: R HXT11 N366F
SEQ ID NO: 140: F HXT11 N366E
SEQ ID NO: 141: R HXT11 N366E
SEQ ID NO: 142: F HXT11 N366K
SEQ ID NO: 143: R HXT11 N366K
SEQ ID NO:144: F HXT11 N366M
SEQ ID NO: 145: R HXT11 N366M
SEQ ID NO: 146: F HXT11 N366W
SEQ ID NO: 147: R HXT11 N366W
SEQ ID NO: 148: F HXT11 N366Y
SEQ ID NO: 149: R HXT11 N366Y

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

The invention relates to a method of identifying amino acid positions in permease polypeptides, preferably hexose permease polypeptides, more preferably hexose permease polypeptides from yeast and fungi, even more preferably in *Saccharomyces cerevisiae* Hxt or Gal2 permease polypeptides, which can be mutated to alter the sugar specificity of the permease.

The invention relates to a polypeptide having one or more substitution at a position corresponding to position 339 or 376 of SEQ ID NO: 59, wherein the polypeptide is a member of the Major Facilitator Superfamily (MFS). In an embodiment, the substitution is at position corresponding to 376 and wherein the amino acid at that position is replaced by an amino acid that has a van der Waals volume of 80 to 138 Å$^3$ and a side chain hydrophobicity of 10 to 100 $\Delta t_R$ (T, C, V, M, L, I, F)

In an embodiment, the substitution is at position corresponding to 376 and wherein the amino acid at that position is replaced by an amino acid that has a van der Waals volume of 80 to 138 Å$^3$ and a side chain hydrophobicity of 40 to 100 $\Delta t_R$. (C, V, M, L, I, F).

In an embodiment, the substitution is at position corresponding to 376 and wherein the amino acid at that position is replaced by an amino acid that has a van der Waals volume of 90 to 138 Å$^3$ and a side chain hydrophobicity of 10 to 100 $\Delta t_R$ (T, V, M, L, I, F)

In an embodiment, the substitution is at position corresponding to 376 and wherein the amino acid at that position is replaced by an amino acid that has a van der Waals volume of 100 to 138 Å$^3$ and a side chain hydrophobicity of 60 to 100 $\Delta t_R$ (V, M, L, I, F).

In an embodiment, the substitution is at position corresponding to 376 and wherein the amino acid at that position is replaced by an amino acid that has a van der Waals volume of 100 to 130 Å$^3$ and a side chain hydrophobicity of 60 to 100 $\Delta t_R$ (V, M, L, I).

In an embodiment, the substitution is at position corresponding to 376 and wherein the amino acid at that position is replaced by an amino acid that has a van der Waals volume of 120 to 130 Å$^3$ and a side chain hydrophobicity of 60 to 100 $\Delta t_R$ (M, L, I).

In an embodiment, the substitution is at position corresponding to 376 and wherein the amino acid at that position is replaced by an amino acid that has a van der Waals volume of 120 to 130 Å$^3$ and a side chain hydrophobicity of 80 to 100 $\Delta t_R$ (L, I).

In an embodiment, the substitution is at position corresponding to 376 and wherein the amino acid at that position is replaced by an amino acid that has a van der Waals volume of 100 to 130 Å$^3$ and a side chain hydrophobicity of 60 to 80 $\Delta t_R$ (V, M).

In an embodiment, the substitution is at position corresponding to 376 and wherein the amino acid at that position is replaced by an amino acid that has a van der Waals volume of 100 to 130 Å$^3$ and a side chain hydrophobicity of 60 to 98 $\Delta t_R$ (V, M, L).

In an embodiment, the substitution is N376T, N376C, N376V, N376M, N376L, N376I, or N376F.

In an embodiment polypeptide has a substitution is at position corresponding to 339 and wherein the amino acid at that position is replaced by an amino acid that has a side chain hydrophobicity of −30 to 10 $\Delta t_R$ (G, S, N, Q, H, K, R).

In an embodiment polypeptide has a substitution is at position corresponding to 339 and wherein the amino acid at that position is replaced by an amino acid that has a side chain hydrophobicity of −30 to 10 $\Delta t_R$ and a van der Waals volume of 60 to 160 Å$^3$. (S, N, Q, H, K, R).

In an embodiment polypeptide has a substitution is at position corresponding to 339 and wherein the amino acid at that position is replaced by an amino acid that has a side chain hydrophobicity of −30 to 10 $\Delta t_R$ and a van der Waals volume of 80 to 160 Å$^3$. (N, Q, H, K, R).

In an embodiment polypeptide has a substitution is at position corresponding to 339 and wherein the amino acid at that position is replaced by an amino acid that has a side chain hydrophobicity of −30 to 10 $\Delta t_R$ and a van der Waals volume of 100 to 160 Å$^3$. (Q, H, K, R).

In an embodiment polypeptide has a substitution is at position corresponding to 339 and wherein the amino acid at that position is replaced by an amino acid that has a side chain hydrophobicity of −30 to 0 $\Delta t_R$ and a van der Waals volume of 100 to 160 Å$^3$. (Q, K, R).

In an embodiment polypeptide has a substitution is at position corresponding to 339 and wherein the amino acid at that position is replaced by an amino acid that has a side chain hydrophobicity of −30 to 0 $\Delta t_R$ and a van der Waals volume of 120 to 160 Å$^3$. (K, R).

In an embodiment polypeptide has a substitution is at position corresponding to 339 and wherein the amino acid at that position is replaced by an amino acid that has a side chain hydrophobicity of −30 to 10 $\Delta t_R$ and a van der Waals volume of 80 to 120 Å$^3$. (N, Q, H).

In an embodiment polypeptide has a substitution is at position corresponding to 339 and wherein the amino acid at that position is replaced by an amino acid that has a side chain hydrophobicity of −30 to 10 $\Delta t_R$ and a van der Waals volume of 80 to 120 Å$^3$. (N, Q).

In an embodiment, the substitution is M339G, M339S, M339N, M339Q, M339H, M339K, M339R, or M339V.

In an embodiment the polypeptide has one or more amino acid corresponding to 339N/V and/or 376I/M/V.

The permeases belong to the Major Facilitator Superfamily (MFS). This is defined hereinbelow. Cellular transport systems allow the uptake of essential nutrients and ions, and excretion of products of metabolism and deleterious substances. In addition, transport systems play a role in the communication between cells and the environment. Also, they are an essential part of the cell system to yield or consume energy-supplying molecules, such as ATP.

The transport of solutes by primary active transporters is energy-driven in the first place, such as by energy supplied from ATP hydrolysis, photon absorption, electron flow, substrate decarboxylation, or methyl transfer. If charged molecules are pumped in one direction as a consequence of the consumption of a primary cellular energy source, an electrochemical potential is the result. The resulting chemiosmotic gradient can then be used to drive the transport of additional molecules via secondary carrier structures which just facilitate the transport of one or more molecules across the membrane.

The last two decades the existence of a multitude of previously unknown protein families of primary and secondary transporters has been clarified by the emergence of genomics strategies and making use of the many performed biochemical and molecular genetics studies. The two main transporter families of which proteins were found throughout all living organism are of the ATP-binding cassette (ABC) superfamily and the major facilitator superfamily (MFS), also known as the uniporter-symporter-antiporter family. Whereas ABC family permeases consist of multiple components and are primary active transporters, capable of transporting both small molecules and macromolecules only after generating energy through ATP hydrolysis, the MFS transporters consist of a single polypeptide of a secondary carrier which facilitates transport of small solutes in response to a chemiosmotic ion gradient. ABC superfamily and MFS proteins account for almost half of the solute transporters encoded within the microbe genomes (reviewed by Pao et al, 1998, Microbiol Mol Biol Rev.; 62 pp. 1-34, and Saier et al, 1999, J Mol Microbiol Biotechnol, 1 pp. 257-279).

Suitable permease polypeptide sequences can contain one or more of the following motifs:

a)
G-R-x(3)-G-x(3)-G-x(11)-E-x(5)-[LIVM]-R-G-x(12)-[GA];

b)
R-x(14)-G-x(2)-Y-x(2)-[YF]-[YF]-[GSAL];.

c)
V-x(15)-[GNR]-[RH]-R-x(2)-[LM]-x(2)-[GA]

Motif (a) is corresponds to residues 179-221 in Gal2; motif (b) is corresponds to residues 330-353 in Gal2; motif (c) is corresponds to residues 375-399 in Gal2.

In an embodiment the polypeptide comprises a motif G-R-x(3)-G-x(3)-G-x(11)-E-x(5)-[LIVM]-R-G-x(12)-[GA].

The claimed method comprises modeling a permease polypeptide sequence onto the published crystal structure of the xylose- or glucose-bound *Escherichia coli* xylose permease XylE (respectively, PDB code 4GBY & 4GBZ in the PDB database, www.pdb.org) to identify the amino acid positions in the channel of the permease that directly interact with the bound sugar (called the first-shell residues in the art), and the residues that interact with the first shell residues (called the second shell residues in the art). Suitable modeling software to construct such models are YASARA, Prime (Schrodinger Inc.) or MODELLER using the default settings. Alternatively, the sugar-specificity-altering first and second shell amino acid positions in a permease polypeptide sequence can be identified by a global pairwise alignment of the permease sequence with the Gal2 sequence SEQ ID NO: 59 using the NEEDLE protocol described below. An example alignment for Gal2 and Hxt's from *Saccharomyces cerevisiae* is given in FIG. 10, which shows how alignment can be used to identify the corresponding amino acid positions in the different yeast Hxt's. The amino acid positions herein thus refer to SEQ ID NO: 59 that describes Gal2 or to corresponding amino acid positions in other polypeptides, in particular other permease polypeptides. For example, the corresponding position of the position N376 in Gal2 (SEQ ID NO; 59) in Hxt1 is N370, in Hxt2 N361, in Hxt3 N367, in Hxt4SC N376, in Hxt4RN N376, in Hxt5 N391, in Hxt6/7 N370, in Hxt8 N372, in Hxt9 N366, in Hxt10 N354, in Hxt11 N366, in Hxt12 N256, in Hxt13 N363, in Hxt14 N387, in Hxt15 N366, in Hxt16 N366 and in Hxt17 N363. Similarly, the corresponding position of N346 in Gal2 (SEQ ID NO:9) in Hxt1 is D340, in Hxt2 N331, in Hxt3 D337, in Hxt4SC D346, in Hxt4RN D346, in Hxt5 D361, in Hxt6/7 D340, in Hxt8 D342, in Hxt9 D336, in Hxt10 C324, in Hxt11 D336, in Hxt12 D226, in Hxt13 E333, in Hxt14 I357, in Hxt15 E336, in Hxt16 E336 and in Hxt17 E333. This can be similary done for other MFS Superfamily transporters, so that corresponding positions in these polypeptides corresponding to the positions in SEQ ID NO: 59 can be obtained. This is supported by the data of examples 6-20.

A person skilled in the art can subsequently mutate the identified amino acid positions in the permease polypeptide to all other 19 amino acids, and screen for improved C5 sugar uptake and/or reduced C6 sugar uptake of the mutant permease, as described in Example 4 and 5.

For instance, for a polypeptide having a mutation at a position corresponding to one or more position corresponding to N376 of SEQ ID NO: 59, the mutations at the positions corresponding to N376 may be a substitution with C, P, G, A, V, L, 1, M, F, W, Y, H, S, T, N, Q, D, E, K, R or a deletion. X may be any amino acid, X(2) means two X.

Herein, Gal2 is a facilitated diffusion transporter required for both the high-affinity galactokinase-dependent and low-affinity galactokinase-independent galactose transport processes. It belongs to the major facilitator superfamily, sugar transporter (TC 2.A.1.1) family. "Permease polypeptide", is also designated herein as "polypeptide permease" or "polypeptide". "Permease polypeptide polynucleotide", is herein a polynucleotide that encodes the permease polypeptide.

In an embodiment of the invention, the permease polypeptide has at least 35%, at least 40%, at least 45%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with SEQ ID NO: 59.

Herein mutations are indicated by one letter amino acids and positions of these amino acids. For example, A6 herein indicates an amino acid (one letter code) at a certain position in SEQ ID NO: 59, here A (Alanine) at position 6 of the protein. A6 (L/N/Q/G/V/I/Y/S/E/K) indicates herein mutation of amino acid at a certain position, here A (Alanine) at position 6 of the protein is exchanged for any of L (Leucine), N (Asparagine), Q (Glutamine), G (Glycine), V (Valine), I (Isoleucine), Y (Tyrosine), S (Serine), E (Glutamic acid) or K (Lysine).

In an embodiment, the polypeptide has xylose transport activity.

In an embodiment the polypeptide has reduced glucose affinity compared to the polypeptide of SEQ ID NO: 59.

The permease polypeptide of the invention may have one or more alternative and/or additional activities other than that of sugar permease activity.

As set out above, a permease polypeptide of the invention will typically have sugar permease activity. However, a permease polypeptide of the invention may have one or more of the activities set out above in addition to or alternative to that activity.

Polynucleotide Sequence

With the permease polypeptide and its amino acid sequence as disclosed herein, the skilled person may determine suitable polynucleotides that encode the permease polypeptide.

In an embodiment the polynucleotide is a variant polynucleotide having at least 35%, at least 40%, at least 45%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with SEQ ID NO: 56, and encodes the polypeptide as described in claims 1 to 11.

The invention therefore provides polynucleotide sequences comprising the gene encoding the permease polypeptide, as well as its coding sequence.

The polynucleotides of the invention may be isolated or synthesized. The permease polypeptides and permease polypeptide polynucleotides herein may be synthetic polypeptides, respectively polynucleotides. The synthetic polynucleotides may be optimized in codon use, preferably according to the methods described in WO2006/077258 and/or PCT/EP2007/055943, which are herein incorporated by reference. PCT/EP2007/055943 addresses codon-pair optimization.

The term refers to a polynucleotide molecule, which is a ribonucleic acid (RNA) or deoxyribonucleic acid (DNA) molecule, either single stranded or double stranded. A polynucleotide may either be present in isolated form, or be comprised in recombinant nucleic acid molecules or vectors, or be comprised in a host cell.

The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art.

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The polynucleotides of the present invention, such as a polynucleotide encoding the permease polypeptide can be isolated or synthesized using standard molecular biology techniques and the sequence information provided herein.

The polynucleotide encoding the permease polypeptide of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Transformation

The polynucleotides according to the invention may be expressed in a suitable host. The invention thus relates to a transformed host cell. In an embodiment, the host cell may be transformed with a nucleic acid construct that comprises a polynucleotide that encodes the polypeptide according to the invention defined before. Therefore standard transformation techniques may be used.

In an embodiment the transformed host cell comprises a heterologous nucleotide that encodes a polypeptide according to claim 1 or encodes a polypeptide having substitution F85QN, T89V, V187A/F, I218S, T219A, Q341S/A, N346V, T380A, F444L/V, T448A, T449F, T451G or W455M of sequence ID NO: 59, and in an embodiment thereof the host cell is *Saccharomyces cerevisiae*.

In an embodiment the transformed host is transformed with a polynucleotide that encodes a polypeptide that is a mutant of a polypeptide that is native in the untransformed host cell.

In an embodiment the polypeptide that is native in the untransformed host cel is a member of the Major Facilitator Superfamily (MFS) transporters, in an embodiment a hexose transporter polypeptide.

In an embodiment he polypeptide that is native in the untransformed host cell is a transporter polypeptide chosen from the list consisting of Gal2, Hxt1, Hxt2, Hxt3, Hxt4, Hxt5, Hxt6, Hxt7, Hxt8, Hxt9, Hxt10, Hxt11, Hxt12, Hxt13, Hxt14, Hxt15, Hxt16 and Hxt17.

In an embodiment, in the polypeptide of the invention has not the amino acid residue X (X may be any amino acid) at a given position A (A maybe any specific position in the polypeptide in SEQ ID NO:59, where X is a mutation in SEQ ID NO: 59, when X is native at the to A corresponding position in a second MFS family polypeptide.

In an embodiment, the polypeptide has not the amino acid residue S, that corresponds to M339S in SEQ ID NO:59, in the corresponding position in HXT1 (i.e. not 333S in HXT1), in HXT2 (i.e. not 324S in HXT2), in HXT3 (i.e. not 330S in HXT3), in HXT4 (i.e. not 339S in HXT4), in HXT5 (i.e not 354S in HXT5), in HXT6 or in HXT7 (i.e. not 333S in HXT6 or HXT7), in HXT8 (i.e. not 335S in HXT8), in HXT9 (i.e. not 329S in HXT9), in HXT10 (i.e. not 317S in HXT10) or in HXT11 (i.e. not 329S in HXT11).

In an embodiment, the polypeptide is a mutant HXT3-6 and has one or more substitutions in HXT3-6, In an embodiment thereof, the polypeptide has substitutions corresponding to N367A/C/D/F/G/I/L/M/S/T/V of SEQ ID NO: 126. In an embodiment, the polypeptide has substitutions corresponding to N367A/I of SEQ ID NO: 126. In an embodiment, the polypeptide has substitutions corresponding to N367A of SEQ ID NO: 126.

In an embodiment, the polypeptide is a mutant HXT11 and has one or more substitiutions in HXT11, In an embodiment thereof, the polypeptide has substitutions corresponding to N366A/C/D/F/G/I/L/M/S/T/V of SEQ ID NO: 123. In an embodiment the polypeptide is a mutant HXT11. In an embodiment the polypeptide has substitutions corresponding to N366/F/I/L/M/T/V of SEQ ID NO: 123. In an embodiment, the polypeptide has substitutions corresponding to N366D/M/T of SEQ ID NO: 123. In an embodiment, the polypeptide has substitutions corresponding to N366M/T of SEQ ID NO: 123. In an embodiment the polypeptide has substitutions corresponding to N366M/T or N366T of SEQ ID NO: 123.

Co-Consumption

In an embodiment the transformed host is capable of co-consumption of glucose and at least one pentose. This pentose may be arabinose or xylose, in an embodiment it is xylose. Co-consumption (or co-fermentation) of two substrates is defined herein as a simultaneous uptake and intracellular conversion of two different carbon sources (e.g. xylose and glucose), at an appreciable level. Said carbon sources are simultaneously converted into products, such as e.g. biomass, ethanol, glycerol, and the like.

Co-consumption of a cell is herein quantified and expressed as co-consumption index. The co-consumption index is herein the co-consumption index for glucose and xylose and is calculated as the sum over the time interval of 0-24 hours (measured at 0, 8, 12, 14, 16, 18, 20, 22 and 24 hours) of the absolute difference of the glucose uptake rate (Qg) and the xylose uptake rate (Qx), expressed as grams of sugar consumed per time unit, in an anaerobic batch culture fermentation at 1.0 g/l dry yeast pitch, 30 degrees C. temperature and wherein the fermentation medium contains 71.8 grams of glucose per liter and 40.0 grams xylose per liter, at the start of the fermentation. See examples 16-18.

In an embodiment, the co-consumption index of the transformed host cell is 27 g/h or less, 25 g/h or less, 23 g/h or less, 20 g/h or less, 18 g/h or less, 16 g/h or less, 14 g/h or less, or 12 g/h or less, The invention further relates to a nucleic acid construct comprising the polynucleotide as described before, e.g. a vector.

Another aspect of the invention thus pertains to vectors, including cloning and expression vectors, comprising a polynucleotide of the invention encoding a permease polypeptide protein or a functional equivalent thereof and methods of growing, transforming or transfecting such vectors in a suitable host cell, for example under conditions in which expression of a permease of the invention occurs. As used herein, the term "vector" refers to a nucleic acid molecule capable of transporting another nucleic acid to which it has been linked.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

It will be appreciated by those skilled in the art that the design of the expression vector can depend on such factors as the choice of the host cell to be transformed, the level of expression of protein desired, etc. The vectors, such as expression vectors, of the invention can be introduced into host cells to thereby produce proteins or peptides, encoded by nucleic acids as described herein. The vectors, such as recombinant expression vectors, of the invention can be designed for expression of permease polypeptide proteins in prokaryotic or eukaryotic cells.

For example, permease polypeptides can be expressed in bacterial cells such as *E. coli*, insect cells (using baculovirus expression vectors), filamentous fungi, yeast cells or mammalian cells. Suitable host cells are discussed further in Goeddel, *Gene Expression Technology: Methods in Enzymology* 185, Academic Press, San Diego, Calif. (1990). Representative examples of appropriate hosts are described hereafter.

Appropriate culture mediums and conditions for the above-described host cells are known in the art.

For most filamentous fungi and yeast, the vector or expression construct is preferably integrated in the genome of the host cell in order to obtain stable transformants. However, for certain yeasts also suitable episomal vectors are available into which the expression construct can be incorporated for stable and high level expression, examples thereof include vectors derived from the 2µ and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome, or at predetermined target loci using homologous recombination, in which case the target loci preferably comprise a highly expressed gene.

Accordingly, expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

When the polypeptide according to the invention is to be secreted from the host cell into the cultivation medium, an appropriate signal sequence can be added to the polypeptide in order to direct the de novo synthesized polypeptide to the secretion route of the host cell. The person skilled in the art knows to select an appropriate signal sequence for a specific host.

The vector may further include sequences flanking the polynucleotide giving rise to RNA which comprise sequences homologous to eukaryotic genomic sequences or viral genomic sequences. This will allow the introduction of the polynucleotides of the invention into the genome of a host cell.

An integrative cloning vector may integrate at random or at a predetermined target locus in the chromosome(s) of the host cell into which it is to be integrated.

The vector system may be a single vector, such as a single plasmid, or two or more vectors, such as two or more plasmids, which together contain the total DNA to be introduced into the genome of the host cell.

The vector may contain a polynucleotide of the invention oriented in an antisense direction to provide for the production of antisense RNA.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual, 2nd, ed. Cold Spring Harbor Laboratory*, Cold Spring Harbor Laboratory Press, Cold Spring Harbor, N.Y., 1989), Davis et al., *Basic Methods in Molecular Biology* (1986) and other laboratory manuals.

As indicated before, the invention provides an isolated polypeptide having the amino acid sequence according to SEQ ID NO: 59 with the mutations indicated in claim 1.

The permease polypeptide according to the invention can be recovered and purified from recombinant cell cultures by methods known in the art. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the polypeptides according to the invention.

Provided also are host cells, comprising a polynucleotide or vector of the invention. The polynucleotide may be heterologous to the genome of the host cell. The term "heterologous", usually with respect to the host cell, means that the polynucleotide does not naturally occur in the genome of the host cell or that the polypeptide is not naturally produced by that cell.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are yeast cells including e.g. *Saccharomyces*, for example *Saccharomyces cerevisiae*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a cell as described above may be used to in the preparation of a polypeptide according to the invention. Such a method typically comprises cultivating a host cell (e. g. transformed or transfected with an expression vector as described above) under conditions to provide for expression (by the vector) of a coding sequence encoding the polypeptide, and optionally recovering the expressed polypeptide. Polynucleotides of the invention can be incorporated into a recombinant replicable vector, e. g. an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

Herein standard isolation, hybridization, transformation and cloning techniques are used (e. g., as described in Sambrook, J., Fritsh, E. F., and Maniatis, T. Molecular Cloning: A Laboratory Manual.2nd, ed., Cold Spring Harbor Laboratory, Cold Spring Harbor Laboratory Press, Cold Spring Harbor, N.Y., 1989).

Homology & Identity

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby,A. Trends in Genetics 16, (6) pp276-277, emboss-.bioinformatics.nl). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity".

The various embodiments of the invention described herein may be cross-combined.

The Sugar Composition

The sugar composition according to the invention comprises glucose, arabinose and xylose. Any sugar composition may be used in the invention that suffices those criteria. Optional sugars in the sugar composition are galactose and mannose. In a preferred embodiment, the sugar composition is a hydrolysate of one or more lignocellulosic material. Lignocelllulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

An overview of some suitable sugar compositions derived from lignocellulose and the sugar composition of their hydrolysates is given in table 1. The listed lignocelluloses include: corn cobs, corn fiber, rice hulls, melon shells, sugar beet pulp, wheat straw, sugar cane bagasse, wood, grass and olive pressings.

TABLE 1

Overview of sugar compositions from lignocellulosic materials.

| Lignocellulosic material | Gal | Xyl | Ara | Man | Glu | Rham | Sum | %. Gal. |
|---|---|---|---|---|---|---|---|---|
| Corn cob a | 10 | 286 | 36 | | 227 | 11 | 570 | 1.7 |
| Corn cob b | 131 | 228 | 160 | | 144 | | 663 | 19.8 |
| Rice hulls a | 9 | 122 | 24 | 18 | 234 | 10 | 417 | 2.2 |
| Rice hulls b | 8 | 120 | 28 | | 209 | 12 | 378 | 2.2 |
| Melon Shells | 6 | 120 | 11 | | 208 | 16 | 361 | 1.7 |
| Sugar beet pulp | 51 | 17 | 209 | 11 | 211 | 24 | 523 | 9.8 |
| Wheat straw Idaho | 15 | 249 | 36 | | 396 | | 696 | 2.2 |
| Corn fiber | 36 | 176 | 113 | | 372 | | 697 | 5.2 |
| Cane Bagasse | 14 | 180 | 24 | 5 | 391 | | 614 | 2.3 |
| Corn stover | 19 | 209 | 29 | | 370 | | 626 | |
| Athel (wood) | 5 | 118 | 7 | 3 | 493 | | 625 | 0.7 |
| Eucalyptus (wood) | 22 | 105 | 8 | 3 | 445 | | 583 | 3.8 |
| CWR (grass) | 8 | 165 | 33 | | 340 | | 546 | 1.4 |
| JTW (grass) | 7 | 169 | 28 | | 311 | | 515 | 1.3 |
| MSW | 4 | 24 | 5 | 20 | 440 | | 493 | 0.9 |
| Reed Canary Grass Veg | 16 | 117 | 30 | 6 | 209 | 1 | 379 | 4.2 |
| Reed Canary Grass Seed | 13 | 163 | 28 | 6 | 265 | 1 | 476 | 2.7 |
| Olive pressing residue | 15 | 111 | 24 | 8 | 329 | | 487 | 3.1 |

Gal = galactose, Xyl = xylose, Ara = arabinose, Man = mannose, Glu = glucose, Rham = rhamnose.
The percentage galactose (% Gal) and literature source is given.

It is clear from table 1 that in these lignocelluloses a high amount of sugar is presence in de form of glucose, xylose, arabinose and galactose. The conversion of glucose, xylose, arabinose and galactose to fermentation product is thus of great economic importance. Also mannose is present in some lignocellulose materials be it usually in lower amounts than the previously mentioned sugars. Advantageously therefore also mannose is converted by the transformed host cell.

The Transformed Host Cell

In an embodiment, the transformed host cell may comprise one or more copies of xylose isomerase gene and/or one or more copies of xylose reductase and/or xylitol dehydrogenase, and two to ten copies of araA, araB and araD, genes, wherein these genes are integrated into the cell genome.

In one embodiment, the transformed host cell comprises genes, for example the above xylose isomerase gene and/or one or more copies of xylose reductase and/or xylitol dehydrogenase, and two to ten copies of araA, araB and araD, genes, are integrated into the transformed host cell genome.

The number of copies may be determined by the skilled person by any known method. In the examples, a suitable method is described.

IN an embodiment, the transformed host cell is able to ferment glucose, arabinose, xylose and galactose.

In an embodiment, the cell is capable of converting 90% or more glucose, xylose arabinose, galactose and mannose available, into a fermentation product. In an embodiment, cell is capable of converting 91% or more, 92% or more, 94% or more, 95% or more, 96% or more, 97% or more, 98% or more or 100% of all glucose, xylose arabinose, galactose and mannose available, into a fermentation product.

In one embodiment of the invention the transformed host cell is able to ferment one or more additional sugar, preferably C5 and/or C6 sugar e.g. mannose. In an embodiment of the invention the transformed host cell comprises one or more of: a xylA-gene, XYL1 gene and XYL2 gene and/or XKS1-gene, to allow the transformed host cell to ferment xylose; deletion of the aldose reductase (GRE3) gene; overexpression of PPP-genes TAL1, TKL1, RPE1 and RKI1 to allow the increase of the flux through the pentose phosphate pathway in the cell.

In an embodiment, the transformed host cell is an industrial cell, more preferably an industrial yeast. An industrial cell and industrial yeast cell may be defined as follows. The living environments of (yeast) cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. In one embodiment, the industrial transformed host cell is constructed on the basis of an industrial host cell, wherein the construction is conducted as described hereinafter. Examples of industrial yeast (*S. cerevisiae*) are Ethanol Red® (Fermentis) Fermiol® (DSM) and Thermosacc® (Lallemand).

In an embodiment the transformed host cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxy-methylfurfural. Examples or phenolic compounds are vannilin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions.

For phenolics: several tens of milligrams per liter, up to a gram per liter, depending on the feedstock, the pretreatment and the hydrolysis conditions.

The transformed host cells according to the invention may be inhibitor tolerant, i.e. they can withstand common inhibitors at the level that they typically have with common pretreatment and hydrolysis conditions, so that the transformed host cells can find broad application, i.e. it has high applicability for different feedstock, different pretreatment methods and different hydrolysis conditions.

In one embodiment, the industrial transformed host cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

In an embodiment, the transformed host cell is marker-free. As used herein, the term "marker" refers to a gene encoding a trait or a phenotype which permits the selection of, or the screening for, a host cell containing the marker. Marker-free means that markers are essentially absent in the transformed host cell. Being marker-free is particularly advantageous when antibiotic markers have been used in construction of the transformed host cell and are removed thereafter. Removal of markers may be done using any suitable prior art technique, e.g intramolecular recombination. A suitable method of marker removal is illustrated in the examples.

A transformed host cell may be able to convert plant biomass, celluloses, hemicelluloses, pectins, starch, starch derivatives, for example into fermentable sugars. Accordingly, a transformed host cell may express one or more enzymes such as a cellulase (an endocellulase or an exocellulase), a hemicellulase (an endo- or exo-xylanase or arabinase) necessary for the conversion of cellulose into glucose monomers and hemicellulose into xylose and arabinose monomers, a pectinase able to convert pectins into glucuronic acid and galacturonic acid or an amylase to convert starch into glucose monomers.

The transformed host cell further may comprise those enzymatic activities required for conversion of pyruvate to a desired fermentation product, such as ethanol, butanol, lactic acid, di-terpene, glycosylated di-terpene, 3-hydroxypropionic acid, acrylic acid, acetic acid, succinic acid, citric acid, fumaric acid, malic acid, itaconic acid, an amino acid, 1,3-propane-diol, ethylene, glycerol, a ß-lactam antibiotic or a cephalosporin.

In an embodiment, the transformed host cell is a cell that is naturally capable of alcoholic fermentation, preferably, anaerobic alcoholic fermentation. A transformed host cell preferably has a high tolerance to ethanol, a high tolerance to low pH (i.e. capable of growth at a pH lower than about 5, about 4, about 3, or about 2.5) and towards organic and/or a high tolerance to elevated temperatures.

Any of the above characteristics or activities of a transformed host cell may be naturally present in the cell or may be introduced or modified by genetic modification.

Construction of the Transformed Host Cell

According to an embodiment, the genes may be introduced in the host cell by introduction into a host cell:
a) a cluster consisting of the genes araA, araB and araD under control of a strong constitutive promoter
b) a cluster consisting of PPP-genes TAL1, TKL1, RPE1 and RKI1, optionally under control of strong constitutive promoter; and deletion of an aldose reductase gene;
c) a cluster consisting of a xylA-gene and a XKS1-gene under control of strong constitutive promoter;

d) a construct comprising a xylA gene under control of a strong constitutive promoter, which has the ability to integrate into the genome on multiple loci;

and adaptive evolution to produce the transformed host cell. The above cell may be constructed using recombinant expression techniques.

Recombinant Expression

The transformed host cell is a recombinant cell. That is to say, a transformed host cell comprises, or is transformed with or is genetically modified with a nucleotide sequence that does not naturally occur in the cell in question.

Techniques for the recombinant expression of enzymes in a cell, as well as for the additional genetic modifications of a transformed host cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of host cells are known from e.g. EP-A-0635 574, WO 98/46772, WO 99/60102, WO 00/37671, WO90/14423, EP-A-0481008, EP-A-0635574 and U.S. Pat. No. 6,265,186.

Typically, the nucleic acid construct may be a plasmid, for instance a low copy plasmid or a high copy plasmid. The cell according to the present invention may comprise a single or multiple copies of the nucleotide sequence encoding a enzyme, for instance by multiple copies of a nucleotide construct or by use of construct which has multiple copies of the enzyme sequence.

The nucleic acid construct may be maintained episomally and thus comprise a sequence for autonomous replication, such as an autosomal replication sequence sequence. A suitable episomal nucleic acid construct may e.g. be based on the yeast 2µ or pKD1 plasmids (Gleer et al., 1991, Biotechnology 9: 968-975), or the AMA plasmids (Fierro et al., 1995, Curr Genet. 29:482-489). Alternatively, each nucleic acid construct may be integrated in one or more copies into the genome of the cell. Integration into the cell's genome may occur at random by non-homologous recombination but preferably, the nucleic acid construct may be integrated into the cell's genome by homologous recombination as is well known in the art (see e.g. WO90/14423, EP-A-0481008, EP-A-0635 574 and U.S. Pat. No. 6,265,186).

Most episomal or 2µ plasmids are relatively unstable in yeast, being lost in approximately $10^{-2}$ or more cells after each generation. Even under conditions of selective growth, only 60% to 95% of the cells retain the episomal plasmid. The copy number of most episomal plasmids ranges from 20-100 per cell of cir$^+$ hosts. However, the plasmids are not equally distributed among the cells, and there is a high variance in the copy number per cell in populations. Strains transformed with integrative plasmids are extremely stable, even in the absence of selective pressure. However, plasmid loss can occur at approximately $10^{-3}$ to $10^{-4}$ frequencies by homologous recombination between tandemly repeated DNA, leading to looping out of the vector sequence. Preferably, the vector design in the case of stable integration is thus, that upon loss of the selection marker genes (which also occurs by intramolecular, homologous recombination) that looping out of the integrated construct is no longer possible. Preferably the genes are thus stably integrated.

Stable integration is herein defined as integration into the genome, wherein looping out of the integrated construct is no longer possible. Preferably selection markers are absent. Typically, the enzyme encoding sequence will be operably linked to one or more nucleic acid sequences, capable of providing for or aiding the transcription and/or translation of the enzyme sequence.

The term "operably linked" refers to a juxtaposition wherein the components described are in a relationship permitting them to function in their intended manner. For instance, a promoter or enhancer is operably linked to a coding sequence the said promoter or enhancer affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

The promoter that could be used to achieve the expression of a nucleotide sequence coding for an enzyme according to the present invention, may be not native to the nucleotide sequence coding for the enzyme to be expressed, i.e. a promoter that is heterologous to the nucleotide sequence (coding sequence) to which it is operably linked. The promoter may, however, be homologous, i.e. endogenous, to the host cell.

Promotors are widely available and known to the skilled person. Suitable examples of such promoters include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADH1, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics. Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3.

In a transformed host cell, the 3'-end of the nucleotide acid sequence encoding enzyme preferably is operably linked to a transcription terminator sequence. Preferably the terminator sequence is operable in a host cell of choice, such as e.g. the yeast species of choice. In any case the choice of the terminator is not critical; it may e.g. be from any yeast gene, although terminators may sometimes work if from a non-yeast, eukaryotic, gene. Usually a nucleotide sequence encoding the enzyme comprises a terminator. Preferably, such terminators are combined with mutations that prevent nonsense mediated mRNA decay in the host transformed host cell (see for example: Shirley et al., 2002, Genetics 161:1465-1482).

The transcription termination sequence further preferably comprises a polyadenylation signal.

Optionally, a selectable marker may be present in a nucleic acid construct suitable for use in the invention. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g. dihydrofolate reductase, hygromycin-B-phosphotransferase, 3'-O-phosphotransferase II (kanamycin, neomycin and G418 resistance). Antibiotic resistance markers may be most convenient for the transformation of polyploid host cells, Also non-antibiotic resistance markers may be used, such as auxotrophic markers (URA3, TRP1, LEU2) or the S. pombe TPI gene (described by Russell P R, 1985, Gene 40: 125-130). In a preferred embodiment the host cells transformed with the nucleic acid constructs are marker gene free. Methods for constructing recombinant marker gene free microbial host cells are disclosed in EP-A-0 635 574 and are based on the use of bidirectional markers such as the A. nidulans amdS (acetamidase) gene or the yeast URA3 and LYS2 genes. Alternatively, a screenable marker such as Green Fluorescent Protein, lacL, luciferase, chloramphenicol acetyltransferase, beta-glucuronidase may be incorporated into the nucleic acid constructs of the invention allowing to screen for transformed cells.

Optional further elements that may be present in the nucleic acid constructs suitable for use in the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence.

The recombination process may thus be executed with known recombination techniques. Various means are known to those skilled in the art for expression and overexpression of enzymes in a transformed host cell. In particular, an enzyme may be overexpressed by increasing the copy number of the gene coding for the enzyme in the host cell, e.g. by integrating additional copies of the gene in the host cell's genome, by expressing the gene from an episomal multicopy expression vector or by introducing a episomal expression vector that comprises multiple copies of the gene.

Alternatively, overexpression of enzymes in the host cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the host cell. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters.

In an embodiment, the transformed host cell is marker-free, which means that no auxotrophic or dominant markers, in particular antibiotic resistance markers, are present in the genome or extra-chromosomally.

The coding sequence used for overexpression of the enzymes mentioned above may preferably be homologous to the host cell. However, coding sequences that are heterologous to the host may be used.

Overexpression of an enzyme, when referring to the production of the enzyme in a genetically modified cell, means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Similarly this usually means that the mRNA coding for the enzymatically active protein is produced in greater amounts, or again rather at a higher steady state level as compared to the unmodified host cell under identical conditions. Preferably in a host, an enzyme to be overexpressed is overexpressed by at least a factor of about 1.1, about 1.2, about 1.5, about 2, about 5, about 10 or about 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

Adaptation

Adaptation is the evolutionary process whereby a population becomes better suited (adapted) to its habitat or habitats. This process takes place over several to many generations, and is one of the basic phenomena of biology.

The term adaptation may also refer to a feature which is especially important for an organism's survival. Such adaptations are produced in a variable population by the better suited forms reproducing more successfully, by natural selection.

Changes in environmental conditions alter the outcome of natural selection, affecting the selective benefits of subsequent adaptations that improve an organism's fitness under the new conditions. In the case of an extreme environmental change, the appearance and fixation of beneficial adaptations can be essential for survival. A large number of different factors, such as e.g. nutrient availability, temperature, the availability of oxygen, etcetera, can drive adaptive evolution.

Fitness

There is a clear relationship between adaptedness (the degree to which an organism is able to live and reproduce in a given set of habitats) and fitness. Fitness is an estimate and a predictor of the rate of natural selection. By the application of natural selection, the relative frequencies of alternative phenotypes will vary in time, if they are heritable.

Genetic Changes

When natural selection acts on the genetic variability of the population, genetic changes are the underlying mechanism. By this means, the population adapts genetically to its circumstances. Genetic changes may result in visible structures, or may adjust the physiological activity of the organism in a way that suits the changed habitat.

It may occur that habitats frequently change. Therefore, it follows that the process of adaptation is never finally complete. In time, it may happen that the environment changes gradually, and the species comes to fit its surroundings better and better. On the other hand, it may happen that changes in the environment occur relatively rapidly, and then the species becomes less and less well adapted. Adaptation is a genetic process, which goes on all the time to some extent, also when the population does not change the habitat or environment.

The Adaptive Evolution

The transformed host cells may in their preparation be subjected to adaptive evolution. A transformed host cell may be adapted to sugar utilisation by selection of mutants, either spontaneous or induced (e.g. by radiation or chemicals), for growth on the desired sugar, preferably as sole carbon source, and more preferably under anaerobic conditions. Selection of mutants may be performed by techniques including serial transfer of cultures as e.g. described by Kuyper et al. (2004, FEMS Yeast Res. 4: 655-664) or by cultivation under selective pressure in a chemostat culture. E.g. in a preferred host cell at least one of the genetic modifications described above, including modifications obtained by selection of mutants, confer to the host cell the ability to grow on the xylose as carbon source, preferably as sole carbon source, and preferably under anaerobic conditions. When XI is used as gene to convert xylose, preferably the cell produce essentially no xylitol, e.g. the xylitol produced is below the detection limit or e.g. less than about 5, about 2, about 1, about 0.5, or about 0.3% of the carbon consumed on a molar basis.

Adaptive evolution is also described e.g. in Wisselink H. W. et al, Applied and Environmental Microbiology August 2007, p. 4881-4891

In one embodiment of adaptive evolution a regimen consisting of repeated batch cultivation with repeated cycles of consecutive growth in different media is applied, e.g. three media with different compositions (glucose, xylose, and arabinose; xylose and arabinose. See Wisselink et al. (2009) Applied and Environmental Microbiology, February 2009, p. 907-914.

Yeast Transformation and Genetic Stability

Genetic engineering, i.e. transformation of yeast cells with recombinant DNA, became feasible for the first time in 1978 [Beggs, 1978; Hinnen et al., 1978]. Recombinant DNA technology in yeast has established itself since then. A multitude of different vector constructs are available. Generally, these plasmid vectors, called shuttle vectors, contain genetic material derived from *E. coli* vectors consisting of an origin of replication and a selectable marker (often the ßlactamase gene, ampR), which enable them to be propagated in *E. coli* prior to transformation into yeast cells. Additionally, the shuttle vectors contain a selectable marker for selection in yeast. Markers can be genes encoding enzymes for the synthesis of a particular amino acid or nucleotide, so that cells carrying the corresponding genomic deletion (or mutation) are complemented for auxotrophy or autotrophy. Alternatively, these vectors contain heterologous dominant resistance markers, which provides recombinant yeast cells (i.e. the cells that have taken up the DNA and express the marker gene) resistance towards certain antibiotics, like g418 (Geneticin), hygromycinB or phleomycin. In addition, these vectors may contain a sequence of (combined) restriction sites (multiple cloning site or MCS) which will allow to clone foreign DNA into these sites, although alternative methods exist as well.

Traditionally, four types of shuttle vectors can be distinguished by the absence or presence of additional genetic elements:

Integrative plasmids (YIp) which by homologous recombination are integrated into the host genome at the locus of the marker or another gene, when this is opened by restriction and the linearized DNA is used for transformation of the yeast cells. This generally results in the presence of one copy of the foreign DNA inserted at this particular site in the genome.

Episomal plasmids (YEp) which carry part of the 2µ plasmid DNA sequence necessary for autonomous replication in yeast cells. Multiple copies of the transformed plasmid are propagated in the yeast cell and maintained as episomes.

Autonomously replicating plasmids (YRp) which carry a yeast origin of replication (ARS, autonomously replicated sequence) that allows the transformed plasmids to be propagated several hundred-fold.

CEN plasmids (YCp) which carry in addition to an ARS sequence a centromeric sequence (derived from one of the nuclear chromosomes) which normally guarantees stable mitotic segregation and usually reduces the copy number of self-replicated plasmid to just one.

These plasmids are being introduced into the yeast cells by transformation. Transformation of yeast cells may be achieved by several different techniques, such as permeabilization of cells with lithium acetate (Ito et al, 1983) and electroporation methods.

In commercial application of recombinant microorganisms, plasmid instability is the most important problem. Instability is the tendency of the transformed cells to lose their engineered properties because of changes to, or loss of, plasmids. This issue is discussed in detail by Zhang et al (Plasmid stability in recombinant *Saccharomyces cerevisiae*. Biotechnology Advances, Vol. 14, No. 4, pp. 401-435, 1996). Strains transformed with integrative plasmids are extremely stable, even in the absence of selective pressure (Sherman, F. dbb.urmc.rochester.edu/labs/sherman_f/yeast/ 9.html and references therein).

The heterologous DNA is usually introduced into the organism in the form of extra-chromosomal plasmids (YEp, YCp and YRp). Unfortunately, it has been found with both bacteria and yeasts that the new characteristics may not be retained, especially if the selection pressure is not applied continuously. This is due to the segregational instability of the hybrid plasmid when recombinant cells grow for a long period of time. This leads to population heterogeneity and clonal variability, and eventually to a cell population in which the majority of the cells has lost the properties that were introduced by transformation. If vectors with auxotrophic markers are being used, cultivation in rich media often leads to rapid loss of the vector, since the vector is only retained in minimal media. The alternative, the use of dominant antibiotic resistance markers, is often not compatible with production processes. The use of antibiotics may not be desired from a registration point of view (the possibility that trace amounts of the antibiotic end up in the end product) or for economic reasons (costs of the use of antibiotics at industrial scale).

Loss of vectors leads to problems in large scale production situations. Alternative methods for introduction of DNA do exist for yeasts, such as the use of integrating plasmids (YIp). The DNA is integrated into the host genome by recombination, resulting in high stability. (Gaunt, P. Stability of recombinant plasmids in yeast. Journal of Biotechnology 9(1988) 173-192). We have found that an integration method using the host transposons are a good alternative. In an embodiment genes may be integrated into the transformed host cell genome. Initial introduction (i.e. before adaptive evolution) of multiple copies be executed in any way known in the art that leads to introduction of the genes. In an embodiment, this may be accomplished using a vector with parts homologous to repeated sequences (transposons), of the host cell. When the host cell is a yeast cell, suitable repeated sequences are the long terminal repeats (LTR) of the Ty element, known as delta sequence. Ty elements fall into two rather similar subfamilies called Ty1 and Ty2. These elements are about 6 kilobases (kb) in length and are bounded by long terminal repeats (LTR), sequences of about 335 base pairs (Boeke J D et al, The *Saccharomyces cerevisiae* Genome Contains Functional and Nonfunctional Copies of Transposon Ty1. Molecular and Cellular Biology, April 1988, p. 1432-1442 Vol. 8, No. 4). In the fully sequenced *S. cerevisiae* strain, S288c, the most abundant transposons are Ty1 (31 copies) and Ty2 (13 copies) (Gabriel A, Dapprich J, Kunkel M, Gresham D, Pratt S C, et al. (2006) Global mapping of transposon location. PLoS Genet 2(12): e212.doi:10.1371/journal.pgen.0020212). These transposons consist of two overlapping open reading frames (ORFs), each of which encode several proteins. The coding regions are flanked by the aforementioned, nearly identical LTRs. Other, but less abundant and more distinct Ty elements in *S. cereviaise* comprise Ty3, Ty4 and Ty5. For each family of full-length Ty elements there are an order of magnitude more solo LTR elements dispersed through the genome. These are thought to arise by LTR-LTR recombination of full-length elements, with looping out of the internal protein encoding regions.

The retrotransposition mechanism of the Ty retrotransposon has been exploited to integrate multiple copies throughout the genome (Boeke et al., 1988; Jacobs et al., 1988). The long terminal repeats (LTR) of the Ty element, known as delta sequences, are also good targets for integration by homologous recombination as they exist in about 150-200 copies that are either Ty associated or solo sites (Boeke, 1989; Kingsman and Kingsman, 1988). (Parekh R. N. (1996). An Integrating Vector for Tunable, High Copy, Stable Integration into the Dispersed Ty DELTA Sites of *Saccharomyces cerevisiae*. Biotechnol. Prog. 1996, 12, 16-21). By adaptive evolution, the number of copies may change.

The Host Cell

The host cell may be any host cell suitable for production of a useful product. A host cell may be any suitable cell, such as a prokaryotic cell, such as a bacterium, or a eukaryotic cell. Typically, the cell will be a eukaryotic cell, for example a yeast or a filamentous fungus.

Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form.

Yeasts may either grow by budding of a unicellular thallus or may grow by fission of the organism. A preferred yeast as a transformed host cell may belong to the genera *Saccharomyces, Kluyveromyces, Candida, Pichia, Schizosaccharomyces, Hansenula, Kloeckera, Schwanniomyces* or *Yarrowia*. Preferably the yeast is one capable of anaerobic fermentation, more preferably one capable of anaerobic alcoholic fermentation.

Filamentous fungi are herein defined as eukaryotic microorganisms that include all filamentous forms of the subdivision Eumycotina. These fungi are characterized by a vegetative mycelium composed of chitin, cellulose, and other complex polysaccharides. The filamentous fungi of the suitable for use as a cell of the present invention are morphologically, physiologically, and genetically distinct from yeasts. Filamentous fungal cells may be advantageously used since most fungi do not require sterile conditions for propagation and are insensitive to bacteriophage infections. Vegetative growth by filamentous fungi is by hyphal elongation and carbon catabolism of most filamentous fungi is obligately aerobic. Preferred filamentous fungi as a host cell may belong to the genus *Aspergillus, Trichoderma, Humicola, Acremoniurra, Fusarium* or *Penicillium*. More preferably, the filamentous fungal cell may be a *Aspergillus niger, Aspergillus oryzae*, a *Penicillium chrysogenum*, or *Rhizopus oryzae* cell.

In one embodiment the host cell may be yeast.

Preferably the host is an industrial host, more preferably an industrial yeast. An industrial host and industrial yeast cell may be defined as follows. The living environments of yeast cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. Examples of industrial yeast (*S. cerevisiae*) are Ethanol Red® (Fermentis) Fermiol® (DSM) and Thermosacc® (Lallemand).

In an embodiment the host is inhibitor tolerant. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

araA, araB and araD Genes

A transformed host cell is capable of using arabinose. A transformed host cell is therefore, be capable of converting L-arabinose into L-ribulose and/or xylulose 5-phosphate and/or into a desired fermentation product, for example one of those mentioned herein.

Organisms, for example *S. cerevisiae* strains, able to produce ethanol from L-arabinose may be produced by modifying a cell introducing the araA (L-arabinose isomerase), araB (L-ribulokinase) and araD (L-ribulose-5-P4-epimerase) genes from a suitable source. Such genes may be introduced into a transformed host cell is order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591.

PPP-Genes

A transformed host cell may comprise one or more genetic modifications that increases the flux of the pentose phosphate pathway. In particular, the genetic modification(s) may lead to an increased flux through the non-oxidative part of the pentose phosphate pathway. A genetic modification that causes an increased flux of the non-oxidative part of the pentose phosphate pathway is herein understood to mean a modification that increases the flux by at least a factor of about 1.1, about 1.2, about 1.5, about 2, about 5, about 10 or about 20 as compared to the flux in a strain which is genetically identical except for the genetic modification causing the increased flux. The flux of the non-oxidative part of the pentose phosphate pathway may be measured by growing the modified host on xylose as sole carbon source, determining the specific xylose consumption rate and subtracting the specific xylitol production rate from the specific xylose consumption rate, if any xylitol is produced. However, the flux of the non-oxidative part of the pentose phosphate pathway is proportional with the growth rate on xylose as sole carbon source, preferably with the anaerobic growth rate on xylose as sole carbon source. There is a linear relation between the growth rate on xylose as sole carbon source ($\mu_{max}$) and the flux of the non-oxidative part of the pentose phosphate pathway. The specific xylose consumption rate ($Q_s$) is equal to the growth rate ($\mu$) divided by the yield of biomass on sugar ($Y_{xs}$) because the yield of biomass on sugar is constant (under a given set of conditions: anaerobic, growth medium, pH, genetic background of the strain, etc.; i.e. $Q_s = \mu/Y_{xs}$). Therefore the increased flux of the non-oxidative part of the pentose phosphate pathway may be deduced from the increase in maximum growth rate under these conditions unless transport (uptake is limiting).

One or more genetic modifications that increase the flux of the pentose phosphate pathway may be introduced in the host cell in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred host cell, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate epimerase; or at least the enzymes ribulose-5-phosphate isomerase and transketolase; or at least the enzymes ribulose-5-phosphate isomerase and transaldolase; or at least the enzymes ribulose-5-phosphate epimerase and transketolase; or at least the enzymes ribulose-5-phosphate epimerase and transaldolase; or at least the enzymes transketolase and transaldolase; or at least the enzymes ribulose-5-phosphate epimerase, transketolase and transaldolase; or at least the enzymes ribulose-5-phosphate isomerase, transketolase and transaldolase; or at least the enzymes ribulose-5-phosphate isomerase, ribulose-5-phosphate epimerase, and transaldolase; or at least the enzymes ribulose-5-phosphate isomerase, ribulose-5-phosphate epimerase, and transketolase. In one embodiment of the invention each of the enzymes ribulose-5-phosphate isomerase, ribulose-5-phosphate epimerase, transketolase and transaldolase are overexpressed in the host cell. More preferred is a host cell in which the genetic modification comprises at least overexpression of both the enzymes transketolase and transaldolase as such a host cell is already capable of anaerobic growth on xylose. In fact, under some conditions host cells overexpressing only the transketolase and the transaldolase already have the same anaerobic growth rate on xylose as do host cells that overexpress all four of the enzymes, i.e. the ribulose-5-phosphate isomerase, ribulose-5-phosphate epimerase, transketolase and transaldolase. Moreover, host cells overexpressing both of the enzymes ribulose-5-phosphate isomerase and ribulose-5-phosphate epimerase are preferred over host cells overexpressing only the isomerase or only the epimerase as overexpression of only one of these enzymes may produce metabolic imbalances.

The enzyme "ribulose 5-phosphate epimerase" (EC 5.1.3.1) is herein defined as an enzyme that catalyses the epimerisation of D-xylulose 5-phosphate into D-ribulose 5-phosphate and vice versa. The enzyme is also known as phosphoribulose epimerase; erythrose-4-phosphate isomerase; phosphoketopentose 3-epimerase; xylulose phosphate 3-epimerase; phosphoketopentose epimerase; ribulose 5-phosphate 3-epimerase; D-ribulose phosphate-3-epimerase; D-ribulose 5-phosphate epimerase; D-ribulose-5-P 3-epimerase; D-xylulose-5-phosphate 3-epimerase; pentose-5-phosphate 3-epimerase; or D-ribulose-5-phosphate 3-epimerase. A ribulose 5-phosphate epimerase may be further defined by its amino acid sequence. Likewise a ribulose 5-phosphate epimerase may be defined by a nucleotide sequence encoding the enzyme as well as by a nucleotide sequence hybridising to a reference nucleotide sequence encoding a ribulose 5-phosphate epimerase. The nucleotide sequence encoding for ribulose 5-phosphate epimerase is herein designated RPE1.

The enzyme "ribulose 5-phosphate isomerase" (EC 5.3.1.6) is herein defined as an enzyme that catalyses direct isomerisation of D-ribose 5-phosphate into D-ribulose 5-phosphate and vice versa. The enzyme is also known as phosphopentosisomerase; phosphoriboisomerase; ribose phosphate isomerase; 5-phosphoribose isomerase; D-ribose 5-phosphate isomerase; D-ribose-5-phosphate ketol-isomerase; or D-ribose-5-phosphate aldose-ketose-isomerase. A ribulose 5-phosphate isomerase may be further defined by its amino acid sequence. Likewise a ribulose 5-phosphate isomerase may be defined by a nucleotide sequence encoding the enzyme as well as by a nucleotide sequence hybridising to a reference nucleotide sequence encoding a ribulose 5-phosphate isomerase. The nucleotide sequence encoding for ribulose 5-phosphate isomerase is herein designated RKI1.

The enzyme "transketolase" (EC 2.2.1.1) is herein defined as an enzyme that catalyses the reaction: D-ribose 5-phosphate+D-xylulose 5-phosphate<−>sedoheptulose 7-phosphate+D-glyceraldehyde 3-phosphate and vice versa. The enzyme is also known as glycolaldehydetransferase or sedoheptulose-7-phosphate:D-glyceraldehyde-3-phosphate glycolaldehydetransferase. A transketolase may be further defined by its amino acid. Likewise a transketolase may be defined by a nucleotide sequence encoding the enzyme as well as by a nucleotide sequence hybridising to a reference nucleotide sequence encoding a transketolase. The nucleotide sequence encoding for transketolase is herein designated TKL1.

The enzyme "transaldolase" (EC 2.2.1.2) is herein defined as an enzyme that catalyses the reaction: sedoheptulose 7-phosphate+D-glyceraldehyde 3-phosphate<−>D-erythrose 4-phosphate+D-fructose 6-phosphate and vice versa. The enzyme is also known as dihydroxyacetonetransferase; dihydroxyacetone synthase; formaldehyde transketolase; or sedoheptulose-7-phosphate: D-glyceraldehyde-3-phosphate glyceronetransferase. A transaldolase may be further defined by its amino acid sequence. Likewise a transaldolase may be defined by a nucleotide sequence encoding the enzyme as well as by a nucleotide sequence hybridising to a reference nucleotide sequence encoding a transaldolase. The nucleotide sequence encoding for transketolase from is herein designated TAL1.

Xylose Isomerase or Xylose Reductase Genes

According to the invention, one or more copies of one or more xylose isomerase gene and/or one or more xylose reductase and xylitol dehydrogenase are introduced into the genome of the host cell. The presence of these genetic elements confers on the cell the ability to convert xylose by isomerisation or reduction.

In one embodiment, the one or more copies of one or more xylose isomerase gene are introduced into the genome of the host cell.

A "xylose isomerase" (EC 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). A xylose isomerase herein may require a bivalent cation, such as magnesium, manganese or cobalt as a cofactor.

Accordingly, such a transformed host cell is capable of isomerising xylose to xylulose. The ability of isomerising xylose to xylulose is conferred on the host cell by transformation of the host cell with a nucleic acid construct comprising a nucleotide sequence encoding a defined xylose isomerase. A transformed host cell isomerises xylose into xylulose by the direct isomerisation of xylose to xylulose.

A unit (U) of xylose isomerase activity may herein be defined as the amount of enzyme producing 1 nmol of xylulose per minute, under conditions as described by Kuyper et al. (2003, FEMS Yeast Res. 4: 69-78).

The Xylose isomerise gene may have various origin, such as for example *Piromyces* sp. as disclosed in WO2006/009434. Other suitable origins are *Bacteroides*, in particular *Bacteroides uniformis* as described in PCT/EP2009/52623, *Bacillus*, in particular *Bacillus stearothermophilus* as described in PCT/EP2009/052625.

In another embodiment, one or more copies of one or more xylose reductase and xylitol dehydrogenase genes are introduced into the genome of the host cell. In this embodiment the conversion of xylose is conducted in a two step conversion of xylose into xylulose via a xylitol intermediate as catalysed by xylose reductase and xylitol dehydrogenase, respectively. In an embodiment thereof xylose reductase (XR), xylitol dehydrogenase (XDH), and xylokinase (XK) may be overexpressed, and optionally one or more of genes encoding NADPH producing enzymes are up-regulated and one or more of the genes encoding NADH consuming enzymes are up-regulated, as disclosed in WO 2004085627.

XKS1 Gene

A transformed host cell may comprise one or more genetic modifications that increase the specific xylulose kinase activity. Preferably the genetic modification or modifications causes overexpression of a xylulose kinase, e.g. by overexpression of a nucleotide sequence encoding a xylulose kinase. The gene encoding the xylulose kinase may be endogenous to the host cell or may be a xylulose kinase that is heterologous to the host cell. A nucleotide sequence used for overexpression of xylulose kinase in the host cell is a nucleotide sequence encoding a polypeptide with xylulose kinase activity.

The enzyme "xylulose kinase" (EC 2.7.1.17) is herein defined as an enzyme that catalyses the reaction ATP+D-xylulose=ADP+D-xylulose 5-phosphate. The enzyme is also known as a phosphorylating xylulokinase, D-xylulokinase or ATP:D-xylulose 5-phosphotransferase. A xylulose kinase of the invention may be further defined by its amino acid sequence. Likewise a xylulose kinase may be defined by a nucleotide sequence encoding the enzyme as well as by a nucleotide sequence hybridising to a reference nucleotide sequence encoding a xylulose kinase.

In a transformed host cell, a genetic modification or modifications that increase(s) the specific xylulose kinase activity may be combined with any of the modifications increasing the flux of the pentose phosphate pathway as described above. This is not, however, essential.

Thus, a host cell may comprise only a genetic modification or modifications that increase the specific xylulose kinase activity. The various means available in the art for achieving and analysing overexpression of a xylulose kinase in the host cells of the invention are the same as described above for enzymes of the pentose phosphate pathway. Preferably in the host cells of the invention, a xylulose kinase to be overexpressed is overexpressed by at least a factor of about 1.1, about 1.2, about 1.5, about 2, about 5, about 10 or about 20 as compared to a strain which is genetically identical except for the genetic modification(s) causing the overexpression. It is to be understood that these levels of overexpression may apply to the steady state level of the enzyme's activity, the steady state level of the enzyme's protein as well as to the steady state level of the transcript coding for the enzyme.

Aldose Reductase (GRE3) Gene Deletion

In the embodiment, where XI is used as gene to convert xylose, it may be advantageous to reduce aldose reducatase activity. A transformed host cell may therefore comprise one or more genetic modifications that reduce unspecific aldose reductase activity in the host cell. Preferably, unspecific aldose reductase activity is reduced in the host cell by one or more genetic modifications that reduce the expression of or inactivates a gene encoding an unspecific aldose reductase. Preferably, the genetic modification(s) reduce or inactivate the expression of each endogenous copy of a gene encoding an unspecific aldose reductase in the host cell (herein called GRE3 deletion). Transformed host cells may comprise multiple copies of genes encoding unspecific aldose reductases as a result of di-, poly- or aneu-ploidy, and/or the host cell may contain several different (iso) enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell.

A nucleotide sequence encoding an aldose reductase whose activity is to be reduced in the host cell is a nucleotide sequence encoding a polypeptide with aldose reductase activity.

Thus, a host cell comprising only a genetic modification or modifications that reduce(s) unspecific aldose reductase activity in the host cell is specifically included in the invention.

The enzyme "aldose reductase" (EC 1.1.1.21) is herein defined as any enzyme that is capable of reducing xylose or xylulose to xylitol. In the context of the present invention an aldose reductase may be any unspecific aldose reductase that is native (endogenous) to a host cell of the invention and that is capable of reducing xylose or xylulose to xylitol. Unspecific aldose reductases catalyse the reaction:

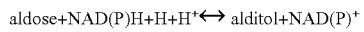

aldose+NAD(P)H+H$^+$ ↔ alditol+NAD(P)$^+$

The enzyme has a wide specificity and is also known as aldose reductase; polyol dehydrogenase (NADP$^+$); alditol: NADP oxidoreductase; alditol:NADP$^+$1-oxidoreductase; NADPH-aldopentose reductase; or NADPH-aldose reductase.

A particular example of such an unspecific aldose reductase that is endogenous to *S. cerevisiae* and that is encoded by the GRE3 gene (Traff et al., 2001, Appl. Environ. Microbiol. 67: 5668-74). Thus, an aldose reductase of the invention may be further defined by its amino acid sequence. Likewise an aldose reductase may be defined by the nucleotide sequences encoding the enzyme as well as by a nucleotide sequence hybridising to a reference nucleotide sequence encoding an aldose reductase.

Bioproducts Production

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i. e., a high acid-, ethanol- and osmo-tolerance, capability of anaerobic growth, and of course its high alcoholic fermentative capacity. Preferred yeast species as host cells include *S. cerevisiae*, *S. bulderi*, *S. barnetti*, *S. exiguus*, *S. uvarum*, *S. diastaticus*, *K. lactis*, *K. marxianus* or *K fragilis*.

A transformed host cell may be a cell suitable for the production of ethanol. A transformed host cell may, however, be suitable for the production of fermentation products other than ethanol Such non-ethanolic fermentation products include in principle any bulk or fine chemical that is producible by a eukaryotic microorganism such as a yeast or a filamentous fungus.

A transformed host cell that may be used for production of non-ethanolic fermentation products is a host cell that contains a genetic modification that results in decreased alcohol dehydrogenase activity.

In an embodiment the transformed host cell may be used in a process wherein sugars originating from lignocellulose are converted into ethanol.

Lignocellulose

Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Enzymatic Hydrolysis

The pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes. The conversion with the cellulases may be executed at ambient temperatures or at higher tempatures, at a reaction time to release sufficient amounts of sugar(s). The result of the enzymatic hydrolysis is hydrolysis product comprising C5/C6 sugars, herein designated as the sugar composition.

Fermentation

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating NAD$^+$.

Thus, in a preferred anaerobic fermentation process pyruvate is used as an electron (and hydrogen acceptor) and is reduced to fermentation products such as ethanol, butanol, lactic acid, di-terpene, glycosylated di-terpene, 3-hydroxypropionic acid, acrylic acid, acetic acid, succinic acid, citric acid, malic acid, fumaric acid, an amino acid, 1,3-propanediol, ethylene, glycerol, a β-lactam antibiotic and a cephalosporin.

The fermentation process is preferably run at a temperature that is optimal for the cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.

The fermentation process according to the present invention may be run under aerobic and anaerobic conditions. In an embodiment, the process is carried out under microaerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention may comprise recovery of the fermentation product.

In a preferred process the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as yeasts are well known in the art The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 g1/L-200 g/L, 40 g/L-200 g/L, 50 g/L-200 g/L, 60 g/L-200 g/L, 70 g/L-200 g/L, 80 g/L-200 g/L, 90 g/L, 80 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical maximum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180=0.511 gr ethanol/gr glucose.

For Butanol (MW 74 gr/mole) or iso butanol, the theoretical maximum yield is 1 mole of butanol per mole of glucose. So Yps max for (iso-)butanol=74/180=0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps gl/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L Accordingly, the invention provides a method for the preparation of a fermentation product, which method comprises:

a. degrading lignocellulose using a method as described herein; and b. fermenting the resulting material, thereby to prepare a fermentation product.

Fermentation Product

The fermentation product of the invention may be any useful product. In one embodiment, it is a product selected from the group consisting of ethanol, n-butanol, isobutanol, lactic acid, di-terpene, glycosylated di-terpene, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase. For example the fermentation products may be produced by cells according to the invention, following prior art cell preparation methods and fermentation processes, which examples however should herein not be construed as limiting. n-butanol may be produced by cells as described in WO2008121701 or WO2008086124; lactic acid as described in US2011053231 or US2010137551; 3-hydroxy-propionic acid as described in WO2010010291; acrylic acid as described in WO2009153047.

Recovery of the Fermentation Product

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol.

The following examples illustrate the invention:

EXAMPLES

Methods

Molecular Biology Techniques and Chemicals.

Restriction enzymes and T4 DNA ligase were acquired from Fermentas. Antibiotics hygromycin (HG), phleomycin (phleo) and geneticin (G418) were acquired from Invivogen. pYL16 and nourseothricin (nour) were acquired from Werner Bioagents. Ampicillin and kanamycin were acquired from Sigma-Aldrich.

For PCR amplifications, Phusion® High-Fidelity DNA Polymerase was used (Finnzymes). PCR fragments were sub-cloned using the TOPO® TA Cloning@ Kit or the Zero Blunt@ TOPO® PCR Cloning Kit (both from Life Technologies). Oligonucleotides used for strain construction were purchased from Sigma-Aldrich.

Plasmids were amplified and maintained in chemically competent TOP10 cells (TOPO® TA Cloning@ Kit, Life Techonologies) following manufacturer's instructions. Plasmids were isolated from E. coli mini cultures using the GeneJET™ Plasmid Miniprep Kit (Fermentas). Genomic DNA was isolated from yeast using the YeaStar™ Genomic DNA Kit (ZymoResearch) following manufacturer's instructions.

Standard molecular biology and yeast genetics techniques were conducted according to textbooks including Sambrook et al. (1989) and Ausubel et al. (1995).

Strains and Maintenance.

For storage of the strains used in this work (Table 2), shake flask cultures were performed in rich medium (YP), consisting of 10 g l$^{-1}$ yeast extract (Oxoid) and 20 g l$^{-1}$ peptone (BD Difco), supplemented with either 2% glucose (YPD), 2% maltose (YPM), or 3% xylose (YPX). Cultures were maintained at 30° C. in an orbital shaker until cultures reached stationary growth phase. After adding glycerol to 30% (v/v), samples from shake-flask cultures were stored in 2 ml aliquots at −80° C.

TABLE 2

Strains used or prepared herein

| Strain | Genotype |
|---|---|
| RN1001 | Mat a, ura3-52, leu2-112, gre3::loxP, loxP-Ptpi:TAL1, loxP-Ptpi::RKI1, loxP-Ptpi-TKL1, loxP-Ptpi-RPE1, delta::Padh1XKS1Tcyc1-LEU2, delta::URA3-Ptpi-xylA-Tcyc1 |
| RN1014 | RN1001 + in vivo engineering on xylose and acetic acid |
| RN1041 | RN1001 his3::loxP |
| RN1053 | RN1041 hxt2::loxP-kanMX-loxP, hxt367::loxP-hphMX-loxP, hxt145::loxP-natMX-loxP, gal2::loxP-zeoMX-loxP |
| YD01227 | RN1014 glk1::lox72; hxk1::loxP; hxk2::lox72; gal1::loxP; his3::loxPnatMXloxP |

OD600 and HPLC Analysis in Shake Flask Culture.

Shake flask cultures were sampled regularly during culture. For OD600 measurements, cultures were diluted appropriately for accurate measurement and optical density was measured at 600 nm wavelength in a Perkin Elmer Spectrophotometer λ2 instrument. Remaining sample was filtrated to separate medium from yeast.

The filtrate was inserted into the appropriate vials for HPLC analysis. The concentrations of glucose, xylose, glycerol, acetic acid and ethanol in the medium were determined using a Shimadzu HPLC system. The system is equipped with column oven CTO-10A-vp and Autoinjector SIL-10AD-vp with a guard column (Bio-Rad H cartridge, Bio-Rad) and an Aminex HPX-87H column (300×7.8 mm; Bio-Rad). Elution took place at 80° C. with 5 mM H2SO4 at 0.6 mL/min. The eluate was monitored using a Refractive Index detector RID-10A (Shimadzu).

Microwell Plate Culture for Growth Curve Profiling.

For micro-well cultivation of strains, the Bioscreen C (Growth Curves Ltd.) was used. Overnight pre-cultures were pelleted, washed with demi water and diluted in demi water to twice the desired OD600 for inoculation. Medium was prepared in twice the concentration as desired. In one well of a honeycomb wellplate, 150 µl medium was mixed with 150 µl cell suspension. Measurements were conducted in triplicate. Settings for the Bioscreen C were maintained at 30° C. incubation T, measurements every 15 min, shaking at type Continuous, amplitude Maximum, and speed Normal. Shaking was set to stop 5 sec before measurement.

Automated Transformation and Colony Picking.

For the generation of transformation of a saturation mutagenesis library into the model strains shake-flask cultures were performed in either YPM for RN1053, or YPX for YD01227 (see below). Yeast cells were pelleted and, subsequently, used in an automated transformation protocol based on Schiestl and Gietz (1989). Transformation mixes were plated on selection medium consisting of yeast nitrogen base (Sigma-Aldrich; 6.7 g l$^{-1}$), agar (BD Biosciences; 15 g l$^{-1}$), supplemented with either 2% maltose (RN1053 transformations) or 3% xylose (YD01227 transformations). Transformation plates were incubated at 30° C., and after colony formation, colonies were re-plated using an automated process transferring colonies to 96 well microtiter plates (MTP) containing the above-referred selection media. MTPs with transformants were incubated at 30° C. until clear growth was observed.

NMR Analysis.

For the quantification of glucose, xylose, glycerol, acetic acid and ethanol in the sample, 100 µl sample is transferred accurately into a suitable vial. Subsequently 100 µl internal standard solution, containing maleic acid (20 g/l), EDTA (40 g/l) and trace amounts of DSS (4,4-dimethyl-4-silapentane-1-sulfonic acid) in D$_2$O, and 450 µL D$_2$O is added.

1D $^1$H NMR spectra are recorded on a Bruker Avance III 700 MHz, equipped with a cryo-probe, using a pulse program with water suppression (power corresponding to 3 Hz) at a temperature of 27° C.

The analyte concentrations are calculated based on the following signals (6 relative to DSS):
α-glucose peak at 5.22 ppm (d, 0.38 H, J=4 Hz),
α-xylose peak at 5.18 ppm (d, 0.37 H, J=4 Hz),
glycerol peak at 3.55 ppm (dd, 2H, $J_{1,2}$=6 Hz and $J_{1a,1b}$=12 Hz)
acetic acid peak at 1.91 ppm (s, 3H)
ethanol peak at 1.17 ppm (t, 3H, J=7 Hz)
The signal user for the standard:
Maleic acid peak at 6.05 ppm (s, 2H)

Example 1—Hexose Transporter Gene Deletions

Deletion Cassettes Construction.

Primers used in plasmid constructions are shown in Table 3; generated plasmids are shown in Table 4. Schemes with restriction sites used for cloning and sites used to release deletion constructs from the plasmid backbone are shown in Table 5.

TABLE 3

Primers (oligonucleotides) used in the examples

| SEQ ID NO: | Internal code | Primer | Sequence (5'→3') | Gene(s) | Purpose |
|---|---|---|---|---|---|
| 1 | 5034 | Kanf | AAGCTTGCCTCGTCCCCGCC | kanMX | Amplification kanMX |
| 2 | 5035 | Kanr | GTCGACACTGGATGGCGGCG | kanMX | Amplification kanMX |
| 3 | 5116 | If2 | ATTCTAGTAACGGCCGCCAGTGTG CTGGAATTCGCCCTTAAGCTTGCC TCGTCCCCGCCG | loxP | Part of loxP flank |
| 45 | 5118 | Ir2 | CATACATTATACGAAGTTATGCGC GCTCTAGATATCGTCGACACTGGA TGGCGGCG | loxP | Part of loxP flank |
| 5 | 5115 | If1 | ATCCGGACGTACGTATAACTTCGT ATAGCATACATTATACGAAGTTATT CTAGTAACGGCCGCCA | loxP | Reamplification/ full loxP flank |
| 6 | 5117 | Ir1 | TCATGACGTCTCGAGGCCTATAAC TTCGTATAGCATACATTATACGAAG TTATGCGCGCT | loxP | Reamplification/ full loxP flank |
| 10 | 115 | Natf | ACATGTAAAATGACCACTCTTGAC GACACGGC | nat1 | Amplification nat1 |
| 11 | 116 | Natr | CAGTACTAGGGGCCAGGGCATGC TC | nat1 | Amplification nat1 |
| 13 | 28 | H3f | TGTACATCCGGAATTCTAGATTGG TGAGCGCTAGGAGTCACTGCC | HIS3 | — |
| 14 | 29 | H3r | CTCGAGTATTTCACACCGCATATG ATCCGTCG | HIS3 | — |
| 16 | 201 | Hx2uf | GACTAGTACCGGTGTTTTCAAAAC CTAGCAACCCC | HXT2 | Upstream flank |
| 17 | 202 | Hx2ur | CGTACGCGTCTTCCGGAAGGGTA CCATCAGATTTCATTTGACC | HXT2 | Upstream flank |
| 18 | 203 | Hx2df | GAAGACACTCGAGACGTCCTTTGT CTGTGAAACCAAGGGC | HXT2 | Downstream flank |
| 19 | 204 | Hx2dr | GTCGACGGGCCCTTATGTTGGTCT TGTTTAGTATGGCCG | HXT2 | Downstream flank |
| 20 | 205 | Hx3uf | AAGCGGCCGCACTAGTACCGGTG AAACAACTCAATAACGATGTGGGA C | HXT3 | Upstream flank |
| 21 | 206 | Hx3ur | ATCCGGACGTCTTCCTCAAGAAAT CAGTTTGGGCGACG | HXT3 | Upstream flank |
| 22 | 210 | Hx4df | AGAAGACGCTCGAGACGTCCCTTA TGGGAAGAAGGTGTTTTGCC | HXT4 | Downstream flank |
| 23 | 211 | Hx4dr | ATGGATCCTAGGGGTTCTTGCAGA GTAAACTGCG | HXT4 | Downstream flank |
| 24 | 212 | Hx5uf | AAGCGGCCGCACTAGTACATGTGA ACTTGAAAACGCTCATCAAGGC | HXT5 | Upstream flank |
| 25 | 213 | Hx5ur | TTCGTACGCGTCTTCCGGAGTAAC ATGAAACCAGAGTACCACG | HXT5 | Upstream flank |
| 26 | 229 | Hx7df | AGAAGACCCTCGAGACGTCCGAC GCTGAAGAAATGACTCACG | HXT7 | Downstream flank |
| 27 | 230 | Hx7dr | AGTCGACGGATCCGTAATTTTTCT TCTTTTAAGTGACGGGCG | HXT7 | Downstream flank |
| 28 | 243 | Gal2ufn | AAGCGGCCGCACTAGTACCGGTG ATCTATATTCGAAAGGGGCGG | GAL2 | Upstream flank |

TABLE 3-continued

Primers (oligonucleotides) used in the examples

| SEQ ID NO: | Internal code | Primer | Sequence (5'→3') | Gene(s) | Purpose |
|---|---|---|---|---|---|
| 29 | 244 | Gal2urn | AACGTACGTCCGGATCATTAGAATACTTTTGAGATTGTGCGCT | GAL2 | Upstream flank |
| 30 | 233 | Ga2df | AGAAGACCCTCGAGACGTCTTACCTTGGAAATCTGAAGGCTGG | GAL2 | Downstream flank |
| 31 | 234 | Ga2dr | GTGGATCCTAGGTAAAACGGTACGAGAAAAGCTCCG | GAL2 | Downstream flank |
| 36 | 281 | Hx3inr2 | GCTCTTTTCACGGAGAAATTCGGG | HXT3-6-7 | Integration check |
| 39 | 289 | Hx2inf | TCTTCGGGAACTAGATAGGTGGC | HXT2 | Integration check |
| 43 | 290 | Hx2inr | GAAGTAATCAGCCACAATACGCC | HXT2 | Integration check |
| 38 | 299 | Hx4inr2 | CCATACTATTTGTCGACTCAAGCGC | HXT5-1-4 | Integration check |
| 39 | 317 | Hx5inf | GGGTTAATTAGTTTTAGGGGCACGG | HXT5-1-4 | Integration check |
| 37 | 323 | Hx7inr1 | GATGAGAATCCTTGGCAACCGC | HXT3-6-7 | Integration check |
| 40 | 324 | Ga2inf1 | TCAATTCGGAAAGCTTCCTTCCGG | GAL2 | Integration check |
| 41 | 325 | Ga2inr1 | CAGTGATAGTTTGGTTCGAGCGG | GAL2 | Integration check |
| 44 | 838 | Glk1-psuc227f | ATGTCATTCGACGACTTACACAAAGCCACTGAGAGAGCGGTCATCCAGGCCCGTCGACCTCGAGTACCGTTCG | GLK1 | Hexokinase flank/Bipartite cassette |
| 45 | 834 | Hxk2-psuc227f | GCCAGAAAGGGTTCCATGGCCGATGTGCCAAAGGAATTGATGCAACAAATCCGTCGACCTCGAGTACCGTTCG | HXK2 | Hexokinase flank/Bipartite cassette |
| 46 | 645 | pSUC227r | GCAATTTCGGCTATACGTAAC | | Bipartite cassette |
| 47 | 839 | Glk1-psuc225r | CAATCTTCAAGTGCACCTTCCTCTCACCCTCGGCACCCAAGGGTGACAAGCCGGATCCTACCGTTCGTATAGC | GLK1 | Hexokinase flank/Bipartite cassette |
| 48 | 835 | Hxk2-psuc225r | GCCAGAAAGGGTTCCATGGCCGATGTGCCAAAGGAATTGATGCAACAAATCCGTCGACCTCGAGTACCGTTCG | HXK2 | Hexokinase flank/Bipartite cassette |
| 49 | 646 | pSUC225f | CGTTCACTCATGGAAAATAGC | | Bipartite cassette |
| 50 | 846 | Hxk1_loxP_f | ATGGTTCATTTAGGTCCAAAGAAACCACAGGCTAGAAAGGGTTCCATGGCCGGATCCACTAGCATAACTTCG | HXK1 | Hexokinase flank/DRM cassette |
| 51 | 847 | Hxk1_loxP_r | ATGGTTCATTTAGGTCCAAAGAAACCACAGGCTAGAAAGGGTTCCATGGCCGGATCCACTAGCATAACTTCG | HXK1 | Hexokinase flank/DRM cassette |
| 52 | 848 | Gal1_loxP_f | ATGACTAAATCTCATTCAGAAGAAGTGATTGTACCTGAGTTCAATTCTAGCGGATCCACTAGCATAACTTCG | GAL1 | Hexokinase flank/DRM cassette |

TABLE 3-continued

Primers (oligonucleotides) used in the examples

| SEQ ID NO: | Internal code | Primer | Sequence (5'→3') | Gene(s) | Purpose |
|---|---|---|---|---|---|
| 53 | 849 | Gal1_loxP_r | TTATAATTCATATAGACAGCTGCCC AATGCTGGTTTAGAGACGATGATA GTTGGGCCGCCAGTGTGATGG | GAL1 | Hexokinase flank/DRM cassette |

TABLE 4

Plasmids used in the strain construction

| Number | Construct | Purpose | SEQ ID NO: |
|---|---|---|---|
| pRN201 | pCR-BLUNT-loxP-kanMX-loxP | Dominant resistance marker | 7 |
| pRN251 | pCR-BLUNT-loxP-hphMX-loxP | Dominant resistance marker | 8 |
| pRN365 | pCR-BLUNT-loxP-natMX-loxP | Dominant resistance marker | 9 |
| pRN447 | pCR-BLUNT-loxP-zeoMX-loxP | Dominant resistance marker | 12 |
| pRN247 | pCR-BLUNT-his3:loxP-kanMX-loxP | HIS3 deletion construct | 15 |
| pRN485 | pCR-BLUNT-gal2:loxP-zeoMX-loxP | GAL2 deletion construct | 32 |
| pRN566 | pCR-BLUNT-hxt367:loxP-hphMX-loxP | HXT3-HXT6-HXT7 cluster deletion construct | 33 |
| pRN569 | pCR-BLUNT-hxt514:loxP-natMX-loxP | HXT5-HXT1-HXT4 cluster deletion contruct | 34 |
| pRN635 | pCR-BLUNT-hxt2:loxP-kanMX-loxP | HXT2 deletion construct | 35 |
| pRN993 | pRN978-P$_{HXT7(-491)}$-GAL2-T$_{ADH1}$ | GAL2 expression vector | 57 |
| pDB1250 | pRN978-P$_{HXT7(-491)}$-synt.wt-GAL2-T$_{ADH1}$ | Synthetic wild-type GAL2 expression vector | 58 |
| pRN187 | pCRE-zeoMX (based on pSH65) | CRE recombinase expression vector | 60 |
| pRN486 | pCR-BLUNT-HIS3::loxPnatMXloxP | HIS3 deletion construct | 61 |

TABLE 5

Cloning scheme

| Construct | Fragment | Cloning Sites | Release Sites |
|---|---|---|---|
| pRN247 | HIS3 upstream<br>loxP-kanMX-loxP<br>HIS3 downstream | SacI-DraI<br>StuI-BsiWI<br>BsiWI-ApaI | XhoI-BsrGI |
| pRN485 | GAL2 upstream<br>loxP-zeoMX-loxP<br>GAL2 downstream | NotI-BsiWI<br>BsiWI-XhoI<br>XhoI-BamHI | BamHI-SpeI-PmlI |
| pRN566 | HXT3 upstream<br>loxP-hphMX-loxP<br>HXT7 downstream | SpeI-BsiWI<br>BsiWI-XhoI<br>XhoI-BamHI | BamHI-AgeI-NaeI |
| pRN569 | HXT5 upstream<br>loxP-natMX-loxP<br>HXT4 downstream | NotI-BspEI<br>BspEI-XhoI<br>XhoI-BamHI | BamHI-NotI-ApaLI |
| pRN635 | HXT2 upstream<br>loxP-kanMX-loxP<br>HXT2 downstream | SpeI-BsiWI<br>BsiWI-XhoI<br>XhoI-EcoRI | AgeI-NotI-BspHI |

The kanMX marker was amplified from the plasmid pFA6-kanMX4 (www-sequence.stanford.edu/group/yeast_deletion_project/kanmx 4.txt) using primers SEQ ID NO's 1 and 2. Subsequently, the kanMX marker was floxed through adding loxP flanks by PCR amplification with primers SEQ ID NO's 3 and 4. Re-amplification was done with primers SEQ ID NO's 5 and 6. The resulting loxP-kanMX-IoxP fragment was cloned in pCR-BLUNT resulting in pRN201 (SEQ ID NO: 7).

For the construction of pRN251 (SEQ ID NO: 8), hphMX was isolated from pGRE3:hphMX (Kuyper et al, 2005). To delete a MluI site as appropriate restriction site in the vicinity of hphMX, pGRE3:hphMX was cut with Eco321 and re-ligated. Subsequently, hphMX was cloned as XhoI-MluI fragment into pRN201 digested with SalI and MluI to replace kanMX.

For the construction of pRN365 (SEQ ID NO: 9), the Streptomyces noursei nat1 gene was PCR-amplified from pYL16 (Werner Bioagents) using primers with SEQ ID NO:'s 10 and -11. The PscI-ScaI nat1 fragment together with the Acc65I-NcoI pRN201-fragment were cloned into pRN201, already linearized with Acc65I and ScaI, in order to replace kanR for nat1.

For the construction of pRN447 (SEQ ID NO: 12), pRN201 was digested with PmlI. This served two ends. Firstly, the Streptoalloteichus hindustanus ble (zeocin or phleomycin resistance gene) ORF was isolated, and secondly, after re-ligation of the PmlI-digested pRN201 an NcoI site was deleted. Subsequently, ble as NcoI-PmlI fragment and part of pRN201 as BamHI-NcoI vector fragment were cloned into the re-ligated pRN201 (missing ble), digested with BamHI and ScaI resulting in pRN447.

For the HIS3 deletion construct, primers SEQ ID13 and -14 were used to amplify the HIS3 locus from yeast genomic DNA. Sites used to cut out the HIS3 flanks and to ligate these to the floxed kanMX marker are shown in Table 5. The ligation product was digested with SacI and ApaI and cloned into pCR-BLUNT digested with SacI and ApaI. The resulting plasmid is pRN247 (SEQ ID NO: 15).

For the deletion of the eight main hexose transporters (HXT1-7 and GAL2 in S. cerevisiae, four deletion constructs were generated (see Table 4). Each deletion construct contained a different floxed dominant resistance marker. For each HXT gene 400-700 bp flanks were amplified using the primers listed in Table 3 (SEQ ID NO:'s 16-31) using RN1001 genomic DNA as template. The upstream flank, the dominant resistance marker and the downstream marker were ligated using the fragments and cloning sites listed under Table 5. The ligations were amplified using the forward primers 2 combinations SEQ ID NO:'s 16+19, SEQ ID NO:'s 20+27, SEQ ID NO:'s 24+23, and SEQ ID NO:'s 28+31). The fused PCR fragments were cloned into pCR-BLUNT to obtain pRN485, pRN566, pRN569, pRN635 (SEQ ID NO:'s 32-35, respectively). To obtain high yields of plasmid DNA, the plasmids were isolated from 50 mL *E. coli* cultures using NucleoBond® Xtra Midi kit (Bioké, Leiden, the Netherlands). Before transformation to yeast, deletion constructs were released from plasmid backbone by digestion with the release restriction sites listed in Table 5.

Strain Construction.

The xylose-fermenting strain RN1001 was made histidine auxotroph by the insertion of loxP-kanMX-loxP (released from pRN247; SEQ NO ID15) at the HIS3 locus. Subsequently, the marker was removed through transient expression of plasmid pRN187 (derived from pSH65 expressing galactose-inducible cre recombinase; SEQ ID NO 60). Introduction of pRN187 was selected on phleo and CRE recombinase expression was induced on YP-medium supplemented with galactose. The resulting his3:loxP strain was named RN1041. The hexose transporters were deleted in the following order: 1) HXT3-HXT6-HXT7cluster, 2) HXT5-HXT1-HXT4 cluster, 3) GAL2, 4) HXT2. The deletion constructs were linearized or released from the plasmid backbone by cutting with the enzyme combinations listed in Table 5 and these were integrated in the genome of RN1041. All transformations were plated on yeast extract (10 g/L), peptone (20 g/L) agar (15 g/L) medium supplemented with 20 g/L maltose. Maltose was added to the medium, because the uptake of this disaccharide goes via an alternative transport system than the glucose transport system (Wieczorke et al, 1999). With each deletion of a (cluster of) HXT gene(s), an additional marker was inserted in the order: 1) hphMX, 2) natMX, 3) zeoMX, 4) kanMX. With each inserted additional marker the respective antibiotic was additionally supplemented to the medium in the following order: 1) HG, 2) HG and nour, 3) HG, nour and phleo, 4) HG, nour, phleo and G418. After integration of all four deletion constructs, a single colony was isolated under selection of all four antibiotics. Correct integrations were verified by PCR analysis on genomic DNA isolates. Primers outside of the integration site were used (combinations SEQ ID NO:'s 36+37, SEQ ID NO:'s 38+39, SEQ ID NO:'s 40+41, SEQ ID NO:'s 42+43; sequences listed in Table 3).

Strain Characterization.

Figure 2:
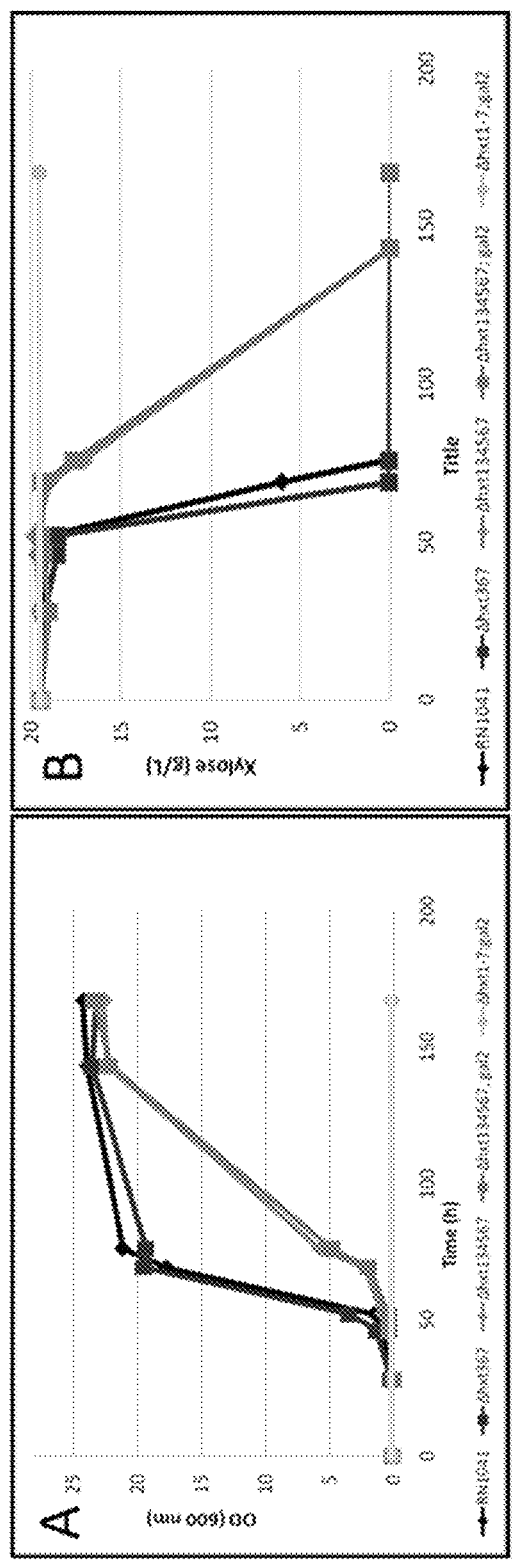
FIG. 2 shows results of aerobic shake flask cultures hexose transporter mutants on Verduyn-urea+20 g l$^{-1}$ xylose. (A) Optical density measurements at 600 nm wavelength, (B) xylose concentrations (g l$^{-1}$).

To characterize the (intermediate) hexose transporter strains, shake flask cultures were performed. Cultures were inoculated at OD600=0.1. The resulting strain, RN1053 (Δhxt1-7; gal2-mutant RN1041; see Table 2 for exact genotype), showed a retarded growth pattern on Verduyn-urea (mineral medium according to Verduyn using urea as nitrogen source; Luttik et al, 2001) supplemented with 0.2 g l$^{-1}$ histidine (Sigma-Aldrich; Verduyn-urea-his; to complement for the histidine auxotrophy) and 15 g l$^{-1}$ glucose and 20 g l$^{-1}$ xylose only starting to grow slowly on glucose only after 60 hours; interestingly, when glucose was present in the medium xylose was finished as well after 150 hrs (FIG. 1) indicating that one or more of the cryptic hexose transporter genes (HXT8-17) was induced on glucose and facilitated xylose transport (FIG. 1). However, on xylose as sole carbon source RN1053 did not grow on Verduyn-urea (+20 g l-1% xylose during the culturing period (FIG. 2) indicating the strain is useable as model strain for testing putative xylose transporters. RN10153 was further maintained on YPM.

Example 2—Hexokinase Gene Deletions

Deletion Cassettes Construction.

For deletion of hexokinase genes oligonucleotides were designed (SEQ ID NO:'s in Table 3) comprised of 60 nucleotide flanking sequences homologous to the hexokinase gene locus and of 20 nucleotides homologous to a floxed dominant resistance marker cassette. The oligonucleotides were used to amplify the deletion constructs. Subsequent PCR products were column filter-purified (Fermentas GeneJet Kit) and used for transformations experiments. Three types of deletion cassettes were used: firstly, for GLK1 and HXK2 deletions a bipartite system was used. One fragment consisted of a lox66 site, KanMX, GAL1 promoter upstream of CRE, and the 5'-part of CRE (CRE1) amplified from pSUC227 with one gene-specific primer (SEQ ID NO: 44 for GLK1 and SEQ ID NO: 45 for HXK2) and one pSUC227-specific primer (SEQ ID NO: 46); the second fragment consisted of the 3'-part of CRE (CRE2) with overlap on CRE1, and a lox71 site, amplified from pSUC225 with again one gene-specific primers (SEQ ID NO: 47 for GLK1 and SEQ ID48 for HXK2) and one pSUC225-specific primer SEQ ID NO: 49. Through homologous recombination the two fragments integrate as lox66-kanMX-CRE-lox71 at the hexokinase locus (pSUC225 and pSUC227 sequences and method provided in PCT/EP2013/055047). Secondly, for HXK1 (primers SEQ ID NO:'s 50-51) and GAL1 (primers SEQ ID NO:'s 52-53) deletions, a floxed dominant resistance marker (DRM) was amplified with flanking sequences homologous to the respective hexokinase to replace the coding region at the locus; as templates for the PCR amplifications of the DRM cassettes pRN774 (loxP-hphMX-loxP; SEQ ID NO: 54) and pRN775 (loxP-natMx-loxP; SEQ ID NO: 55) were used, respectively. Thirdly, for HIS3 deletion to allow for complementation of the auxotrophic phenotype by transporter episomal plasmids, a similar construct with HIS3-homologous flanks was integrated as was used to generate RN1041 (RN1001-his3:loxP, in strain family RN1053; see above Example 1). In this case the construct beared natMX as dominant resistance marker instead of kanMX (SEQ ID NO 61).

Strain Construction.

Figure 3:
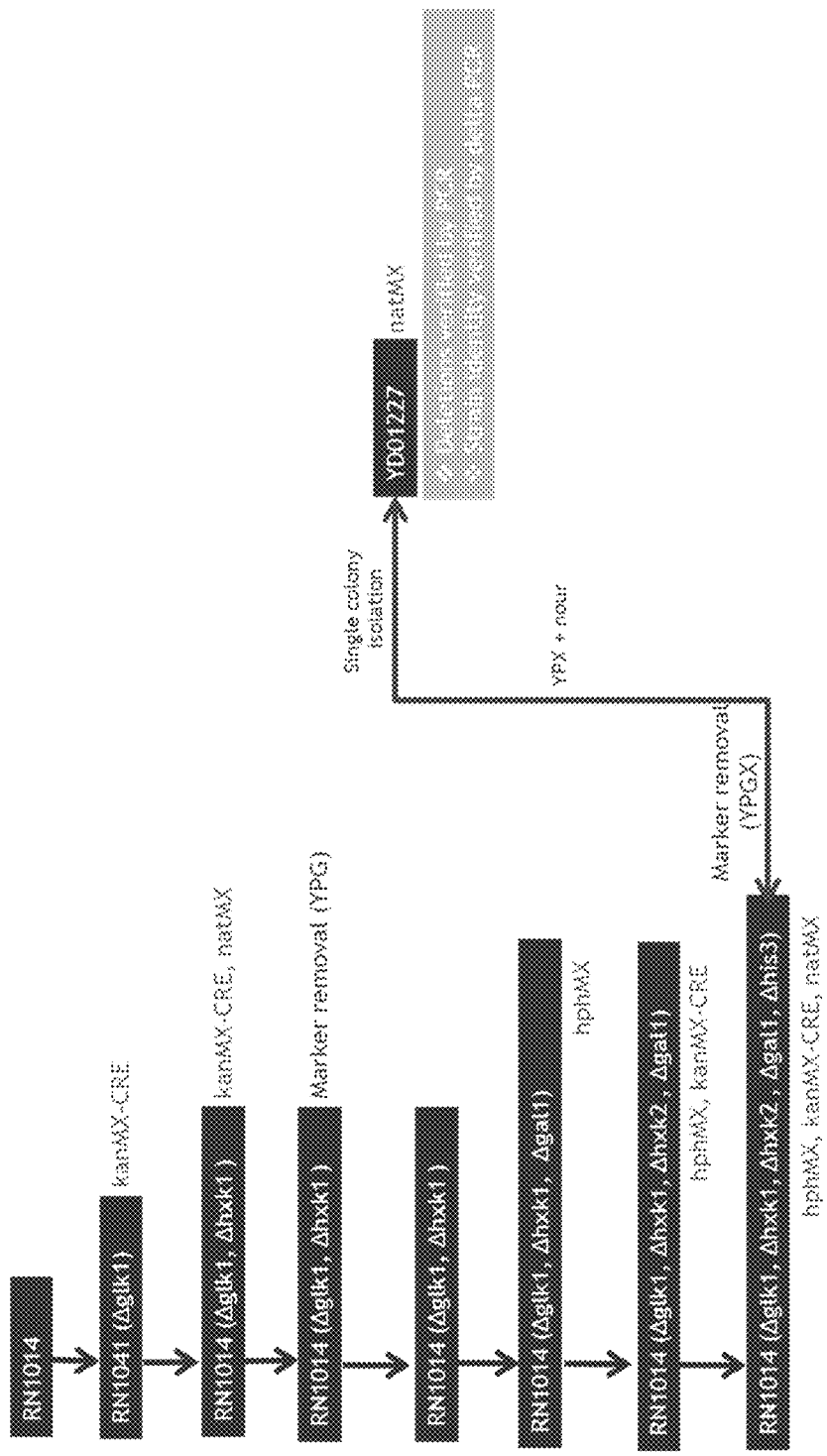
FIG. 3 shows the strain construction scheme for strain YD01227

For the generation of a strain incapable of hexose metabolism but capable of hexose transport, hexokinase gene deletions were made in the xylose-fermenting strain RN1014 (Table 2; FIG. 3 for deletion scheme).

As mentioned, in the case of GLK1 and HXK2, the disruption cassettes were bipartite. Through homologous recombination the two fragments integrate as lox66-kanMX-CRE-lox71 at the hexokinase locus. The integration was selected on YPD supplemented with G418. The disruption cassettes for HXK1 and GAL1 consisted of one fragment: either loxP-natMX-loxP or loxP-hphMX-loxP, respectively. RN1014 was transformed with the purified PCR products and the integration was selected on the appropriate antibiotic. Additionally, HIS3 was disrupted with a similar construct (SEQ ID NO: 61) used for the generation of RN1053. In this case natMX was the selection marker instead of kanMX.

The genes were deleted in the following order: 1) GLK1, 2) HXK1, 3) GAL1, 4) HXK2 and 5) HIS3. After the deletion of GLK1 and HXK1 both markers were recycled by galactose-induced Cre-mediated recombination. After deletion of HXK2 the intermediate strain was maintained on xylose-containing rich medium (YPX). After HIS3 deletion the integrated hphMX and kanMX markers were removed by galactose-induced CRE recombination. To ensure growth of the strain, 2% xylose was added to YP 2% galactose+ nourseothricin (YPGX). Selection on nourseothricin ensured maintenance of the natMX marker at the HIS3 locus leaving a selection trait to be used possibly later on. After single colony isolation, the strain was verified for its deletions and delta sequence profile by colony PCR, and named YD01227.

Strain Characterization.

Figure 4:
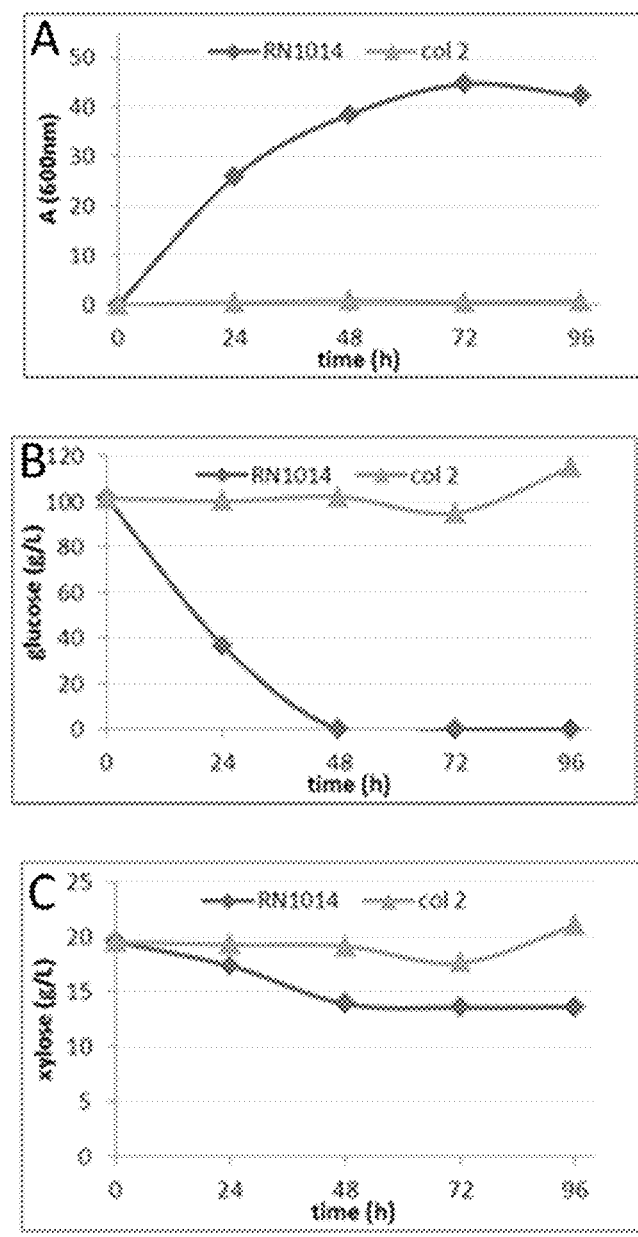
FIG. 4 shows results of aerobic shake flask cultures of quadruple hexose kinase mutant (col 2) and reference strain RN1014 on Verduyn-urea+100 g l$^{-1}$ glucose+20 g l$^{-1}$ xylose. A) Optical density measurements at 600 nm wavelength, (B) glucose concentrations (g l$^{-1}$), (C) xylose concentrations during the culture period.

In aerobic shake flask culture experiments using Verduyn-urea-his, another colony with the same quadruple hexokinase knockout (KO) genotype (col 2) as YD01227 was characterized in a pre-screen for its ability to consume xylose in the absence and presence an excess of glucose (10%), and for its ability to consume glucose (FIG. 4). Cultures were inoculated at OD600=0.1. Both RN1014 and the quadruple hexokinase KO are able to grow on and consume xylose (data not shown). And expectedly, the quadruple hexokinase KO does neither grow on nor consumes glucose, whereas RN1014 does (data not shown). Furthermore, the excess of glucose (10%) prevents the growth on and consumption of xylose for at least 96 hours, whereas RN1014 utilizes xylose (FIG. 4).

Figure 5:
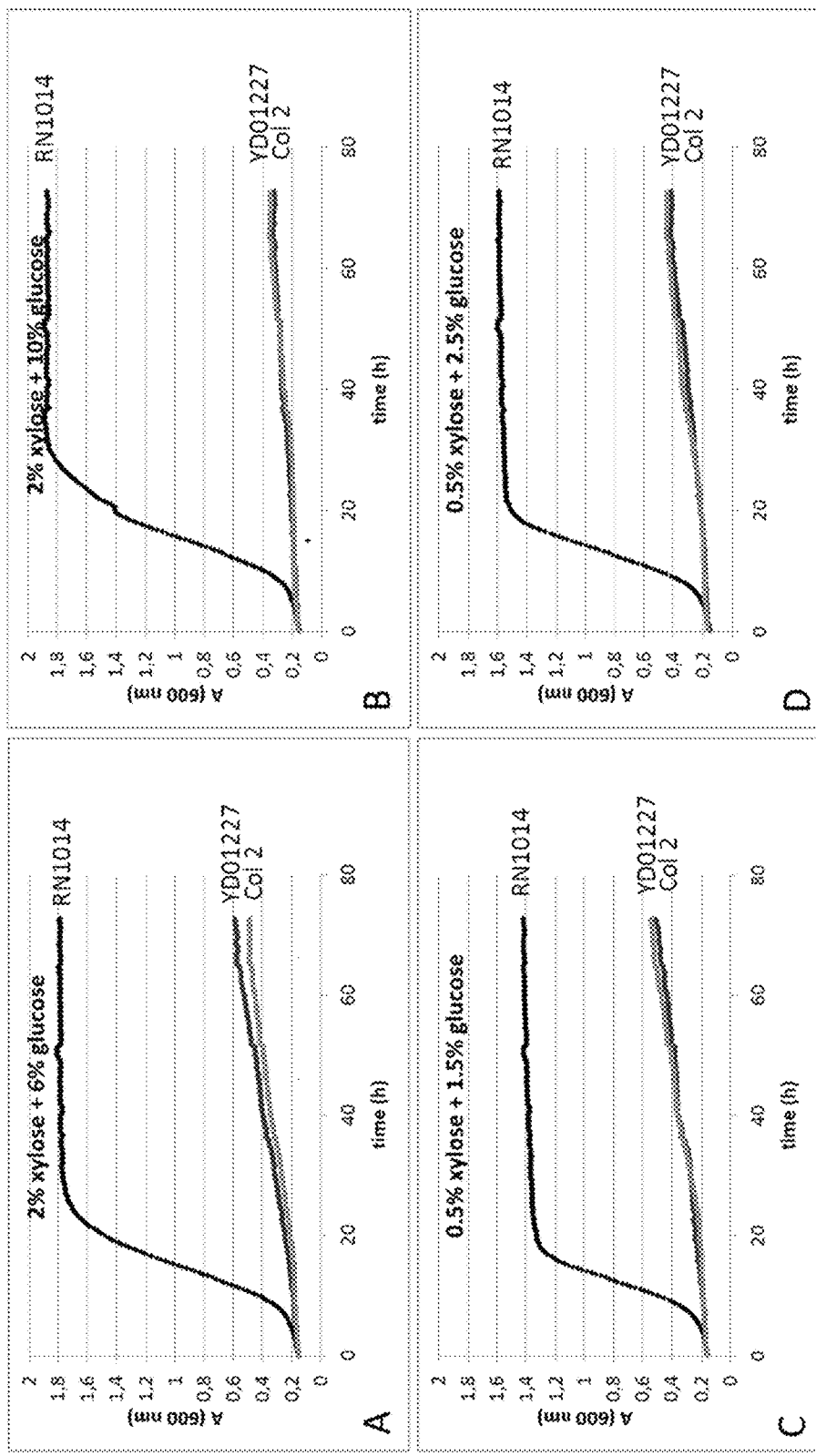
FIG. 5 shows results of micro-well plate cultures on glucose-xylose mixtures. Growth characteristics of reference strain RN1014, and quadruple hexokinase mutants YD01227 and colony 2 (Col 2) with equal genotype on Verduyn-urea supplemented with mixtures of glucose and xylose in the following concentrations: (A) 60+20, (B) 100+20, (C) 15+5, and (D) 25 g l$^{-1}$+5 g l$^{-1}$, respectively. Every 15 minutes, OD600 was measured automatically by a Bioscreen C apparatus. Data points are the average of measurements in triplicate.

In Bioscreen C experiments, YD01227 and the aforementioned col 2 were screened for growth on Verduyn-urea-his supplemented with different sugars and sugar mixtures. Cultures were inoculated at OD600=0.05. YD01227 grew on xylose but was not able to grow on glucose, maltose or galactose (data not shown). The glucose-xylose mixtures were screened to support a choice of medium composition suitable for the screen for pentose-specific transporters. As seen in FIG. 5, with a ratio of glucose:xylose of 5:1 showed the optimal inhibition of growth on xylose for strain YD01227. This was the case for both a high (10:2), as for a low sugar load (2.5:0.5). YD01227 was further maintained on YPX for storage and handling.

Example 3. GAL2 Saturation Mutagenesis Library and Other Constructs

Figure 6:
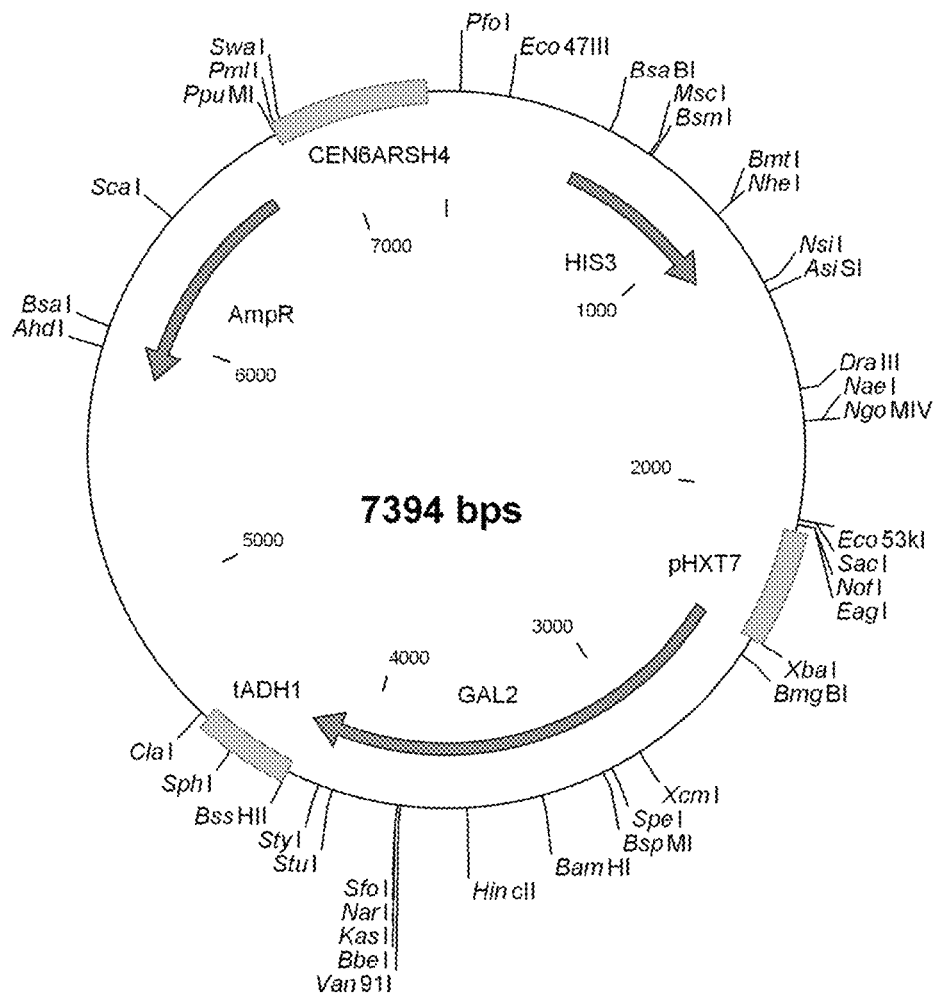
FIG. 6 shows a plasmid map pRN993.

A synthetic DNA construct for wild-type (WT) GAL2 was ordered at GeneArt (SEQ ID NO: 56; Invitrogen) and was used as template for site-directed mutagenesis. The synthetic WT GAL2 DNA construct was cloned into pRN993 (SEQ ID NO: 57) as XbaI-BssHII fragment exchanging another ORF for the synthetic WT GAL2 construct to generate pDB1250 (SEQ ID NO: 58). pDB1250 is a yeast shuttle vector based on pRS313, bearing as most prominent features besides the synthetically made GAL2 ORF: 1) a HIS3 expression cassette to complement the histidine auxotrophy, 2) a CEN.ARSH to maintain 1-2 copies (low copy number) of the expression vector in yeast cells, 3) truncated HXT7 promoter (−491 bp) resulting in medium expression levels of downstream ORF, 4) ADH1 terminator, and 5) ampicillin resistance gene (amp') for selection in *E. coli* TOP10 cells (see above) for cloning purposes (FIG. 6). The saturation mutagenesis library for at least 13 non-wild-type amino acid changes on 30 amino acid positions in Gal2p was ordered from Invitrogen Life Technologies (www.invitrogen.com/site/us/en/home/Products-and-Services/Applications/Cloning/gene-synthesis/directed-evolution/GeneArt-Site-Saturation-Mutagenesis.html); for positions and amino acid changes to the wild-type Gal2p amino acid sequence (SEQ ID NO: 59) see Table 6.

TABLE 6

GAL2 Single Site Saturation Mutagenesis Library

Gal2

| # sites | Position | WT AA | # non wt AA | Non wt AA |
|---|---|---|---|---|
| 1 | 85 | F | 15 | A, C, D, E, G, H, K, M, N, P, Q, R, S, T, V |
| 1 | 89 | T | 18 | A, C, D, E, F, H, I, K, L, M, N, P, Q, R, S, V, W, Y |
| 3 | 187 | V | 17 | A, C, D, E, F, G, H, I, K, L, M, Q, R, S, T, W, V |
| 4 | 191 | A | 19 | C, D, E, F, G, H, K, L, M, N, P, Q, R, S, T, V, W, Y |
| 5 | 214 | Y | 15 | A, C, G, I, K, L, M, N, P, Q, R, S, T, V, W |
| 6 | 215 | Q | 16 | A, C, D, E, F, G, H, I, L, M, N, R, S, V, W, Y |
| 7 | 218 | I | 15 | A, C, D, E, G, H, K, L, M, N, R, S, T, V, W |
| 8 | 219 | T | 15 | A, C, D, E, F, G, I, K, L, M, N P, Q, R, S, V, W |
| 9 | 222 | I | 15 | A, C, D, E, G, H, K, M, P, R, S, T, V, W, Y |
| 10 | 226 | Y | 19 | A, C, D, E, F, G, H, I, K, L, M, N, P, Q, R, S, T, V, W |
| 11 | 338 | Q | 18 | A, C, D, E, F, G, H, I, L, M, N, P, R, S, T, V, W, Y |
| 12 | 339 | M | 19 | A, C, D, E, F, G, H, I, K, L, N, P, Q, R, S, T, V, W, Y |
| 13 | 341 | Q | 13 | D, E, H, I, K, L, M, N, R, S, T, V, Y |
| 14 | 342 | Q | 19 | A, C, D, E, F, G, H, I, K, L, M, N, P, R, S, T, V, W, Y |
| 15 | 343 | L | 19 | A, C, D, E, F, G, H, I, K, M, N, P, Q, R, S, T, V, W, Y |
| 16 | 346 | N | 19 | A, C, D, E, F, G, H, I, K, L, M, P, Q, R, S, T, V, W, Y |
| 17 | 347 | N | 13 | A, D, E, G, H, I, K, L, Q, R, S, T, V |
| 18 | 350 | F | 14 | D, E, H, I, K, L, M, N, Q, R, S, T, V, Y |
| 19 | 373 | G | 19 | A, C, D, E, F, H, I, K, L, M, N, P, Q, R, S, T, V, W, Y |
| 20 | 376 | N | 18 | A, C, D, E, F, H, I, K, L, M, P, Q, R, S, T, V, W, Y |
| 21 | 380 | T | 18 | A, C, D, E, F, G, I, K, L, M, N, P, Q, R, S, V, W, Y |
| 22 | 383 | S | 17 | A, C, D, E, F, G, I, K, L, M, N, Q, R, T, V, W, Y |
| 23 | 444 | F | 19 | A, C, D, E, G, H, I, K, L, M, N, P, Q, R, S, T, V, W, Y |
| 24 | 446 | Y | 13 | D, E, H, I, K, L, M, N, Q, R, S, T, V |
| 25 | 448 | T | 18 | A, C, D, E, F, G, H, I, K, L, M, P, Q, R, S, V, W, Y |
| 26 | 449 | T | 19 | A, C, D, E, F, G, H, I, K, L, M, N, P, Q, R, S, V, W, Y |
| 27 | 451 | A | 18 | C, D, F, G, H, I, K, L, M, N, P, Q, R, S, T, V, W, Y |
| 28 | 455 | W | 18 | A, C, D, E, F, G, I, K, L, M, N, P, Q, R, S, T, V, Y |
| 29 | 478 | N | 16 | A, C, D, F, G, H, I, K, L, P, Q, R, V, W, Y |
| 30 | 479 | W | 18 | C, D, E, F, G, H, I, K, L, M, N, P, Q, R, S, T, V, Y |

Resulting constructs were inserted by custom cloning at GeneArt (Invitrogen, Regensburg, Germany) in pDB1250 (SEQ ID NO: ID58).

Example 4: Glucose Transport Activity Counter-Screening

Aim.

Using the Glucose Transport Activity Counter (GTAC)-screen, i.e. transforming hexokinase-mutant strain YD01227 as host to introduce GAL2 variants and screening the resulting transformants on medium for growth on and consumption of xylose in the presence of a 5 times higher amount of glucose, mutations can be identified that favour xylose above in the presence of a surplus glucose in the Gal2p variant (i.e. higher affinity for xylose than for glucosea reduction or more preferably full removal of glucose transport capability, while keeping xylose transport capability more or less intact).

Transformation and Colony Picking.

YD01227 was transformed with a total of 497 constructs, each one bearing a GAL2 mutant. One construct with wild-type GAL2 sequence (pDB1250; SEQ ID NO: 58) was included as control. For each transformation, 3 colonies, when available, were re-plated to agar medium MTPs amounting to 1450 transformants. The 1450 transformants were screened in three parts. For each part of the screening, wild-type GAL2 was included as control.

Pre-Culture and Screen.

For pre-culture, transformants were transferred by automated process from selection agar medium MTPs to 96 well half-deepwell plates (96HDWP) containing liquid selection medium consisting of mineral medium (according to Verduyn, with urea as nitrogen source) supplemented with 3% xylose. The 96 HDWPs were cultured for 3 days of pre-culture in an orbital shaker at 30° C. and 750 rpm. Subsequently, for each well 20 µl of culture was transferred by automated process to 24 deepwell plates (24 DWPs) containing 2.5 ml Verduyn-urea supplemented with the sugar mixture glucose:xylose in a ratio 5:1 with the following concentrations: 10 g l$^{-1}$ glucose and 2 g l$^{-1}$ xylose (YD10-medium). For each of the three sampling points a series of 24DWPs was inoculated. On each 24DWP, one RN1001 growth control was inoculated to have an indication of plate variation effects. After 24 hours, 72 hours and 96 hours automatic sampling and transfer to 96HDWP was conducted for automated OD-measurement at 600 nm wavelength.

After the last OD measurement after 96 hours, cells were pelleted after centrifugation and 100 µl supernatant was collected by automated process for flow-NMR analysis residual constituents in the medium after culture (see above for method description). For each construct and each time point, the measured residual glucose and xylose concentrations for the different replicates were averaged. In order to compare the different parts of the screen, a relative value was calculated based on the difference to the wild-type residual xylose concentration measured in the particular part of the GTAC screen, according to the following formula:

$$RelXyl = \frac{(\text{residual xylose}_{Gal2\text{-}wildtype} - \text{residual xylose}_{Gal2\text{-}mutant})}{\text{residual xylose}_{Gal2\text{-}wildtype}} \times 100\%$$

Results.

Figure 7:
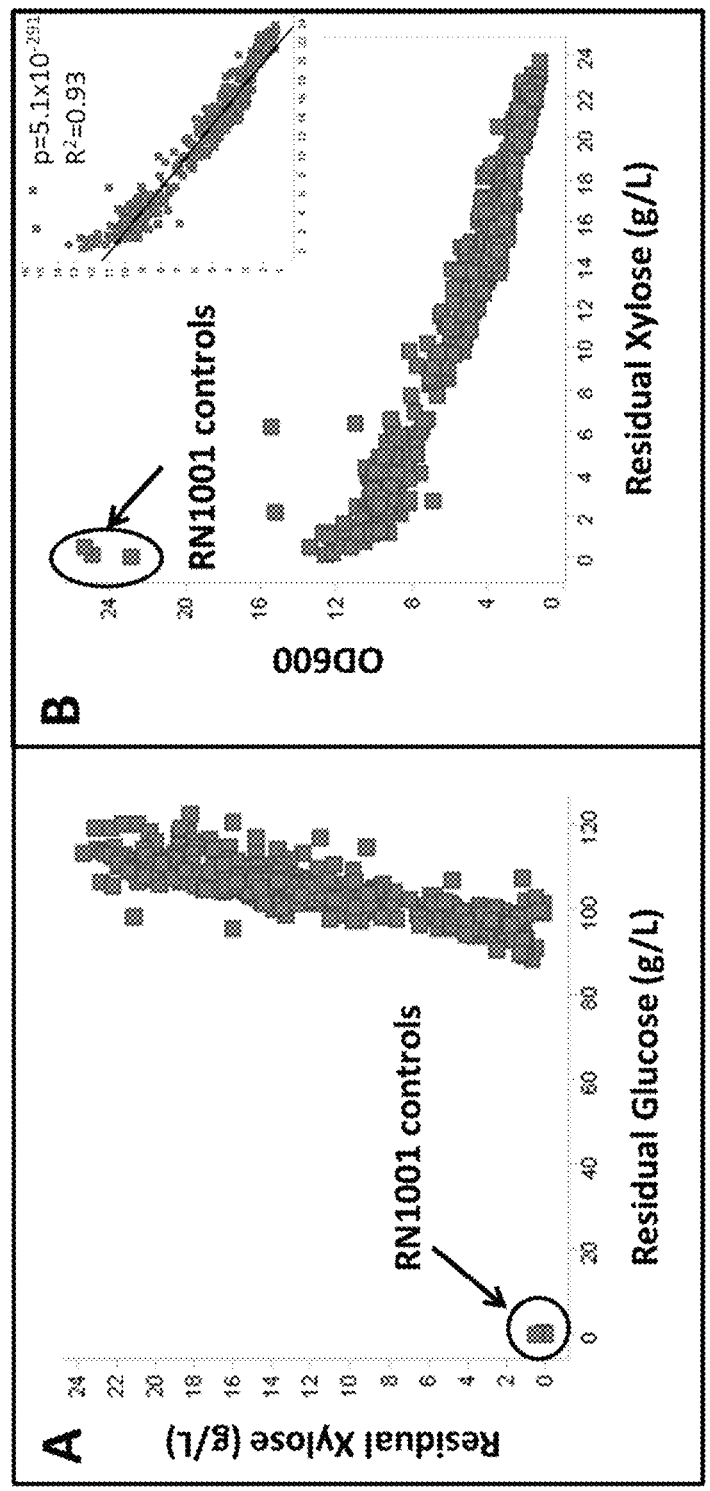
FIG. 7 shows the relationships between residual xylose and glucose concentrations (A), or residual xylose concentrations and growth (OD600; B) in the Glucose Transport Activity Counter Screen (GTAC screen), see examples. Residual xylose concentrations (g l$^{-1}$) were plotted against the residual (A) glucose concentration (g l$^{-1}$) and (B) OD600 at 96 hours. (Inset B) linear regression analysis of shows a good correlation of OD600 and xylose. Each data point represents the average of sugar concentrations of 1 to 3 replicates, or of multiple measurements of RN1001 control strain or medium samples per part of the screen.

Whereas RN1001 displayed complete consumption of both glucose and xylose, YD01227 transformants of wild-type and mutagenesis library GAL2 constructs did not consume glucose and displayed a spectrum of residual xylose concentrations representing their individual ability to consume xylose in the presence of glucose (FIG. 7A). As shown in FIG. 7B, the xylose consumption displayed a high correlation ($R^2$=0.93) with the growth measurements (OD600). Since the screen was conducted in aerobic conditions, and little ethanol formation was shown (data not shown) and growth displayed high correlation with the xylose consumption, the residual xylose concentrations were used as main parameter to compare GAL2 variants with wild-type. The comparison of all tested mutant GAL2 variants versus wild-type GAL2 on xylose consumption (average RelXyl) at 96 hours is listed in Table 7. All mutations affecting glucose transport to the benefit of xylose transport have RelXyl>0 (Table 7). The TOP positions to target for a second round of mutagenesis were sorted based on their average RelXyl score per mutation; specific mutations were sorted on preference based on RelXyl score as well (Table 8).

TABLE 7

Relative OD600 (RelOD600) and xylose consumption (RelXyl) of GTAC Screen. Wild-type GAL2 construct pDB1250 was set to 0. RelOD600 values are the averages of 1-3 replicates and are relative values compared to wild-type.

| Pos | wtAA | MutAA | RelXyl |
|---|---|---|---|
| 85 | F | A | 1.45 |
|  |  | C | 0.66 |
|  |  | D | −1.89 |
|  |  | E | −13.09 |
|  |  | G | −1.06 |
|  |  | H | 1.76 |
|  |  | K | −20.81 |
|  |  | M | 7.03 |
|  |  | N | 1.96 |
|  |  | P | 2.83 |
|  |  | Q | 37.68 |
|  |  | R | −1.93 |
|  |  | S | 19.81 |
|  |  | T | 50.51 |
|  |  | V | 32.76 |
| 89 | T | A | 11.68 |
|  |  | C | 13.22 |
|  |  | D | 19.68 |
|  |  | F | −9.97 |
|  |  | H | 25.59 |
|  |  | I | −17.32 |
|  |  | K | −24.84 |
|  |  | L | 12.38 |
|  |  | M | −8.38 |
|  |  | N | 9.88 |
|  |  | Q | −16.03 |
|  |  | R | −16.11 |
|  |  | S | −11.44 |
|  |  | V | 41.06 |
|  |  | Y | −2.89 |
| 187 | V | A | 26.84 |
|  |  | C | 9.98 |
|  |  | D | 3.76 |
|  |  | E | 6.21 |
|  |  | F | 14.53 |
|  |  | G | 10.01 |
|  |  | H | 8.32 |
|  |  | I | 6.69 |
|  |  | K | 4.09 |
|  |  | L | 4.12 |
|  |  | M | 1.85 |
|  |  | Q | 10.17 |
|  |  | R | 3.05 |
|  |  | S | 7.54 |
|  |  | T | 10.41 |
|  |  | W | 1.81 |
|  |  | Y | 1.22 |

TABLE 7-continued

Relative OD600 (RelOD600) and xylose consumption (RelXyl) of GTAC Screen. Wild-type GAL2 construct pDB1250 was set to 0. RelOD600 values are the averages of 1-3 replicates and are relative values compared to wild-type.

| Pos | wtAA | MutAA | RelXyl |
|-----|------|-------|--------|
| 191 | A | C | 4.70 |
|  |  | D | 12.43 |
|  |  | E | -2.61 |
|  |  | F | 5.49 |
|  |  | G | 15.83 |
|  |  | H | 2.83 |
|  |  | I | 11.93 |
|  |  | K | 1.94 |
|  |  | L | -8.25 |
|  |  | M | -14.37 |
|  |  | N | 20.35 |
|  |  | P | 14.89 |
|  |  | Q | 2.94 |
|  |  | R | -1.09 |
|  |  | S | 3.09 |
|  |  | T | 10.61 |
|  |  | V | 4.52 |
|  |  | W | 2.49 |
|  |  | Y | 1.93 |
| 214 | Y | A | -12.81 |
|  |  | C | -5.85 |
|  |  | G | 18.41 |
|  |  | I | -12.07 |
|  |  | K | -4.66 |
|  |  | L | 35.33 |
|  |  | M | 23.92 |
|  |  | N | 32.71 |
|  |  | P | 18.44 |
|  |  | Q | 39.94 |
|  |  | R | 25.50 |
|  |  | S | 14.91 |
|  |  | V | 55.48 |
|  |  | W | 47.35 |
| 215 | Q | A | 2.01 |
|  |  | C | 9.90 |
|  |  | D | 13.62 |
|  |  | F | 10.12 |
|  |  | G | -9.62 |
|  |  | H | -18.18 |
|  |  | I | 17.72 |
|  |  | L | 24.63 |
|  |  | M | 21.59 |
|  |  | N | -11.47 |
|  |  | S | 2.14 |
|  |  | V | -8.22 |
|  |  | W | -20.47 |
|  |  | Y | -8.07 |
| 218 | I | A | 17.98 |
|  |  | C | 5.52 |
|  |  | D | 4.64 |
|  |  | E | 8.44 |
|  |  | G | 4.62 |
|  |  | H | 9.88 |
|  |  | K | 27.86 |
|  |  | L | 9.73 |
|  |  | M | 5.80 |
|  |  | N | 24.31 |
|  |  | R | -0.73 |
|  |  | S | 24.96 |
|  |  | T | -2.65 |
|  |  | V | 7.69 |
|  |  | W | -2.10 |
| 219 | T | A | 52.55 |
|  |  | C | 25.05 |
|  |  | D | 18.04 |
|  |  | E | -14.58 |
|  |  | F | 43.86 |
|  |  | G | 46.45 |
|  |  | I | -11.07 |
|  |  | K | -4.44 |
|  |  | M | -18.28 |
|  |  | N | 7.85 |
|  |  | Q | -22.81 |
|  |  | R | -24.62 |
|  |  | S | 4.90 |
|  |  | W | -16.77 |
| 222 | I | A | 11.37 |
|  |  | C | 13.45 |
|  |  | D | 20.91 |
|  |  | E | 3.35 |
|  |  | G | 3.75 |
|  |  | H | 9.73 |
|  |  | K | -4.92 |
|  |  | M | 4.39 |
|  |  | P | 0.97 |
|  |  | S | 1.85 |
|  |  | T | -1.59 |
|  |  | V | 8.42 |
|  |  | W | -8.04 |
|  |  | Y | 7.87 |
| 226 | Y | A | 63.63 |
|  |  | C | 62.07 |
|  |  | D | 81.68 |
|  |  | E | 70.43 |
|  |  | G | 39.06 |
|  |  | H | 5.10 |
|  |  | I | 32.79 |
|  |  | K | -1.86 |
|  |  | L | 42.48 |
|  |  | M | 74.04 |
|  |  | N | 62.81 |
|  |  | P | 49.78 |
|  |  | Q | 56.23 |
|  |  | R | 65.53 |
|  |  | S | 14.97 |
|  |  | T | 7.27 |
|  |  | V | -11.15 |
|  |  | W | 44.48 |
| 338 | Q | A | 38.18 |
|  |  | C | 52.66 |
|  |  | D | 33.17 |
|  |  | E | 46.93 |
|  |  | F | 46.65 |
|  |  | G | 13.80 |
|  |  | H | 26.28 |
|  |  | I | 28.32 |
|  |  | L | 33.08 |
|  |  | M | -2.53 |
|  |  | N | 22.26 |
|  |  | P | 3.96 |
|  |  | R | 39.83 |
|  |  | S | 3.96 |
|  |  | T | 11.84 |
|  |  | V | 24.84 |
|  |  | W | 35.55 |
|  |  | Y | 19.90 |
| 339 | M | A | 50.56 |
|  |  | C | 30.36 |
|  |  | D | 46.71 |
|  |  | E | 10.48 |
|  |  | F | 63.75 |
|  |  | G | 73.03 |
|  |  | H | 67.99 |
|  |  | I | 40.96 |
|  |  | K | 71.92 |
|  |  | L | 67.43 |
|  |  | N | 83.73 |
|  |  | P | 12.77 |
|  |  | Q | 77.74 |
|  |  | R | 70.25 |
|  |  | S | 81.65 |
|  |  | T | 57.02 |
|  |  | V | 82.35 |
|  |  | W | -23.02 |
|  |  | Y | 37.43 |

TABLE 7-continued

Relative OD600 (RelOD600) and xylose consumption (RelXyl) of GTAC Screen. Wild-type GAL2 construct pDB1250 was set to 0. RelOD600 values are the averages of 1-3 replicates and are relative values compared to wild-type.

| Pos | wtAA | MutAA | RelXyl |
|---|---|---|---|
| 341 | Q | D | −20.08 |
|  |  | E | −3.38 |
|  |  | H | −22.19 |
|  |  | L | 46.71 |
|  |  | M | 23.17 |
|  |  | N | 11.77 |
|  |  | R | −5.18 |
|  |  | S | 15.78 |
|  |  | T | 28.67 |
|  |  | Y | 19.78 |
| 342 | Q | A | 61.47 |
|  |  | C | 64.63 |
|  |  | D | 48.62 |
|  |  | E | 34.90 |
|  |  | F | 45.61 |
|  |  | G | 14.10 |
|  |  | H | 46.28 |
|  |  | I | 16.81 |
|  |  | K | 41.75 |
|  |  | L | 37.38 |
|  |  | M | 27.70 |
|  |  | N | 32.30 |
|  |  | P | 44.88 |
|  |  | R | 23.95 |
|  |  | S | 68.48 |
|  |  | T | 50.54 |
|  |  | V | 24.39 |
|  |  | W | 59.43 |
|  |  | Y | 76.45 |
| 343 | L | A | 9.67 |
|  |  | C | 8.74 |
|  |  | D | 9.41 |
|  |  | E | 2.39 |
|  |  | F | 15.49 |
|  |  | G | 11.87 |
|  |  | H | 16.96 |
|  |  | I | 10.67 |
|  |  | K | 40.15 |
|  |  | M | 16.94 |
|  |  | N | 14.03 |
|  |  | P | 26.08 |
|  |  | Q | 8.73 |
|  |  | R | 29.11 |
|  |  | S | 20.28 |
|  |  | T | 14.38 |
|  |  | V | −6.06 |
|  |  | W | 7.76 |
|  |  | Y | 20.43 |
| 346 | N | A | 21.99 |
|  |  | C | 17.11 |
|  |  | D | 8.88 |
|  |  | E | −8.32 |
|  |  | F | 9.91 |
|  |  | G | 8.42 |
|  |  | H | 26.01 |
|  |  | I | 17.12 |
|  |  | K | 17.48 |
|  |  | L | 6.48 |
|  |  | M | 13.19 |
|  |  | Q | 19.93 |
|  |  | R | 7.94 |
|  |  | S | 23.37 |
|  |  | T | 23.19 |
|  |  | V | 47.09 |
|  |  | W | 45.58 |
|  |  | Y | 41.70 |
| 347 | N | A | 44.64 |
|  |  | D | 26.67 |
|  |  | E | 25.36 |
|  |  | G | −22.71 |
|  |  | H | 11.18 |
|  |  | I | 27.33 |
|  |  | K | −22.05 |
|  |  | L | 7.79 |
|  |  | Q | −14.96 |
|  |  | R | −15.36 |
|  |  | S | −15.56 |
|  |  | T | −19.33 |
|  |  | V | −28.12 |
| 350 | Y | D | 2.93 |
|  |  | E | −13.15 |
|  |  | H | −19.99 |
|  |  | I | −10.76 |
|  |  | K | 3.00 |
|  |  | L | 40.49 |
|  |  | M | 5.01 |
|  |  | N | 13.57 |
|  |  | Q | 0.66 |
|  |  | R | 57.58 |
|  |  | S | 15.25 |
|  |  | T | 21.64 |
|  |  | V | 13.39 |
|  |  | Y | −7.36 |
| 373 | G | A | 25.90 |
|  |  | C | 36.56 |
|  |  | D | 36.22 |
|  |  | E | 41.01 |
|  |  | F | 15.15 |
|  |  | H | 6.96 |
|  |  | I | 9.10 |
|  |  | K | 20.72 |
|  |  | L | 51.94 |
|  |  | M | 35.03 |
|  |  | N | 38.49 |
|  |  | P | 35.75 |
|  |  | Q | 5.50 |
|  |  | R | 8.35 |
|  |  | S | 11.62 |
|  |  | T | 10.67 |
|  |  | V | 21.91 |
|  |  | W | 22.96 |
|  |  | Y | 31.04 |
| 376 | N | A | 36.70 |
|  |  | C | 78.63 |
|  |  | D | 19.23 |
|  |  | E | 20.15 |
|  |  | F | 92.62 |
|  |  | H | 39.30 |
|  |  | I | 99.46 |
|  |  | K | 7.53 |
|  |  | L | 93.69 |
|  |  | M | 97.33 |
|  |  | P | 51.70 |
|  |  | Q | 24.24 |
|  |  | R | 27.86 |
|  |  | S | 59.39 |
|  |  | T | 99.01 |
|  |  | V | 96.57 |
|  |  | W | 13.51 |
|  |  | Y | 43.95 |
| 380 | T | A | 53.06 |
|  |  | C | 42.34 |
|  |  | D | 37.28 |
|  |  | E | −29.92 |
|  |  | F | 54.67 |
|  |  | G | 34.22 |
|  |  | I | 47.40 |
|  |  | K | 42.12 |
|  |  | L | 39.25 |
|  |  | M | 74.78 |
|  |  | N | 49.79 |
|  |  | P | 43.28 |
|  |  | Q | 43.31 |
|  |  | R | 42.31 |
|  |  | S | 42.03 |
|  |  | V | 42.53 |

TABLE 7-continued

Relative OD600 (RelOD600) and xylose consumption (RelXyl) of GTAC Screen. Wild-type GAL2 construct pDB1250 was set to 0. RelOD600 values are the averages of 1-3 replicates and are relative values compared to wild-type.

| Pos | wtAA | MutAA | RelXyl |
|---|---|---|---|
|  |  | W | 51.16 |
|  |  | Y | 25.09 |
| 383 | S | A | 57.21 |
|  |  | C | 67.78 |
|  |  | D | 29.42 |
|  |  | E | 54.55 |
|  |  | F | 52.71 |
|  |  | G | 39.71 |
|  |  | I | 25.88 |
|  |  | K | 49.19 |
|  |  | L | 37.72 |
|  |  | M | 52.64 |
|  |  | N | 58.14 |
|  |  | Q | 83.94 |
|  |  | R | 61.78 |
|  |  | T | 71.85 |
|  |  | V | 19.38 |
|  |  | W | 65.32 |
|  |  | Y | 62.76 |
| 444 | F | A | 32.41 |
|  |  | C | 14.64 |
|  |  | D | 13.21 |
|  |  | E | 16.38 |
|  |  | G | 12.78 |
|  |  | H | 25.62 |
|  |  | I | 31.95 |
|  |  | K | 28.79 |
|  |  | L | 39.43 |
|  |  | M | 17.30 |
|  |  | N | 5.43 |
|  |  | P | 15.65 |
|  |  | Q | 19.63 |
|  |  | R | 0.06 |
|  |  | S | 10.94 |
|  |  | T | 7.44 |
|  |  | V | 37.29 |
|  |  | W | 2.94 |
|  |  | Y | 32.56 |
| 446 | F | D | 10.80 |
|  |  | E | 10.63 |
|  |  | H | 16.93 |
|  |  | I | 8.65 |
|  |  | K | -3.40 |
|  |  | L | 22.78 |
|  |  | M | 18.62 |
|  |  | N | 14.99 |
|  |  | Q | 34.25 |
|  |  | R | -8.44 |
|  |  | S | -20.59 |
|  |  | T | -16.07 |
|  |  | V | -9.48 |
| 448 | T | A | 76.95 |
|  |  | C | 58.53 |
|  |  | D | 66.10 |
|  |  | E | 53.25 |
|  |  | F | 61.94 |
|  |  | G | 65.05 |
|  |  | H | 67.00 |
|  |  | I | 58.01 |
|  |  | K | 54.82 |
|  |  | L | 63.49 |
|  |  | M | 77.64 |
|  |  | P | 64.39 |
|  |  | Q | 58.15 |
|  |  | R | 33.80 |
|  |  | S | 59.40 |
|  |  | V | 53.50 |
|  |  | W | 56.69 |
|  |  | Y | 47.73 |
| 449 | T | A | 57.64 |
|  |  | C | 50.44 |
|  |  | D | 55.89 |
|  |  | E | 37.14 |
|  |  | F | 92.65 |
|  |  | G | 61.00 |
|  |  | H | 82.47 |
|  |  | I | 71.71 |
|  |  | K | 79.30 |
|  |  | L | 81.03 |
|  |  | M | 89.29 |
|  |  | N | 84.60 |
|  |  | P | 37.06 |
|  |  | Q | 81.19 |
|  |  | R | 82.14 |
|  |  | S | 83.15 |
|  |  | V | 74.98 |
|  |  | W | 80.75 |
|  |  | Y | 79.80 |
| 451 | T | C | 10.57 |
|  |  | D | 9.68 |
|  |  | E | 15.39 |
|  |  | F | 13.38 |
|  |  | G | 43.34 |
|  |  | H | 7.65 |
|  |  | I | 17.96 |
|  |  | K | 8.59 |
|  |  | L | 11.00 |
|  |  | M | 5.68 |
|  |  | N | 14.56 |
|  |  | P | 11.89 |
|  |  | Q | 8.63 |
|  |  | R | 4.46 |
|  |  | S | 13.08 |
|  |  | T | 2.10 |
|  |  | V | 4.99 |
|  |  | W | 15.25 |
|  |  | Y | 1.62 |
| 455 | W | A | 1.31 |
|  |  | C | 1.19 |
|  |  | D | -6.13 |
|  |  | E | 19.68 |
|  |  | F | -1.57 |
|  |  | G | 0.73 |
|  |  | I | -2.70 |
|  |  | K | 6.91 |
|  |  | L | 19.08 |
|  |  | M | 19.92 |
|  |  | N | 19.10 |
|  |  | P | 14.76 |
|  |  | Q | 3.03 |
|  |  | R | -14.86 |
|  |  | S | 8.05 |
|  |  | T | 19.75 |
|  |  | V | 10.66 |
|  |  | Y | 7.30 |
| 478 | N | A | -11.71 |
|  |  | C | -1.14 |
|  |  | D | -3.08 |
|  |  | F | 30.35 |
|  |  | G | 8.29 |
|  |  | H | -15.02 |
|  |  | I | 10.06 |
|  |  | K | 9.95 |
|  |  | L | -3.27 |
|  |  | P | 30.98 |
|  |  | Q | 4.37 |
|  |  | R | 11.41 |
|  |  | V | 21.91 |
|  |  | W | 3.25 |
|  |  | Y | 4.98 |
| 479 | W | C | 13.20 |
|  |  | D | 6.12 |
|  |  | E | 11.20 |
|  |  | F | 1.41 |
|  |  | G | 1.34 |
|  |  | H | 6.90 |

TABLE 7-continued

Relative OD600 (RelOD600) and xylose consumption (RelXyl) of GTAC Screen. Wild-type GAL2 construct pDB1250 was set to 0. RelOD600 values are the averages of 1-3 replicates and are relative values compared to wild-type.

Figure 11:
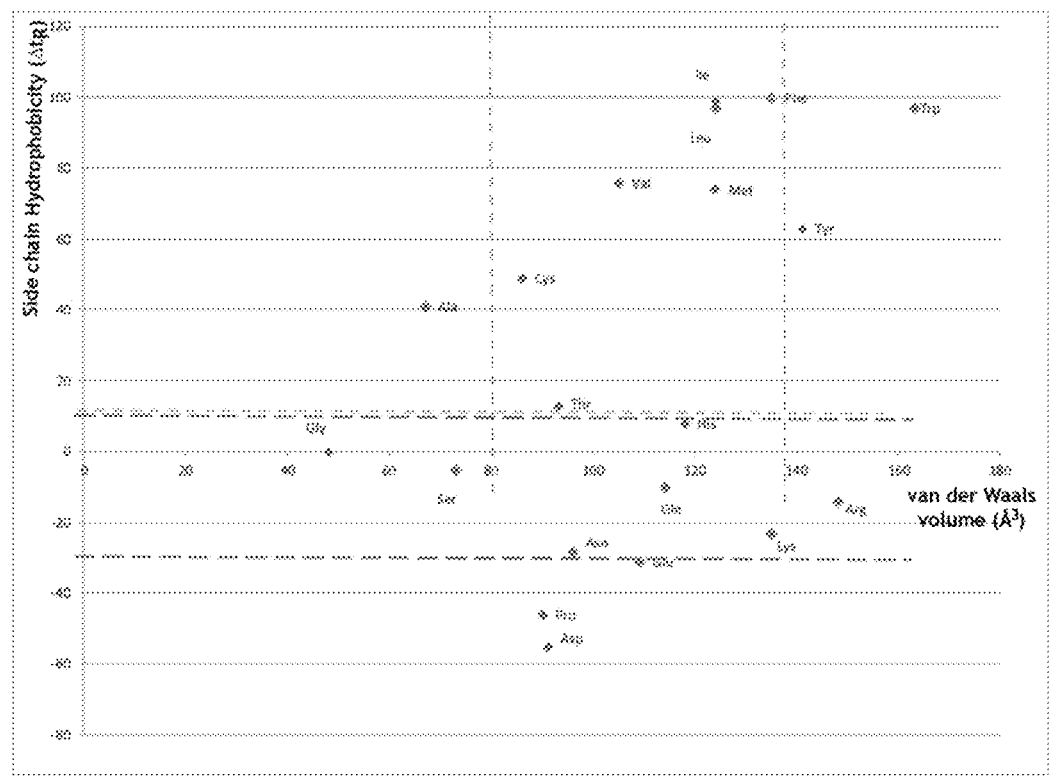
FIG. 11 shows plot of amino acid van der Waals volume (Å$^3$) (Y-axis) against amino acid hydrophobicity ($\Delta t_R$) (X-axis). Advantageous amino acids (reduced glucose transport activity) for position corresponding to 376 in SEQ ID NO: 59 are within the area defined by the short striped lines and for position 339 by the long strips lines. Values for van der Waals volume used herein are described in: www.proteinsandproteomics.org/content/free/tables_1/t able08.pdf. The corresponding literature is N. J. Darby, Thomas E. Creighton, Protein Structure (1993) Oxford University Press. The values for hydrophobicity ($\Delta t_R$) of amino acids are herein used as described in onlinelibrary.wiley.com/doi/10.1002/psc.310010507/pdf. The reference corresponding to this is Monera, O. D. et al, Journal of Peptide Science 1995; 1(5):319-329.

| Pos | wtAA | MutAA | RelXyl |
|---|---|---|---|
| | | I | 1.50 |
| | | K | 5.54 |
| | | L | 7.80 |
| | | M | 5.47 |
| | | N | 2.20 |
| | | P | 7.07 |
| | | Q | 15.50 |
| | | R | 1.63 |
| | | S | 18.50 |
| | | T | 21.51 |
| | | V | 5.89 |
| | | Y | 8.63 | acid that has a hydrophobicity of −30 to 10 $\Delta t_R$ results in mutants with reduced glucose transport activity. This is illustrated by FIG. 11.

The values for van der Waals volume ($Å^3$) for amino acids are herein used as described in: www.proteinsandproteomics.org/content/free/tables_1/t able08.pdf. The corresponding literature is N. J. Darby, Thomas E. Creighton, Protein Structure (1993) Oxford University Press. The values for hydrophobicity ($\Delta t_R$) of amino acids are herein used as described in onlinelibrary.wiley.com/doi/10.1002/psc.310010507/pdf. The reference corresponding to this is Monera, O. D. et al, Journal of Peptide Science 1995; 1(5):319-329.

Example 5: Xylose Transport Activity Screening

Aim.

Using the Xylose Transport Activity (XTA) screen, i.e. using hexose transporter-mutant strain RN1053 as host to

TABLE 8

Gal2p positions and mutations identified in the GTAC screen are ordered on preference. SCORE TOP HIT is the RelXyl score for the amino acid substitution within a position yielding the clearest improvement compared to wild-type Gal2p This allows a sorting of the most influential mutations and relevant positions to target in Gal2p to eliminate glucose affinity.

| GTAC | Position | wt AA | Most preferred | Preferred | Least preferred | Inactive | SCORE TOP HIT |
|---|---|---|---|---|---|---|---|
| Most preferred | 376 | N | FILMTV | ACHPSY | DEKQRW | | 99.46 |
| | 449 | T | FM | HIKLNQRSVWY | ACDEGP | | 92.65 |
| | 383 | S | CQRTWY | AEFKMN | DGILV | | 83.94 |
| | 339 | M | NQSV | AFGHKLRT | CDEIPY | W | 83.73 |
| | 226 | Y | ACDMNR | EQ | GHILPSTW | KV | 81.68 |
| | 448 | T | AM | CDEFGHIKLPQSVW | RY | | 77.64 |
| | 342 | Q | ACSWY | DFHKPT | EGILMNRV | | 76.45 |
| | 380 | T | AFMW | CDGIKLNPQRSV | Y | E | 74.78 |
| | 350 | F | LR | NSTV | DKMQ | EHIY | 57.58 |
| | 214 | Y | VW | LNQ | GMPRS | ACIK | 55.48 |
| | 338 | Q | CEF | ADHILRW | GNPSTVY | M | 52.66 |
| | 219 | T | AFG | CD | NS | EIKMQRW | 52.55 |
| | 373 | G | L | ACDEMNPVWY | FHIKQRST | | 51.94 |
| | 85 | F | QTV | S | ACHMNP | DEGKR | 50.51 |
| Preferred | 346 | N | VWY | AHST | CDFGIKLMQR | E | 47.09 |
| | 341 | Q | L | MT | NSY | DEHR | 46.71 |
| | 347 | N | A | DEI | HL | GKQRSTV | 44.64 |
| | 451 | A | G | CDEFILNPSW | HKMQRTVY | | 43.34 |
| | 89 | T | DHV | ACL | N | FIKMQRSY | 41.06 |
| | 343 | L | K | PRSY | ACDEFGHIMNQTW | V | 40.15 |
| | 444 | F | AILVY | HK | CDEGMNPQSTW | R | 39.43 |
| | 446 | F | Q | HLMN | DEI | KRSTV | 34.25 |
| | 478 | N | FP | V | GIKQRWY | ACDHL | 30.98 |
| Least preferred | 218 | I | KNS | AHL | CDEGMV | RTW | 27.86 |
| | 187 | V | A | CFGQT | DEHIKLMRSWY | | 26.84 |
| | 215 | Q | LM | CDF | AIS | GHNVWY | 24.63 |
| | 479 | W | QST | CE | DFGHIKLMNPRVY | | 21.51 |
| | 222 | I | D | ACH | EGMPSVY | KTW | 20.91 |
| | 191 | A | N | DGIPT | CFHKQSVWY | ELMR | 20.35 |
| | 455 | W | ELMNT | PV | ACGKQSY | DFIR | 19.92 |

Figure 8:
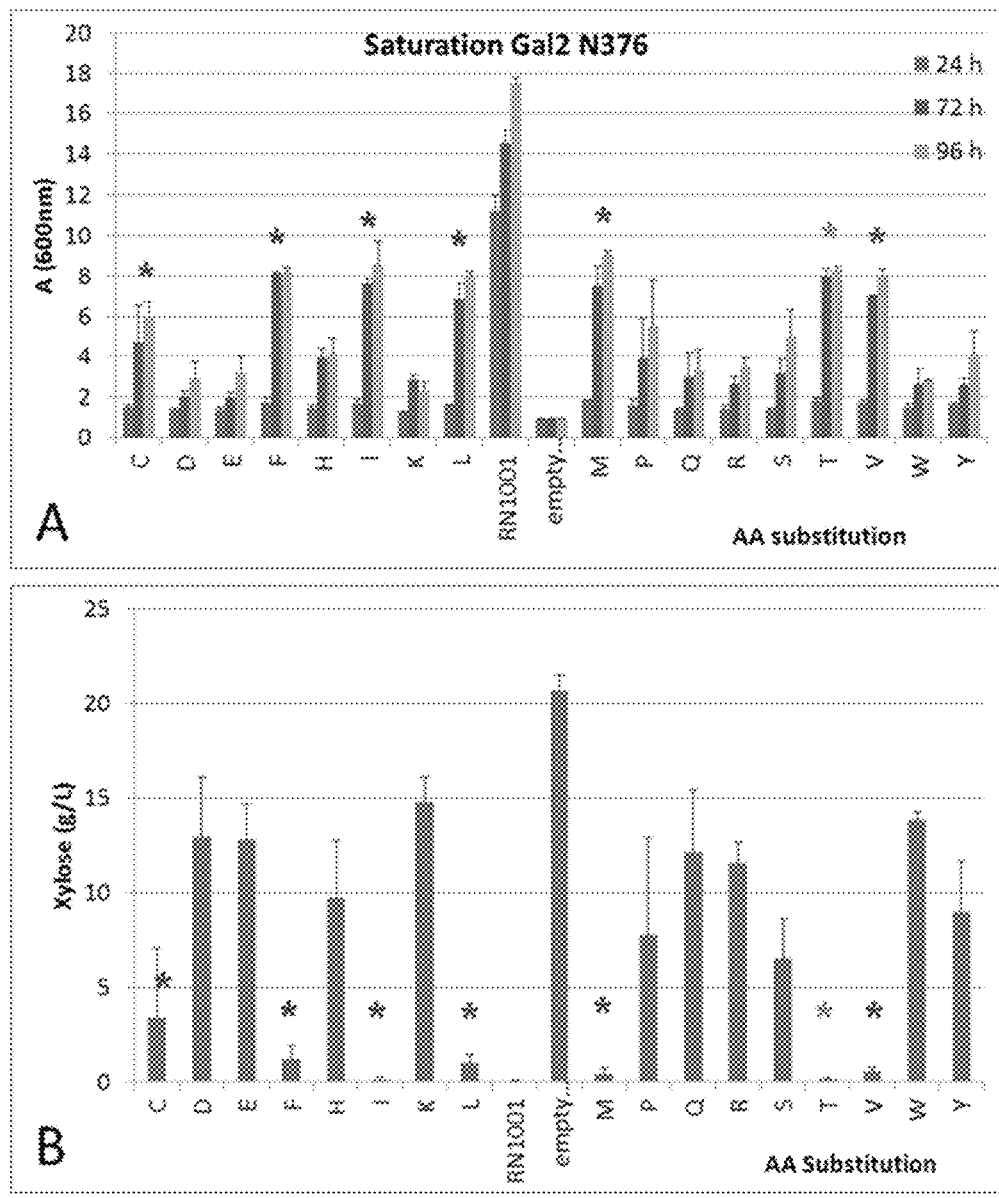
FIG. 8 shows growth and xylose consumption of Gal2-N376-mutant variants in the GTAC screen. (A) OD600 measurements at time points 24, 72 and 96 hours, and (B) residual xylose concentrations (g l$^{-1}$) measured for the Gal2-N376-mutant variants, RN1001 control strain and empty samples (YD10 medium-only) during the GTAC Screen. Each column represents the average OD600 or residual xylose concentration of 3 transformants; error bars represent the standard error of the mean. Asterisks indicate amino acids with large hydrophobic side chains with a clear effect.

The most prominent mutations were found at position 376 when the wild-type amino acid Asn was exchanged for amino acids with large hydrophobic side chains such as Phe, Ile, Leu, Met, Thr, or Val; these variants facilitated clear growth and almost full xylose consumption and almost no transport activity for glucose in the GTAC screen (FIG. 8). We have found that advantageous amino acids at position 376 have a van der Waals volume of 85 to 138 $Å^3$ and a hydrophobicity of 10 to 100 $\Delta t_R$ or in an embodiment a van der Waals volume of 100 to 138 $Å^3$ and a hydrophobicity of 10 to 100 $\Delta t_R$. A further important embodiment is specific amino acids at position 339, where we have found an amino introduce GAL2 variants and screening the resulting transformants on medium for growth on low xylose (1 g $l^{-1}$) concentrations, mutations can be identified that increase the xylose transport activity in the Gal2p variant. Activity of transport can be defined by more than one parameter, for instance, the affinity of the transporter (expressed by the Michaelis constant, i.e. $K_m$), or the rate of the transporter (expressed as $V_{max}$). It is also possible that a mutation increases the expression of the tranporter, and thus improves xylose transport activity in the host cell.

Transformation and Colony Picking.

RN1053 was transformed with a total of 468 constructs, each one bearing a GAL2 mutant. One construct with wild-type GAL2 sequence (SEQ. ID58) was included as control. For each transformation, 1-3 colonies were re-plated to agar medium MTPs amounting to 1229 transformants. The 1229 transformants were screened in two parts. For each part of the screening, wild-type GAL2 was included as control.

Pre-Culture and Screen.

For the pre-culture, transformants resulting from automated transformation and colony picking were transferred by automated process from selection agar medium MTPs to 96HDWP containing in each well 250 µl Verduyn-urea supplemented with 2% maltose. After 3 days of pre-culture in an orbital shaker at 30° C. and 750 rpm, 5 µl of culture was transferred to three different 96HDWP containing 250 µl Verduyn-urea supplemented with 1 g l$^{-1}$ xylose (RN01-medium), each 96 HDWP representing a sampling point. On each plate (24 DWP or 96 HDWP) at least one RN1001 growth control was inoculated to have an indication of plate-to-plate effects. After 24 hours, 72 hours and 96 hours a series of 96HDWPs was harvested for automated OD-measurement at 600 nm. For each construct and each time point the OD600 values for the different replicates was averaged. In order to compare the different parts of the screen, a relative value was calculated based on the difference to the wild-type OD600 value measured in the particular part of the XTA screen, according to the following formula:

$$RelOD600 = \frac{(OD600_{Gal2\text{-}mutant} - OD600_{Gal2\text{-}wildtype})}{OD600_{Gal2\text{-}wildtype}} \times 100\%$$

Results.

Figure 9:
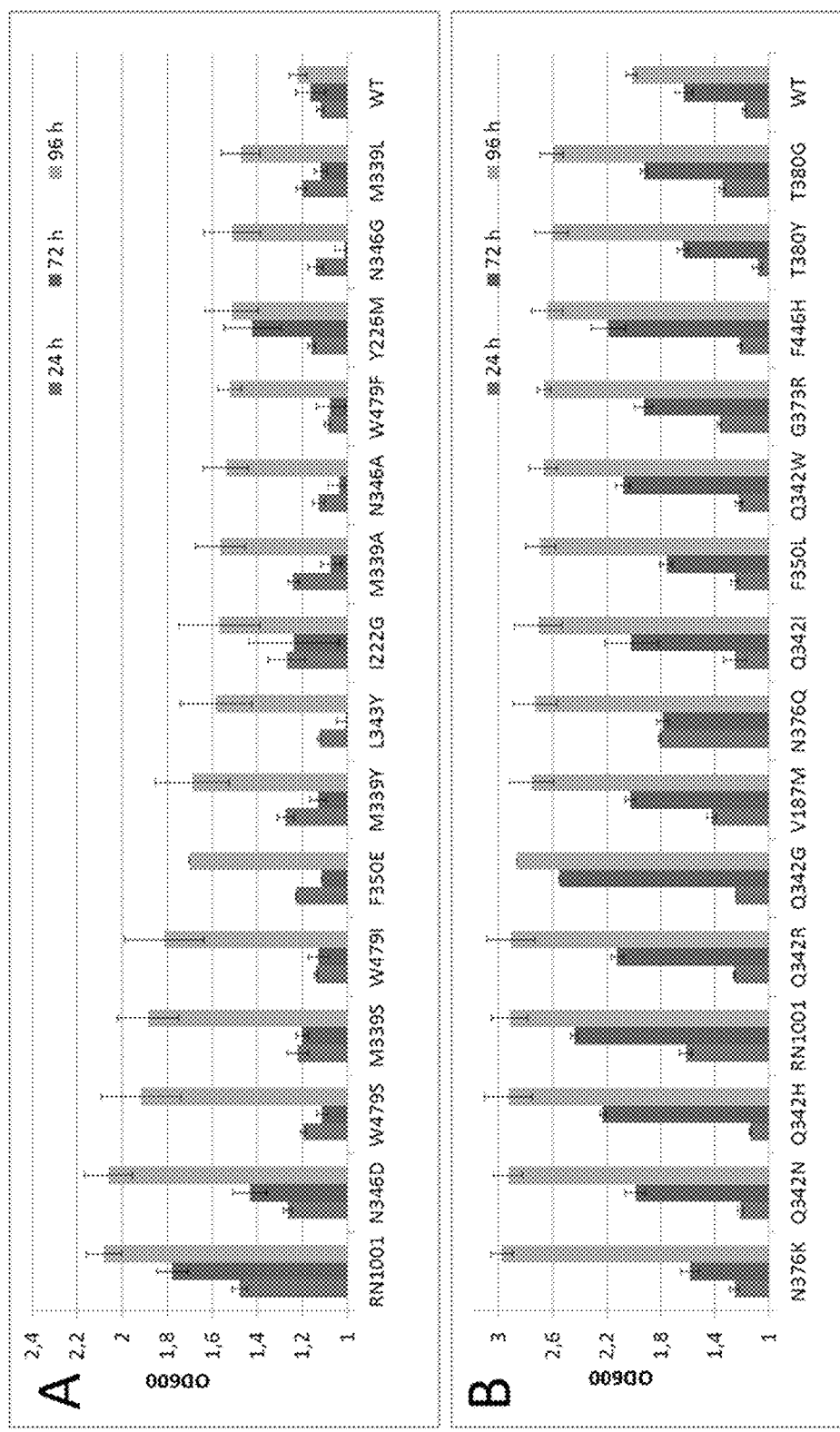
FIG. 9 shows growth profiles of TOP15 Xylose Transport Activity (XTA) Screening (see examples). OD600 values of the three sampling points for the TOP15 strains/variants from (A) Part A and (B) Part B of the XTA Screen. Each column represents the average OD600 of 3 transformants; error bars represent the standard error of the mean.

In both parts of the XTA screen RN1001 is part of the TOP15 positions based on the growth profile compared to wild-type Gal2p; RN1001 has the full complement of hexose transporters and the presence of RN1001 in the TOP15 in both parts of the XTA Screen (FIG. 9), indicates that one or more endogenous hexose transporters in yeast facilitate high affinity xylose uptake in contrast with the wild-type Gal2 RN1053-transformants which displayed poorer growth profiles. The mutant variants with the single amino acid changes present in the TOP15 displayed an increased affinity to xylose compared to wild-type Gal2p and developed towards the RN1001 growth profile or even showed similar or improved growth characteristics on low xylose concentrations. Interestingly, when aligning amino acid sequences of the S. cerevisiae hexose transporter family, some of the Gal2p mutations found in the TOP15, e.g. N346D and M339S, are to be found in the wild-type sequences of Hxt2 (S324) and Hxt11 (D336 and S329), respectively. The comparison of all tested mutant GAL2 variants versus wild-type GAL2 on growth (average RelOD600) at 96 hours is listed in Table 8. All mutations with RelOD600>0 are proposed to have a positive effect on the xylose affinity.

TABLE 9

Average RelOD600 values for the screened Gal2p mutants in the XTA Screen.
Wild-type GAL2 construct pDB1250 was set to 0.
RelOD600 values are the averages of
1-3 replicates and are relative values compared to wild-type.

| Pos | wtAA | MutAA | RelOD600 |
|---|---|---|---|
| 85 | F | A | -2.50 |
|  |  | C | -1.81 |

TABLE 9-continued

Average RelOD600 values for the screened Gal2p mutants in the XTA Screen.
Wild-type GAL2 construct pDB1250 was set to 0.
RelOD600 values are the averages of
1-3 replicates and are relative values compared to wild-type.

| Pos | wtAA | MutAA | RelOD600 |
|---|---|---|---|
|  |  | D | -32.03 |
|  |  | E | -37.55 |
|  |  | G | -51.06 |
|  |  | H | -35.08 |
|  |  | K | -27.75 |
|  |  | N | -6.14 |
|  |  | P | -23.27 |
|  |  | Q | -0.27 |
|  |  | R | -18.30 |
|  |  | S | 7.30 |
|  |  | T | -6.07 |
|  |  | V | 2.40 |
| 89 | T | A | -1.12 |
|  |  | C | 19.39 |
|  |  | E | -13.89 |
|  |  | I | -20.86 |
|  |  | K | -13.89 |
|  |  | L | 1.12 |
|  |  | M | -9.48 |
|  |  | N | -8.70 |
|  |  | Q | -4.57 |
|  |  | R | -10.12 |
|  |  | V | 3.11 |
|  |  | W | -43.47 |
|  |  | Y | 0.01 |
| 187 | V | A | -10.62 |
|  |  | C | 14.34 |
|  |  | D | -5.07 |
|  |  | E | -2.94 |
|  |  | F | -6.14 |
|  |  | G | 14.77 |
|  |  | H | -2.79 |
|  |  | I | 15.55 |
|  |  | L | 10.08 |
|  |  | M | 36.83 |
|  |  | Q | 26.77 |
|  |  | R | -11.36 |
|  |  | S | -28.01 |
|  |  | T | -10.54 |
|  |  | W | -17.20 |
|  |  | Y | 11.95 |
| 191 | A | C | 5.10 |
|  |  | D | 7.05 |
|  |  | E | 0.58 |
|  |  | F | -1.81 |
|  |  | G | -4.01 |
|  |  | H | -12.93 |
|  |  | I | 10.13 |
|  |  | K | 7.11 |
|  |  | M | -4.82 |
|  |  | N | 4.60 |
|  |  | P | 1.90 |
|  |  | Q | -8.47 |
|  |  | R | 3.34 |
|  |  | S | -19.15 |
|  |  | T | -2.00 |
|  |  | V | -9.91 |
|  |  | W | 4.10 |
|  |  | Y | -15.24 |
| 214 | Y | A | -3.04 |
|  |  | C | -12.04 |
|  |  | G | -6.92 |
|  |  | I | -6.92 |
|  |  | K | -4.15 |
|  |  | L | 6.02 |
|  |  | M | -26.59 |
|  |  | N | -9.60 |
|  |  | P | 5.35 |
|  |  | Q | -26.44 |
|  |  | R | -29.77 |
|  |  | S | -37.90 |
|  |  | W | -21.91 |

TABLE 9-continued

Average RelOD600 values for the screened Gal2p mutants in the XTA Screen.
Wild-type GAL2 construct pDB1250 was set to 0.
RelOD600 values are the averages of 1-3 replicates and are relative values compared to wild-type.

| Pos | wtAA | MutAA | RelOD600 |
|---|---|---|---|
| 215 | Q | A | 1.54 |
|  |  | C | 5.92 |
|  |  | D | 25.93 |
|  |  | E | 20.81 |
|  |  | F | 3.28 |
|  |  | I | −5.50 |
|  |  | L | 8.24 |
|  |  | M | 11.19 |
|  |  | R | −48.74 |
|  |  | S | 16.66 |
|  |  | V | −21.07 |
|  |  | W | −39.22 |
|  |  | Y | −24.30 |
| 218 | I | A | −15.52 |
|  |  | C | −13.03 |
|  |  | D | −19.50 |
|  |  | E | −15.31 |
|  |  | G | −9.12 |
|  |  | H | −9.12 |
|  |  | K | −10.19 |
|  |  | L | −15.45 |
|  |  | M | −24.27 |
|  |  | N | −23.20 |
|  |  | R | −13.39 |
|  |  | S | −13.60 |
|  |  | T | −15.95 |
|  |  | V | −4.00 |
|  |  | W | 40.30 |
| 219 | T | A | −6.71 |
|  |  | C | −20.53 |
|  |  | D | −21.69 |
|  |  | E | 3.47 |
|  |  | F | −17.01 |
|  |  | G | −35.80 |
|  |  | I | −47.23 |
|  |  | L | 3.78 |
|  |  | M | −20.00 |
|  |  | N | −13.93 |
|  |  | P | −18.27 |
|  |  | Q | −14.25 |
|  |  | R | 7.17 |
|  |  | S | −18.08 |
|  |  | V | 11.19 |
|  |  | W | −15.13 |
| 222 | I | A | −7.91 |
|  |  | C | −6.92 |
|  |  | D | −12.54 |
|  |  | E | −16.80 |
|  |  | G | 28.78 |
|  |  | H | −13.50 |
|  |  | K | −48.17 |
|  |  | M | 20.18 |
|  |  | P | 11.01 |
|  |  | R | −0.62 |
|  |  | S | 3.03 |
|  |  | T | 10.25 |
|  |  | V | −12.55 |
|  |  | W | 11.38 |
|  |  | Y | 23.82 |
| 226 | Y | A | 23.92 |
|  |  | C | −6.78 |
|  |  | D | −12.89 |
|  |  | E | 5.10 |
|  |  | F | −28.04 |
|  |  | G | −4.64 |
|  |  | H | −11.26 |
|  |  | I | −12.46 |
|  |  | K | −10.55 |
|  |  | M | 24.16 |
|  |  | N | −4.86 |
|  |  | P | 20.39 |
|  |  | Q | 0.33 |
|  |  | R | −9.19 |
|  |  | S | −5.78 |
|  |  | T | 23.80 |
|  |  | W | −5.71 |
| 338 | Q | A | 4.10 |
|  |  | C | 10.88 |
|  |  | D | 7.99 |
|  |  | E | 3.59 |
|  |  | F | 0.45 |
|  |  | G | 5.29 |
|  |  | H | 11.63 |
|  |  | I | 12.95 |
|  |  | L | 0.58 |
|  |  | M | 4.79 |
|  |  | N | 14.12 |
|  |  | P | 2.21 |
|  |  | R | 15.03 |
|  |  | S | −17.02 |
|  |  | T | −26.76 |
|  |  | V | −11.33 |
|  |  | W | −6.92 |
|  |  | Y | −17.30 |
| 339 | M | A | 28.42 |
|  |  | C | 20.32 |
|  |  | D | −0.09 |
|  |  | E | 18.97 |
|  |  | F | 4.17 |
|  |  | G | −20.00 |
|  |  | H | −14.46 |
|  |  | I | −17.55 |
|  |  | K | −11.75 |
|  |  | L | 21.03 |
|  |  | N | 4.25 |
|  |  | P | −4.64 |
|  |  | Q | −3.65 |
|  |  | R | −7.91 |
|  |  | S | 54.52 |
|  |  | T | 10.79 |
|  |  | V | −11.90 |
|  |  | W | 6.56 |
|  |  | Y | 38.66 |
| 341 | Q | D | −10.62 |
|  |  | E | −8.13 |
|  |  | H | 2.89 |
|  |  | K | −21.66 |
|  |  | L | −22.79 |
|  |  | M | −11.30 |
|  |  | N | −13.31 |
|  |  | R | −10.76 |
|  |  | S | 7.16 |
|  |  | T | −3.08 |
|  |  | V | 18.89 |
|  |  | Y | 9.37 |
| 342 | Q | A | −15.66 |
|  |  | C | 2.04 |
|  |  | D | −12.54 |
|  |  | E | −9.23 |
|  |  | F | 33.22 |
|  |  | G | 42.01 |
|  |  | H | 45.21 |
|  |  | I | 34.38 |
|  |  | K | 12.92 |
|  |  | L | 28.91 |
|  |  | M | 7.99 |
|  |  | N | 45.31 |
|  |  | P | −7.15 |
|  |  | R | 44.36 |
|  |  | S | 22.25 |
|  |  | T | 20.62 |
|  |  | V | −16.07 |
|  |  | W | 32.62 |
|  |  | Y | −21.41 |

TABLE 9-continued

Average RelOD600 values for the screened Gal2p mutants in the XTA Screen.
Wild-type GAL2 construct pDB1250 was set to 0.
RelOD600 values are the averages of 1-3 replicates and are relative values compared to wild-type.

| Pos | wtAA | MutAA | RelOD600 |
|---|---|---|---|
| 343 | L | A | 15.98 |
|  |  | C | 7.16 |
|  |  | D | −12.82 |
|  |  | E | 9.65 |
|  |  | F | −6.07 |
|  |  | G | −6.63 |
|  |  | H | −9.83 |
|  |  | I | 19.04 |
|  |  | K | 2.40 |
|  |  | M | −0.73 |
|  |  | N | 0.97 |
|  |  | P | 4.53 |
|  |  | Q | 19.53 |
|  |  | R | −10.62 |
|  |  | S | 10.72 |
|  |  | T | −6.46 |
|  |  | W | 0.69 |
|  |  | Y | 29.99 |
| 346 | N | A | 26.36 |
|  |  | C | 15.73 |
|  |  | D | 69.10 |
|  |  | F | 10.15 |
|  |  | G | 24.01 |
|  |  | H | −4.93 |
|  |  | I | 0.76 |
|  |  | K | −1.66 |
|  |  | P | −0.80 |
|  |  | Q | −5.28 |
|  |  | R | −7.84 |
|  |  | V | −44.97 |
|  |  | Y | −3.51 |
| 347 | N | D | 5.29 |
|  |  | E | −24.11 |
|  |  | G | 7.59 |
|  |  | H | −4.57 |
|  |  | I | −3.08 |
|  |  | K | 9.65 |
|  |  | L | 14.52 |
|  |  | Q | 6.55 |
|  |  | R | −1.93 |
|  |  | S | 18.92 |
|  |  | T | 2.61 |
|  |  | V | 6.09 |
| 350 | Y | D | −2.08 |
|  |  | E | 39.52 |
|  |  | I | −28.19 |
|  |  | L | 33.56 |
|  |  | M | 7.09 |
|  |  | Q | 6.95 |
|  |  | R | −40.48 |
|  |  | S | 7.93 |
|  |  | T | −6.33 |
|  |  | V | −15.81 |
|  |  | W | −9.27 |
| 373 | G | A | −51.50 |
|  |  | E | −50.72 |
|  |  | F | −47.17 |
|  |  | H | −37.99 |
|  |  | I | 2.84 |
|  |  | K | 15.40 |
|  |  | L | 18.36 |
|  |  | M | 14.21 |
|  |  | N | 21.06 |
|  |  | Q | 14.02 |
|  |  | R | 32.18 |
|  |  | S | 18.92 |
|  |  | T | −11.04 |
|  |  | V | −6.71 |
|  |  | W | −5.20 |
|  |  | Y | 1.21 |
| 376 | N | A | 10.19 |
|  |  | C | 24.67 |
|  |  | D | 8.93 |
|  |  | E | 10.19 |
|  |  | F | −13.02 |
|  |  | H | −13.78 |
|  |  | I | 14.59 |
|  |  | K | 47.76 |
|  |  | L | −9.63 |
|  |  | M | 6.29 |
|  |  | P | 29.04 |
|  |  | Q | 35.51 |
|  |  | R | −23.42 |
|  |  | S | 44.42 |
|  |  | V | −42.40 |
|  |  | W | −15.74 |
|  |  | Y | −21.28 |
| 380 | T | A | 3.56 |
|  |  | C | 8.37 |
|  |  | D | 24.95 |
|  |  | E | 14.21 |
|  |  | F | −17.33 |
|  |  | G | 29.22 |
|  |  | I | 20.81 |
|  |  | K | 14.34 |
|  |  | L | 23.45 |
|  |  | M | 29.16 |
|  |  | N | −50.25 |
|  |  | P | −7.46 |
|  |  | Q | −15.32 |
|  |  | R | −0.55 |
|  |  | S | −6.02 |
|  |  | V | −6.21 |
|  |  | W | 14.78 |
|  |  | Y | 29.48 |
| 383 | S | A | 16.05 |
|  |  | C | 3.32 |
|  |  | D | −2.94 |
|  |  | E | 1.97 |
|  |  | F | −15.10 |
|  |  | G | −4.50 |
|  |  | I | 2.40 |
|  |  | K | −47.86 |
|  |  | L | 3.59 |
|  |  | M | −2.56 |
|  |  | N | −44.72 |
|  |  | Q | 14.40 |
|  |  | R | 21.37 |
|  |  | T | −28.26 |
|  |  | V | 24.58 |
|  |  | W | 26.71 |
|  |  | Y | 27.84 |
| 444 | F | C | −6.49 |
|  |  | D | −2.08 |
|  |  | E | −16.16 |
|  |  | G | 1.54 |
|  |  | H | −16.38 |
|  |  | I | −20.29 |
|  |  | K | −24.06 |
|  |  | L | −10.19 |
|  |  | M | −7.20 |
|  |  | N | −9.76 |
|  |  | P | −18.79 |
|  |  | Q | −27.18 |
|  |  | S | −14.45602 |
|  |  | W | −16.94 |
|  |  | Y | −18.08 |
| 446 | F | D | 19.61 |
|  |  | E | −36.17 |
|  |  | H | 30.98 |
|  |  | I | 0.83 |
|  |  | L | −40.55 |
|  |  | M | −2.58 |
|  |  | N | −10.90 |

TABLE 9-continued

Average RelOD600 values for the screened Gal2p mutants in the XTA Screen.
Wild-type GAL2 construct pDB1250 was set to 0.
RelOD600 values are the averages of
1-3 replicates and are relative values compared to wild-type.

| Pos | wtAA | MutAA | RelOD600 |
|---|---|---|---|
| | | Q | -35.54 |
| | | R | -37.62 |
| | | S | -2.94 |
| | | T | -39.41 |
| | | V | -47.79 |
| 448 | T | A | 10.57 |
| | | C | 0.08 |
| | | D | 15.78 |
| | | E | 19.55 |
| | | F | -6.65 |
| | | G | 16.91 |
| | | H | 25.64 |
| | | I | -0.18 |
| | | K | 26.65 |
| | | L | 22.31 |
| | | M | 0.77 |
| | | P | 12.58 |
| | | Q | 14.08 |
| | | R | 29.22 |
| | | S | 11.19 |
| | | V | |
| | | W | 8.09 |
| | | Y | -2.01 |
| 449 | T | A | 4.67 |
| | | C | 6.59 |
| | | D | -2.58 |
| | | E | -2.08 |
| | | F | 16.48 |
| | | G | 11.00 |
| | | H | 16.26 |
| | | I | 9.51 |
| | | K | -3.51 |
| | | L | 11.29 |
| | | M | -15.59 |
| | | N | -7.13 |
| | | P | 8.73 |
| | | Q | 13.21 |
| | | R | -10.33 |
| | | S | 15.48 |
| | | V | 14.41 |
| | | W | -5.78 |
| | | Y | -5.57 |
| 451 | T | C | -33.23 |
| | | D | -23.20 |
| | | F | -4.75 |
| | | G | -16.94 |
| | | H | -41.76 |
| | | I | -40.26 |
| | | K | -8.91 |
| | | L | -23.73 |
| | | N | -6.07 |
| | | P | -6.14 |
| | | Q | -8.22 |
| | | R | -6.21 |

TABLE 9-continued

Average RelOD600 values for the screened Gal2p mutants in the XTA Screen.
Wild-type GAL2 construct pDB1250 was set to 0.
RelOD600 values are the averages of
1-3 replicates and are relative values compared to wild-type.

| Pos | wtAA | MutAA | RelOD600 |
|---|---|---|---|
| | | S | 2.90 |
| | | T | -11.42 |
| | | V | -5.89 |
| | | W | 4.10 |
| | | Y | 3.91 |
| 455 | W | C | -14.75 |
| | | D | 8.18 |
| | | E | 4.22 |
| | | F | -2.31 |
| | | G | -10.67 |
| | | I | 5.45 |
| | | K | 8.12 |
| | | L | -5.96 |
| | | M | 6.39 |
| | | N | -9.22 |
| | | P | 0.83 |
| | | Q | 0.95 |
| | | R | -48.55 |
| | | S | -4.82 |
| | | T | -9.44 |
| | | V | -2.06 |
| | | Y | -19.81 |
| 478 | N | A | -25.74 |
| | | C | -14.75 |
| | | D | -9.91 |
| | | F | 6.86 |
| | | G | 0.01 |
| | | H | -13.12 |
| | | I | 8.81 |
| | | K | -24.30 |
| | | P | -20.47 |
| | | Q | 14.40 |
| | | R | -27.44 |
| | | W | -13.40 |
| | | Y | 6.77 |
| 479 | W | C | -12.96 |
| | | D | 15.20 |
| | | E | 18.40 |
| | | F | 24.87 |
| | | H | 1.83 |
| | | I | 48.83 |
| | | K | 8.58 |
| | | L | -3.79 |
| | | M | 7.87 |
| | | N | 8.05 |
| | | P | -42.40 |
| | | Q | -33.73 |
| | | R | 13.42 |
| | | S | 57.22 |
| | | T | 15.48 |
| | | V | -12.54 |
| | | Y | 12.07 |

TABLE 10

Gal2p positions and mutations identified in the XTA screening are ordered on preference. SCORE TOP HIT is the RelXyl score for the amino acid substitution within a position yielding the clearest improvement compared to wild-type Gal2p This allows a sorting of the most influential mutations and relevant positions to target in Gal2p to increase xylose transport activity.

| XTA | Mutations | | | | | SCORE |
|---|---|---|---|---|---|---|
| | Position | wt AA | Most preferred | Preferred | Least preferred | Inactive | TOP HIT |
| Most Preferred | 346 | N | D | AG | CF | HIKPQRVY | 69.10 |
| | 479 | W | S | I | DEFHKMNRTY | CLPQV | 57.22 |
| | 339 | M | SY | ACEL | FNTW | DGHIKPQRV | 54.52 |

TABLE 10-continued

Gal2p positions and mutations identified in the XTA screening are ordered on preference. SCORE TOP HIT is the RelXyl score for the amino acid substitution within a position yielding the clearest improvement compared to wild-type Gal2p This allows a sorting of the most influential mutations and relevant positions to target in Gal2p to increase xylose transport activity.

| XTA | | | Mutations | | | SCORE |
|---|---|---|---|---|---|---|
| | Position | wt AA | Most preferred | Preferred | Least preferred | Inactive | TOP HIT |
| | 342 | Q | GHNR | FILW | CKMST | ADEPVY | 47.76 |
| | 376 | N | KS | CPQ | ADEIM | FHLRVWY | 47.76 |
| Preferred | 218 | I | W | | | ACDEGHKLMNRSTV | 40.30 |
| | 350 | F | E | L | MQS | DIRTVY | 39.52 |
| | 187 | V | MQ | CGI | LY | ADEFHRSTW | 36.83 |
| | 373 | G | R | KLMNQS | IY | AEFHTVW | 32.18 |
| | 446 | F | H | D | | EILMNQRSTV | 30.98 |
| Least preferred | 343 | L | Y | AIQ | CEKSP | DFGHMNRTW | 29.99 |
| | 380 | T | GMY | DIL | ACEKW | FNPQRSV | 29.48 |
| | 448 | T | HKR | EL | ADGPQSW | MCFIVY | 29.22 |
| | 222 | I | G | MY | PTW | ACDEHKRSV | 28.78 |
| | 383 | S | VWY | AQR | CEIL | DFGKMNT | 27.84 |
| | 215 | Q | DE | S | ACFL | IMRVWY | 25.93 |
| | 226 | Y | AMPT | | E | CDFGHIKNQRSW | 24.16 |
| | 89 | T | C | | LVY | AEIKMNQRW | 19.39 |
| | 347 | N | S | KL | DGQTV | EHIR | 18.92 |
| | 449 | T | FH | QSV | ACGILP | DEKMNRWY | 16.48 |
| | 338 | Q | NR | CDHI | AEFGLMP | STVWY | 15.03 |
| | 478 | N | Q | FIY | | ACDGHKPRW | 14.40 |
| | 191 | A | I | DK | CENPRW | FGHMQSTVY | 10.13 |
| | 341 | Q | V | SY | H | DEKLMNRT | 9.37 |
| | 455 | W | DK | EIM | | CFGLNPQRSTVY | 8.18 |
| | 85 | F | S | V | | ACDEGHKNPQRT | 7.30 |
| | 219 | T | V | R | EL | ACDFGIMNPQSW | 7.17 |
| | 214 | Y | LP | | | ACGIKMNQRSW | 6.02 |
| | 451 | A | WY | S | | CDFGHIKLNPQRTV | 4.10 |
| | 444 | F | | | G | CDEHIKLMNPQSWY | 1.54 |

Examples 6 to 15

Methods

Molecular Biology Techniques and Chemicals.

Restriction enzymes and T4 DNA ligase were acquired from Fermentas (Fisher Scientific, Landsmeer, the Netherlands). Primers used in the studies (SEQ ID NO: 1-55) are indicated in Table 11. Standard molecular biology and yeast genetics techniques were conducted according to textbooks including Sambrook et al. (2001; Molecular cloning: a laboratory manual, third edition, Cold Spring Harbor Press, Cold Spring Harbor, N.Y., N.Y., USA) and Ausubel et al. (1995; Current Protocols in Molecular Biology).

PCR Amplification and Cloning.

For PCR amplifications, Phusion® High-Fidelity PCR Master Mix with HF buffer was used (Finnzymes; Fisher Scientific, Landsmeer, the Netherlands). Primers used for cloning and sequencing are indicated in Table 11 (SEQ ID NO: 37-55). HXT2, HXT3-6, and HXT11 PCR fragments were cloned into the yeast expression vector pRS313-P7T7 (SEQ ID NO 56), based on the shuttle vector pRS313 (Sikorski & Hieter, 1989, A system of shuttle vectors and yeast host strains designed for efficient manipulation of DNA in Saccharomyces cerevisiae. Genetics, 122, pp. 19-27). Construct pRS313-P7T7 bears the truncated HXT7 promoter (Hauf et al, 2000, Simultaneous genomic overexpression of seven glycolytic enzymes in the yeast Saccharomyces cerevisiae. Enzyme Microb Technol, 26:688-698) and the HXT7 terminator. In between the promoter and the terminator, a multiple cloning site (MCS) exists. Resulting PCR fragments, were digested by restriction enzyme combinations (as further indicated in the Examples below) and cloned by standard molecular biology techniques into the yeast expression vector. HXT11 was also cloned into pRS313-P7T7-GFP (resulting in SEQ ID NO: 57) for localization studies of the GFP-tagged Hxt11 protein using fluorescence microscopy (Example 5). pDB1250 contained the GAL2 ORF (SEQ ID NO:60) between the truncated HXT7 promoter and the ADH1 terminator (for reference of sequence pDB1250 see SEQ ID NO: 58. Plasmids were amplified and maintained in DH5α cells following manufacturer's instructions. Plasmids were isolated from E. coli mini cultures using the GeneElute plasmid Miniprep kit (Sigma-Aldrich, Zwijndrecht, the Netherlands). Gene/Protein sequences and constructs used and generated during these studies are listed in Table 12.

TABLE 11 oligonucleotides used in the examples

| Name | Sequence (5'→3') | purpose | SEQ ID NO |
|---|---|---|---|
| ActinF | GGATTCTGAGGTTGCTGCTTTGG | Real time PCR | 62 |

TABLE 11-continued oligonucleotides used in the examples

| Name | Sequence (5'→3') | purpose | SEQ ID NO |
|---|---|---|---|
| ActinR | GAGCTTCATCACCAACGTAGGAG | Real time PCR | 63 |
| HXT1F | TGTTCTCTGTACACCGTTGACCG | Real time PCR | 64 |
| HXT1R | AGATCATACAGTTACCAGCACCC | Real time PCR | 65 |
| HXT2F | CTTCGCATCCACTTTCGTG | Real time PCR | 66 |
| HXT2R | AATCATGACGTTACCGGCAGCC | Real time PCR | 67 |
| HXT3F | GAAGCTAGAGCTGCTGGTTCAGC | Real time PCR | 68 |
| HXT3R | ACAACGACATAAGGAATTGGAGCC | Real time PCR | 69 |
| HXT4F | ATGGAGAGTTCCATTAGGTCTAGG | Real time PCR | 70 |
| HXT4R | ATAACAGCTGGATCGTCTGCGC | Real time PCR | 71 |
| HXT5F | TTGCTATGTCGTCTATGCCTCTG | Real time PCR | 72 |
| HXT5R | AGATAAGGACATAGGCAACGGG | Real time PCR | 73 |
| HXT7F | GGGTGCTGCATCCATGACTGC | Real time PCR | 74 |
| HXT7R | ACAACGACATAAGGAATTGGAGCC | Real time PCR | 75 |
| HXT8F | GTACTACTATCTTCAAATCTGTCGG | Real time PCR | 76 |
| HXT8R | CTTGTGACGCCAACGGAGGCG | Real time PCR | 77 |
| HXT9F | CCATTGAGAGGTTTGGACGCCG | Real time PCR | 78 |
| HXT9R | ACACAATCATACAGTTACCGGCG | Real time PCR | 79 |
| HXT10F | GGAATGCAAGACTCTTTCGAGAC | Real time PCR | 80 |
| HXT10R | CTAGTGACGCCAACGGTGGCG | Real time PCR | 81 |
| HXT11F | GCCACTCAATGGAGAGTCGGC | Real time PCR | 82 |
| HXT11R | CAACTAGCAAGGCTGGATCGTC | Real time PCR | 83 |
| HXT12F | CACCATCTTCAAATCTGTCGGTC | Real time PCR | 84 |
| HXT12R | CAATCATACAGTTACCGGCACCC | Real time PCR | 85 |
| HXT13F | CCCTCATGGCCAGGACGGTC | Real time PCR | 86 |
| HXT13R | TTGCCATAACCAGTTGCATGCAG | Real time PCR | 87 |

TABLE 11-continued oligonucleotides used in the examples

| Name | Sequence (5'→3') | purpose | SEQ ID NO |
|------|------------------|---------|-----------|
| HXT14F | GCCTTAGTAGTGTACTGCATCGGT | Real time PCR | 88 |
| HXT14R | TGATACGTAGATACCATGGAGCC | Real time PCR | 89 |
| HXT15F | GAGGCCTGTGTCTCCATCGCC | Real time PCR | 90 |
| HXT15R | CACAAGAATACCTGTGATCAAACG | Real time PCR | 91 |
| HXT16F | CAAGGAAGTATAGTAATACTGCGC | Real time PCR | 92 |
| HXT16R | TTGGCGATGGAGACACAGGCC | Real time PCR | 93 |
| HXT17F | TAACACTGCACAATGGAGAGTCC | Real time PCR | 94 |
| HXT17R | TGAGTACCCATGGATCCTCTGG | Real time PCR | 95 |
| GAL2F | TCAATGGAGAGTTCCATTAGGGC | Real time PCR | 96 |
| GAL2R | CTGGACGGCAGGATCCTCTGG | Real time PCR | 97 |
| KOP11* | *AATAATCATTGCACAATTTAGTTCTAAACGCTTTTGTTATTACTCAATAT*<u>CCGTTTTAAGAGCTTGGTGAGCGCTAGGAGTC</u> | KO HXT11 | 98 |
| KOT11* | *TCGTCAATTTTTTTTTTTGCTTTTTTACCAATTTACCGAAAACTAGAAGA*<u>GAGTTCAAGAGAAAAAAAAAGAAAAAGCAAAAAGAAAAAAGGAAAGCGCGC</u> | KO HXT11 | 99 |
| iHXT11F | GGCCTCTAGATCAGCTGGAAAAGAACCTCTTGTAAATTG | Inverse HXT11 | 100 |
| iHXT11R | GCTAGGATCCATGTCAGGTGTTAATAATACATCCGCAAATG | Inverse HXT11 | 101 |
| HXT11F | GGCCTCTAGAATGTCAGGTGTTAATAATACATCCGC | Cloning | 102 |
| HXT12F | GGCCTCTAGAATGGGTTTGATTGTCTCAATATTCAAC | Cloning | 103 |
| HXT11/12R | CGATGGATCCTCAGCTGGAAAAGAACCTCTTGTAAATTG | cloning | 104 |
| HXT1 XbaI | GCATTCTAGAATGAATTCAACTCCCGATCTAATATC | cloning | 105 |
| R HXT1 Cfr9i | TGCATCCCGGGTTATTTCCTGCTAAACAAACTCTTGTA | cloning | 106 |
| F HXT2 Xbai | GTCCTCTAGAATGTCTGAATTCGCTACTAGCCG | cloning | 107 |
| R HXT2 Cfr9i | CATCGCCCGGGTTATTCCTCGGAAACTCTTTTTTCTTTTG | cloning | 108 |
| F HXT3 XbaI | GCATTCTAGAATGAATTCAACTCCAGATTTAATATCTC | cloning | 109 |
| R HXT6 Cfr9I | CATCGCCCGGGTTATTTGGTGCTGAACATTCTCTTG | cloning | 110 |
| F HXT4 XbaI | GTCCTCTAGAATGTCTGAAGAAGCTGCCTATCAAG | cloning | 111 |

TABLE 11-continued oligonucleotides used in the examples

| Name | Sequence (5'→3') | purpose | SEQ ID NO |
|---|---|---|---|
| R HXT4RN Cfr9I | TATCGCCCGGGTTAATTAACTGACCTACTTTTTTCCGA | cloning | 112 |
| F HXT5 XbaI | GTCCTCTAGAATGTCGGAACTTGAAAACGCTCATC | cloning | 113 |
| R HXT5 Cfr9I | GCATCCCGGGTTATTTTCTTTAGTGAACATCCTTTTATA | cloning | 114 |
| F HXT7 XbaI | GTCCTCTAGAATGTCACAAGACGCTGCTATTGCA | cloning | 115 |
| R HXT7 Cfr9I | CATCGCCCGGGTTATTTGGTGCTGAACATTCTCTTG | cloning | 116 |

*In italics the HXT11 flanking sequence, and underlined the HIS3 sequence

RNA Extraction and cDNA Synthesis.

Total RNA was isolated from yeast cells in exponential phase by a glass-bead disruption/Trizol extraction procedure. Yeast pellets from 2 ml of cell culture were mixed with 0.2 ml of glass beads (diameter, 0.45 mm) and 0.9 ml of Trizol with 125 µl chloroform, and disrupted in a Fastprep FP120 (Bio-101, Thermo Savant, Calif., USA) by a 45-second burst at speed 6. 1 µg of total RNA was used to synthesize cDNA using the iScript Kit (Bio-Rad, Veenendaal, the Netherlands).

Real-Time PCR.

The HXT1-HXT17 and GAL2-specific real-time PCRs were performed, respectively, using SensiMix SYBR & Fluorescein kit (GC Biotech, Alphen aan den Rijn, the Netherlands) and the MyiQ iCYCLER Real Time PCR instrument (BIO-Rad, Veenendaal, the Netherlands). Each 25-µl reaction contained 12.5 µl of SYBR green Master Mix, 4 µl cDNA, 0.5 µl of each primer (10 nM) and 7.5 µl of sterile deionized water. The PCR conditions were 10 min at 95° C. followed by 39 cycles of amplification (15 sec at 95° C., 30 sec at 60° C., 30 sec at 72° C.). The primers shown in Table 11 were utilized to amplify the cDNA fragments by PCR amplification (SEQ ID NO's 1-36).

Error Prone PCR.

Error-prone PCR experiments were performed following the indications provided by the DNA Taq polymerase (Thermo Fischer) using 10 ng of template in 100 µl of PCR mix containing 5.5 mM MgCl2 and 0.15 mM MnCl2.

Strain Maintenance, Cultivation and Evolutionary Engineering.

Strains generated in these studies are listed in Table 13. For storage of the strains used in this work (Table 2), shake flask cultures were performed in rich medium (YP), consisting of 10 g $l^{-1}$ yeast extract (Oxoid) and 20 g $l^{-1}$ peptone (BD Difco), supplemented with either 2% glucose (YPD), 2% maltose (YPM; in case of RN1053-derivatives), or 3% xylose (YPX; in case of YD01227-derivatives). Cultures were maintained at 30° C. in an orbital shaker until cultures reached stationary growth phase. After adding glycerol to 30% (v/v), samples from shake-flask cultures were stored in 2 ml aliquots at −80° C.

For strain characterizations and evolutionary engineering, cultivations were conducted using mineral medium according to Verduyn using urea as nitrogen source (Verduyn-urea Luttik et al, 2001, J Bacteriol, 182:501-517) at pH 4.5 supplemented with the desired sugar (mixtures). In cultures of the model strains RN1053 or YD01227, Verduyn-urea was supplemented with 0.2 g $l^{-1}$ histidine (Sigma-Aldrich; Verduyn-urea-his) to complement for the histidine auxotrophy.

Cultivations of strains for characterization of growth and sugar consumption profiles were conducted in shake flasks, a Bioscreen C reader using honeycomb well plates (Growth Curves Ltd, represented by Thermo Fisher Scientific BV, Breda, the Netherlands). Cultures were maintained at a temperature of 30° C. Specifically for the purpose of evolutionary engineering, chemostat cultures were grown in a 3 L stirred tank bioreactor (Applikon, Schiedam, the Netherlands) filled with 500 ml of Verduyn-urea-his supplemented with the required carbon sources at a temperature of 30° C. Starting Dissolved Oxygen (DO) setpoint was 5%, stirring was performed at 400 rpm and the starting OD600 was 0.2.

TABLE 12 plasmids and gene/protein sequences

| Plasmid/gene/protein | Sequence type | SEQ ID NO or reference | Example |
|---|---|---|---|
| pRS313-P7T7 (empty vector control) | Artificial DNA | 117 | 7, 8, 9, 10, 11, 13, 15 |
| pRS313-P7TA-GAL2 (pDB1250) | Articifial DNA | | 12 |
| pRS313-P7T7-iHXT11 | Articifial DNA | | 7 |

TABLE 12-continued plasmids and gene/protein sequences

| Plasmid/gene/protein | Sequence type | SEQ ID NO or reference | Example |
|---|---|---|---|
| pRS313-P7T7-HXT11 | Articifial DNA | | 8, 9, 10 |
| pRS313-P7T7-HXT12 | Articifial DNA | | 8 |
| pRS313-P7T7-HXT2 | Articifial DNA | | 9, 10 |
| pRS313-P7T7-HXT11-GFP | Articifial DNA | 118 | 10 |
| pRS313-P7T7-mHXT11(N366D) | Articifial DNA | | 11 |
| pRS313-P7T7-HXT36 | Articifial DNA | | 15 |
| pRS313-P7T7-mHXT36(N367I) | Articifial DNA | | 15 |
| HXT11 | DNA S. cerevisiae | 119 | 7, 8, 9, 10, 11, 12 |
| HXT2 | DNA S. cerevisiae | 120 | 9, 10 |
| GAL2 | DNA S. cerevisiae | 121 | 12 |
| HXT3-6 | DNA S. cerevisiae | 122 | 15 |
| Hxt11p | Protein, S. Cerevisiae | 123 | 7, 8, 9, 10, 11, 12 |
| Hxt2p | Protein, S. Cerevisiae | 124 | 9 |
| Gal2p | Protein, S. Cerevisiae | 125 | 10 |
| Hxt36p | Protein, S. Cerevisiae | 126 | 15 |

TABLE 13

Strains used or prepared herein

| Strain | Genotype | Example |
|---|---|---|
| RN1001 | Mat a, ura3-52, leu2-112, gre3::loxP, loxP-Ptpi:TAL1, loxP-Ptpi::RKI1, loxP-Ptpi-TKL1, loxP-Ptpi-RPE1, delta::Padh1XKS1Tcyc1-LEU2, delta::URA3-Ptpi-xylA-Tcyc1 | 10 |
| RN1014 | RN1001 + in vivo engineering on xylose and acetic acid | Reference |
| RN1041 | RN1001 his3::loxP | WO2013081456 |
| RN1041-empty | RN1041, pRS313-P7T7 (empty vector control) | 8, 11 |
| RN1053 | RN1041 hxt2::loxP-kanMX-loxP, hxt367::loxP-hphMX-loxP, hxt145::loxP-natMX-loxP, gal2::loxP-zeoMX-loxP | 6, 7 |
| RN1053-X2 | RN1053 single colony selected on YPX after chemostat evolutionary engineering on 2% xylose | 6, 7 |
| RN1053-X2-hxt11Δ | RN1053-X2, hxt11::HIS3 | 7 |
| RN1053-empty | RN1053, pRS313-P7T7 (empty vector control) | 8, 9, 10, 15 |
| RN1053-HXT2 | RN1053, pRS313-P7T7-HXT2 | 9 |
| RN1053-HXT3-6 | RN1053, pRS13-P7T7-HXT3-6 | 15 |
| RN1053-mHXT3-6(N367I) | RN1053, pRS13-P7T7-mHXT3-6(N367I) | 15 |
| RN1053-HXT11 | RN1053, pRS13-P7T7-HXT11 | 8, 9, 10, 11, 13 |
| RN1053-mHXT11-N366D | RN1053, pRS313-P7T7-mHXT11(N366D) | 13 |
| RN1053-iHXT11 | RN1053-pRS313-P7T7-iHXT11 | 7 |
| RN1053-HXT11-GFP | RN1053, pRS313-P7T7-HXT11-GFP | 10 |
| RN1053-HXT12 | RN1053, pRS13-P7T7-HXT12 | 8 |
| YD01227 (ori) | RN1014 glk1::lox72; hxk1::loxP; hxk2::lox72; gal1::loxP; his3::loxPnatMXlox P | 14 |
| YD01227-evoA, -B, and -C | YD01227, three single colonies selected on plates with 1% xylose + 10% glucose after chemostat evolutionary engineering runs (see Example 14) | 14 |
| YD01227-empty | YD01227, pRS313-P7T7 (empty vector control) | 13 |
| YD01227-HXT2 | YD01227, pDB1162 (pRS313-P7T7-HXT2) | 12 |
| YD01227-GAL2 | YD01227, pDB1250 (pRS313-P7TA-GAL2) | 12 |
| YD01227-HXT11 | YD01227, pDB1152 (pRS313-P7T7-HXT11) | 12, 13 |
| YD01227-mHXT11(N366D) | YD01227, pRS313-P7T7-mHXT11(N366D) | 13 |

Analytical Methods.

Cell growth was monitored by optical density (OD) at 600 nm using UV-visible spectrophotometer (Novaspec PLUS). The concentrations of glucose, xylose, ethanol were measured in supernatant of cultures (separated from cell pellet after centrifugation at 4000 rpm for 5 min) by High Performance Liquid Chromatography (Shimadzu, Kyoto, Japan) using an Aminex HPX-87H column (Bio-Rad) and a refractive index detector (Shimadzu, Kyoto, Japan). The temperature of the column and detector was maintained at 65° C. The mobile phase was 0.005 N H2SO4 at a flow rate of 0.55 ml/min.

Sugar Uptake Measurement.

The uptake of radio-labeled xylose was measured as follows: the cells were grown for 24 hours in shake flasks in Verduyn-urea supplemented with 2% xylose and 0.05% maltose and were collected by centrifugation (3,000 rpm, 3 min, 20° C.), washed and re-suspended in Verduyn-urea. [14C] xylose or [14C] glucose (CAMPRO scientific, Veenendaal, the Netherlands stocks were added to the cell suspension. The reaction was stopped, for xylose after 1 minute and for glucose after 15 seconds, by addition of 5 ml of 0.1M lithium chloride, and the cell suspension was filtered (0.45 µm HV membrane filter, Millipore, France). The filters were washed with another 5 ml of lithium chloride and counted with Liquid Scintillation Counter in the emulsifier scintillator plus (Perkin-Elmer, USA). Uptake experiments for YD01227-ori and YD01227-evo were done with 0.5, 2, 6, 20, 40 mM xylose or 0.1, 0.4, 1.5, 6, 20, 80 mM glucose. Glucose competition studies for RN1053-HXT3-6 and RN1053-mHXT3-6(N367I), RN1053-HXT11 and RN1053-mHXT11 (N366D) were performed with [14C] xylose stock and with unlabeled glucose. The final xylose and glucose concentrations were 50 mM and 50-500 mM, respectively.

Fluorescence Microscopy.

Plasmid pRS313-P7T7-HXT11-GFP (SEQ ID NO 57) was transformed into strain RN1053 and RN1041. Fresh colonies were inoculated into minimal medium with xylose or glucose. A fresh liquid cell culture taken in exponential growth phase (at an optical density of 10 at 600 nm) was subjected to fluorescence microscopy under a Nikon Eclipse-Ti microscope equipped with a 100× oil immersion objective, a filter set for GFP, and a Nikon DS-5Mc cooled camera. We routinely examined at least 100 cells per sample, and each experiment was replicated at least three times.

Automated Transformation and Colony Picking.

For the generation of transformation of a saturation mutagenesis library into YD01227, shake-flask cultures were performed in either YPM for RN1053, or YPX for YD01227 (see below). Yeast cells were pelleted and, subsequently, used in an automated transformation protocol based on Gietz, R. D. and Woods, R. A. (Gietz, R. D. and Woods, R. A. 2006, Yeast transformation by the LiAc/SS Carrier DNA/PEG method. Methods Mol. Biol., 313:107-120). Transformation mixtures were plated on selection medium consisting of yeast nitrogen base (Sigma-Aldrich; 6.7 g l$^{-1}$), agar (BD Biosciences; 15 g l$^{-1}$), supplemented with either 2% maltose (RN1053 transformations) or 3% xylose (YD01227 transformations). Transformation plates were incubated at 30° C., and after colony formation, colonies were re-plated using an automated process transferring colonies to 96 well microtiter plates (MTP) containing the above-referred selection media. MTPs with transformants were incubated at 30° C. until clear growth was observed.

NMR Analysis.

For the quantification of glucose, xylose, glycerol, acetic acid and ethanol in the sample, 100 µl sample is transferred accurately into a suitable vial. Subsequently 100 µl internal standard solution, containing maleic acid (20 g/l), EDTA (40 g/l) and trace amounts of DSS (4,4-dimethyl-4-silapentane-1-sulfonic acid) in D$_2$O, and 450 µL D$_2$O is added.
1D $^1$H NMR spectra are recorded on a Bruker Avance III 700 MHz, equipped with a cryo-probe, using a pulse program with water suppression (power corresponding to 3 Hz) at a temperature of 27° C.

The analyte concentrations are calculated based on the following signals (δ relative to DSS):
α-glucose peak at 5.22 ppm (d, 0.38 H, J=4 Hz),
α-xylose peak at 5.18 ppm (d, 0.37 H, J=4 Hz),
glycerol peak at 3.55 ppm (dd, 2H, $J_{1,2}$=6 Hz and 0.1 $J_{1a,1b}$=12 Hz)
acetic acid peak at 1.91 ppm (s, 3H)
ethanol peak at 1.17 ppm (t, 3H, J=7 Hz)
The signal user for the standard:
Maleic acid peak at 6.05 ppm (s, 2H)

Example 6

Elevated Expression of S. Cerevisiae Hxt11 in Evolved Xylose Transport-Negative Strain with Restored Ability to Grow on Xylose RN1053 Chemostat Culture.

Uptake of xylose in Saccharomyces cerevisiae is facilitated by a distinct subgroup of hexose transporters (Hamacher et al, 2002, Characterization of the xylose-transporting properties of yeast hexose transporters and their influence on xylose utilization. Microbiology, 148: 2783-2788). We have constructed a deletion mutant with xylose-fermenting capabilities (RN1053) which lacks the major hexose transporters HXT1-HXT7 and GAL2. As a result of the deletions, RN1053 is not able to utilize xylose (as described in Example 1). Saccharomyces cerevisiae possesses more HXT genes than the eight major ones (HXT8-17) of which not much is known rather than their expression is low or negligible (Sedlak & Ho, 2004, Characterization of the effectiveness of hexose transporters for transporting xylose during glucose and xylose co-fermentation by a recombinant Saccharomyces yeast. Yeast, 21, pp. 671-684) or that they have been connected to physiological roles other than sugar transport (Nourani et al 1997 Multiple-drug-resistance phenomenon in the yeast Saccharomyces cerevisiae: involvement of two hexose transporters. Mol Cell Biol, 17: 5453-5460). Therefore we refer to them as the cryptic HXT genes. An attempt was made to select for possible spontaneous mutations in cryptic HXT loci resulting in improved expression or possibly improved affinity for xylose. In order to do so, strain RN1053 was grown in an anaerobic, xylose-limited chemostat culture at a dilution rate of 0.05 h-1. The evolved strains by chemostat cultivation, RN1053-X2, was isolated on 2% xylose plate. A single colony was selected for cultivation in aerobic shake-flask on Verduyn-urea-his supplemented with 2% xylose for 96 h for comparison to the original RN1053 strain. The growth curves of RN1053-X2 and RN1053 strain were represented in FIG. 12A. The evolved strain RN1053-X2 was able to grow on 2% xylose, whereas the original strain RN1053 did not grow on the xylose medium. A reason could be that one or more of the cryptic HXT-genes (HXT8-HXT17) was up-regulated on xylose medium during the chemostat culture facilitating the uptake of xylose.

Expression Profiling Evolved RN1053-X2.

The expression patterns of HXT8-HXT17 in the evolved strain RN1053-X2 and original strain RN1053 were compared during batch cultivations on 2% xylose medium. The transcription level of HXT11 and HXT12 were dramatically increased by up to 8-fold in the evolved strain RN1053-X2 from the beginning of exponential phase (FIG. 12B) and reached a maximum level at day 3, compared to original strain RN1053. The chemostat was effective for the evolution of mutants to enhance xylose consumption by expressing HXT11 and/or HXT12 transporter genes in strain RN1053. However, expression level of other HXT-genes (i.e. HXT8-HXT10, and HXT13-HXT17) were repressed on xylose medium, compared to wild-type of RN1053.

The first limiting step of xylose metabolism is its transport across the plasma membrane (Kahar P, Taku K, Tanaka S, 2011. Enhancement of xylose uptake in 2-deoxyglucose tolerant mutant of *Saccharomyces cerevisiae*. J. Biosci. Bioeng. 111:557-63). It was reported that expression of HXT transporter genes of *S. cerevisiae* was regulated in response to different levels of extracellular glucose (Ozcan & Johnston, 1999. Function and regulation of yeast hexose transporters. Microbiol. Mol. Biol. Rev. 63:554-569). Possibly, mutations in the promoters or regulatory genes are the basis of enhanced expression of the cryptic HXT genes in the RN1053-X2 strain evolved in the chemostat culture on xylose.

Example 7

Knocking Out/Down Hxt11 in Evolved Rn1053 Abolishes Newly Acquired Ability to Grow on Xylose Knockout and silencing of HXT11 in the strain RN1053-X2. For the deletion construct of HXT11, $P_{HIS3}$-HIS3-$T_{HIS3}$ expression cassette was amplified from the plasmid template pRS313-P7T7 (SEQ ID NO 117) using oligonucleotides KOP11 (SEQ ID NO 98) and KOT11 (SEQ ID NO 99) consisting of HXT11 flanking sequences for integration at HXT11 locus and HIS3 sequence to amplify the expression cassette.

In order to determine whether Hxt11p was responsible for the spontaneous growth on xylose, we deleted HXT11 in the evolved strain RN1053-X2 by succession of one-step gene deletion complementing for the HIS3 marker upon deletion of HXT11. HXT11 mRNA levels decreased considerably after knockout construct was introduced (FIG. 13a). When HXT11 was disrupted in the strain RN1053-X2, the strain lost its newly acquired ability to grow on xylose medium (FIG. 13b). In addition, the HXT11 expression level of knockout strains decreased to 60%. Most probably, still HXT11 levels were measured since also expressed HXT12 transcripts in the RN1053-X2 strain are about 98% homologous to HXT11 (FIG. 13a).

Antisense RNA technique is very useful for the repression of translation of a target protein by scavenging target mRNA in microorganisms. Translation repression can be promoted by antisense sequences that hybridize to messenger RNA. The antisense mechanism involves ribosome interference, in which the ribosome cannot bind to the nucleotides of the mRNA (Park et al 2001. Antisense-mediated inhibition of arginase [CAR1] gene expression in *Saccharomyces cerevisiae*. J. Biosci. Bioeng. 92:481-484). This method is more convenient for inhibiting gene expression than the gene disruption method. For expression of inverse HXT11 (iHXT11), iHXT11 was amplified using primers iHXT11F (SEQ ID NO: 100) and iHXT11R (SEQ ID NO: 101) and cloned as BamHI-XbaI fragment inversely between the truncated HXT7 promoter and HXT7 terminator in the pRS313-P7T7 vector (FIG. 13c; SEQ ID NO: 117). The construct was introduced into RN1053-X2 to express antisense HXT11 RNA which hinders the translation of HXT11 mRNA into protein. The iHXT11 was overexpressed in the strain RN1053-X2, and the strain lost its ability to grow on xylose medium (FIG. 13d).

These knock-out/knock-down experiments clearly indicate that the evolved strain RN1053-X2 started to consume xylose due to the increase in HXT11 expression and the probable functional expression of Hxt11p on the yeast membrane.

Example 8

Overexpressing Hxt11 in Rn1053 Restores Growth on Xylose

Over-Expression HXT11 and HXT12 in RN1053.

To determine whether strains expressing HXT11 or HXT12 are capable of growth on xylose, both HXT-genes were expressed individually in the original RN1053 strain which is incapable to grow on xylose because of the deletion of the eight major hexose transporters (HXT1-HXT7 and GAL2). For these experiments RN1041-empty, RN1053-empty, RN1053-HXT11 and RN1053-HXT12 were used (see Table 13). RN1053-HXT11 and RN1053 HXT12 were constructed in the following manner: the open-reading frames for the HXT11 and HXT12 genes were PCR-amplified from cDNA of the wild-type RN1053 using primers HXT11F (SEQ ID NO: 102), HXT12F (SEQ ID NO: 103) and HXT11/12R (SEQ ID NO: 104); PCR fragments were sequenced and were found 100% homologous to the respective CEN.PK113-7D gene sequences (*Saccharomyces* Genome Database, www.yeastgenome.org; HXT11 sequence SEQ ID NO; 119); the PCR fragments were cut using restriction enzymes XbaI and BamHI and cloned in yeast expression vector pRS313-P7T7 (SEQ ID NO: 117; FIG. 13C; Table 12). The HXT11 and HXT12 expression construct of the transporters were transformed into RN1053 using a standard yeast genetic technique according to the Gietz method (Gietz and Woods 2006, Yeast transformation by the LiAc/SS Carrier DNA/PEG method. Methods Mol. Biol 313 pp. 107-120). Transformants isolated from single colonies resulted in strains RN1053-HXT11 and RN1053-HXT12. Both strains were inoculated into maltose medium, followed by cultures in shake flask on liquid media containing 2% xylose and/or 2% glucose. Only RN1053-HXT11 and RN1041 displayed clear growth within 48 hours, whereas RN1053-empty and RN1053-HXT12 displayed hardly any growth in this period (FIG. 14a). The growth of RN1053-HXT11 started earlier and displayed faster growth than that of reference strain RN1041-empty (with wild-type HXT background) in xylose medium (FIG. 14b). However, the introduction of HXT12 sequence in RN1053 did not allow growth on xylose medium. In the *Saccharomyces* genome database reference strain S288C, HXT12 is considered a pseudogene because of a frame shift mutation (www.yeastgenome.org; ORFs YIL170W and YIL171W).

This experiment showed clearly that the spontaneous growth on xylose of RN1053-X2 was caused by higher expression of HXT11 and that HXT11 is an efficient xylose transporter, if expressed.

Example 9

Hxt11p Facilitates Xylose Transport with Intrinsic Higher Level of Xylose Specificity than Hxt2p Xylose Uptake by Hxt11p.

Figure 15:
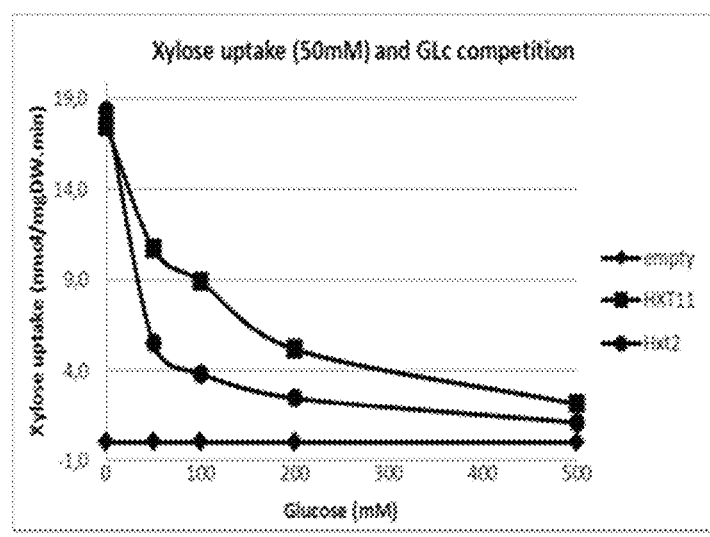
FIG. 15 shows xylose uptake studies on RN1053-HXT11 (HXT11), RN1053-HXT2 (Hxt2), RN1053-empty (empty) with or without increasing concentrations of competing glucose (0-500 mM).

To determine whether HXT11 is capable of xylose transport in the absence and presence of glucose, uptake studies using radiolabeled 14C-xylose were performed. For these experiments the strains RN1053-empty, RN1053-HXT11 and RN1053-HXT2 were used (see Table 13). HXT2 is known for its xylose transport capabilities (Saloheimo et al, 2007, Xylose transport studies with xylose-utilizing *Saccharomyces cerevisiae* strains expressing heterologous and homologous permeases. Appl Microbiol Biotechnol. 74:1041-1052; Sedlak and Ho, 2004, Characterization of the effectiveness of hexose transporters for transporting xylose during glucose and xylose co-fermentation by a recombinant *Saccharomyces* yeast. Yeast, 21:671-684). Construction of RN1053-HXT11 was described in the previous example. RN1053-HXT2 was constructed in the following manner: HXT2 (SEQ ID NO: 120) was PCR-amplified from RN1001 genome (Table 12) using primers F HXT2 XbaI (SEQ ID NO:107) and R HXT2 Cfr9I (SEQ ID NO: 108). Resulting PCR fragment was sequence-verified and cloned into pRS313-P7-T7 (SEQ ID NO: 117) as XbaI-Cfr9I fragment. RN1053 was transformed with resulting construct pRS313-P7T7-HXT2 (see Table 12) generating a transformant derived from a single colony named strain RN1053-HXT2 (Table 13). To determine if Hxt11p increased xylose uptake in the strain RN1053, xylose uptake was measured using $^{14}C$ in the cells expressing the transporters. In the presence of glucose, strains expressing HXT11 accumulated up to 50% more xylose compared to strains expressing HXT2 in the presence of glucose (FIG. 15). In addition, xylose uptake of RN1053-HXT11 was increased up to 4.5-fold, compared to RN1053-HXT2 (FIG. 15). These experiments show that Hxt11p is capable of transporting xylose across the yeast plasma membrane. Even more, Hxt11p harnesses an intrinsic higher specificity towards xylose that could not be easily competed by glucose as compared to previously identified xylose transporters within the yeast genome such as Hxt2p.

Example 10

Hxt11p is Functionally Expressed in the Yeast Plasma Membrane

Functional Expression of HXT11 in RN1053.

Detection of the Hxt11p by immunoblot analysis will not completely demonstrate the functional expression of the protein. For functional expression of a hexose transporter protein, it must reside in the plasma membrane. In order to monitor the expression and targeting of Hxt11p, a chimeric Hxt11p-GFP protein was engineered and examined by fluorometry and fluorescence microscopy. For these studies RN1053-HXT11-GFP, RN1041-HXT11-GFP, RN1053-HXT11 and RN1053-empty were used (Table 13). For the construction of the HXT11-GFP expressing strains, RN1053 and RN1041 were transformed with the expression vector bearing this chimeric Hxt11-GFP protein (pRS313-P7T7-HXT11-GFP; SEQ ID NO: 118; Table 12). The Hxt11p+GFP fusion protein is a functional hexose transporter: it restored growth on 2% xylose to the strain RN1053 (FIG. 16a). In addition, Hxt11p+GFP fluorescence of RN1053-HXT11-GFP and RN1041-HXT11-GFP was localized to the plasma membrane on xylose or glucose medium (FIG. 16b). These experiments show that Hxt11p-GFP is functional as xylose transporter and that Hxt11p is expressed functionally in the plasma membrane.

Example 11

HXT11 Expression in Rn1053 Facilitates Faster Co-Fermentation of Glucose and Xylose in Industrially Relevant Concentrations Fermentation Profile of RN1053-HXT11 in Glucose-Xylose Mixtures.

To determine the fermentation behavior on a glucose-xylose mixture of a strain functionally expressing HXT11 in a HXT deletion background (hxt1-7, gal2) in comparison to a strain expressing the wild-type HXT landscape, fermentations were conducted on Verduyn-urea supplemented with industrially relevant glucose-xylose concentrations (80 and 40 g $l^{-1}$ respectively). For these fermentations RN1053-HXT11 and RN1041-empty were used (see Table 13).

As shown in FIG. 17a, xylose of RN1041 was not co-fermented with glucose; whereas the degree of glucose-xylose co-fermentation was enhanced in strain RN1053-HXT11 as shown in FIG. 17b. Furthermore, xylose fermentation was completely exhausted in HXT11-RN1053, whereas 10 g/L of xylose was still remaining in RN1041 at 40 h; in addition, the xylose consumption of RN1053-HXT11 was dramatically increased at 2% residual glucose, and ethanol concentration was increased from 63.92 g/L to 72.33 g/L at the end of the fermentation (FIG. 17ab).

This example shows that a strain in which the major hexose transporters are deleted but expressing HXT11 displays faster xylose utilization than a strain with a wild-type hexose transporter background without HXT11.

Example 12

Wild-Type Hxt11 Expression Supports Growth on Xylose in Glucose Transport Counter-Activity Screen Aim.

Using the Glucose Transport Activity Counter (GTAC)-screen, i.e. transforming hexokinase-mutant strain YD01227 as host to introduce transporters and screening the resulting transformants on medium for growth on and consumption of xylose in the presence of a 5 times higher amount of glucose, xylose transporters can be identified that exhibit an improved ability to transport xylose in the presence of a surplus of glucose (i.e. a higher affinity for xylose than for glucose; a reduction or more preferably full removal of glucose transport capability, while keeping xylose transport capability at least at the same level).

Transformation and Colony Picking.

YD01227 was transformed with constructs bearing wild-type GAL2 (pDB1250, EPA-29355), HXT2 (pDB1162; see Example 9 for construction plasmid) and HXT11 (pRS313-P7T7-HXT11, see for construction Example 8) constructs. For each transformation, 3 colonies, when available, were re-plated using automated colony picking to YNB+3% xylose agar medium MTPs and grown at 30° C. until visible colony growth was visible in the agar puncture.

Pre-Culture and Screen.

For pre-culture, transformants were transferred by automated process from selection agar medium MTPs to 96 well half-deepwell plates (96HDWP) containing liquid selection medium consisting of mineral medium (according to Verduyn, with urea as nitrogen source) supplemented with 3% xylose. The 96 well HDWPs were incubated for 3 days (pre-culture) in an orbital shaker at 30° C. and 750 rpm. Subsequently, for each sample, 20 µl of culture was transferred to 24 well deepwell plates (24 DWPs) containing 2.5 ml Verduyn-urea supplemented with the sugar mixture glucose:xylose in a ratio 5:1 with the following concentrations: 10 g $l^{-1}$ glucose and 2 g $l^{-1}$ xylose (YD10-medium). For each of the three sampling points a series of 24 well DWPs was inoculated. On each 24DWP, one RN1001 growth control was inoculated to have an indication of plate variation effects between different 24DWPs. After 24 hours, 72 hours and 96 hours automatic sampling, transfer to 96HDWP was conducted for automated OD-measurement at 600 nm wavelength. After the last OD measurement after 96 hours, cells were pelleted after centrifugation and 100 µl supernatant was collected for flow-NMR analysis of residual sugars and ethanol formation in the medium, after incubation (see above for method description).

Results.

Whereas RN1001 displayed growth from 24 hours onward (FIG. 18a) and complete consumption of both glucose and xylose (FIG. 18b, 18c), YD01227 transformants expressing GAL2, HXT2 and HXT11 constructs did not consume glucose (FIG. 18c) due to the deletion of hexo- and glucokinase activities. The latter strains also displayed diverse growth profiles (FIG. 18a) over time and diverse residual xylose concentrations representing their individual ability to consume xylose (FIG. 18b) in the presence of glucose. YD01227 expressing the HXT11 construct (YD01227-HXT11) displayed clear growth at 72 hours (FIG. 18a) and substantial xylose consumption with 4.83±1.26 g $l^{-1}$ (n=3) xylose residing in the medium after 96 hours from the 22.7±0.12 g $l^{-1}$ (n=43) present in the medium at the beginning of the experiment; YD01227-GAL2 and YD01227-HXT2 displayed hardly any growth and not much xylose was consumed in comparison to YD01227-HXT11, with respectively 18.34±0.39 and 21.29±0.32 g $l^{-1}$ xylose residing in the medium after 96 hours of incubation (FIG. 18b).

This example shows that HXT11 supports considerable biomass formation and xylose consumption in the presence of glucose indicating that HXT11 expression in the hexokinase mutant YD01227 enables a more xylose-specific component in the sugar transport than exerted by GAL2 or HXT2 expression, both proven xylose transporters in the *S. cerevisiae* transportome (Saloheimo et al, 2007, Xylose transport studies with xylose-utilizing *Saccharomyces cerevisiae* strains expressing heterologous and homologous permeases. Appl Microbiol Biotechnol., 74:1041-1052; Sedlak and Ho, 2004, Characterization of the effectiveness of hexose transporters for transporting xylose during glucose and xylose co-fermentation by a recombinant *Saccharomyces* yeast. Yeast 21:671-684; Hamacher et al, 2002, Characterization of the xylose-transporting properties of yeast hexose transporters and their influence on xylose utilization. Microbiology, 148:2783-2788).

Example 13

Improved Hxt11 Mutant Obtained from Hxt11 Error Prone Library Screened in YD01227

To improve xylose uptake in the presence of glucose, error-prone PCR was conducted to generate a HXT11 mutant library encoding variants of Hxt11p which were screened for competitive xylose transport in the presence of glucose in the YD01227 strain (see Table 3 herein). The concentration of Mn2+ in the PCR reaction mixture was 0.15 mM, and it was added following the standard error-prone PCR protocol (Cirino, P. C et al. 2003. Generating mutant libraries using error-prone PCR. Methods Mol. Biol., 231, pp. 3-9) using primers HXT11F (SEQ ID NO: 41), and HXT11/12R (SEQ ID NO: 43). The library was cloned into pRS313-P7T7 as XbaI-BamHI fragments. Strain YD01227 was transformed with the HXT11-library and three thousand transformants were screened on Verduyn-urea medium supplemented with a 1:15 ratio of xylose (1%) and glucose (15%) in 96-well plate format using Synergy MX (BioTek Instruments, Inc, USA). From these 3000 mutants, eight mutants were obtained out-performing wild-type Hxt11p on screening medium. A representative clone was shown in FIG. 19a. The plasmids were isolated from YD01227 by using protocol according to Chowdhury (Chowdhury, K. 1991. One step 'miniprep' method for the isolation of plasmid DNA. Nucl. Acids Res 19, pp. 2792), and re-sequenced. All eight mutants were found to carry a plasmid bearing mutant sequences which translated into a protein containing the same mutation in Hxt11 (wild-type amino acid sequence Hxt11p SEQ ID NO: 62) leading to amino acid change at position 366 Asn (N) into Asp (D). In shake flask experiments the N366D mutant (YD01227-mHXT11 [N366D]; see Table 13) also displayed faster growth in the screening medium compared to YD01227-HXT11, as shown in FIG. 19a. pRS313-P7T7-mHXT11(N366D) construct was re-transformed to RN1053 resulting in RN1053-mHXT11(N366D). The RN1053 expressing HXT11-N366D mutant was not affected with respect to xylose utilization on 2% xylose medium, compared to RN1053 expressing the wild-type HXT11 gene, since similar growth curves were observed (FIG. 19b).

Sugar Uptake of Strain RN1053 with Hxt11 and N366D Mutant.

Xylose and glucose transport kinetics were determined in the xylose utilizing *S. cerevisiae* strain RN1053 expressing the transporters Hxt11 and mHxt11p-(N366D). The measured xylose transport rate was plotted against glucose or xylose concentration. The affinity for glucose of RN1053-mHXT11(N366D) was strongly decreased up to 2-fold compared to RN1053-HXT11, whereas the affinity for xylose of RN1053-mHXT11(N366D) was also slightly decreased up to 1.2-fold, compared to RN1053-HXT11 (FIGS. 19c, 19d). In addition, in the presence of increasing concentrations of glucose strains expressing the N366D mutant accumulated up to 75% more xylose compared to strains expressing Hxt11 (FIG. 19e).

Fermentation of Xylose in the Presence of Glucose.

Fermentation experiments of sugar mixtures were performed comparing RN1053-mHXT11(N366D) to RN1053-HXT11 and RN1041-empty.

In a first experiment on Verduyn-urea supplemented with 100 g/L of glucose and 60 g/L of xylose, as shown in FIGS. 19f, 19g, 19h, and 19i glucose utilization, biomass formation (OD600), and ethanol production of RN1053-mHXT11 (N366D) were delayed during the fermentation, compared to RN1041 and RN1053-HXT11. It seems that glucose consumption by RN1053-mHXT11(N366D) was strongly decreased at early exponential phase compared to RN1053-HXT11 (FIG. 19g). In addition, xylose consumption of RN1053-mHXT11(N366D) was not decreased (FIG. 19h) although the cell density of RN1053-mHXT11(N366D) was lower than that of RN1041, and RN1053-HXT11 (FIG. 19f).

In a second fermentation experiment on Verduyn-urea supplemented with lower sugar concentrations (80 g $l^{-1}$ of glucose and 40 g l$^{-1}$ of xylose) comparing RN1053-mHXT11(N366D) to RN1053-HXT11, a clear difference in sugar consumption profile was observed (FIGS. 19$j$, 19$k$, 19$l$). Whereas the glucose consumption profile displayed a faster glucose consumption rate during the phase that the glucose is declining rapidly (between 0 and 35 hours; $q_{gluc(RN1053-HXT11)}$ 2.22 g/l/h vs. g/l/h vs. $q_{gluc(RN1053-mHXT11[N366D])}$) 2.04 g/l/h/, 8.5% decline in $q_{gluc}$), whereas the xylose consumption rate has greatly increased during that same time window ($q_{xyl(RN1053-HXT11)}$ of 0.23 g/l/h vs. $q_{xyl(RN1053-mHXT11[N366D])}$ of 0.38 g/l/h, 65% incline in $q_{xyl}$). During the phase that mainly xylose was fermented (35-73 hrs) the xylose consumption rates were almost identical ($q_{xyl(RN1053-HXT11)}$ of 0.36 g/l/h vs. $q_{xyl(RN1053-mHXT11[N366D])}$ of 0.37 g/l/h). The maximal xylose consumption rate was higher and reached earlier in the fermentation for RN1053-mHXT11(N366D) (0.65 g/l/h at 23 hrs) than for RN1053-HXT11 (0.50 g/l/h at 35 hrs). At the end of the fermentation run (period of 72 hrs typical for industrial fermentations) the RN1053-HXT11 consumed 51% of the xylose whereas RN1053-mHXT11(N366D) consumed 63%. The ethanol titers measured at the end of the fermentation were 4.4% higher for the RN1053 expressing the N366D mutant than for RN1053 expressing wild-type HXT11. Considering that the input of sugars into the fermentation was almost identical, one could imagine that higher yields were obtained from this glucose-xylose mixture with sugar concentrations typical for industrially relevant batch fermentations, and more specifically higher yields from the xylose fraction.

These fermentation experiments indicate that compared to its wild-type reference sequence the presence of a xylose-specific transporter variant engineered from S. cerevisiae hexose transporter HXT11 on the membrane increases the xylose consumption rate during the glucose phase, where the glucose consumption rate declined somewhat, and that in the end higher ethanol yields were obtained on a typical glucose-xylose mixture typical for relevant industrially relevant hydrolysates.

Example 14

Evolved Hexokinase Mutant Consumes Xylose in Presence of Glucose

Evolutionary Engineering of Strain YD01227.

For the evolutionary engineering, strain YD01227 was used for evolutionary engineering on glucose-xylose mixtures to evolve for xylose assimilation in the presence of glucose aiming at isolating spontaneous mutants in hexose transport or the regulation of the expression and/or activity of hexose transport.

Figure 20:
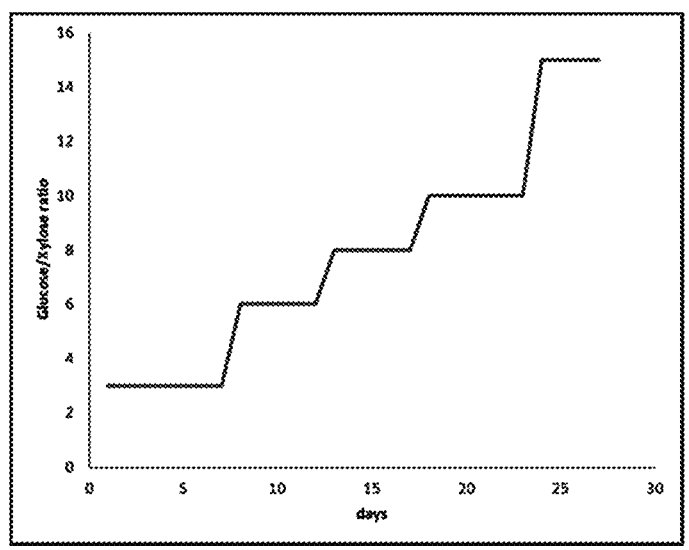
FIG. 20 shows the scheme for the glucose/xylose ratio in the Verduyn-urea-his medium during chemostat cultivation (days) of YD01227.

YD01227 was inoculated for 16 hours in shake flask with Verduyn-urea-his supplemented with 2% xylose. At the start of the evolutionary engineering, YD01227 was diluted to an OD600 of 0.2 and DO setpoint at 5% in Verduyn-urea-his containing 1% xylose, 3% glucose. Carbondioxide outflow was monitored. At various time points samples were taken for analysis of glucose and xylose concentrations. It was determined whether strain YD01227 was growing solely on xylose or on both glucose and xylose. The glucose to xylose ratio, at the start of the evolutionary engineering, was kept to low to a ratio (glucose 3%, xylose 1%), which still allowed YD01227 growth at the beginning of the experiment. However, this was at significantly lower growth rates if compared to growth on only 1% xylose. In this setup the strain consumes the xylose which leads to higher glucose: xylose ratios and, therefore, a drop in growth rate. When the $CO_2$ production dropped, additional xylose (5 ml of 50% xylose to 500 ml fermentor volume) was added to maintain growth. At an OD600 of 20, which was reached on average after 5-6 days, the culture was diluted into fresh Verduyn-urea-his in a higher glucose to xylose ratio, if growth rates had significantly improved in the previous cycle. In total, in a time frame of 27 days, the strain was serial diluted 5 times in 1% Xyl/3% Glc (1:3), 1.5% Xyl/9% Glc (1:6), 1% Xyl/8% Glc (1:8), 1% Xyl/10% Glc (1:10) and 0.57% Xyl/10% Glc (1:15), respectively. Before inoculation in 1% xylose and 8% glucose the setpoint for DO was lowered into 0% (anaerobic growth) in order to maintain a lower growth rate. In FIG. 20 the scheme for the glucose/xylose ratio in the Verduyn-urea-his medium during chemostat cultivation (days) of YD01227 is given. After 27 days samples were taken of the evolved YD01227 strain and plated 1% xylose and 10% glucose with the original YD01227 as negative control. Whereas the original YD01227 showed only small colonies the colonies of the evolved YD01227 strain were 10-15 times larger.

Xylose Growth and Xylose Uptake with/without Glucose Competition.

Figure 21:
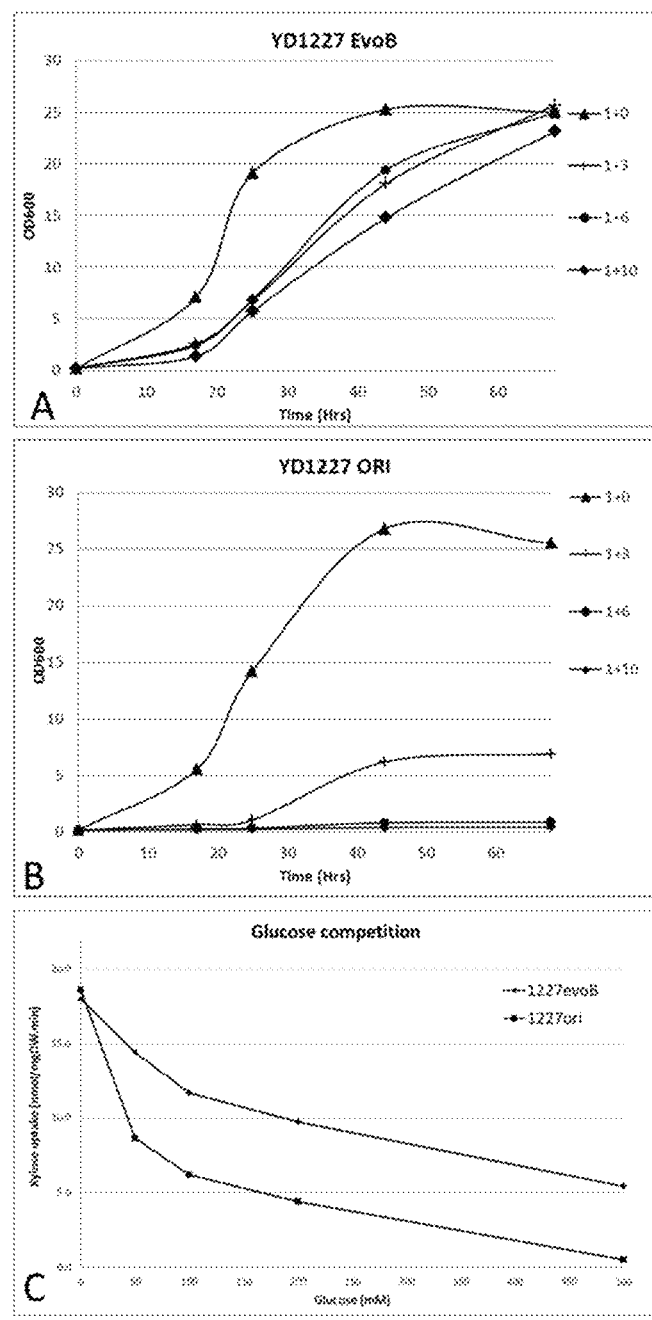
FIG. 21 shows growth profiles of shake flask cultures on Verduyn-urea-his supplemented with 1% xylose without (closed triangles; 1+0) or with (3% glucose, stripe, 1+3; 6% glucose, closed circles, 1+6; 10% glucose, closed diamonds, 1+10) increasing glucose concentrations with YD01227-evo (A) and YD01227-ori (B). (C)$^{14}$C-xylose uptake study of YD01227-ori (1227-ori, closed squares) or YD01227-evo (1227-evo, closed diamonds) with or without increasing glucose concentrations (0-500 mM).

After re-streaking the evolved YD01227 strain on a 1% xylose and 10% glucose plate, three colonies (EvoA, EvoB and EvoC) were analyzed for growth in shake flasks on 1% xylose in the presence of respectively 0%, 3%, 6% and 10% glucose. YD01227 EvoB had the highest growth rate on xylose at 6% en 10% glucose and was compared with the original YD01227 strain (FIG. 21$a$, 21$b$). In the original YD01227 strain (YD01227 ORI in FIG. 21$b$) the growth rate is already partly inhibited at 3% glucose and completely inhibited at 6% and 10% glucose however the YD01227 EvoB strain shows only minor inhibition in growth rate at all glucose concentrations and this seems unrelated to the amount of glucose added (FIG. 21$a$). The same two strains were used in a $^{14}C$ xylose (50 mM) uptake experiment in which the xylose uptake is inhibited by glucose (FIG. 21$c$). The uptake of xylose without the addition of glucose in both strains is the same however as soon as glucose was added to both strains the uptake of xylose in the YD01227 EvoB strain was not as inhibited as the uptake in the original YD01227 strain. In a 1:10 ratio the xylose uptake in the original YD01227 strain is completely abolished whereas in the YD01227 EvoB strain still 5 nmol/mgDW·min is taken up.

Example 15

Single Nucleotide Polymorphism in Hxt3-6 Chimera Allows for Xylose Consumption in the Presence of Glucose in Evolved Hexokinase Mutant Expression of the HXTs in the Evolved YD01227 Strain.

Figure 22:
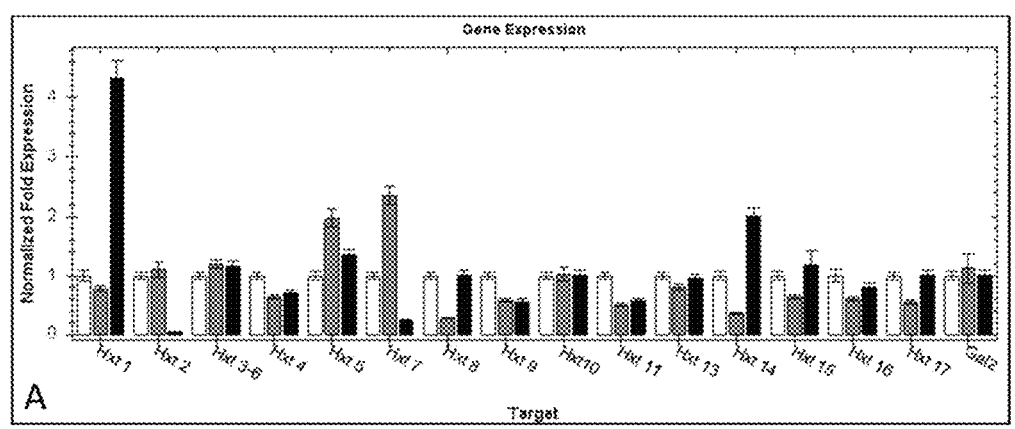
FIG. 22 shows (A) mRNA expression profile of YD01227-ori (white bars), YD01227-evoB on Verduyn-urea-his supplemented with a sugar mixture in a ratio xylose:glucose 1:3 (gray bars) and 1:10 (black bars). Data were expressed as normalized expression (relative to ACT1 and relative to YD01227-ori, which was set to 1).

The expression levels of HXT1-17 and GAL2 in the evolved YD01227 EvoB and original YD01227 strains were compared during batch cultivations on Verduyn-urea-his containing 1% xylose and 3% glucose (FIG. 22$a$). Primers (SEQ ID NO: 2-37) were used in the real time PCR characterization of the expression of HXTs in YD01227 and evolved derivative. Furthermore, the expression levels in the YD01227 EvoB strain were also analyzed on Verduyn-urea-his containing 1% xylose and 10% glucose. The absolute C(t) values (data not shown) show that the HXT1-7 genes are the only HXT genes that are intermediately or highly expressed of which the HXT3-6 chimera (specific deletion in strain lineage intragenic and intergenic HXT3 and HXT6 sequences resulting in one HXT36 chimeric sequence) has the highest expression levels. None of the analyzed sugar transporters is up-regulated in the YD01227 EvoB strain compared to the original YD01227 strain. The up-regulation seen in the HXT1 gene in YD01227 EvoB 1% xylose and 10% glucose is caused by the high glucose concentration in this sample which is quite well known (Ozcan & Johnston, 1995, Three different regulatory mechanisms enable yeast hexose transporter (HXT) genes to be induced by different levels of glucose. Mol Cell Biol 15, pp. 1564-1572). This high glucose concentration also leads to the down-regulation of HXT2 and HXT7 in YD01227 EvoB. Both the up-regulation in HXT1 and down-regulation of HXT2 and HXT7, are described in literature (Boles & Hollenberger 1997, Kinetic characterization of individual hexose transporters of *Saccharomyces cerevisiae* and their relation to the triggering mechanisms of glucose repression, FEMS Microbiol Rev 21, pp. 85-111).

Sequencing of the Highly Expressed HXT Genes.

HXT1-7 were amplified from cDNA which was isolated from the YD01227 EvoB culture on 1% xylose and 3% glucose using the primers SEQ ID NO: 49-60. The PCR products from these genes were sequenced. No mutations were revealed in HXT1, HXT2 and HXT4, one silent mutation in HXT5 and HXT7 and a mutation leading to amino acid change at position 367 (Asn into Ile; N367I) in chimera HXT3-6. Somewhere in the YD01227 strain lineage a deletion occurred between the neighboring loci of HXT3 and HXT6 in which intragenic and intergenic sequences were deleted (part of 3' part of HXT3 ORF, HXT3 terminator, HXT6 promoter, HXT6 ORF) resulting in one HXT36 chimeric sequence which is in frame and can be expressed as mRNA and translated into functional protein. The translated chimeric protein Hxt3-6p of which the first 438 amino acids are identical to the CEN.PK Hxt3p amino acid sequence, whereas the 130 amino acids towards the C-terminus are identical to Hxt6p in CEN.PK. Genomic rearrangements in the HXT3-6-7 locus have been documented in the past, e.g. HXT6/7 chimeric sequences resulting from chemostat cultures on low glucose concentrations, and are proposed to be caused by homologous recombination due to the highly homologous stretches of sequences in this cluster of hexose transporters (Brown et al 1998. Multiple duplications of yeast hexose transport genes in response to selection in a glucose-limited environment. Mol Biol Evol 15:931-942). The N367I point mutation is located in trans membrane domain (TMD) 8 which is known to contain residues responsible for the affinity for glucose (Kasahara & Kasahara, 2003. Transmembrane segments 1, 5, 7 and 8 are required for high-affinity glucose transport by *S. cerevisiae* Hxt2 transporter. Biochem J. 372:247-252, reconfirmed by this patent application).

Examples 16-18

Methods

Methods not mentioned in the section of Examples 16 and 17 were already described in section Examples 6-15. Oligonucleotides used in the studies described in Example 16 and 17 are depicted in Table 14. The saturated mutagenesis of position N367 in HXT36 was done using PCR with Phusion® High-Fidelity PCR Master Mix with HF buffer using primer pairs F HXT36 BcuI (SEQ ID NO 127)/R HXT36 367NNN (SEQ ID NO 128) and F HXT36 367NNN (SEQ ID NO 129)/R HXT36 BamHI (SEQ ID NO 130). The fragments of 1119 and 623 base pairs were subsequently used in an overlap PCR using the outside primers F HXT36 BcuI and R HXT36 BamHI and cloned into pRS313P7T7 using BcuI and BamHI. Sequencing of 48 *E. coli* clones yielded N367S (tcc), N367P (ccc), N367G (ggg), N367Y (tac), N367A (gcc), N367H (cac), N367R (agg), N367F (ttt), N367E (gag), and N367V (gtg). The remaining 8 amino acids at position 367 were amplified and cloned with overlap PCR using specific primers in which the NNN was replaced by tta (L), tgt (C), tgg (W), atg (M), act (T), aag (K), gat (D) and cag (Q).

The carboxyl-terminal GFP fusions with HXT36 and HXT36-N367I mutant were made by amplification of the corresponding genes with the Phusion® High-Fidelity PCR Master Mix (HF buffer) using primers F HXT36 BcuI (SEQ ID NO 127) and R HXT36 BamHI-stop (SEQ ID NO 131). The GFP gene itself was amplified with F GFP BamHI (SEQ ID NO 132) and R GFP C/al (SEQ ID NO 133). HXT36 and HXT36-N367I were digested with the restriction enzymes BcuI and BamHI and GFP was digested with BamHI and ClaI. The HXT36 genes were separately ligated in a two-fragment ligation together with GFP into pRS313-P7T7 which was cut with BcuI and ClaI.

For the fermentations of Example 18, strains were grown, in duplo, in 50 ml Schott bottles filled to the rim with 68 ml fermentation medium containing 0.5% D-glucose and 0.5% D-xylose and kept completely closed at 30° C. in a water bath. Stirring speed, with a magnet stirrer, was 200 rpm and the strains were inoculated at a starting OD600 of approximately 8.0. At regular intervals samples were taken for OD600 measurements and HPLC analysis.

TABLE 14

Oligonucleotides used in cloning and sequencing.

| SEQ ID NO | Name | Sequence (5'→3') |
|---|---|---|
| 127 | F HXT36 Bcui | GCATACTAGTATGAATTCAACTCCAGATTTAATATCC |
| 128 | R HXT36 367NNN | CAACAAGTAGAGAAGAAnnnGACGACACCG |
| 129 | F HXT36 367NNN | CGGTGTCGTCnnnTTCTTCTCTACTTGTTG |
| 130 | R HXT36 BamHi | ACGTGGATCCTTATTTGGTGCTGAACATTCTCTTGT |
| 131 | R HXT36 BamHI-stop | CCATGGATCCTTTGGTGCTGAACATTCTCTTGTAC |
| 132 | F GFP BamHI | AAAGGATCCATGGTGAGCAAGGGCGAGGAGC |
| 133 | R GFP ClaI | AAAATCGATTTACTTGTACAGCTCGTCC |

Example 16

Decrease in $V_{max}$ (of Hxt3-6 N367I is not the Result of Decreased Expression of Mutant as Shown by Gfp-Tagging Studies To ensure that this lower $V_{max}$ is not due to a decrease in expression, chimers were made in which GFP was fused to the C-terminus of the HXT36 and the HXT36-N367I mutant. Both fusions were transformed to the RN1053 strain, and fluorescence imaging revealed that the proteins are uniformly distributed over the plasma membrane (FIGS.

Figure 23:
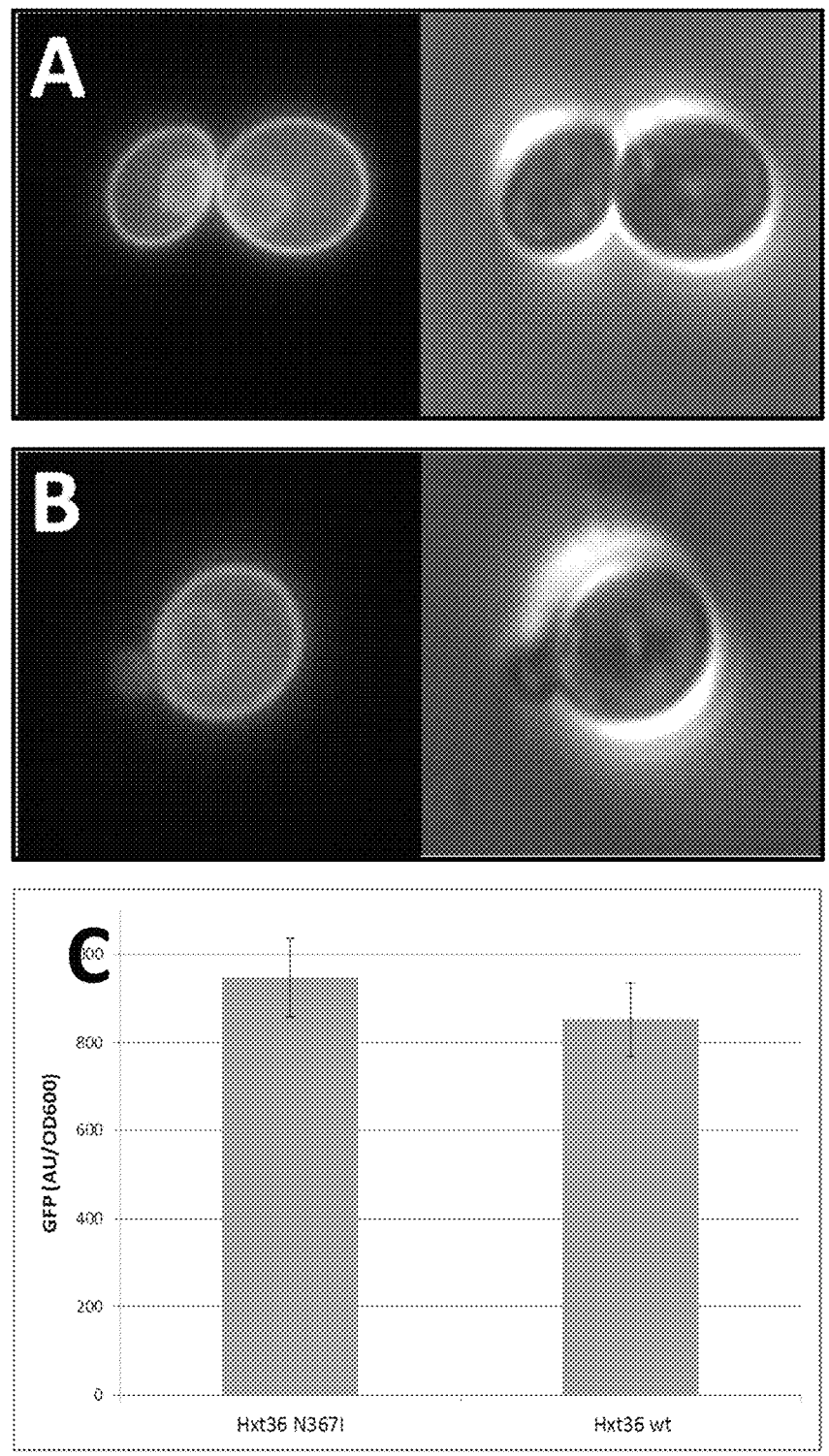
FIG. 23 Fluorescence images of strain RN1053 expressing GFP fusion proteins of Hxt36 (A) and Hxt36-N367I (B). Images were analyzed on a Nikon Eclipse-Ti microscope. (C) Total amount of GFP fluorescence (in AU/OD600) in both strains.

23A and 23B). Since the same levels of GFP were recorded, Hxt36p and Hxt36p-N367I are expressed to similar extents. (FIG. 23C).

Example 17

Figure 24:
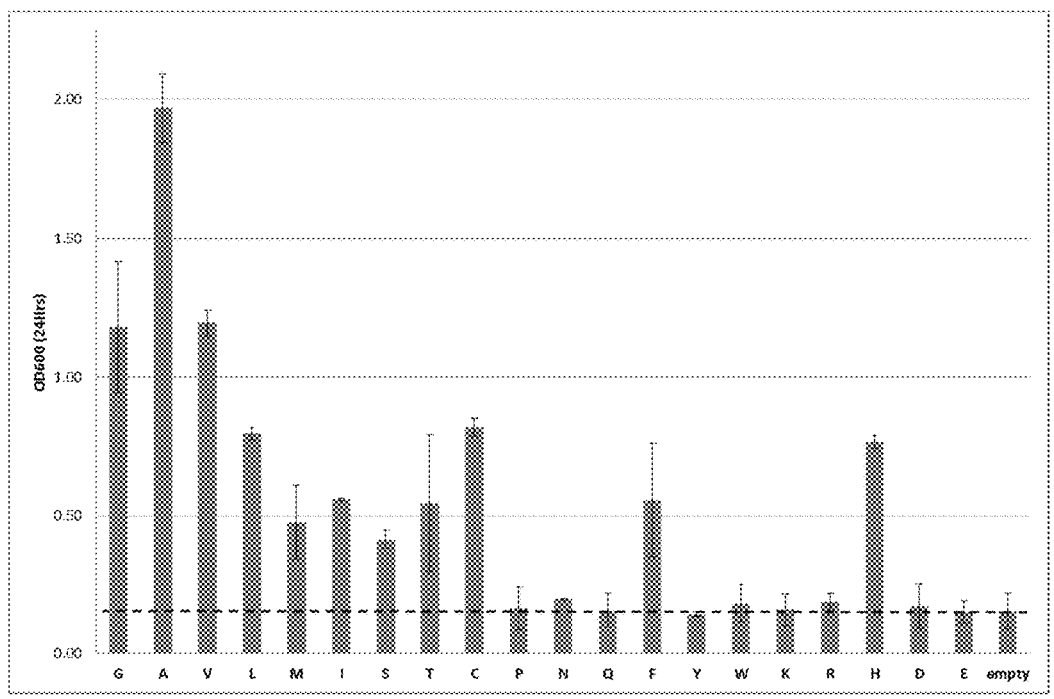
FIG. 24 Growth of the YD01227 strain containing vectors expressing HXT36 transporters with all possible amino acid substitutions at position 367. Cells were grown on 1% xylose and 10% xylose, and YD01227 transformed with the empty vector pRS313-P7T7 was used as a control.

Saturation Mutagenesis on Position Asparagin-367 in Hxt3-6 Chimera for the Exploration of the Sequence Space Reveals Alanine as Potent Residue in Enhanced Transporter with Enhanced Xylose Transport Capacity To explore the sequence space of position N367 (corresponding to position N376 in SEQ ID NO: 59), all amino acid substitutions were individually introduced into the HXT36 gene. The individual HXT36-N367X mutants were transformed to the YD01227 hexokinase deletion strain and tested for growth on minimal medium containing 1% D-xylose and 10% D-glucose. The transformant bearing the original HXT36-N367I mutant showed an $OD_{600}$ of 0.56 after 24 hrs whereas the HXT36 wild-type was unable to grow under these conditions (FIG. 24). The fastest growing transformant beared the Hxt36p N367A mutant, which reached an $OD_{600}$ of almost 2. Also the transformants expressing the HXT36 mutants the other nonpolar aliphatic amino acid substitutions (glycine, valine, leucine and methionine) where able to grow on D-xylose in the presence of 10% D-glucose. On the other hand, the phenylalanine and histidine mutants showed a reduced growth rate whereas strong polar and charged amino acid substitutions did not support growth (FIG. 24). These data show that the N367 (corresponding to N376 in Gal2p and N366 in Hxt11p) is a critical residue in determining the specificity of Hxt36p for glucose versus xylose.

Figure 25:
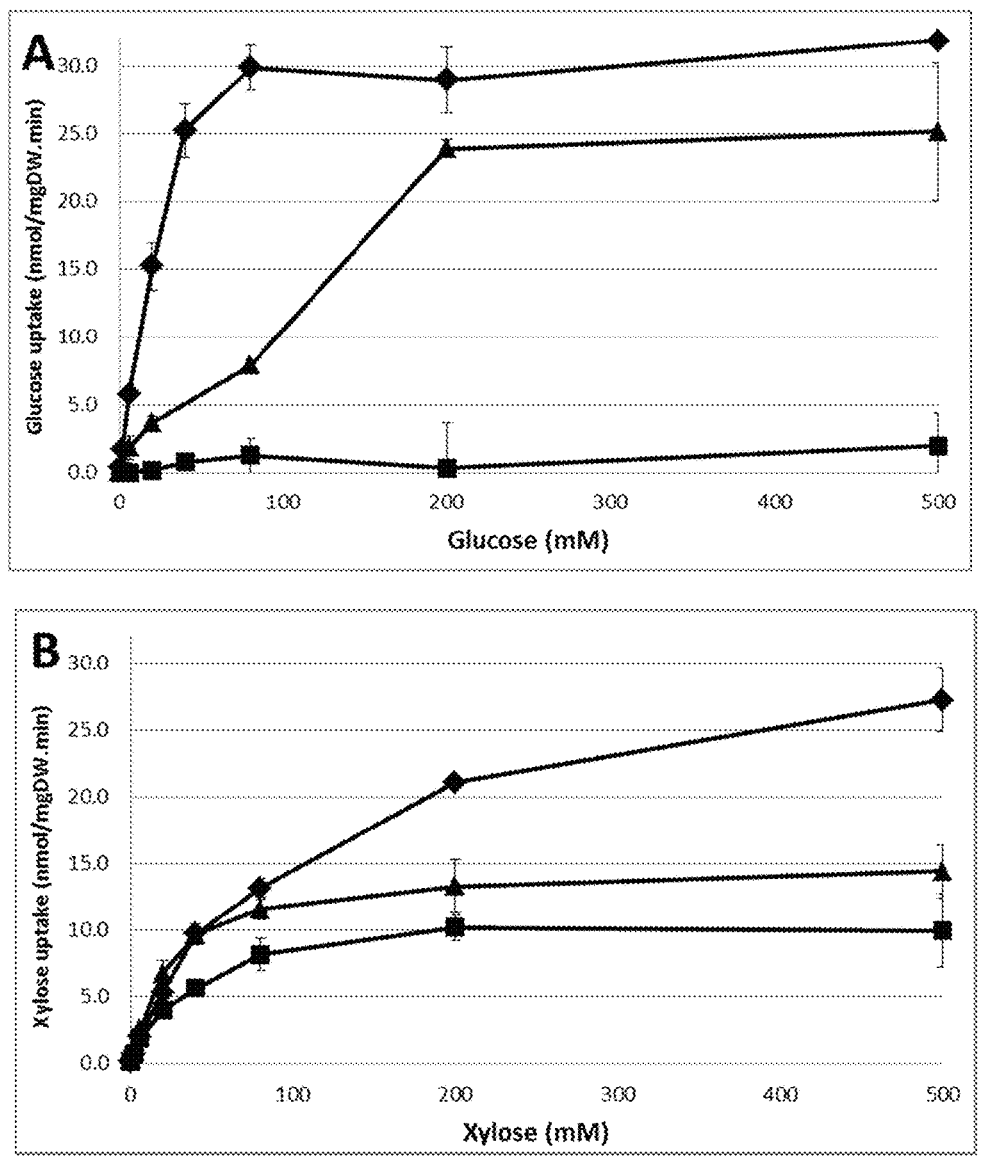
FIG. 25 Uptake experiments to determine the $K_m$ and $V_{max}$ for glucose (panel A) and xylose (panel B). Uptake was measured in nmol/mgDW·min in the RN1053-HXT36 strain (diamonds), the RN1053-HXT36-N367I strain (squares) and in the RN1053-HXT36-N367A strain (triangles). The uptake levels of the RN1053-empty strain were, for both sugars, subtracted from the RN1053-HXT36, RN1053-HXT36-N367I and RN1053-HXT36-N367A strains.

The Hxt36p N367A and N367I mutants were analyzed further to determine their transporter kinetics. Herein, the transporters were expressed in strain RN1053 that is equipped with a low background glucose transport activity. The $K_m$ and $V_{max}$ for D-glucose uptake by HXT36 was about 6 mM and 32 nmol/mgDW·min, respectively (Table 15 and FIG. 25). Remarkably, the Hxt36p N367I mutant was completely defective in D-glucose uptake, while the affinity for D-xylose uptake was improved 2.7-fold (i.e., from 108 to 40 mM) compared to Hxt36p (Table 15). The mutation, however, also caused a near to 3-fold decrease in the $V_{max}$ for D-xylose uptake.

Also the transport activity of the Hxt36p-N367A mutant was examined which showed the fastest growth on D-xylose. This transporter still showed some glucose uptake although with a very poor $K_m$ (171 mM versus 6 mM). Compared to the N367I mutant, the N367A mutation caused both an improvement of the $K_m$ and $V_{max}$ values for D-xylose uptake to 25 mM and 15.3 nmol/mgDW·min, respectively.

Example 18

Figure 26:
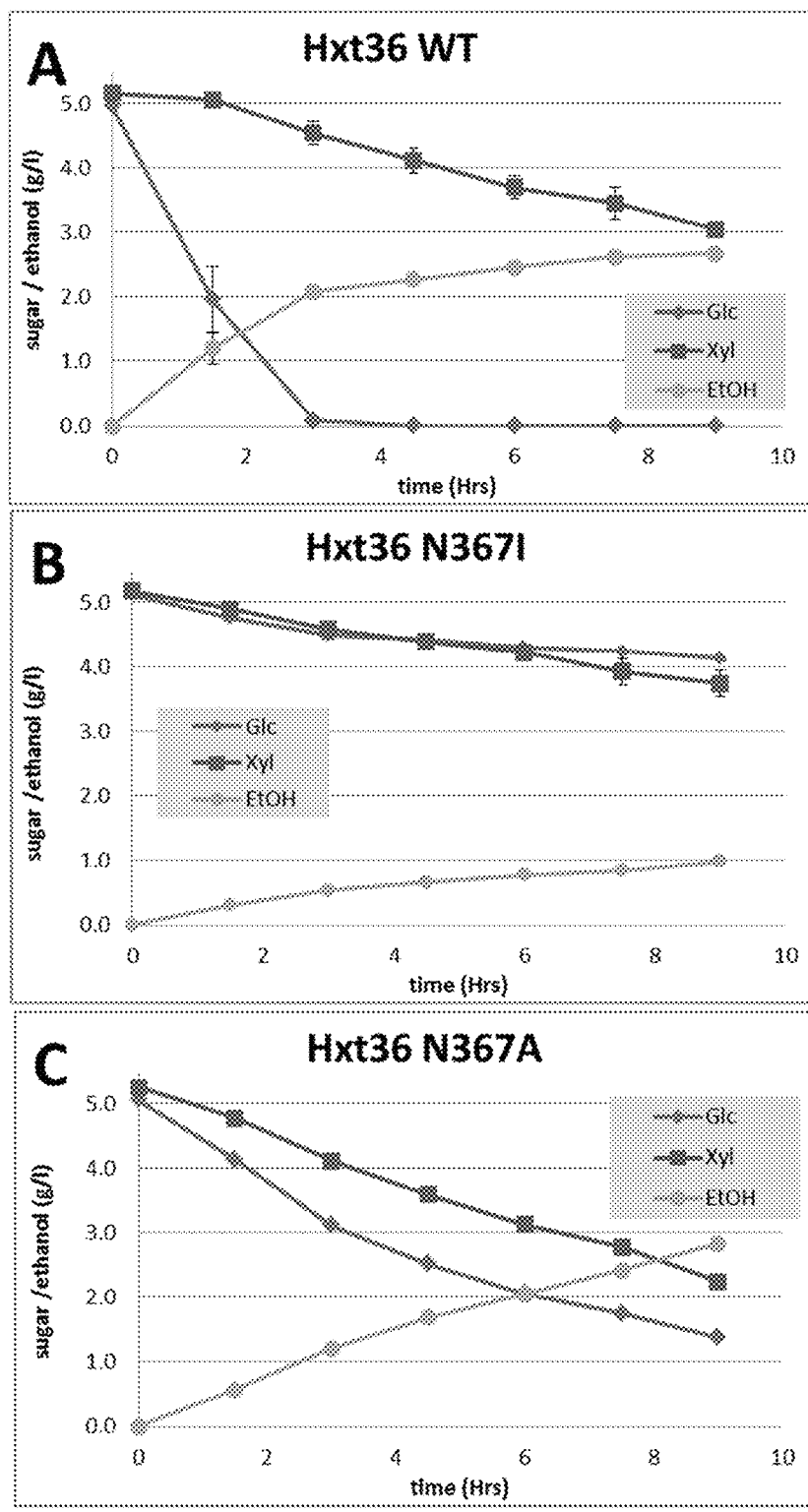
FIG. 26 Growth of the RN1053 strain expressing HXT36 (A), HXT36-N367I (B) and HXT36-N367A (C) on 5 g L$^{-1}$ D-glucose and 5 g l$^{-1}$ D-xylose. The residual D-glucose (diamonds), D-xylose (squares) and ethanol (circles) were measured in g/l.

Co-Fermentation of D-Glucose and D-Xylose by an Engineered S. Cerevisiae Strain with Altered Transport Characteristics In order to investigate co-fermentation of D-glucose and D-xylose, the RN1053 strain harboring the wild-type Hxt36, Hxt36-N367I and Hxt36p-N367A, were grown on 5 g $L^{-1}$ D-glucose/5 g $L^{-1}$ D-xylose at a higher industrially relevant starting $OD_{600}$ of approximately 8.0. Sugar consumption and ethanol concentrations were followed through time (FIG. 26). The strain containing the Hxt36-N367I transporter grows on D-xylose but because of the severe D-glucose uptake defect (FIG. 26B), it only shows some background level of D-glucose consumption that is similar to that of the original RN1053 strain without any re-introduced transporter (data not shown). The strain harboring the Hxt36-N367A mutant showed an improved D-glucose and D-xylose co-consumption (FIG. 26C) as compared to the strain containing the Hxt36 wild-type transporter (FIG. 26A). Moreover, also the total sugar consumption increased because of the co-consumption of glucose and xylose by the Hxt36p-N367A-expressing RN1053 yielding a higher ethanol concentration (2.83 g $L^{-1}$) than wild-type Hxt36p-expressing RN1053 (2.67 g $L^{-1}$) after 9 hours of fermentation.

TABLE 15

$K_m$ and $V_{max}$ values for D-glucose and D-xylose uptake by Hxt36p transporters expressed in strain RN1053.

| | $K_m$ (mM) | | $V_{max}$ (nmol/mgDW · min) | |
|---|---|---|---|---|
| | Glucose | Xylose | Glucose | Xylose |
| HXT36 | 6.13 ± 0.02 | 107.9 ± 12.1 | 31.7 ± 0.07 | 32.9 ± 3.1 |
| HXT36-N367I | —[a] | 39.8 ± 5.6 | —[a] | 12.1 ± 1.63 |
| HXT36-N367A | 170.7 ± 37.8 | 24.9 ± 3.4 | 37.2 ± 4.4 | 15.3 ± 0.2 |

[a]Could not be determined

Examples 19 and 20

Material and Methods

Methods not mentioned in the section of Examples 19 and 20 were already described in sections of Examples 6-18. Oligonucleotides used in the studies described in Example 19 and 20 are depicted in Table 16.

Mutagenesis of N366X.

The saturated mutagenesis of position N366 in HXT11 was done using PCR with Phusion® High-Fidelity PCR Master Mix with HF buffer using primer pairs F HXT11 XbaI/R HXT11 366NNN and F HXT11 366NNN/R HXT11 BamHI (see Table 16). The fragments of 1113 and 591 base pairs were subsequently used in an overlap PCR using the outside primers F HXT11 XbaI and R HXT11 BamHI and cloned into pRS313P7T7 using XbaI and BamHI. Sequencing of 48 E. coli clones yielded N367S (tct), N367P (cca), N367G (ggt), N367A (gcc), N367H (cac), N367R (cgc), N367L (ttg), N367C (tgt), N367T (acg), N367D (gat), N367Q (caa), and N367V (gtg). The remaining 6 amino acids at position 366 were amplified and cloned as mentioned above with overlap PCR using specific primers in which the NNN was replaced by ttt (F), gag (E), tgg (W), atg (M), aaa (K), and N367Y (tat).

Using the generated HXT11 variant sequences generated by the saturation mutagenesis PCR, HXT11-N366x-GFP-fusion constructs to study cellular localization of HXT11 variants were prepared similarly (with oligonucleotides, restriction sites and pRS313-P7T7-GFP backbone vector) as described in the methods for Example 10 (p. 96).

Fermentation Experiments.

Yeast cultures were pre-cultured in mineral medium containing 2% maltose. Cells at mid-exponential phase were harvested and inoculated after washing twice with sterilized water. Fermentation experiments were performed using 100 ml of mineral medium containing 7% glucose and 4% xylose in 120 ml bottle at 30° C. with an initial OD600 of 5 under oxygen limited conditions. Stirring speed, with a magnetic stirrer, was 200 rpm. All of the bottle fermentation experiments were repeated independently.

TABLE 16

Primers used for saturation mutagenesis of S. cerevisiae HXT11.

| Name | SEQ ID NO | Sequence (5'→3') |
|---|---|---|
| F HXT11 XbaI | 134 | GGCCTCTAGAATGTCAGGTGTTAATAATACATCCGC |
| R HXT11 Bam HI | 135 | CGATGGATCCTCAGCTGGAAAAGAACCTCTTGTAAATTG |
| F HXT11 366NNN | 136 | CGGTGTGGTTnnnTTTTTCTCTTCATTC |
| R HXT11 366NNN | 137 | GAATGAAGAGAAAAAnnnAACCACACCG |
| F HXT11 N366F | 138 | CGGTGTGGTTtttTTTTTCTCTTCATTC |
| R HXT11 N366F | 139 | GAATGAAGAGAAAAAaaaAACCACACCG |
| F HXT11 N366E | 140 | CGGTGTGGTTgagTTTTTCTCTTCATTC |
| R HXT11 N366E | 141 | GAATGAAGAGAAAAActcAACCACACCG |
| F HXT11 N366K | 142 | CGGTGTGGTTaaaTTTTTCTCTTCATTC |
| R HXT11 N366K | 143 | GAATGAAGAGAAAAAtttAACCACACCG |
| F HXT11 N366M | 144 | CGGTGTGGTTatgTTTTTCTCTTCATTC |
| R HXT11 N366M | 145 | GAATGAAGAGAAAAAcatAACCACACCG |
| F HXT11 N366W | 146 | CGGTGTGGTTtggTTTTTCTCTTCATTC |
| R HXT11 N366W | 147 | GAATGAAGAGAAAAAccaAACCACACCG |
| F HXT11 N366Y | 148 | CGGTGTGGTTtatTTTTTCTCTTCATTC |
| R HXT11 N366Y | 149 | GAATGAAGAGAAAAAataAACCACACCG | n is any nucleotide

Example 19

Figure 27:
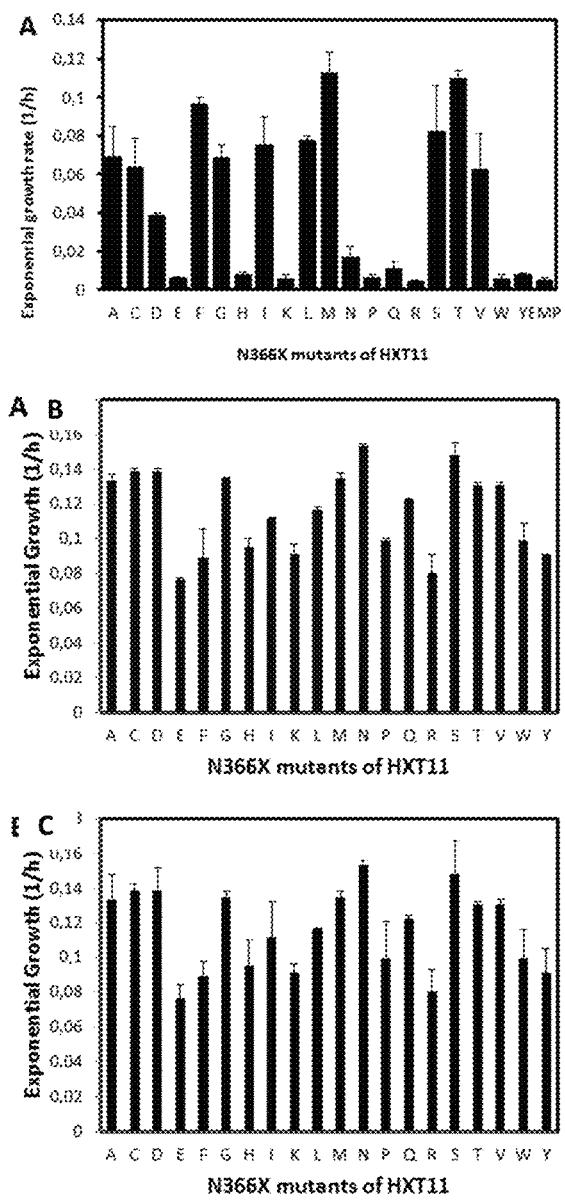
FIG. 27 Characterization of xylose specificity of HXT11-N366X mutants. (A) Maximal Exponential growth rate (1/h) of HXT11-N366X mutants in the strain YD01227. Maximal exponential growth rate (1/h) for N366X mutants expressed in RN1053 on glucose (B) or xylose (C).
Figure 28:
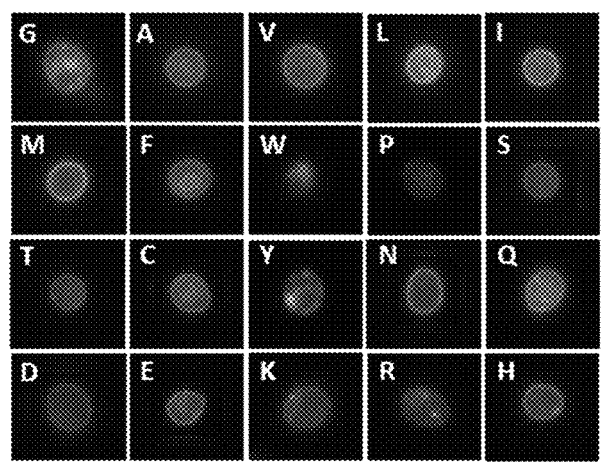
FIG. 28 Fluorescence images of strain RN1053 expressing GFP fusion proteins of HXT11 N366X mutants grown on 2% maltose. Letters in left upper hand of picture depict the amino acid on position 366 of the respective Hxt11 variant.

N366 Mutations in Hxt11 Improve Xylose Utilization in the Presence of Glucose The N366D mutation in Hxt11 improved xylose uptake in the presence of glucose because of a reduction in the glucose transport affinity. In order to assess the importance of this position, N366 was replaced with each of the other 19 amino acids to generate a series of N366X mutants. The corresponding genes were expressed in strain YD01227 and evaluated for their ability to utilize 1% xylose in the presence of 10 glucose using 96-well plates. Here, 10% glucose was used instead of 15% to increase the sensitivity of the assay in order to discriminate between the performance of the various mutants. Growth rates on xylose in the presence of a 10-fold excess glucose was improved when N366 was substituted by a methionine (M) or threonine (T) residue (FIG. 27A), and was up to 3-fold higher than the N366D substitution. Amino acids with a positive charged or bulky hydrophobic side chain did not support growth on xylose under the screening condition. The mutants were also tested for growth on glucose and expressed in strain RN1053. The N366M and N366T Hxt11 mutants showed similar growth on glucose or as compared to the wild-type Hxt11 (FIGS. 27B and 27C). In addition, the expression level of all individual mutants was determined using GFP-tagged Hxt11 proteins (FIG. 28). All of the Hxt11-GFP proteins were highly expressed on membrane, except that with the GFP-tagged N366W and N366Y Hxt11 proteins, a cytosolic and likely vacuolar localization seems apparent. This suggests protein-misfolding and faulty targeting to the membrane by these mutants explaining the low activity in the growth experiments with xylose and glucose. However, the wild-type and N366M and N366T Hxt11 mutant protein localized to the plasma membrane. Overall, these data indicate that N366 is a critical residue in determining the specificity of Hxt11 for xylose versus glucose.

The xylose and glucose transport kinetics via Hxt11 and the N366T and N366M Hxt11 mutants were determined for the genes expressed in the xylose utilizing S. cerevisiae strain RN1053. Compared to the wild-type Hxt11, the affinity for glucose transport by N366T and N366M Hxt11 was reduced up to 5 and 4-fold, respectively. In contrast, the affinity for xylose by these mutants was improved by up to 2-fold (Table 17) relative to Hxt11. The $V_{max}$ for glucose uptake by the N366T Hxt11 mutant was increased by about 40% as compared to wild-type Hxt11, while the $V_{max}$ was unchanged for the N366M Hxt11 protein. Importantly, the $V_{max}$ for xylose of the mutants remained largely unchanged compared to Hxt11.

TABLE 17

$K_m$ and $V_{max}$ values for D-glucose and D-xylose uptake by Hxt11 transporters expressed in strain RN1053.

| | $K_m$ (mM) | | $V_{max}$ (nmol/mg DW · min) | |
|---|---|---|---|---|
| | Glucose | Xylose | Glucose | Xylose |
| Hxt11 | 33.4 ± 2.1 | 84.2 ± 10.0 | 82.3 ± 3.8 | 44.5 ± 1.7 |
| Hxt11-N366D | 87.0 ± 6.4 | 106.7 ± 21.7 | 98.9 ± 5.7 | 45.5 ± 1.0 |
| Hxt11-N366T | 194.4 ± 47.9 | 46.7 ± 2.7 | 125.6 ± 3.7 | 40.1 ± 2.4 |
| Hxt11-N366M | 144.9 ± 36.0 | 50.1 ± 9.7 | 75.3 ± 8.6 | 34.2 ± 3.4 |
| Hxt2 | n.d. | 51.2 ± 0.1 | n.d. | 12.5 ± 0.2 | n.d., not determined

Example 20

Figure 29:
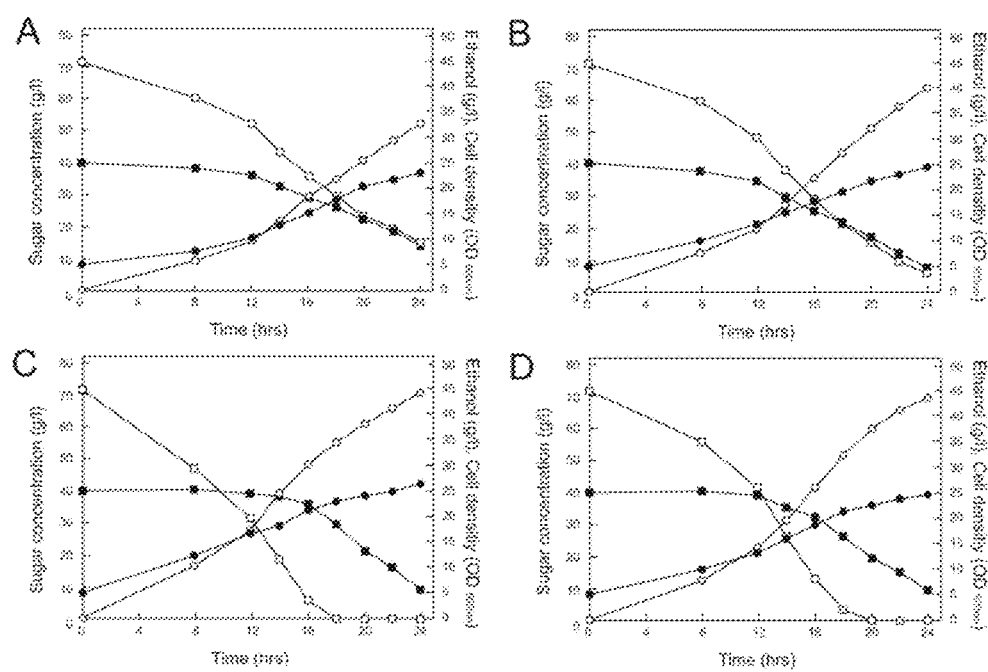
FIG. 29 Fermentations on Verduyn-urea supplemented with xylose (40 g L$^{-1}$) and glucose (71.8 g L$^{-1}$) of (A) RN1053 HXT11-N366M, (B) RN1053 HXT11-N366T, (C) RN1001 and (D) RN1053 HXT11-N366N. Symbols: glucose (♦), xylose (■), ethanol (▲), cell density (●). (A), (B), (C) and (D) are the panels of FIG. 29.

Co-Fermentation of D-Glucose and D-Xylose by Engineered S. Cerevisiae Strains Expressing Hxt11 Variants Because of the marked effects of the N366 mutations in Hxt11 on glucose transport without interfering with xylose transport, the mutants were further examined for their ability to co-metabolize xylose and glucose under industrial conditions, i.e., 7% glucose and 4% xylose, respectively. Herein, the mutants were expressed in strain RN1053, and growth was compared to the Hxt11 wild-type and strain RN1001 containing a full complement of endogenous transporters. The two mutants supported a near to perfect co-consumption of glucose and xylose (FIGS. 29A and 29B) in contrast to the RN1001 strain (FIG. 29C) and RN1053 wild-type Hxt11 (FIG. 29D) and that showed delayed consumption of xylose. These data demonstrate that the mutagenesis of the N366 position of Hxt11 yields mutants that mediate a balanced uptake of glucose and xylose thereby supporting co-consumption of the hexose and pentose sugars. Best results were obtained for mutant N366T HXT11.

Co-Consumption

Co-consumption of a cell is herein quantified and expressed as co-consumption index. The co-consumption index was herein the co-consumption index for glucose and xylose and was calculated as the sum over the time interval of 0-24 hours (it was measured at 0, 8, 12, 14, 16, 18, 20, 22 and 24 hours) of the absolute difference of the glucose uptake rate (Qg) and the xylose uptake rate (Qx), expressed as grams of sugar consumed per time unit. The fermentation was an anaerobic batch culture fermentation at 1.0 g/l dry yeast pitch, 30 degrees C. temperature and wherein the fermentation medium contains 71.8 grams of glucose per liter and 40.0 grams xylose per liter, at the start of the fermentation. A low value for co-consumption index indicates high co-consumption, a high value less co-consumption.

These fermentation data and calculations for the strains RN1001, RN1053 HXT11, RN1053 HXT11 (N366M) and RN1053 HXT11 (N366T) are given in table 18.

TABLE 18

Fermentation data and calculation of co-consumption index for the the strains RN1001, RN1053 HXT11, RN1053 HXT11 (N366M) and RN1053 HXT11 (N366T)

| Time | Average Glucose | Xylose | Qg (g/h) | Qx (g/h) | abs(Qg − Qx) | sum(abs(Qg − Qx)) | corr(glucose, xylose) |
|---|---|---|---|---|---|---|---|
| DS68616 | | | | | | | |
| 0 | 71.8 | 39.9 | | | | | |
| 8 | 46.9 | 39.8 | 3.12 | 0.02 | 3.10 | 29.1 | 0.69 |
| 12 | 31.0 | 38.7 | 3.97 | 0.27 | 3.70 | | |
| 14 | 18.4 | 37.8 | 6.31 | 0.46 | 5.85 | | |
| 16 | 5.42 | 35.9 | 6.47 | 0.94 | 5.53 | | |
| 18 | 0 | 29.1 | 2.71 | 3.39 | 0.68 | | |
| 20 | 0 | 20.7 | 0 | 4.25 | 4.25 | | |
| 22 | 0 | 15.4 | 0 | 2.632 | 2.63 | | |
| 24 | 0 | 8.60 | 0 | 3.40 | 3.40 | | |
| HXT11 | | | | | | | |
| 0 | 71.8 | 39.9 | | | | | |
| 8 | 55.4 | 40.0 | 2.06 | 0.00 | 2.06 | 25.0 | 0.84 |
| 12 | 41.1 | 38.6 | 3.55 | 0.345 | 3.21 | | |
| 14 | 25.5 | 35.2 | 7.84 | 1.70 | 6.15 | | |
| 16 | 12.5 | 32.3 | 6.49 | 1.47 | 5.02 | | |
| 18 | 2.85 | 26.0 | 4.82 | 3.12 | 1.70 | | |
| 20 | 0 | 19.4 | 1.42 | 3.34 | 1.91 | | |
| 22 | 0 | 14.3 | 0 | 2.51 | 2.51 | | |
| 24 | 0 | 9.44 | 0 | 2.45 | 2.45 | | |
| HXT11 (N366M) | | | | | | | |
| 0 | 71.8 | 39.9 | | | | | |
| 8 | 60.2 | 38.2 | 1.45 | 0.220 | 1.23 | 11.2 | 0.977 |
| 12 | 52.5 | 35.6 | 1.93 | 0.644 | 1.29 | | |
| 14 | 42.7 | 31.3 | 4.87 | 2.15 | 2.72 | | |
| 16 | 35.6 | 28.8 | 3.55 | 1.23 | 2.32 | | |
| 18 | 29.4 | 26.0 | 3.09 | 1.44 | 1.66 | | |
| 20 | 23.3 | 22.3 | 3.05 | 1.82 | 1.24 | | |
| 22 | 18.5 | 18.7 | 2.42 | 1.83 | 0.592 | | |
| 24 | 14.1 | 14.5 | 2.18 | 2.07 | 0.117 | | |
| HXT11(N366T) | | | | | | | |
| 0 | 71.8 | 39.9 | | | | | |
| 8 | 59.1 | 36.7 | 1.59 | 0.409 | 1.18 | 11.8 | 0.977 |
| 12 | 47.7 | 33.5 | 2.84 | 0.798 | 2.05 | | |
| 14 | 37.5 | 28.6 | 5.13 | 2.41 | 2.71 | | |
| 16 | 28.6 | 24.7 | 4.42 | 1.99 | 2.43 | | |
| 18 | 21.3 | 20.7 | 3.68 | 1.97 | 1.72 | | |
| 20 | 14.2 | 15.9 | 3.55 | 2.44 | 1.11 | | |
| 22 | 8.87 | 11.1 | 2.65 | 2.38 | 0.268 | | |
| 24 | 4.94 | 6.56 | 1.96 | 2.26 | 0.3 | | |

The co-consumption index of the strains RN1001, RN1053 HXT11, RN1053 HXT11 (N366M) and RN1053 HXT11 (N366T) was determined as in table 18. Summarizing, the results for co-consumption index are given in table 19.

TABLE 19

Co-consumption index of strains

| Strain | Co-consumption index (sum abs (Qg*-Qx*) (g/h)) |
|---|---|
| RN1001 | 29.1 |
| RN1053 HXT11 | 25.0 |

TABLE 19-continued

Co-consumption index of strains

| Strain | Co-consumption index (sum abs (Qg*-Qx*) (g/h)) |
| --- | --- |
| RN1053 HXT11 (N366M) | 11.2 |
| RN1053 HXT11 (N366T) | 11.8 |

REFERENCES

Ausubel et al. 1995 Current Protocols in Molecular Biology, John Wiley & Sons, Inc.

Becker J, Boles E. 2003 A modified *Saccharomyces cerevisiae* strain that consumes L-Arabinose and produces ethanol. *Appl Environ Microbiol.* 69: 4144-4150.

Hamacher T, Becker J, Gárdonyi M, Hahn-Hägerdal B, Boles E. 2002 Characterization of the xylose-transporting properties of yeast hexose transporters and their influence on xylose utilization. *Microbiology* 148: 2783-2788.

Kasahara T, Kasahara M. 2000 Three aromatic amino acid residues critical for galactose transport in yeast Gal2 transporter. *J Biol Chem.* 275: 4422-4428.

Kasahara T, Maeda M, Boles E, Kasahara M. 2009 Identification of a key residue determining substrate affinity in the human glucose transporter GLUT1. Biochim Biophys Acta. 1788: 1051-1055.

Kasahara T, Kasahara M. 2010 Identification of a key residue determining substrate affinity in the yeast glucose transporter Hxt7: a two-dimensional comprehensive study. J Biol Chem. 285: 26263-26268.

Kuyper M, Hartog M M, Toirkens M J, Almering M J, Winkler A A, van Dijken J P, Pronk J T 2005 Metabolic engineering of a xylose-isomerase-expressing *Saccharomyces cerevisiae* strain for rapid anaerobic xylose fermentation. FEMS Yeast Research 5: 399-409.

Luttik M A, Kötter P, Salomons F A, van der Klei I J, van Dijken J P, Pronk J T 2000 The *Saccharomyces cerevisiae* ICL2 gene encodes a mitochondrial 2-methylisocitrate lyase involved in propionyl-coenzyme A metabolism. Journal of Bacteriology 182: 7007-7013.

Nelissen B, De Wachter R, Goffeau A. 1997 Classification of all putative permeases and other membrane plurispanners of the major facilitator superfamily encoded by the complete genome of *Saccharomyces cerevisiae*. FEMS Microbiol Rev. 21: 113-134.

Sambrook et al. 1989 Molecular Cloning, a Laboratory Manual

Schiestl R H and Gietz R D 1989 High efficiency transformation of intact yeast cells using single stranded nucleic acids as a carrier. Current Genetics 16: 339-346.

Wieczorke R, Krampe S, Weierstall T, Freidel K, Hollenberg C P, Boles E 1999 Concurrent knock-out of at least 20 transporter genes is required to block uptake of hexoses in *Saccharomyces cerevisiae*. FEBS Letters 464: 123-128.

Young E, Poucher A, Corner A, Bailey A, Alper H. 2011 Functional survey for heterologous sugar transport proteins, using *Saccharomyces cerevisiae* as a host. Appl Environ Microbiol. 77: 3311-3319

The invention claimed is:

1. A *Saccharomyces* cell transformed with a polynucleotide encoding a polypeptide having at least 90% sequence identity with SEQ ID NO:59, comprising:
   a) one or more substitution at a position corresponding to position 376 of SEQ ID NO:59, selected from the group consisting of N376M, N376T, N376C, N376L, N376I, N376F, and N376V; and
   b) one or more of the following amino acid motifs:
      i) G-R-x(3)-G-x(3)-G-x(11)-E-x(5)-[LIVM]-R-G-x(12)-[GA], corresponding to residues 179-221 of SEQ ID NO:59;
      ii) R-x(14)-G-x(2)-Y-x(2)-[YF]-[YF]-[GSAL], corresponding to residues 330-353 of SEQ ID NO:59; and
      iii) V-x(15)-[GNR]-[RH]-R-x(2)-[LM]-x(2)-[GA], corresponding to residues 375-399 of SEQ ID NO:59;
   wherein the polypeptide has sugar transporter activity.

2. The *Saccharomyces* cell according to claim 1, wherein the polypeptide encodes amino acid motifs i), ii), and iii).

3. The *Saccharomyces* cell according to claim 2, wherein the polypeptide is a mutant of a polypeptide that is native in an untransformed *Saccharomyces* cell, selected from the group consisting of Gal2, Hxt1, Hxt2, Hxt3, Hxt4, Hxt5, Hxt6, Hxt7, Hxt8, Hxt9, Hxt10, Hxt11, Hxt12, Hxt13, Hxt14, Hxt15, Hxt16, and Hxt17.

4. The *Saccharomyces* cell according to claim 1, wherein the polypeptide has reduced glucose transport activity compared to the polypeptide of SEQ ID NO:59.

5. The *Saccharomyces* cell according to claim 1, wherein the polypeptide has improved xylose transport activity compared to the polypeptide of SEQ ID NO:59.

6. The *Saccharomyces* cell according to claim 1, wherein the *Saccharomyces* cell has decreased glucose transport activity and improved xylose transport activity compared to a *Saccharomyces* cell expressing SEQ ID NO:59.

7. The *Saccharomyces* cell polypeptide according to claim 2, wherein the polypeptide is a mutant of a polypeptide that is native in an untransformed *Saccharomyces* cell, selected from the group consisting of SEQ ID NOs: 59 and 150 through 167.

8. A nucleic acid construct encoding a polypeptide having at least 90% sequence identity with SEQ ID NO:59, comprising:
   a) one or more substitution at a position corresponding to position 376 of SEQ ID NO:59, selected from the group consisting of N376M, N376T, N376C, N376L, N376I, N376F, and N376V; and
   b) one or more of the following amino acid motifs:
      i) G-R-x(3)-G-x(3)-G-x(11)-E-x(5)-[LIVM]-R-G-x(12)-[GA], corresponding to residues 179-221 of SEQ ID NO:59;
      ii) R-x(14)-G-x(2)-Y-x(2)-[YF]-[YF]-[GSAL], corresponding to residues 330-353 of SEQ ID NO:59; and
      iii) V-x(15)-[GNR]-[RH]-R-x(2)-[LM]-x(2)-[GA], corresponding to residues 375-399 of SEQ ID NO:59;
   wherein the polypeptide has sugar transporter activity.

9. The transformed *Saccharomyces* cell according to claim 1, which belongs to the species *Saccharomyces cerevisiae*.

10. The transformed *Saccharomyces* cell according to claim 1, wherein the polynucleotide encodes a polypeptide that is a mutant of a polypeptide that is native in an untransformed *Saccharomyces* cell.

11. The transformed *Saccharomyces* cell according to claim 10, wherein the polypeptide that is native in the untransformed *Saccharomyces* cell has sugar transporter activity.

12. The transformed *Saccharomyces* cell according to claim 10, wherein the polypeptide that is native in the untransformed *Saccharomyces* cell is a hexose transporter polypeptide.

13. The transformed *Saccharomyces* cell according to claim 11, wherein the polypeptide that is native in the untransformed *Saccharomyces* cell is a hexose transporter polypeptide.

14. The transformed *Saccharomyces* cell according to claim 13, wherein the polypeptide that is native in the untransformed host cell is a polypeptide selected from the group consisting of Gal2, Hxt1, Hxt2, Hxt3, Hxt4, Hxt5, Hxt6, Hxt7, Hxt8, Hxt9, Hxt10, Hxt11, Hxt12, Hxt13, Hxt14, Hxt15, Hxt16, and Hxt17.

15. The transformed *Saccharomyces* cell of claim 1 that, when subjected to the Glucose Transport Activity Counter Screen (GTAC) protocol, consumes xylose from a medium comprising xylose and glucose, while glucose is still present in the medium.

16. The transformed *Saccharomyces* cell according to claim 15 that, when subjected to the Glucose Transport Activity Counter Screen (GTAC) protocol, consumes xylose faster than said transformed *Saccharomyces* cell consumes glucose.

17. A polypeptide having at least 90% sequence identity with SEQ ID NO:59, comprising:
   a) a substitution corresponding to N376T of SEQ ID NO:59; and
   b) one or more of the following amino acid motifs:
      i) G-R-x(3)-G-x(3)-G-x(11)-E-x(5)-[LIVM]-R-G-x(12)-[GA], corresponding to residues 179-221 of SEQ ID NO:59;
      ii) R-x(14)-G-x(2)-Y-x(2)-[YF]-[YF]-[GSAL], corresponding to residues 330-353 of SEQ ID NO:59; and
      iii) V-x(15)-[GNR]-[RH]-R-x(2)-[LM]-x(2)-[GA], corresponding to residues 375-399 of SEQ ID NO:59;
   wherein the polypeptide has xylose transporter activity.

18. The polypeptide according to claim 17, wherein the polypeptide is expressed in an eukaryotic cell and the eukaryotic cell is used to ferment xylose in the presence of glucose.

19. A process for degradation of ligno-cellulosic or hemi-cellulosic material, wherein ligno-cellulosic or hemi-cellulosic material is contacted with an enzyme composition, wherein one or more sugar is produced, and wherein produced sugar is fermented to give ethanol as a fermentation product, wherein the fermentation is conducted with the transformed *Saccharomyces* cell of claim 1.

20. The process according to claim 19, wherein produced sugar comprises xylose and glucose and wherein the *Saccharomyces* cell co-ferments xylose and glucose.

21. A process for the degradation of ligno-cellulosic or hemi-cellulosic material, wherein ligno-cellulosic or hemi-cellulosic material is contacted with an enzyme composition, wherein one or more sugar is produced, and wherein the produced sugar is fermented to give ethanol as a fermentation product, wherein the fermentation is conducted with the transformed *Saccharomyces* cell of claim 1.

22. The *Saccharomyces* cell of claim 1, wherein the polynucleotide encodes a polypeptide having at least 95% sequence identity with SEQ ID NO:59.

23. The *Saccharomyces* cell of claim 1, wherein the polynucleotide encodes a polypeptide having at least 98% sequence identity with SEQ ID NO:59.

24. The *Saccharomyces* cell of claim 1, wherein the polynucleotide encodes a polypeptide having at least 99% sequence identity with SEQ ID NO:59.

25. The nucleic acid construct of claim 8, encoding a polypeptide having at least 95% sequence identity with SEQ ID NO:59.

26. The nucleic acid construct of claim 8, encoding a polypeptide having at least 98% sequence identity with SEQ ID NO:59.

27. The nucleic acid construct of claim 8, encoding a polypeptide having at least 99% sequence identity with SEQ ID NO:59.

28. The polypeptide of claim 17, having at least 95% sequence identity with SEQ ID NO:59.

29. The polypeptide of claim 17, having at least 98% sequence identity with SEQ ID NO:59.

30. The polypeptide of claim 17, having at least 99% sequence identity with SEQ ID NO:59.

* * * * *

```
                         SEQUENCE LISTING

<160> NUMBER OF SEQ ID NOS: 167

<210> SEQ ID NO 1
<211> LENGTH: 20
<212> TYPE: DNA
<213> ORGANISM: Artificial Sequence
<220> FEATURE:
<223> OTHER INFORMATION: primer 5034-kanf
<220> FEATURE:
<221> NAME/KEY: source
<222> LOCATION: (1)..(20)
<223> OTHER INFORMATION: /organism="Artificial Sequence"
      /note="primer 5034-kanf" /mol_type="unassigned DNA"

<400> SEQUENCE: 1
aagcttgcct cgtccccgcc                                               20

<210> SEQ ID NO 2
<211> LENGTH: 20
<212> TYPE: DNA
<213> ORGANISM: Artificial Sequence
<220> FEATURE:
<223> OTHER INFORMATION: primer 5035-kanr
<220> FEATURE:
<221> NAME/KEY: source
<222> LOCATION: (1)..(20)
<223> OTHER INFORMATION: /organism="Artificial Sequence"
      /note="primer 5035-kanr" /mol_type="unassigned DNA"

<400> SEQUENCE: 2
gtcgacactg gatggcggcg                                               20

<210> SEQ ID NO 3
<211> LENGTH: 60
<212> TYPE: DNA
<213> ORGANISM: Artificial Sequence
```

```
<220> FEATURE:
<223> OTHER INFORMATION: note="primer 5116-lf2"
<220> FEATURE:
<221> NAME/KEY: source
<222> LOCATION: (1)..(60)
<223> OTHER INFORMATION: /organism="Artificial Sequence"
      /note="primer 5116-lf2" /mol_type="unassigned DNA"

<400> SEQUENCE: 3
attctagtaa cggccgccag tgtgctggaa ttcgcccta agcttgcctc gtccccgccg    60

<210> SEQ ID NO 4
<211> LENGTH: 56
<212> TYPE: DNA
<213> ORGANISM: Artificial Sequence
<220> FEATURE:
<223> OTHER INFORMATION: primer 5118-lr2
<220> FEATURE:
<221> NAME/KEY: source
<222> LOCATION: (1)..(56)
<223> OTHER INFORMATION: /organism="Artificial Sequence"
      /note="primer 5118-lr2" /mol_type="unassigned DNA"

<400> SEQUENCE: 4
catacattat acgaagttat gcgcgctcta gatatcgtcg acactggatg gcggcg    56

<210> SEQ ID NO 5
<211> LENGTH: 65
<212> TYPE: DNA
<213> ORGANISM: Artificial Sequence
<220> FEATURE:
<223> OTHER INFORMATION: primer 5115-lf1
<220> FEATURE:
<221> NAME/KEY: source
<222> LOCATION: (1)..(65)
<223> OTHER INFORMATION: /organism="Artificial Sequence"
      /note="primer 5115-lf1" /mol_type="unassigned DNA"

<400> SEQUENCE: 5
atccggacgt acgtataact tcgtatagca tacattatac gaagttattc tagtaacggc    60
cgcca                                                                65

<210> SEQ ID NO 6
<211> LENGTH: 60
<212> TYPE: DNA
<213> ORGANISM: Artificial Sequence
<220> FEATURE:
<223> OTHER INFORMATION: primer 5117-lr1
<220> FEATURE:
<221> NAME/KEY: source
<222> LOCATION: (1)..(60)
<223> OTHER INFORMATION: /organism="Artificial Sequence"
      /note="primer 5117-lr1" /mol_type="unassigned DNA"

<400> SEQUENCE: 6
tcatgacgtc tcgaggccta aacttcgta tagcatacat tatacgaagt tatgcgcgct    60

<210> SEQ ID NO 7
<211> LENGTH: 5082
<212> TYPE: DNA
<213> ORGANISM: Artificial Sequence
<220> FEATURE:
<223> OTHER INFORMATION: pRN201; TOPO-BLUNT-loxP-kanMX-loxP
<220> FEATURE:
<221> NAME/KEY: source
<222> LOCATION: (1)..(5082)
<223> OTHER INFORMATION: /organism="Artificial Sequence" /note="pRN201;
      TOPO-BLUNT-loxP-kanMX-loxP" /mol_type="unassigned DNA"

<400> SEQUENCE: 7
```

```
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagctat   240
ttaggtgaca ctatagaata ctcaagctat gcatcaagct tggtaccgag ctcggatcca   300
ctagtaacgg ccgccagtgt gctggaattc gcccttatcc ggacgtacgt ataacttcgt   360
atagcataca ttatacgaag ttattctagt aacggccgcc agtgtgctgg aattcgccct   420
taagcttgcc tcgtccccgc cgggtcaccc ggccagcgac atggaggccc agaataccct   480
ccttgacagt cttgacgtgc gcagctcagg gcatgatgt gactgtcgcc cgtacattta   540
gcccatacat ccccatgtat aatcatttgc atccatacat tttgatggcc gcacggcgcg   600
aagcaaaaat tacggctcct cgctgcagac ctgcgagcag ggaaacgctc ccctcacaga   660
cgcgttgaat tgtccccacg ccgcgcccct gtagagaaat ataaaaggtt aggatttgcc   720
actgaggttc ttctttcata tacttccttt taaaatcttg ctaggataca gttctcacat   780
cacatccgaa cataaacaac catgggtaag gaaaagactc acgtttcgag gccgcgatta   840
aattccaaca tggatgctga tttatatggg tataaatggg ctcgcgataa tgtcgggcaa   900
tcaggtgcga caatctatcg attgtatggg aagcccgatg cgccagagtt gtttctgaaa   960
catggcaaag gtagcgttgc caatgatgtt acagatgaga tggtcagact aaactggctg  1020
acggaattta tgcctcttcc gaccatcaag cattttatcc gtactcctga tgatgcatgg  1080
ttactcacca ctgcgatccc cggcaaaaca gcattccagg tattagaaga atatcctgat  1140
tcaggtgaaa atattgttga tgcgctggca gtgttcctgc gccggttgca ttcgattcct  1200
gtttgtaatt gtccttttaa cagcgatcgc gtatttcgtc tcgctcaggc gcaatcacga  1260
atgaataacg gtttggttga tgcgagtgat tttgatgacg agcgtaatgg ctggcctgtt  1320
gaacaagtct ggaaagaaat gcataagctt ttgccattct caccggattc agtcgtcact  1380
catggtgatt tctcacttga taaccttatt tttgacgagg ggaaattaat aggttgtatt  1440
gatgttggac gagtcggaat cgcagaccga taccaggatc ttgccatcct atggaactgc  1500
ctcggtgagt tttctccttc attacagaaa cggctttttc aaaaatatgg tattgataat  1560
cctgatatga taaattgca gtttcatttg atgctcgatg agttttttcta atcagtactg  1620 acaataaaaa gattcttgtt ttcaagaact tgtcatttgt atagtttttt tatattgtag  1680
ttgttctatt ttaatcaaat gttagcgtga tttatatttt ttttcgcctc gacatcatct  1740
gcccagatgc agttaagtgc gcagaaagta atatcatgcg tcaatcgtat gtgaatgctg  1800
gtcgctatac tgctgtcgat tcgatactaa cgccgccatc cagtgtcgac gatatctaga  1860
gcgcgcataa cttcgtataa tgtatgctat acgaagttat aggcctcgag acgtcatgaa  1920
agggcgaatt ctgagatatc catcacactg gcggccgctc gagcatgcat ctagagggcc  1980
caattcgccc tatagtgagt cgtattacaa ttcactggcc gtcgttttac aacgtcgtga  2040
ctgggaaaac cctggcgtta cccaacttaa tcgccttgca gcacatcccc ctttcgccag  2100
ctggcgtaat agcgaagagg cccgcaccga tcgcccttcc caacagttgc gcagcctata  2160
cgtacggcag tttaaggttt acacctataa aagagagagc cgttatcgtc tgtttgtgga  2220
tgtacagagt gatattattg acacgccggg gcgacggatg gtgatccccc tggccagtgc  2280
acgtctgctg tcagataaag tctcccgtga actttacccg gtggtgcata tcggggatga  2340
```

-continued

```
aagctggcgc atgatgacca ccgatatggc cagtgtgccg gtctccgtta tcggggaaga    2400
agtggctgat ctcagccacc gcgaaaatga catcaaaaac gccattaacc tgatgttctg    2460
gggaatataa atgtcaggca tgagattatc aaaaaggatc ttcacctaga tccttttcac    2520
gtagaaagcc agtccgcaga aacggtgctg accccggatg aatgtcagct actgggctat    2580
ctggacaagg gaaaacgcaa gcgcaaagag aaagcaggta gcttgcagtg ggcttacatg    2640
gcgatagcta gactgggcgg ttttatggac agcaagcgaa ccggaattgc cagctggggc    2700
gccctctggt aaggttggga agccctgcaa agtaaactgg atggctttct cgccgccaag    2760
gatctgatgg cgcaggggat caagctctga tcaagagaca ggatgaggat cgtttcgcat    2820
gattgaacaa gatggattgc acgcaggttc tccggccgct tgggtggaga ggctattcgg    2880
ctatgactgg gcacaacaga caatcggctg ctctgatgcc gccgtgttcc ggctgtcagc    2940 gcagggcgc ccggttcttt ttgtcaagac cgacctgtcc ggtgccctga atgaactgca    3000
agacgaggca gcgcggctat cgtggctggc cacgacgggc gttccttgcg cagctgtgct    3060
cgacgttgtc actgaagcgg gaagggactg gctgctattg ggcgaagtgc cggggcagga    3120
tctcctgtca tctcacccttg ctcctgccga gaaagtatcc atcatggctg atgcaatgcg    3180
gcggctgcat acgcttgatc cggctacctg cccattcgac caccaagcga acatcgcat    3240 cgagcgagca cgtactcgga tggaagccgg tcttgtcgat caggatgatc tggacgaaga    3300
gcatcagggg ctcgcgccag ccgaactgtt cgccaggctc aaggcgagca tgcccgacgg    3360
cgaggatctc gtcgtgaccc atggcgatgc ctgcttgccg aatatcatgg tggaaaatgg    3420
ccgcttttct ggattcatcg actgtggccg gctgggtgtg gcggaccgct atcaggacat    3480
agcgttggct acccgtgata ttgctgaaga gcttggcggc gaatgggctg accgcttcct    3540
cgtgctttac ggtatcgccg ctcccgattc gcagcgcatc gccttctatc gccttcttga    3600
cgagttcttc tgaattatta acgcttacaa tttcctgatg cggtattttc tccttacgca    3660
tctgtgcggt atttcacacc gcatacaggt ggcactttc ggggaaatgt gcgcggaacc    3720
cctatttgtt tatttttcta aatacattca aatatgtatc cgctcatgag acaataaccc    3780
tgataaatgc ttcaataata gcacgtgagg agggccacca tggccaagtt gaccagtgcc    3840
gttccggtgc tcaccgcgcg cgacgtcgcc ggagcggtcg agttctggac cgaccggctc    3900
gggttctccc gggacttcgt ggaggacgac ttcgccggtg tggtccggga cgacgtgacc    3960
ctgttcatca gcgcggtcca ggaccaggtg gtgccggaca cacccctggc ctgggtgtgg    4020
gtgcgcggcc tggacgagct gtacgccgag tggtcggagg tcgtgtccac gaacttccgg    4080
gacgcctccg ggcggccat gaccgagatc ggcgagcagc cgtgggggcg ggagttcgcc    4140
ctgcgcgacc cggccggcaa ctgcgtgcac ttcgtggccg aggagcagga ctgacacgtg    4200
ctaaaacttc attttttaatt taaaaggatc taggtgaaga tccttttga taatctcatg    4260 accaaaatcc cttaacgtga gttttcgttc cactgagcgt cagacccgt agaaaagatc    4320 aaaggatctt cttgagatcc ttttttctg cgcgtaatct gctgcttgca acaaaaaaa    4380 ccaccgctac cagcggtggt ttgtttgccg gatcaagagc taccaactct ttttccgaag    4440
gtaactggct tcagcagagc gcagatacca aatactgtcc ttctagtgta gccgtagtta    4500
ggccaccact tcaagaactc tgtagcaccg cctacatacc tcgctctgct aatcctgtta    4560
ccagtggctg ctgccagtgg cgataagtcg tgtcttaccg ggttggactc aagacgatag    4620
ttaccggata aggcgcagcg gtcgggctga acggggggtt cgtgcacaca gcccagcttg    4680
gagcgaacga cctacaccga actgagatac ctacagcgtg agctatgaga aagcgccacg    4740
```

```
cttcccgaag ggagaaaggc ggacaggtat ccggtaagcg gcagggtcgg aacaggagag      4800
cgcacgaggg agcttccagg gggaaacgcc tggtatcttt atagtcctgt cgggtttcgc      4860
cacctctgac ttgagcgtcg attttttgtga tgctcgtcag gggggcggag cctatggaaa     4920
aacgccagca acgcggcctt tttacggttc ctgggctttt gctggccttt tgctcacatg      4980
ttctttcctg cgttatcccc tgattctgtg ataaccgta ttaccgcctt tgagtgagct       5040
gataccgctc gccgcagccg aacgaccgag cgcagcgagt ca                         5082
```

<210> SEQ ID NO 8
<211> LENGTH: 5352
<212> TYPE: DNA
<213> ORGANISM: Artificial Sequence
<220> FEATURE:
<223> OTHER INFORMATION: pRN251; TOPO-BLUNT-loxP-hphMX-loxP
<220> FEATURE:
<221> NAME/KEY: source
<222> LOCATION: (1)..(5352)
<223> OTHER INFORMATION: /organism="Artificial Sequence" /note="pRN251;
      TOPO-BLUNT-loxP-hphMX-loxP" /mol_type="unassigned DNA"

<400> SEQUENCE: 8

```
agcgcccaat acgcaaaccg cctctccccg cgcgttggcc gattcattaa tgcagctggc        60
acgacaggtt tcccgactgg aaagcgggca gtgagcgcaa cgcaattaat gtgagttagc       120
tcactcatta ggcaccccag gctttacact ttatgcttcc ggctcgtatg ttgtgtggaa       180
ttgtgagcgg ataacaattt cacacaggaa acagctatga ccatgattac gccaagctat       240
ttaggtgaca ctatagaata ctcaagctat gcatcaagct tggtaccgag ctcggatcca       300
ctagtaacgg ccgccagtgt gctggaattc gccctttcat gacgtctcga ggcctataac       360
ttcgtatagc atacattata cgaagttatg cgcgctctag atatcgtcga gcggccgcca       420
gtgtgatgga tatcatcgat gaattcgagc tcgttttcga cactggatgg cggcgttagt       480
atcgaatcga cagcagtata gcgaccagca ttcacatacg attgacgcat gatattactt       540
tctgcgcact taacttcgca tctgggcaga tgatgtcgag gcgaaaaaaa atataaatca       600
cgctaacatt tgattaaaat agaacaacta caatataaaa aaactataca aatgacaagt      660
tcttgaaaac aagaatcttt ttattgtcag tactgattat tccttttgccc tcggacgagt      720 gctgggggcgt cggtttccac tatcggcgag tacttctaca cagccatcgg tccagacggc      780
cgcgcttctg cgggcgattt gtgtacgccc gacagtcccg gctccggatc ggacgattgc      840
gtcgcatcga ccctgcgccc aagctgcatc atcgaaattg ccgtcaacca agctctgata      900
gagttggtca agaccaatgc ggagcatata cgcccggagc cgcggcgatc ctgcaagctc      960
cggatgcctc cgctcgaagt agcgcgtctg ctgctccata caagccaacc acggcctcca     1020
gaagaagatg ttggcgacct cgtattggga atccccgaac atcgcctcgc tccagtcaat     1080
gaccgctgtt atgcggccat tgtccgtcag acattgttg gagccgaaat ccgcgtgcac      1140
gaggtgccgg acttcggggc agtcctcggc ccaaagcatc agctcatcga gagcctgcgc     1200
gacggacgca ctgacggtgt cgtccatcac agtttgccag tgatacacat ggggatcagc     1260
aatcgcgcat atgaaatcac gccatgtagt gtattgaccg attccttgcg gtccgaatgg     1320
gccgaacccg ctcgtctggc taagatcggc cgcagcgatc gcatccatgg cctccgcgac     1380
cggctgcaga acagcgggca gttcggtttc aggcaggtct tgcaacgtga caccctgtgc     1440
acggcgggag atgcaatagg tcaggctctc gctgaattcc ccaatgtcaa gcacttccgg     1500
aatcgggagc gcggccgatg caaagtgccg ataaacataa cgatctttgt agaaaccatc     1560
```

-continued

```
ggcgcagcta tttacccgca ggacatatcc acgccctcct acatcgaagc tgaaagcacg    1620
agattcttcg ccctccgaga gctgcatcag gtcggagacg ctgtcgaact tttcgatcag    1680
aaacttctcg acagacgtcg cggtgagttc aggcttttta cccatggttg tttatgttcg    1740
gatgtgatgt gagaactgta tcctagcaag attttaaaag gaagtatatg aaagaagaac    1800
ctcagtggca aatcctaacc ttttatattt ctctacaggg gcgcggcgtg gggacaattc    1860
acgcgtctgt gaggggagcg tttccctgct cgcaggtctg cagcgaggag ccgtaatttt    1920
tgcttcgcgc cgtgcggcca tcaaaatgta tggatgcaaa tgattataca tggggatgta    1980
tgggctaaat gtacgggcga cagtcacatc atgcccctga gctgcgcacg tcaagactgt    2040
caaggagggt attctgggcc tccatgtcgc tggccgggtg acccggcggg gacgaggcaa    2100
gcttaagggc gaattccagc acactggcgg ccgttactag aataacttcg tataatgtat    2160
gctatacgaa gttatacgta cgtccggata agggcgaatt ctgagatatc catcacactg    2220
gcggccgctc gagcatgcat ctagagggcc caattcgccc tatagtgagt cgtattacaa    2280
ttcactggcc gtcgttttac aacgtcgtga ctgggaaaac cctggcgtta cccaacttaa    2340
tcgccttgca gcacatcccc ctttcgccag ctggcgtaat agcgaagagg cccgcaccga    2400
tcgcccttcc caacagttgc gcagcctata cgtacggcag tttaaggttt acacctataa    2460
aagagagagc cgttatcgtc tgtttgtgga tgtacagagt gatattattg acacgccggg    2520
gcgacggatg gtgatccccc tggccagtgc acgtctgctg tcagataaag tctcccgtga    2580
actttacccg gtggtgcata tcggggatga aagctggcgc atgatgacca ccgatatggc    2640
cagtgtgccg gtctccgtta tcggggaaga agtggctgat ctcagccacc gcgaaaatga    2700
catcaaaaac gccattaacc tgatgttctg gggaatataa atgtcaggca tgagattatc    2760 aaaaggatc ttcacctaga tccttttcac gtagaaagcc agtccgcaga aacggtgctg    2820
accccggatg aatgtcagct actgggctat ctggacaagg gaaaacgcaa gcgcaaagag    2880
aaagcaggta gcttgcagtg gcttacatg gcgatagcta gactgggcgg ttttatggac    2940
agcaagcgaa ccggaattgc cagctggggc gccctctggt aaggttggga agccctgcaa    3000
agtaaactgg atggctttct cgccgccaag gatctgatgg cgcaggggat caagctctga    3060
tcaagacaca ggatgaggat cgtttcgcat gattgaacaa gatggattgc acgcaggttc    3120
tccggccgct tgggtggaga ggctattcgg ctatgactgg gcacaacaga caatcggctg    3180
ctctgatgcc gccgtgttcc ggctgtcagc gcaggggcgc ccggttcttt tgtcaagac    3240 cgacctgtcc ggtgccctga atgaactgca agacgaggca gcgcggctat cgtggctggc    3300
cacgacgggc gttccttgcg cagctgtgct cgacgttgtc actgaagcgg gaagggactg    3360
gctgctattg ggcgaagtgc cggggcagga tctcctgtca tctcaccttg ctcctgccga    3420
gaaagtatcc atcatggctg atgcaatgcg gcggctgcat acgcttgatc cggctacctg    3480
cccattcgac caccaagcga aacatcgcat cgagcgagca cgtactcgga tggaagccgg    3540
tcttgtcgat caggatgatc tggacgaaga gcatcagggg ctcgcgccag ccgaactgtt    3600
cgccaggctc aaggcgagca tgcccgacgg cgaggatctc gtcgtgaccc atggcgatgc    3660
ctgcttgccg aatatcatgg tggaaaatgg ccgcttttct ggattcatcg actgtggccg    3720
gctgggtgtg gcggaccgct atcaggacat agcgttggct acccgtgata ttgctgaaga    3780
gcttggcggc gaatgggctg accgcttcct cgtgctttac ggtatcgccg ctcccgattc    3840
gcagcgcatc gccttctatc gccttcttga cgagttcttc tgaattatta acgcttacaa    3900
```

| | |
|---|---|
| tttcctgatg cggtattttc tccttacgca tctgtgcggt atttcacacc gcatacaggt | 3960 |
| ggcactttc ggggaaatgt gcgcggaacc cctatttgtt tattttcta aatacattca | 4020 |
| aatatgtatc cgctcatgag acaataaccc tgataaatgc ttcaataata gcacgtgagg | 4080 |
| agggccacca tggccaagtt gaccagtgcc gttccggtgc tcaccgcgcg cgacgtcgcc | 4140 |
| ggagcggtcg agttctggac cgaccggctc gggttctccc gggacttcgt ggaggacgac | 4200 |
| ttcgccggtg tggtccggga cgacgtgacc ctgttcatca gcgcggtcca ggaccaggtg | 4260 |
| gtgccggaca cacccctggc ctgggtgtgg gtgcgcggcc tggacgagct gtacgccgag | 4320 |
| tggtcggagt cgtgtccac gaacttccgg gacgcctccg gccggccat gaccgagatc | 4380 |
| ggcgagcagc cgtgggggcg ggagttcgcc ctgcgcgacc cggccggcaa ctgcgtgcac | 4440 |
| ttcgtggccg aggagcagga ctgacacgtg ctaaaacttc attttaatt taaaaggatc | 4500 |
| taggtgaaga tccttttga taatctcatg accaaaatcc cttaacgtga gttttcgttc | 4560 |
| cactgagcgt cagaccccgt agaaaagatc aaaggatctt cttgagatcc tttttttctg | 4620 |
| cgcgtaatct gctgcttgca acaaaaaaa ccaccgctac cagcggtggt ttgtttgccg | 4680 |
| gatcaagagc taccaactct ttttccgaag gtaactggct tcagcagagc gcagatacca | 4740 |
| aatactgtcc ttctagtgta gccgtagtta ggccaccact tcaagaactc tgtagcaccg | 4800 |
| cctacatacc tcgctctgct aatcctgtta ccagtggctg ctgccagtgg cgataagtcg | 4860 |
| tgtcttaccg ggttggactc aagacgatag ttaccggata aggcgcagcg gtcgggctga | 4920 |
| acggggggtt cgtgcacaca gcccagcttg gagcgaacga cctacaccga actgagatac | 4980 |
| ctacagcgtg agctatgaga aagcgccacg cttcccgaag ggagaaaggc ggacaggtat | 5040 |
| ccggtaagcg gcagggtcgg aacaggagag cgcacgaggg agcttccagg gggaaacgcc | 5100 |
| tggtatcttt atagtcctgt cgggtttcgc cacctctgac ttgagcgtcg attttgtga | 5160 |
| tgctcgtcag ggggcggag cctatggaaa aacgccagca acgcggcctt tttacggttc | 5220 |
| ctgggctttt gctggccttt tgctcacatg ttctttcctg cgttatcccc tgattctgtg | 5280 |
| gataaccgta ttaccgcctt tgagtgagct gataccgctc gccgcagccg aacgaccgag | 5340 |
| cgcagcgagt ca | 5352 |

<210> SEQ ID NO 9
<211> LENGTH: 4847
<212> TYPE: DNA
<213> ORGANISM: Artificial Sequence
<220> FEATURE:
<223> OTHER INFORMATION: pRN365; TOPO-BLUNT-loxP-natMX-loxP
<220> FEATURE:
<221> NAME/KEY: source
<222> LOCATION: (1)..(4847)
<223> OTHER INFORMATION: /organism="Artificial Sequence" /note="pRN365; TOPO-BLUNT-loxP-natMX-loxP" /mol_type="unassigned DNA"

<400> SEQUENCE: 9

| | |
|---|---|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagctat | 240 |
| ttaggtgaca ctatagaata tcaagctat gcatcaagct tggtaccgag ctcggatcca | 300 |
| ctagtaacgg ccgccagtgt gctggaattc gcccttatcc ggacgtacgt ataacttcgt | 360 |
| atagcataca ttatacgaag ttattctagt aacggccgcc agtgtgctgg aattcgccct | 420 |

```
taagcttgcc tcgtccccgc cgggtcaccc ggccagcgac atggaggccc agaataccct    480
ccttgacagt cttgacgtgc gcagctcagg ggcatgatgt gactgtcgcc cgtacattta    540
gcccatacat ccccatgtat aatcatttgc atccatacat tttgatggcc gcacggcgcg    600
aagcaaaaat tacggctcct cgctgcagac ctgcgagcag ggaaacgctc ccctcacaga    660
cgcgttgaat tgtccccacg ccgcgcccct gtagagaaat ataaaaggtt aggatttgcc    720
actgaggttc ttcttttcata tacttccttt taaaatcttg ctaggataca gttctcacat    780
cacatccgaa cataaacaac catgtaaaat gaccactctt gacgacacgg cttaccggta    840
ccgcaccagt gtcccggggg acgccgaggc catcgaggca ctggatgggt ccttcaccac    900
cgacaccgtc ttccgcgtca ccgccaccgg ggacggcttc accctgcggg aggtgccggt    960
ggacccgccc ctgaccaagg tgttcccga cgacgaatcg gacgcgaat cggacgccgg   1020
ggaggacggc gacccggact cccggacgtt cgtcgcgtac ggggacgacg gcgacctggc   1080
gggcttcgtg gtcgtctcgt actccggctg gaaccgccgg ctgaccgtcg aggacatcga   1140
ggtcgccccg gagcaccggg ggcacggggt cgggcgcgcg ttgatggggc tcgcgacgga   1200
gttcgcccgc gagcggggcg ccgggcacct ctggctggag gtcaccaacg tcaacgcacc   1260
ggcgatccac gcgtaccggc ggatgggggtt caccctctgc ggcctggaca ccgccctgta   1320
cgacggcacc gcctcggacg gcgagcaggc gctctacatg agcatgccct gcccctagta   1380
ctgacaataa aaagattctt gttttcaaga acttgtcatt tgtatagttt ttttatattg   1440
tagttgttct attttaatca aatgttagcg tgatttatat ttttttcgc ctcgacatca   1500
tctgcccaga tgcgaagtta agtgcgcaga aagtaatatc atgcgtcaat cgtatgtgaa   1560
tgctggtcgc tatactgctg tcgattcgat actaacgccg ccatccagtg tcgacgatat   1620
ctagagcgcg cataacttcg tataatgtat gctatacgaa gttataggcc tcgagacgtc   1680
atgaaagggc gaattctgag atatccatca cactggcggc cgctcgagca tgcatctaga   1740
gggcccaatt cgccctatag tgagtcgtat tacaattcac tggccgtcgt tttacaacgt   1800
cgtgactggg aaaaccctgg cgttacccaa cttaatcgcc ttgcagcaca tccccctttc   1860
gccagctggc gtaatagcga agaggcccgc accgatcgcc cttcccaaca gttgcgcagc   1920
ctatacgtac ggcagtttaa ggtttacacc tataaagag agagccgtta tcgtctgttt   1980
gtggatgtac agagtgatat tattgacacg ccggggcgac ggatggtgat cccctggcc    2040
agtgcacgtc tgctgtcaga taaagtctcc cgtgaacttt acccggtggt gcatatcggg   2100
gatgaaagct ggcgcatgat gaccaccgat atggccagtg tgccggtctc cgttatcggg   2160
gaagaagtgg ctgatctcag ccaccgcgaa aatgacatca aaaacgccat taacctgatg   2220
ttctggggaa tataaatgtc aggcatgaga ttatcaaaaa ggatcttcac ctagatcctt   2280
ttcacgtaga aagccagtcc gcagaaacgg tgctgacccc ggatgaatgt cagctactgg   2340
gctatctgga caagggaaaa cgcaagcgca aagagaaagc aggtagcttg cagtgggctt   2400
acatggcgat agctagactg gcggttttta tggacagcaa gcgaaccgga attgccagct   2460
ggggcgccct ctggtaaggt tgggaagccc tgcaaagtaa actggatggc tttctcgccg   2520
ccaaggatct gatggcgcag gggatcaagc tctgatcaag agacaggatg aggatcgttt   2580
cgcatgattg aacaagatgg attgcacgca ggttctccgg ccgcttgggt ggagaggcta   2640
ttcggctatg actgggcaca acagacaatc ggctgctctg atgccgccgt gttccggctg   2700
tcagcgcagg ggcgcccggt tctttttgtc aagaccgacc tgtccggtgc cctgaatgaa   2760
ctgcaagacg aggcagcgcg gctatcgtgg ctggccacga cgggcgttcc ttgcgcagct   2820
```

```
gtgctcgacg ttgtcactga agcgggaagg gactggctgc tattgggcga agtgccgggg    2880
caggatctcc tgtcatctca ccttgctcct gccgagaaag tatccatcat ggctgatgca    2940
atgcggcggc tgcatacgct tgatccggct acctgcccat tcgaccacca agcgaaacat    3000
cgcatcgagc gagcacgtac tcggatggaa gccggtcttg tcgatcagga tgatctggac    3060
gaagagcatc aggggctcgc gccagccgaa ctgttcgcca ggctcaaggc gagcatgccc    3120
gacggcgagg atctcgtcgt gacccatggc gatgcctgct tgccgaatat catggtggaa    3180
aatggccgct tttctggatt catcgactgt ggccggctgg gtgtggcgga ccgctatcag    3240
gacatagcgt tggctacccg tgatattgct gaagagcttg cgggcgaatg ggctgaccgc    3300
ttcctcgtgc tttacggtat cgccgctccc gattcgcagc gcatcgcctt ctatcgcctt    3360
cttgacgagt tcttctgaat tattaacgct tacaatttcc tgatgcggta ttttctcctt    3420
acgcatctgt gcggtatttc acaccgcata caggtggcac ttttcgggga aatgtgcgcg    3480 gaaccctat tgtttattt ttctaaatac attcaaatat gtatccgctc atgagacaat    3540
aaccctgata aatgcttcaa taatagcacg tgaggagggc caccatggcc aagttgacca    3600
gtgccgttcc ggtgctcacc gcgcgcgacg tcgccgagc ggtcgagttc tggaccgacc    3660
ggctcgggtt ctcccgggac ttcgtggagg acgacttcgc cggtgtggtc cgggacgacg    3720
tgaccctgtt catcagcgcg gtccaggacc aggtggtgcc ggacaacacc ctggcctggg    3780
tgtgggtgcg cggcctggac gagctgtacg ccgagtggtc ggaggtcgtg tccacgaact    3840
tccgggacgc ctccgggccg gccatgaccg agatcggcga gcagccgtgg gggcgggagt    3900
tcgccctgcg cgacccggcc ggcaactgcg tgcacttcgt ggccgaggag caggactgac    3960
acgtgctaaa acttcatttt taatttaaaa ggatctaggt gaagatcctt tttgataatc    4020
tcatgaccaa aatcccttaa cgtgagtttt cgttccactg agcgtcagac cccgtagaaa    4080
agatcaaagg atcttcttga gatccttttt ttctgcgcgt aatctgctgc ttgcaaacaa    4140
aaaaaccacc gctaccagcg gtggtttgtt tgccggatca agagctacca actctttttc    4200
cgaaggtaac tggcttcagc agagcgcaga taccaaatac tgtccttcta gtgtagccgt    4260
agttaggcca ccacttcaag aactctgtag caccgcctac atacctcgct ctgctaatcc    4320
tgttaccagt ggctgctgcc agtggcgata agtcgtgtct taccgggttg gactcaagac    4380
gatagttacc ggataaggcg cagcggtcgg gctgaacggg gggttcgtgc acacagccca    4440
gcttggagcg aacgacctac accgaactga gatacctaca gcgtgagcta tgagaaagcg    4500
ccacgcttcc cgaagggaga aaggcggaca ggtatccggt aagcggcagg gtcggaacag    4560
gagagcgcac gagggagctt ccaggggaa acgcctggta tctttatagt cctgtcgggt    4620
ttcgccacct ctgacttgag cgtcgatttt tgtgatgctc gtcaggggg cggagcctat    4680 ggaaaaacgc cagcaacgcg gcctttttac ggttcctggg cttttgctgg ccttttgctc    4740
acatgttctt tcctgcgtta tcccctgatt ctgtggataa ccgtattacc gcctttgagt    4800
gagctgatac cgctcgccgc agccgaacga ccgagcgcag cgagtca                 4847
```

<210> SEQ ID NO 10
<211> LENGTH: 32
<212> TYPE: DNA
<213> ORGANISM: Artificial Sequence
<220> FEATURE:
<223> OTHER INFORMATION: primer 115-natf
<220> FEATURE:
<221> NAME/KEY: source
<222> LOCATION: (1)..(32)

```
<223> OTHER INFORMATION: /organism="Artificial Sequence"
     /note="primer 115-natf" /mol_type="unassigned DNA"

<400> SEQUENCE: 10
acatgtaaaa tgaccactct tgacgacacg gc                              32

<210> SEQ ID NO 11
<211> LENGTH: 25
<212> TYPE: DNA
<213> ORGANISM: Artificial Sequence
<220> FEATURE:
<223> OTHER INFORMATION: primer 116-natr
<220> FEATURE:
<221> NAME/KEY: source
<222> LOCATION: (1)..(25)
<223> OTHER INFORMATION: /organism="Artificial Sequence"
     /note="primer 116-natr" /mol_type="unassigned DNA"

<400> SEQUENCE: 11
cagtactagg ggccagggca tgctc                                      25

<210> SEQ ID NO 12
<211> LENGTH: 4254
<212> TYPE: DNA
<213> ORGANISM: Artificial Sequence
<220> FEATURE:
<223> OTHER INFORMATION: pRN447; TOPO-BLUNT-loxP-zeoMX-loxP
<220> FEATURE:
<221> NAME/KEY: source
<222> LOCATION: (1)..(4254)
<223> OTHER INFORMATION: /organism="Artificial Sequence" /note="pRN447;
     TOPO-BLUNT-loxP-zeoMX-loxP" /mol_type="unassigned DNA"

<400> SEQUENCE: 12
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagctat   240
ttaggtgaca ctatagaata ctcaagctat gcatcaagct tggtaccgag ctcggatcca   300
ctagtaacgg ccgccagtgt gctggaattc gcccttatcc ggacgtacgt ataacttcgt   360
atagcataca ttatacgaag ttattctagt aacggccgcc agtgtgctgg aattcgccct   420
taagcttgcc tcgtccccgc cgggtcaccc ggccagcgac atggaggccc agaatacccc   480
ccttgacagt cttgacgtgc gcagctcagg ggcatgatgt gactgtcgcc cgtacattta   540
gcccatacat ccccatgtat aatcatttgc atccatacat tttgatggcc gcacggcgcg   600
aagcaaaaat tacggctcct cgctgcagac ctgcgagcag ggaaacgctc ccctcacaga   660
cgcgttgaat tgtccccacg ccgcgcccct gtagagaaat ataaaaggtt aggatttgcc   720
actgaggttc ttctttcata tacttccttt taaaatcttg ctaggataca gttctcacat   780
cacatccgaa cataaacaac catggccaag ttgaccagtg ccgttccggt gctcaccgcg   840
cgcgacgtcg ccggagcggt cgagttctgg accgaccggc tcgggttctc ccgggacttc   900
gtggaggacg acttcgccgg tgtggtccgg gacgacgtga ccctgttcat cagcgcggtc   960
caggaccagg tggtgccgga caacaccctg gcctgggtgt gggtgcgcgg cctggacgag  1020
ctgtacgccg agtggtcgga ggtcgtgtcc acgaacttcc gggacgcctc cgggccggcc  1080
atgaccgaga tcggcgagca gccgtggggg cgggagttcg ccctgcgcga cccggccggc  1140
aactgcgtgc acttcgtggc cgaggagcag gactgacaca ctgacaataa aaagattctt  1200
```

-continued

```
gttttcaaga acttgtcatt tgtatagttt ttttatattg tagttgttct attttaatca    1260
aatgttagcg tgatttatat ttttttttcgc ctcgacatca tctgcccaga tgcgaagtta    1320
agtgcgcaga aagtaatatc atgcgtcaat cgtatgtgaa tgctggtcgc tatactgctg    1380
tcgattcgat actaacgccg ccatccagtg tcgacgatat ctagagcgcg cataacttcg    1440
tataatgtat gctatacgaa gttataggcc tcgagacgtc atgaaagggc gaattctgag    1500
atatccatca cactggcggc cgctcgagca tgcatctaga gggcccaatt cgccctatag    1560
tgagtcgtat tacaattcac tggccgtcgt tttacaacgt cgtgactggg aaaaccctgg    1620
cgttacccaa cttaatcgcc ttgcagcaca tccccctttc gccagctggc gtaatagcga    1680
agaggcccgc accgatcgcc cttcccaaca gttgcgcagc ctatacgtac ggcagtttaa    1740
ggtttacacc tataaaagag agagccgtta tcgtctgttt gtggatgtac agagtgatat    1800
tattgacacg ccggggcgac ggatggtgat cccctggcc agtgcacgtc tgctgtcaga    1860
taaagtctcc cgtgaacttt acccggtggt gcatatcggg gatgaaagct ggcgcatgat    1920
gaccaccgat atggccagtg tgccggtctc cgttatcggg gaagaagtgg ctgatctcag    1980
ccaccgcgaa aatgacatca aaaacgccat taacctgatg ttctggggaa tataaatgtc    2040
aggcatgaga ttatcaaaaa ggatcttcac ctagatcctt ttcacgtaga aagccagtcc    2100
gcagaaacgg tgctgacccc ggatgaatgt cagctactgg gctatctgga caagggaaaa    2160
cgcaagcgca aagagaaagc aggtagcttg cagtgggctt acatggcgat agctagactg    2220
ggcggtttta tggacagcaa gcgaaccgga attgccagct ggggcgccct ctggtaaggt    2280
tgggaagccc tgcaaagtaa actggatggc tttctcgccg ccaaggatct gatggcgcag    2340
gggatcaagc tctgatcaag agacaggatg aggatcgttt cgcatgattg aacaagatgg    2400
attgcacgca ggttctccgg ccgcttgggt ggagaggcta ttcggctatg actgggcaca    2460
acagacaatc ggctgctctg atgccgccgt gttccggctg tcagcgcagg ggcgcccggt    2520
tcttttttgtc aagaccgacc tgtccggtgc cctgaatgaa ctgcaagacg aggcagcgcg    2580
gctatcgtgg ctggccacga cgggcgttcc ttgcgcagct gtgctcgacg ttgtcactga    2640
agcgggaagg gactggctgc tattgggcga agtgccgggg caggatctcc tgtcatctca    2700
ccttgctcct gccgagaaag tatccatcat ggctgatgca atgcggcggc tgcatacgct    2760
tgatccggct acctgcccat tcgaccacca agcgaaacat cgcatcgagc gagcacgtac    2820
tcggatggaa gccggtcttg tcgatcagga tgatctggac gaagagcatc aggggctcgc    2880
gccagccgaa ctgttcgcca ggctcaaggc gagcatgccc gacggcgagg atctcgtcgt    2940
gacccatggc gatgcctgct tgccgaatat catggtggaa aatggccgct ttctggatt    3000
catcgactgt ggccggctgg gtgtggcgga ccgctatcag acatagcgt tggctacccg    3060
tgatattgct gaagagcttg gcggcgaatg ggctgaccgc ttcctcgtgc tttacggtat    3120
cgccgctccc gattcgcagc gcatcgcctt ctatcgcctt cttgacgagt tcttctgaat    3180
tattaacgct tacaatttcc tgatgcggta ttttctcctt acgcatctgt gcggtatttc    3240
acaccgcata caggtggcac ttttcgggga atgtgcgcg aaccccctat ttgtttattt    3300
ttctaaatac attcaaatat gtatccgctc atgagacaat aaccctgata aatgcttcaa    3360
taatagcacg tgctaaaact tcattttaa tttaaaagga tctaggtgaa gatcctttt    3420
gataatctca tgaccaaaat cccttaacgt gagttttcgt tccactgagc gtcagacccc    3480
gtagaaaaga tcaaaggatc ttcttgagat cctttttttc tgcgcgtaat ctgctgcttg    3540
caaacaaaaa aaccaccgct accagcggtg gtttgtttgc cggatcaaga gctaccaact    3600
```

```
cttttttccga aggtaactgg cttcagcaga gcgcagatac caaatactgt ccttctagtg    3660
tagccgtagt taggccacca cttcaagaac tctgtagcac cgcctacata cctcgctctg    3720
ctaatcctgt taccagtggc tgctgccagt ggcgataagt cgtgtcttac cgggttggac    3780
tcaagacgat agttaccgga taaggcgcag cggtcgggct gaacggggggg ttcgtgcaca    3840 cagcccagct tggagcgaac gacctacacc gaactgagat acctacagcg tgagctatga    3900
gaaagcgcca cgcttcccga agggagaaag gcggacaggt atccggtaag cggcagggtc    3960
ggaacaggag agcgcacgag ggagcttcca gggggaaacg cctggtatct ttatagtcct    4020
gtcgggtttc gccacctctg acttgagcgt cgatttttgt gatgctcgtc aggggggcgg    4080
agcctatgga aaaacgccag caacgcggcc ttttacggt tcctgggctt tgctggcct    4140 tttgctcaca tgttctttcc tgcgttatcc cctgattctg tggataaccg tattaccgcc    4200
tttgagtgag ctgataccgc tcgccgcagc cgaacgaccg agcgcagcga gtca          4254
```

<210> SEQ ID NO 13
<211> LENGTH: 45
<212> TYPE: DNA
<213> ORGANISM: Artificial Sequence
<220> FEATURE:
<223> OTHER INFORMATION: primer 28-H3f
<220> FEATURE:
<221> NAME/KEY: source
<222> LOCATION: (1)..(45)
<223> OTHER INFORMATION: /organism="Artificial Sequence"
    /note="primer 28-H3f" /mol_type="unassigned DNA"

<400> SEQUENCE: 13

```
tgtacatccg gaattctaga ttggtgagcg ctaggagtca ctgcc                     45
```

<210> SEQ ID NO 14
<211> LENGTH: 32
<212> TYPE: DNA
<213> ORGANISM: Artificial Sequence
<220> FEATURE:
<223> OTHER INFORMATION: primer 29-H3r
<220> FEATURE:
<221> NAME/KEY: source
<222> LOCATION: (1)..(32)
<223> OTHER INFORMATION: /organism="Artificial Sequence"
    /note="primer 29-H3r" /mol_type="unassigned DNA"

<400> SEQUENCE: 14

```
ctcgagtatt tcacaccgca tatgatccgt cg                                   32
```

<210> SEQ ID NO 15
<211> LENGTH: 6000
<212> TYPE: DNA
<213> ORGANISM: Artificial Sequence
<220> FEATURE:
<223> OTHER INFORMATION: pRN247 (TOPO- BLUNT-HIS3::loxPkanMXloxP
<220> FEATURE:
<221> NAME/KEY: source
<222> LOCATION: (1)..(6000)
<223> OTHER INFORMATION: /organism="Artificial Sequence"
    /note="pRN247 (TOPO- BLUNT-HIS3::loxPkanMXloxP)"
    /mol_type="unassigned DNA"

<400> SEQUENCE: 15

```
ggccgccaga tcttccggat ggctcgagtt tttcagcaag atcgcgagta tttcacaccg      60
catatgatcc gtcgagttca agagaaaaaa aagaaaaag caaaaagaaa aaggaaagc      120 gcgcctcgtt cagaatgaca cgtatagaat gatgcattac cttgtcatct tcagtatcat     180
```

```
actgttcgta tacatactta ctgacattca taggtataca tatatacaca tgtatatata    240
tcgtatgctg cagcttttaaa taatcggtgt cactacataa gaacaccttt ggtggaggga    300
acatcgttgg taccattggg cgaggtggct tctcttatgg caaccgcaag agccttgaac    360
gcactctcac tacggtgatg atcattcttg cctcgcagac aatcaacgtg gagggtaatt    420
ctgctagcct ctgcaaagct ttcaagaaaa tgcgggatca tctcgcaaga gagatctcct    480
actttctccc tttgcaaacc aagttcgaca actgcgtacg tataacttcg tatagcatac    540
attatacgaa gttattctag taacggccgc cagtgtgctg gaattcgccc ttaagcttgc    600
ctcgtccccg ccgggtcacc cggccagcga catggaggcc cagaataccc tccttgacag    660
tcttgacgtg cgcagctcag gggcatgatg tgactgtcgc ccgtacattt agcccataca    720
tccccatgta taatcatttg catccataca ttttgatggc cgcacggcgc gaagcaaaaa    780
ttacggctcc tcgctgcaga cctgcgagca gggaaacgct cccctcacag acgcgttgaa    840
ttgtccccac gccgcgcccc tgtagagaaa tataaaaggt taggatttgc cactgaggtt    900
cttctttcat atacttcctt ttaaaatctt gctaggatac agttctcaca tcacatccga    960
acataaacaa ccatgggtaa ggaaaagact cacgtttcga ggccgcgatt aaattccaac   1020
atggatgctg atttatatgg gtataaatgg ctcgcgata atgtcgggca atcaggtgcg   1080
acaatctatc gattgtatgg gaagcccgat gcgccagagt tgtttctgaa acatggcaaa   1140
ggtagcgttg ccaatgatgt tacagatgag atggtcagac taaactggct gacggaattt   1200
atgcctcttc cgaccatcaa gcattttatc cgtactcctg atgatgcatg gttactcacc   1260
actgcgatcc ccgcaaaac agcattccag gtattagaag aatatcctga ttcaggtgaa   1320
aatattgttg atgcgctggc agtgttcctg cgccggttgc attcgattcc tgtttgtaat   1380 tgtccttttta acagcgatcg cgtatttcgt ctcgctcagg cgcaatcacg aatgaataac   1440
ggtttggttg atgcgagtga ttttgatgac gagcgtaatg ctggcctgt tgaacaagtc    1500 tggaaagaaa tgcataagct tttgccattc tcaccggatt cagtcgtcac tcatggtgat   1560
ttctcacttg ataaccttat ttttgacgag gggaaattaa taggttgtat tgatgttgga   1620
cgagtcggaa tcgcagaccg ataccaggat cttgccatcc tatggaactg cctcggtgag   1680
ttttctcctt cattacagaa acggcttttt caaaaatatg gtattgataa tcctgatatg   1740
aataaattgc agtttcattt gatgctcgat gagttttttct aatcagtact gacaataaaa   1800
agattcttgt tttcaagaac ttgtcatttg tatagttttt ttatattgta gttgttctat   1860
tttaatcaaa tgttagcgtg atttatattt ttttcgcct cgacatcatc tgcccagatg   1920
cgaagttaag tgcgcagaaa gtaatatcat gcgtcaatcg tatgtgaatg ctggtcgcta   1980
tactgctgtc gattcgatac taacgccgcc atccagtgtc gacgatatct agagcgcgca   2040
taacttcgta taatgtatgc tatacgaagt tataggaaag gatcgcaat ctgaatcttg    2100 gtttcatttg taatacgctt tactagggct ttctgctctg tcatctttgc cttcgtttat   2160
cttgcctgct catttttag tatattcttc gaagaaatca cattacttta tataatgtat   2220
aattcattat gtgataatgc caatcgctaa gaaaaaaaa gagtcatccg ctaggtggaa   2280 aaaaaaaat gaaaatcatt accgaggcat aaaaaaatat agagtgtact agaggaggcc   2340
aagagtaata gaaaagaaa attgcgggaa aggactgtgt tatgacttcc ctgactaatg   2400
ccgtgttcaa acgatacctg gcagtgactc ctagcgctca ccaatctaga attccggatg   2460
tacaatcttt ctagagatc tcctacaata ttctcagctg cttaagggcg aattctgaga   2520
tatccatcac actggcggcc gctcgagcat gcatctagag ggcccaattc gccctatagt   2580
```

```
gagtcgtatt acaattcact ggccgtcgtt ttacaacgtc gtgactggga aaaccctggc    2640
gttacccaac ttaatcgcct tgcagcacat cccccttttcg ccagctggcg taatagcgaa   2700
gaggcccgca ccgatcgccc ttcccaacag ttgcgcagcc tatacgtacg gcagtttaag   2760
gtttacacct ataaaagaga gagccgttat cgtctgtttg tggatgtaca gagtgatatt   2820
attgacacgc cggggcgacg gatggtgatc cccctggcca gtgcacgtct gctgtcagat   2880
aaagtctccc gtgaacttta cccggtggtg catatcgggg atgaaagctg gcgcatgatg   2940
accaccgata tggccagtgt gccggtctcc gttatcgggg aagaagtggc tgatctcagc   3000
caccgcgaaa atgacatcaa aaacgccatt aacctgatgt tctggggaat ataaatgtca   3060
ggcatgagat tatcaaaaag gatcttcacc tagatccttt tcacgtagaa agccagtccg   3120
cagaaacggt gctgacccccg gatgaatgtc agctactggg ctatctggac aagggaaaac  3180
gcaagcgcaa agagaaagca ggtagcttgc agtgggctta catggcgata gctagactgg   3240
gcggttttat ggacagcaag cgaaccggaa ttgccagctg gggcgccctc tggtaaggtt   3300
gggaagccct gcaaagtaaa ctggatggct ttctcgccgc caaggatctg atggcgcagg   3360
ggatcaagct ctgatcaaga gacaggatga ggatcgtttc gcatgattga acaagatgga   3420
ttgcacgcag gttctccggc cgcttgggtg gagaggctat tcggctatga ctgggcacaa   3480
cagacaatcg gctgctctga tgccgccgtg ttccggctgt cagcgcaggg gcgcccggtt   3540
cttttttgtca agaccgacct gtccggtgcc ctgaatgaac tgcaagacga ggcagcgcgg  3600
ctatcgtggc tggccacgac gggcgttcct tgcgcagctg tgctcgacgt tgtcactgaa   3660
gcgggaaggg actggctgct attgggcgaa gtgccggggc aggatctcct gtcatctcac   3720
cttgctcctg ccgagaaagt atccatcatg gctgatgcaa tgcggcggct gcatacgctt   3780
gatccggcta cctgcccatt cgaccaccaa gcgaaacatc gcatcgagcg agcacgtact   3840
cggatggaag ccggtcttgt cgatcaggat gatctggacg aagagcatca ggggctcgcg   3900
ccagccgaac tgttcgccag gctcaaggcg agcatgcccg acggcgagga tctcgtcgtg   3960
acccatggcg atgcctgctt gccgaatatc atggtggaaa atggccgctt ttctggattc   4020
atcgactgtg gccggctggg tgtggcggac cgctatcagg acatagcgtt ggctacccgt   4080
gatattgctg aagagcttgg cggcgaatgg gctgaccgct tcctcgtgct ttacggtatc   4140
gccgctcccg attcgcagcg catcgccttc tatcgccttc ttgacgagtt cttctgaatt   4200
attaacgctt acaatttcct gatgcggtat tttctcctta cgcatctgtg cggtatttca   4260
caccgcatac aggtggcact tttcggggaa atgtgcgcgg aacccctatt tgtttatttt   4320
tctaaataca ttcaaatatg tatccgctca tgagacaata accctgataa atgcttcaat   4380
aatagcacgt gaggagggcc accatggcca agttgaccag tgccgttccg gtgctcaccg   4440
cgcgcgacgt cgccggagcg gtcgagttct ggaccgaccg gctcgggttc tcccgggact   4500
tcgtggagga cgacttcgcc ggtgtggtcc gggacgacgt gaccctgttc atcagcgcgg   4560
tccaggacca ggtggtgccg gacaacaccc tggcctgggt gtgggtgcgc ggcctggacg   4620
agctgtacgc cgagtggtcg gaggtcgtgt ccacgaactt ccgggacgcc tccgggccgg   4680
ccatgaccga gatcggcgag cagccgtggg ggcgggagtt cgccctgcgc gacccggccg   4740
gcaactgcgt gcacttcgtg gccgaggagc aggactgaca cgtgctaaaa cttcattttt   4800
aatttaaaag gatctaggtg aagatccttt ttgataatct catgaccaaa atcccttaac   4860
gtgagttttc gttccactga gcgtcagacc ccgtagaaaa gatcaaagga tcttcttgag   4920
```

```
atcctttttt tctgcgcgta atctgctgct tgcaaacaaa aaaaccaccg ctaccagcgg      4980
tggtttgttt gccggatcaa gagctaccaa ctcttttcc gaaggtaact ggcttcagca       5040
gagcgcagat accaaatact gtccttctag tgtagccgta gttaggccac cacttcaaga     5100
actctgtagc accgcctaca tacctcgctc tgctaatcct gttaccagtg gctgctgcca     5160
gtggcgataa gtcgtgtctt accgggttgg actcaagacg atagttaccg gataaggcgc     5220
agcggtcggg ctgaacgggg ggttcgtgca cacagcccag cttggagcga acgacctaca     5280
ccgaactgag atacctacag cgtgagctat gagaaagcgc cacgcttccc gaagggagaa     5340
aggcggacag gtatccggta agcggcaggg tcggaacagg agagcgcacg agggagcttc     5400 caggggaaa cgcctggtat ctttatagtc ctgtcgggtt tcgccacctc tgacttgagc      5460 gtcgatttt gtgatgctcg tcaggggggc ggagcctatg gaaaaacgcc agcaacgcgg      5520
cctttttacg gttcctgggc ttttgctggc cttttgctca catgttcttt cctgcgttat     5580
cccctgattc tgtggataac cgtattaccg cctttgagtg agctgatacc gctcgccgca     5640
gccgaacgac cgagcgcagc gagtcaagcg cccaatacga aaccgcctc tccccgcgcg      5700 ttggccgatt cattaatgca gctggcacga caggtttccc gactggaaag cgggcagtga    5760
gcgcaacgca attaatgtga gttagctcac tcattaggca ccccaggctt tacactttat   5820
gcttccggct cgtatgttgt gtggaattgt gagcggataa caatttcaca caggaaacag   5880
ctatgaccat gattacgcca agctatttag gtgacactat agaatactca agctatgcat  5940
caagcttggt accgagctcg gatccactag taacggccgc cagtgtgctg gaattcgccc   6000
```

<210> SEQ ID NO 16
<211> LENGTH: 35
<212> TYPE: DNA
<213> ORGANISM: Artificial Sequence
<220> FEATURE:
<223> OTHER INFORMATION: primer 201-Hx2uf
<220> FEATURE:
<221> NAME/KEY: source
<222> LOCATION: (1)..(35)
<223> OTHER INFORMATION: /organism="Artificial Sequence"
    /note="primer 201-Hx2uf" /mol_type="unassigned DNA"

<400> SEQUENCE: 16
gactagtacc ggtgttttca aaacctagca acccc                              35

<210> SEQ ID NO 17
<211> LENGTH: 43
<212> TYPE: DNA
<213> ORGANISM: Artificial Sequence
<220> FEATURE:
<223> OTHER INFORMATION: primer 202-Hx2ur
<220> FEATURE:
<221> NAME/KEY: source
<222> LOCATION: (1)..(43)
<223> OTHER INFORMATION: /organism="Artificial Sequence"
    /note="primer 202-Hx2ur" /mol_type="unassigned DNA"

<400> SEQUENCE: 17
cgtacgcgtc ttccggaagg gtaccatcag atttcatttg acc                     43

<210> SEQ ID NO 18
<211> LENGTH: 40
<212> TYPE: DNA
<213> ORGANISM: Artificial Sequence
<220> FEATURE:
<223> OTHER INFORMATION: primer 203-Hx2df
<220> FEATURE:
<221> NAME/KEY: source

```
<222> LOCATION: (1)..(40)
<223> OTHER INFORMATION: /organism="Artificial Sequence"
      /note="primer 203-Hx2df" /mol_type="unassigned DNA"

<400> SEQUENCE: 18
gaagacactc gagacgtcct ttgtctgtga aaccaagggc                              40

<210> SEQ ID NO 19
<211> LENGTH: 39
<212> TYPE: DNA
<213> ORGANISM: Artificial Sequence
<220> FEATURE:
<223> OTHER INFORMATION: primer 204-Hx2dr
<220> FEATURE:
<221> NAME/KEY: source
<222> LOCATION: (1)..(39)
<223> OTHER INFORMATION: /organism="Artificial Sequence"
      /note="primer 204-Hx2dr" /mol_type="unassigned DNA"

<400> SEQUENCE: 19
gtcgacgggc ccttatgttg gtcttgttta gtatggccg                               39

<210> SEQ ID NO 20
<211> LENGTH: 48
<212> TYPE: DNA
<213> ORGANISM: Artificial Sequence
<220> FEATURE:
<223> OTHER INFORMATION: primer 205-Hx3uf
<220> FEATURE:
<221> NAME/KEY: source
<222> LOCATION: (1)..(48)
<223> OTHER INFORMATION: /organism="Artificial Sequence"
      /note="primer 205-Hx3uf" /mol_type="unassigned DNA"

<400> SEQUENCE: 20
aagcggccgc actagtaccg gtgaaacaac tcaataacga tgtgggac                     48

<210> SEQ ID NO 21
<211> LENGTH: 38
<212> TYPE: DNA
<213> ORGANISM: Artificial Sequence
<220> FEATURE:
<223> OTHER INFORMATION: primer
      206-Hx3urATCCGGACGTCTTCCTCAAGAAATCAGTTTGGGCGACG
<220> FEATURE:
<221> NAME/KEY: source
<222> LOCATION: (1)..(38)
<223> OTHER INFORMATION: /organism="Artificial Sequence" /note="primer
      206-Hx3urATCCGGACGTCTTCCTCAAGAAATCAGTTTGGGCGACG"
      /mol_type="unassigned DNA"

<400> SEQUENCE: 21
atccggacgt cttcctcaag aaatcagttt gggcgacg                                38

<210> SEQ ID NO 22
<211> LENGTH: 44
<212> TYPE: DNA
<213> ORGANISM: Artificial Sequence
<220> FEATURE:
<223> OTHER INFORMATION: primer 210-Hx4df
<220> FEATURE:
<221> NAME/KEY: source
<222> LOCATION: (1)..(44)
<223> OTHER INFORMATION: /organism="Artificial Sequence"
      /note="primer 210-Hx4df" /mol_type="unassigned DNA"

<400> SEQUENCE: 22
agaagacgct cgagacgtcc cttatgggaa gaaggtgttt tgcc                         44
```

```
<210> SEQ ID NO 23
<211> LENGTH: 34
<212> TYPE: DNA
<213> ORGANISM: Artificial Sequence
<220> FEATURE:
<223> OTHER INFORMATION: primer 211-Hx4dr"
<220> FEATURE:
<221> NAME/KEY: source
<222> LOCATION: (1)..(34)
<223> OTHER INFORMATION: /organism="Artificial Sequence"
      /note="primer 211-Hx4dr" /mol_type="unassigned DNA"

<400> SEQUENCE: 23
atggatccta ggggttcttg cagagtaaac tgcg                              34

<210> SEQ ID NO 24
<211> LENGTH: 46
<212> TYPE: DNA
<213> ORGANISM: Artificial Sequence
<220> FEATURE:
<223> OTHER INFORMATION: primer 212-Hx5uf
<220> FEATURE:
<221> NAME/KEY: source
<222> LOCATION: (1)..(46)
<223> OTHER INFORMATION: /organism="Artificial Sequence"
      /note="primer 212-Hx5uf" /mol_type="unassigned DNA"

<400> SEQUENCE: 24
aagcggccgc actagtacat gtgaacttga aaacgctcat caaggc                 46

<210> SEQ ID NO 25
<211> LENGTH: 43
<212> TYPE: DNA
<213> ORGANISM: Artificial Sequence
<220> FEATURE:
<223> OTHER INFORMATION: primer 213-Hx5ur
<220> FEATURE:
<221> NAME/KEY: source
<222> LOCATION: (1)..(43)
<223> OTHER INFORMATION: /organism="Artificial Sequence"
      /note="primer 213-Hx5ur" /mol_type="unassigned DNA"

<400> SEQUENCE: 25
ttcgtacgcg tcttccggag taacatgaaa ccagagtacc acg                    43

<210> SEQ ID NO 26
<211> LENGTH: 42
<212> TYPE: DNA
<213> ORGANISM: Artificial Sequence
<220> FEATURE:
<223> OTHER INFORMATION: primer 229-Hx7df
<220> FEATURE:
<221> NAME/KEY: source
<222> LOCATION: (1)..(42)
<223> OTHER INFORMATION: /organism="Artificial Sequence"
      /note="primer 229-Hx7df" /mol_type="unassigned DNA"

<400> SEQUENCE: 26
agaagaccct cgagacgtcc gacgctgaag aaatgactca cg                     42

<210> SEQ ID NO 27
<211> LENGTH: 42
<212> TYPE: DNA
<213> ORGANISM: Artificial Sequence
<220> FEATURE:
<223> OTHER INFORMATION: primer 230-Hx7dr
<220> FEATURE:
<221> NAME/KEY: source
<222> LOCATION: (1)..(42)
<223> OTHER INFORMATION: /organism="Artificial Sequence"
      /note="primer 230-Hx7dr" /mol_type="unassigned DNA"
```

<400> SEQUENCE: 27
agtcgacgga tccgtaattt ttcttctttt aagtgacggg cg                    42

<210> SEQ ID NO 28
<211> LENGTH: 44
<212> TYPE: DNA
<213> ORGANISM: Artificial Sequence
<220> FEATURE:
<223> OTHER INFORMATION: primer 243-Gal2ufn
<220> FEATURE:
<221> NAME/KEY: source
<222> LOCATION: (1)..(44)
<223> OTHER INFORMATION: /organism="Artificial Sequence"
      /note="primer 243-Gal2ufn" /mol_type="unassigned DNA"

<400> SEQUENCE: 28
aagcggccgc actagtaccg gtgatctata ttcgaaaggg gcgg                  44

<210> SEQ ID NO 29
<211> LENGTH: 43
<212> TYPE: DNA
<213> ORGANISM: Artificial Sequence
<220> FEATURE:
<223> OTHER INFORMATION: primer 244-Gal2urn
<220> FEATURE:
<221> NAME/KEY: source
<222> LOCATION: (1)..(43)
<223> OTHER INFORMATION: /organism="Artificial Sequence"
      /note="primer 244-Gal2urn" /mol_type="unassigned DNA"

<400> SEQUENCE: 29
aacgtacgtc cggatcatta gaatactttt gagattgtgc gct                   43

<210> SEQ ID NO 30
<211> LENGTH: 43
<212> TYPE: DNA
<213> ORGANISM: Artificial Sequence
<220> FEATURE:
<223> OTHER INFORMATION: primer 233-Ga2df
<220> FEATURE:
<221> NAME/KEY: source
<222> LOCATION: (1)..(43)
<223> OTHER INFORMATION: /organism="Artificial Sequence"
      /note="primer 233-Ga2df" /mol_type="unassigned DNA"

<400> SEQUENCE: 30
agaagaccct cgagacgtct taccttggaa atctgaaggc tgg                   43

<210> SEQ ID NO 31
<211> LENGTH: 36
<212> TYPE: DNA
<213> ORGANISM: Artificial Sequence
<220> FEATURE:
<223> OTHER INFORMATION: primer 234-Ga2dr
<220> FEATURE:
<221> NAME/KEY: source
<222> LOCATION: (1)..(36)
<223> OTHER INFORMATION: /organism="Artificial Sequence"
      /note="primer 234-Ga2dr" /mol_type="unassigned DNA"

<400> SEQUENCE: 31
gtggatccta ggtaaaacgg tacgagaaaa gctccg                           36

<210> SEQ ID NO 32
<211> LENGTH: 5959
<212> TYPE: DNA
<213> ORGANISM: Artificial Sequence
<220> FEATURE:

<223> OTHER INFORMATION: pRN485; TOPO-BLUNT-GAL2::loxPzeoMXloxP
<220> FEATURE:
<221> NAME/KEY: source
<222> LOCATION: (1)..(5959)
<223> OTHER INFORMATION: /organism="Artificial Sequence" /note="pRN485; TOPO-BLUNT-GAL2::loxPzeoMXloxP" /mol_type="unassigned DNA"

<400> SEQUENCE: 32

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctat     240
ttaggtgaca ctatagaata ctcaagctat gcatcaagct tggtaccgag ctcggatcca     300
ctagtaacgg ccgccagtgt gctggaattc gcccttgtgg atcctaggaa tggatgatgg     360
taaaacggta cgagaaaagc tccgagacgt tgaattgaat attaataggt tgcaggttga     420
tataaaagaa ataaggaaa tgcttgttac actgataaac aaatgactga aaaaagcaac      480
tcctggatcg ttcgaacatt ctcactccat taattgtatg ttagctcagg aattcaactg     540
gaagaaagtc caggcaagta cctgacttat tttctagagg accccccaga gataagtctg     600
gtgatgtggt cctttaataa tttcataggg acaattcatt ttgcgttttt aattttgctc     660
ggtgaacaaa ggatggcaga gcatgttatc gttttctttt ttttttcctg ttttagagaa     720
aaaggttata tatgtaataa tactctgata tatgtacaca ataataggt ttaggtaagg      780
aatttatata atcgtaagga tatcattgat aagggaaatt ttttttttt ttttcaaac      840
aaatactatg ataattaaaa tgaagaaaaa acgtcagtca tgaaaaatta agagagatga     900
tggagcgtct cacttcaaac gcattattct agcatggcct tgtaccacgg tttgtcgtca     960
tgttgtaaat cctctaaatc gtaattatta cctcttctgg atgaaggaat ccagccttca    1020
gatttccaag gtaagacgtc tcgaggccta aacttcgta tagcatacat tatacgaagt     1080
tatgcgcgct ctagatatcg tcgacactgg atggcggcgt tagtatcgaa tcgacagcag    1140
tatagcgacc agcattcaca tacgattgac gcatgatatt actttctgcg cacttaactt    1200
cgcatctggg cagatgatgt cgaggcgaaa aaaaatataa atcacgctaa catttgatta    1260
aaatagaaca actacaatat aaaaaaacta tacaaatgac aagttcttga aaacaagaat    1320
ctttttattg tcagtgtgtc agtcctgctc ctcggccacg aagtgcacgc agttgccggc    1380
cgggtcgcgc agggcgaact cccgccccca cggctgctcg ccgatctcgg tcatggccgg    1440
cccggaggcg tccggaagt tcgtggacac gacctccgac cactcggcgt acagctcgtc    1500
caggccgcgc acccacaccc aggccagggt gttgtccggc accacctggt cctggaccgc    1560
gctgatgaac agggtcacgt cgtcccggac cacaccggcg aagtcgtcct ccacgaagtc    1620
ccgggagaac ccgagccggt cggtccagaa ctcgaccgct ccggcgacgt cgcgcgcggt    1680
gagcaccgga acggcactgg tcaacttggc catggttgtt tatgttcgga tgtgatgtga    1740
gaactgtatc ctagcaagat tttaaaagga agtatatgaa agaagaacct cagtggcaaa    1800
tcctaacctt ttatatttct ctacaggggc gcggcgtggg gacaattcaa cgcgtctgtg    1860
aggggagcgt ttccctgctc gcaggtctgc agcgaggagc cgtaattttt gcttcgcgcc    1920
gtgcggccat caaatgtat ggatgcaaat gattatacat ggggatgtat gggctaaatg    1980
tacgggcgac agtcacatca tgcccctgag ctgcgcacgt caagactgtc aaggagggta    2040
ttctgggcct ccatgtcgct ggccgggtga cccggcgggg acgaggcaag cttaagggcg    2100
```

```
aattccagca cactggcggc cgttactaga ataacttcgt ataatgtatg ctatacgaag   2160
ttatacgtac gtccggatca ttagaatact tttgagattg tgcgcttaaa tgggaatctt   2220
tactgagtga agagatcacg tcttcaccag cttggggttg ctgtgaaaca acaggcatat   2280
tgttctcctc aactgccatt atgaaagaat tatttttttt attatgttaa tcttgtgttt   2340
acttaactat tactattctt gatgataatt gaataaggtg cataatgaag agcaattcac   2400
aacaccaaat tttcaatcca attactgatt gtttatatat gtctacaaaa cttatcctat   2460
ctccacattt tagcctgcga aatgtttgtt ttttgaacaa tagctctcca gaatgttgta   2520
taatttaaga atatgtgcac agttaacttt ctagcaggag tataatgcca tttgctcccc   2580
atcttgagat gggaagggct taactaatct cggttcggag tgatccgccc cgatactgcc   2640
ttctgcctta atatcgtcca aggcacatgg acccctgaac ggcgcagata tctccgcacg   2700
gacgaaagac cgccggtgcc ttcctgaggc aaccgcccct ttcgaatata gatcaccggt   2760
actagtgcgg ccgcttaagg gcgaattctg cagatatcca tcacactggc ggccgctcga   2820
gcatgcatct agagggccca attcgcccta tagtgagtcg tattacaatt cactggccgt   2880
cgttttacaa cgtcgtgact gggaaaaccc tggcgttacc caacttaatc gccttgcagc   2940 acatcccccct ttcgccagct ggcgtaatag cgaagaggcc cgcaccgatc gcccttccca   3000
acagttgcgc agcctatacg tacggcagtt taaggtttac acctataaaa gagagagccg   3060
ttatcgtctg tttgtggatg tacagagtga tattattgac acgccggggc gacggatggt   3120 gatcccctg gccagtgcac gtctgctgtc agataaagtc tcccgtgaac tttacccggt   3180
ggtgcatatc ggggatgaaa gctggcgcat gatgaccacc gatatggcca gtgtgccggt   3240
ctccgttatc ggggaagaag tggctgatct cagccaccgc gaaaatgaca tcaaaaacgc   3300
cattaacctg atgttctggg aatataaat gtcaggcatg agattatcaa aaaggatctt   3360
cacctagatc cttttcacgt agaaagccag tccgcagaaa cggtgctgac cccggatgaa   3420
tgtcagctac tgggctatct ggacaaggga aaacgcaagc gcaaagagaa agcaggtagc   3480
ttgcagtggg cttacatggc gatagctaga ctgggcggtt ttatggacag caagcgaacc   3540
ggaattgcca gctggggcgc cctctggtaa ggttgggaag ccctgcaaag taaactggat   3600
ggctttctcg ccgccaagga tctgatggcg caggggatca agctctgatc aagagacagg   3660
atgaggatcg tttcgcatga ttgaacaaga tggattgcac gcaggttctc cggccgcttg   3720
ggtggagagg ctattcggct atgactgggc acaacagaca atcggctgct ctgatgccgc   3780
cgtgttccgg ctgtcagcgc aggggcgccc ggttcttttt gtcaagaccg acctgtccgg   3840
tgccctgaat gaactgcaag acgaggcagc gcggctatcg tggctggcca cgacgggcgt   3900
tccttgcgca gctgtgctcg acgttgtcac tgaagcggga agggactggc tgctattggg   3960
cgaagtgccg gggcaggatc tcctgtcatc tcaccttgct cctgccgaga agtatccat   4020 catggctgat gcaatgcggc ggctgcatac gcttgatccg gctacctgcc cattcgacca   4080
ccaagcgaaa catcgcatcg agcgagcacg tactcggatg aagccggtc ttgtcgatca   4140 ggatgatctg gacgaagagc atcaggggct cgcgccagcc gaactgttcg ccaggctcaa   4200
ggcgagcatg cccgacggcg aggatctcgt cgtgacccat ggcgatgcct gcttgccgaa   4260
tatcatggtg gaaaatggcc gcttttctgg attcatcgac tgtggccggc tgggtgtggc   4320
ggaccgctat caggacatag cgttggctac ccgtgatatt gctgaagagc ttggcggcga   4380
atgggctgac cgcttcctcg tgctttacgg tatcgccgct cccgattcgc agcgcatcgc   4440
cttctatcgc cttcttgacg agttcttctg aattattaac gcttacaatt tcctgatgcg   4500
```

```
gtattttctc cttacgcatc tgtgcggtat ttcacaccgc atacaggtgg cacttttcgg    4560
ggaaatgtgc gcggaacccc tatttgttta tttttctaaa tacattcaaa tatgtatccg    4620
ctcatgagac aataaccctg ataaatgctt caataatagc acgtgaggag ggccaccatg    4680
gccaagttga ccagtgccgt tccggtgctc accgcgcgcg acgtcgccgg agcggtcgag    4740
ttctggaccg accggctcgg gttctcccgg gacttcgtgg aggacgactt cgccggtgtg    4800
gtccgggacg acgtgaccct gttcatcagc gcggtccagg accaggtggt gccggacaac    4860
accctggcct gggtgtgggt gcgcggcctg gacgagctgt acgccgagtg gtcggaggtc    4920
gtgtccacga acttccggga cgcctccggg ccggccatga ccgagatcgg cgagcagccg    4980
tgggggcggg agttcgccct gcgcgacccg gccggcaact gcgtgcactt cgtggccgag    5040
gagcaggact gacacgtgct aaaacttcat ttttaattta aaaggatcta ggtgaagatc    5100
ctttttgata atctcatgac caaaatccct taacgtgagt tttcgttcca ctgagcgtca    5160
gaccccgtag aaaagatcaa aggatcttct tgagatcctt ttttttctgcg cgtaatctgc    5220 tgcttgcaaa caaaaaaacc accgctacca gcggtggttt gtttgccgga tcaagagcta    5280
ccaactcttt ttccgaaggt aactggcttc agcagagcgc agataccaaa tactgtcctt    5340
ctagtgtagc cgtagttagg ccaccacttc aagaactctg tagcaccgcc tacatacctc    5400
gctctgctaa tcctgttacc agtggctgct gccagtggcg ataagtcgtg tcttaccggg    5460
ttggactcaa gacgatagtt accggataag gcgcagcggt cgggctgaac ggggggttcg    5520
tgcacacagc ccagcttgga gcgaacgacc tacaccgaac tgagatacct acagcgtgag    5580
ctatgagaaa gcgccacgct tcccgaaggg agaaaggcgg acaggtatcc ggtaagcggc    5640
agggtcggaa caggagagcg cacgagggag cttccagggg gaaacgcctg gtatctttat    5700
agtcctgtcg ggtttcgcca cctctgactt gagcgtcgat ttttgtgatg ctcgtcaggg    5760
gggcggagcc tatggaaaaa cgccagcaac gcggcctttt tacggttcct ggcttttgc    5820 tggccttttg ctcacatgtt ctttcctgcg ttatccctg attctgtgga taaccgtatt    5880
accgcctttg agtgagctga taccgctcgc cgcagccgaa cgaccgagcg cagcgagtca    5940
gtgagcgagg aagcggaag                                                  5959
```

<210> SEQ ID NO 33
<211> LENGTH: 6384
<212> TYPE: DNA
<213> ORGANISM: Artificial Sequence
<220> FEATURE:
<223> OTHER INFORMATION: pRN566; TOPO-BLUNT-HXT367::loxP-hphMX-loxP
<220> FEATURE:
<221> NAME/KEY: source
<222> LOCATION: (1)..(6384)
<223> OTHER INFORMATION: /organism="Artificial Sequence" /note="pRN566;
    TOPO-BLUNT-HXT367::loxP-hphMX-loxP" /mol_type="unassigned DNA"

<400> SEQUENCE: 33

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctat     240
ttaggtgaca ctatagaata ctcaagctat gcatcaagct tggtaccgag ctcggatcca     300
ctagtaccgg tgaaacaact caataacgat gtgggacatt gggggcccac tcaaaaaatc     360
tggggactat atccccagag aatttctcca gaagagaaga aaagtcaaag ttttttttcg     420
```

-continued

```
cttgggggtt gcatataaat acaggcgctg ttttatcttc agcatgaata ttccataatt    480
ttacttaata gcttttcata aataatagaa tcacaaacaa aatttacatc tgagttaaac    540
aatcatgaat tcaactccag atttaatatc tccacaaaag tcaagtgaga attcgaatgc    600
tgacctgcct tcgaatagct ctcaggtaat gaacatgcct gaagaaaaag gtgttcaaga    660
tgatttccaa gctgaggccg accaagtact taccaaccca aatacaggta aggtgcata    720 tgtcactgtg tctatctgtt gtgttatggt tgccttcggt ggtttcgttt cggttggga    780 tactggtacc atttctggtt tcgtcgccca aactgatttc ttgaggaaga cgtccggacg    840
tacgtataac ttcgtatagc atacattata cgaagttatt ctagtaacgg ccgccagtgt    900
gctggaattc gcccttaagc ttgcctcgtc cccgccgggt cacccggcca gcgacatgga    960
ggcccagaat accctccttg acagtcttga cgtgcgcagc tcagggcat gatgtgactg    1020 tcgcccgtac atttagccca tacatcccca tgtataatca tttgcatcca tacattttga    1080
tggccgcacg gcgcgaagca aaaattacgg ctcctcgctg cagacctgcg agcagggaaa    1140
cgctcccctc acagacgcgt gaattgtccc cacgccgcgc ccctgtagag aaatataaaa    1200
ggttaggatt tgccactgag gttcttcttt catatacttc cttttaaaat cttgctagga    1260
tacagttctc acatcacatc cgaacataaa caaccatggg taaaaagcct gaactcaccg    1320
cgacgtctgt cgagaagttt ctgatcgaaa agttcgacag cgtctccgac ctgatgcagc    1380
tctcggaggg cgaagaatct cgtgctttca gcttcgatgt aggagggcgt ggatatgtcc    1440
tgcgggtaaa tagctgcgcc gatggtttct acaaagatcg ttatgtttat cggcactttg    1500
catcggccgc gctcccgatt ccggaagtgc ttgacattgg ggaattcagc gagagcctga    1560
cctattgcat ctcccgccgt gcacagggtg tcacgttgca agacctgcct gaaaccgaac    1620
tgcccgctgt tctgcagccg gtcgcggagg ccatggatgc gatcgctgcg gccgatctta    1680
gccagacgag cgggttcggc ccattcggac cgcaaggaat cggtcaatac actacatggc    1740
gtgatttcat atgcgcgatt gctgatcccc atgtgtatca ctggcaaact gtgatggacg    1800
acaccgtcag tgcgtccgtc gcgcaggctc tcgatgagct gatgctttgg gccgaggact    1860
gccccgaagt ccggcacctc gtgcacgcgg atttcggctc caacaatgtc ctgacggaca    1920
atggccgcat aacagcggtc attgactgga gcgaggcgat gttcggggat tcccaatacg    1980
aggtcgccaa catcttcttc tggaggccgt ggttggcttg tatggagcag cagacgcgct    2040
acttcgagcg gaggcatccg gagcttgcag gatcgccgcg gctccgggcg tatatgctcc    2100
gcattggtct tgaccaactc tatcagagct tggttgacgg caatttcgat gatgcagctt    2160
gggcgcaggg tcgatgcgac gcaatcgtcc gatccggagc cgggactgtc gggcgtacac    2220
aaatcgcccg cagaagcgcg gccgtctgga ccgatgctg tgtagaagta ctcgccgata    2280
gtggaaaccg acgccccagc actcgtccga gggcaaagga ataatcagta ctgacaataa    2340
aaagattctt gttttcaaga acttgtcatt tgtatagttt ttttatattg tagttgttct    2400
attttaatca aatgttagcg tgatttatat ttttttttcgc ctcgacatca tctgcccaga    2460
tgcgaagtta agtgcgcaga aagtaatatc atgcgtcaat cgtatgtgaa tgctggtcgc    2520
tatactgctg tcgattcgat actaacgccg ccatccagtg tcgaaaacga gctcgaattc    2580
atcgatgata tccatcacac tggcggccgc tcgacgatat ctagagcgcg cataacttcg    2640
tataatgtat gctatacgaa gttataggcc tcgagcgtc cgacgctgaa gaatgactc    2700 acgatgacaa gccattgtac aagagaatgt tcagcaccaa ataatttgcg aacacttta    2760
```

```
ttaattcatg atcacgctct aatttgtgca tttgaaatgt actctaattc taattttata    2820
tttttaatga tatcttgaaa agtaaatacg tttttaatat atacaaaata atacagttta    2880
attttcaagt ttttgatcat ttgttctcag aaagttgagt gggacggaga caaagaaact    2940
ttaaagagaa atgcaaagtg ggaagaagtc agttgtttac cgaccgcact gttattcaca    3000
aatattccaa tttttgcctgc agacccacgt ctacaaattt tggttagttt ggtaaatggt    3060
aaggatatag tagagccttt ttgaaatggg aaatatcttc tttttctgta tcccgcttca    3120
aaaagtgtct aatgagtcag ttatttcttt cttactcatc gcccgtcact taaaagaaga    3180
aaaattacgg atccgtcgac taagggcgaa ttctgcagat atccatcaca ctggcggccg    3240
ctcgagcatg catctagagg gcccaattcg ccctatagtg agtcgtatta caattcactg    3300
gccgtcgttt tacaacgtcg tgactgggaa accctggcg ttacccaact taatcgcctt    3360
gcagcacatc cccctttcgc cagctggcgt aatagcgaag aggcccgcac cgatcgccct    3420
tcccaacagt tgcgcagcct atacgtacgg cagtttaagg tttacaccta taaagagag    3480 agccgttatc gtctgtttgt ggatgtacag agtgatatta ttgacacgcc ggggcgacgg    3540
atggtgatcc ccctggccag tgcacgtctg ctgtcagata aagtctcccg tgaactttac    3600
ccggtggtgc atatcgggga tgaaagctgg cgcatgatga ccaccgatat ggccagtgtg    3660
ccggtctccg ttatcgggga agaagtggct gatctcagcc accgcgaaaa tgacatcaaa    3720
aacgccatta acctgatgtt ctggggaata taaatgtcag gcatgagatt atcaaaaagg    3780
atcttcacct agatccttttt cacgtagaaa gccagtccgc agaaacggtg ctgaccccgg    3840
atgaatgtca gctactgggc tatctggaca agggaaaacg caagcgcaaa gagaaagcag    3900
gtagcttgca gtgggcttac atggcgatag ctagactggg cggttttatg gacagcaagc    3960
gaaccggaat tgccagctgg ggcgccctct ggtaaggttg gaagccctg caaagtaaac    4020 tggatggctt tctcgccgcc aaggatctga tggcgcaggg gatcaagctc tgatcaagag    4080
acaggatgag gatcgtttcg catgattgaa caagatggat tgcacgcagg ttctccggcc    4140
gcttgggtgg agaggctatt cggctatgac tgggcacaac agacaatcgg ctgctctgat    4200
gccgccgtgt tccggctgtc agcgcagggg cgcccggttc ttttttgtcaa gaccgacctg    4260 tccggtgccc tgaatgaact gcaagacgag gcagcgcggc tatcgtggct ggccacgacg    4320
ggcgttcctt gcgcagctgt gctcgacgtt gtcactgaag cgggaaggga ctggctgcta    4380
ttgggcgaag tgccggggca ggatctcctg tcatctcacc ttgctcctgc cgagaaagta    4440
tccatcatgg ctgatgcaat gcggcggctg catacgcttg atccggctac ctgcccattc    4500
gaccaccaag cgaaacatcg catcgagcga gcacgtactc ggatggaagc cggtcttgtc    4560
gatcaggatg atctggacga agagcatcag gggctcgcgc cagccgaact gttcgccagg    4620
ctcaaggcga gcatgcccga cggcgaggat ctcgtcgtga cccatggcga tgcctgcttg    4680
ccgaatatca tggtggaaaa tggccgcttt tctggattca tcgactgtgg ccggctgggt    4740
gtggcggacc gctatcagga catagcgttg gctacccgtg atattgctga agagcttggc    4800
ggcgaatggg ctgaccgctt cctcgtgctt tacggtatcg ccgctcccga ttcgcagcgc    4860
atcgccttct atcgccttct tgacgagttc ttctgaatta ttaacgctta caatttcctg    4920
atgcggtatt ttctccttac gcatctgtgc ggtatttcac accgcataca ggtggcactt    4980
ttcggggaaa tgtgcgcgga accccctattt gtttattttt ctaaatacat tcaaatatgt    5040
atccgctcat gagacaataa ccctgataaa tgcttcaata atagcacgtg aggagggcca    5100
ccatggccaa gttgaccagt gccgttccgg tgctcaccgc gcgcgacgtc gccggagcgg    5160
```

```
tcgagttctg gaccgaccgg ctcgggttct cccgggactt cgtggaggac gacttcgccg    5220
gtgtggtccg ggacgacgtg accctgttca tcagcgcggt ccaggaccag gtggtgccgg    5280
acaacaccct ggcctgggtg tgggtgcgcg gcctggacga gctgtacgcc gagtggtcgg    5340
aggtcgtgtc cacgaacttc cgggacgcct ccgggccggc catgaccgag atcggcgagc    5400
agccgtgggg gcgggagttc gccctgcgcg acccggccgg caactgcgtg cacttcgtgg    5460
ccgaggagca ggactgacac gtgctaaaac ttcattttta atttaaaagg atctaggtga    5520
agatcctttt tgataatctc atgaccaaaa tcccttaacg tgagttttcg ttccactgag    5580
cgtcagaccc cgtagaaaag atcaaaggat cttcttgaga tccttttttt ctgcgcgtaa    5640
tctgctgctt gcaaacaaaa aaaccaccgc taccagcggt ggtttgtttg ccggatcaag    5700
agctaccaac tctttttccg aaggtaactg gcttcagcag agcgcagata ccaaatactg    5760
tccttctagt gtagccgtag ttaggccacc acttcaagaa ctctgtagca ccgcctacat    5820
acctcgctct gctaatcctg ttaccagtgg ctgctgccag tggcgataag tcgtgtctta    5880
ccgggttgga ctcaagacga tagttaccgg ataaggcgca gcggtcgggc tgaacggggg    5940
gttcgtgcac acagcccagc ttggagcgaa cgacctacac cgaactgaga tacctacagc    6000
gtgagctatg agaaagcgcc acgcttcccg aagggagaaa ggcggacagg tatccggtaa    6060
gcggcagggt cggaacagga gagcgcacga gggagcttcc agggggaaac gcctggtatc    6120
tttatagtcc tgtcgggttt cgccacctct gacttgagcg tcgatttttg tgatgctcgt    6180
caggggggcg gagcctatgg aaaaacgcca gcaacgcggc cttttacgg ttcctgggct    6240 tttgctggcc ttttgctcac atgttctttc ctgcgttatc ccctgattct gtggataacc    6300
gtattaccgc ctttgagtga gctgataccg ctcgccgcag ccgaacgacc gagcgcagcg    6360
agtcagtgag cgaggaagcg gaag                                          6384
```

<210> SEQ ID NO 34
<211> LENGTH: 6073
<212> TYPE: DNA
<213> ORGANISM: Artificial Sequence
<220> FEATURE:
<223> OTHER INFORMATION: pRN569: TOPO-BLUNT-HXT514::loxP-natMX-loxP
<220> FEATURE:
<221> NAME/KEY: source
<222> LOCATION: (1)..(6073)
<223> OTHER INFORMATION: /organism="Artificial Sequence" /note="pRN569:
      TOPO-BLUNT-HXT514::loxP-natMX-loxP" /mol_type="unassigned DNA"

<400> SEQUENCE: 34

```
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagctat    240
ttaggtgaca ctatagaata ctcaagctat gcatcaagct tggtaccgag ctcggatcca    300
ctagtaacgg ccgccagtgt gctggaattc gcccttatgg atcctagggg ttcttgcaga    360
gtaaactgcg attcttcaga taaactatcc cgaacatatt gacccacttt caggtaggtc    420
attcaaagct ttttgattga cggtagatca agttgtgtt ctacgtattt acgtctttt     480 tgtcgtattt attgatgacc ttttgccatc gttaagtgga gaattcggcc tattcctaac    540
ctcttccaga actttgaaac aaaaaacata attcaaaatt gtagtttgat aaagtattat    600
ctataaacta ttaaatcata aatatatatt tcatagagcg ttaaaaattg aagatcaaat    660
```

```
attattttta ttccttgaag gaagtctata ttatttaatt aactgaccta cttttttccg    720
aacatcttct tgtaaaatgg ttgatcatca tgcattagat catcagcgtt gtagtcagta    780
cctctcttgt ttggtggaac ccaagaaggt gatttccatg gcaaacacc ttcttcccat     840 aagggacgtc tcgaggccta taacttcgta tagcatacat tatacgaagt tatgcgcgct    900
ctagatatcg tcgacactgg atggcggcgt tagtatcgaa tcgacagcag tatagcgacc    960
agcattcaca tacgattgac gcatgatatt actttctgcg cacttaactt cgcatctggg   1020
cagatgatgt cgaggcgaaa aaaatataa atcacgctaa catttgatta aaatagaaca    1080
actacaatat aaaaaaacta tacaaatgac aagttcttga aaacaagaat ctttttattg   1140
tcagtactag gggcagggca tgctcatgta gagcgcctgc tcgccgtccg aggcggtgcc   1200
gtcgtacagg gcggtgtcca ggccgcagag ggtgaacccc atccgccggt acgcgtggat   1260
cgccggtgcg ttgacgttgg tgacctccag ccagaggtgc ccggcgcccc gctcgcgggc   1320
gaactccgtc gcgagcccca tcaacgcgcg cccgaccccg tgccccggt gctccggggc    1380 gacctcgatg tcctcgacgg tcagccggcg gttccagccg gagtacgaga cgaccacgaa   1440
gcccgccagg tcgccgtcgt ccccgtacgc gacgaacgtc cgggagtccg ggtcgccgtc   1500
ctccccggcg tccgattcgt cgtccgattc gtcgtcgggg aacaccttgg tcaggggcgg   1560
gtccaccggc acctcccgca gggtgaagcc gtccccggtg gcggtgacgc ggaagacggt   1620
gtcggtggtg aaggacccat ccagtgcctc gatggcctcg gcgtcccccg ggacactggt   1680
gcggtaccgg taagccgtgt cgtcaagagt ggtcattta catggttgtt tatgttcgga    1740
tgtgatgtga gaactgtatc ctagcaagat tttaaaagga agtatatgaa agaagaacct   1800
cagtggcaaa tcctaacctt ttatatttct ctacagggc gcggcgtggg gacaattcaa    1860
cgcgtctgtg aggggagcgt ttccctgctc gcaggtctgc agcgaggagc cgtaattttt   1920
gcttcgcgcc gtgcgccat caaaatgtat ggatgcaaat gattatacat ggggatgtat    1980
gggctaaatg tacgggcgac agtcacatca tgcccctgag ctgcgcacgt caagactgtc   2040
aaggagggta ttctgggcct ccatgtcgct ggccgggtga cccggcgggg acgaggcaag   2100
cttaagggcg aattccagca cactggcggc cgttactaga taacttcgt ataatgtatg    2160 ctatacgaag ttatacgtac gtccggagta acatgaaacc agagtaccac gcaactgctt   2220
aggcgacact tcagaaatta gcataggcgc caaaactgta ataccaccaa cgcccagtcc   2280
tgagatgatt cttccaatga aatattgata ccatttgtca atggaggcga tttggatgat   2340
gatcccaatt gagtaaatga cgacaacagt catcagacca atcttacgtc catacatatc   2400
accgagcttt gacaaaacta tacctccgat agcgcagccg atgttgaaaa tagaaaccat   2460
caaaccggtt ctgacatcgg aaagataggt agtcccgttt gcacgggtgc tgccaaatcg   2520
cctaatgaag tctgtttgcc tgacaaaacc agatatagta ccagtatccc acccaaacac   2580
gaacccacca aaagcaacca tcaaacagca gacggataca aatagtaaat ccgacttcga   2640
tttcttctct agttggttgt caacctcctt ctgaagctct tccagttcgt ctttgggagg   2700
gccttcatgg gaaatgtaac ttgagacggg tttagcttgt gccaaattat cgttgtaacc   2760
ggcggtacca ggagcagtcg agtttcctga cttctcgttg tatgagttag aatttgtgct   2820
cacagtagca gacccttcca aggggccttg atgagcgttt tcaagttcac atgtactagt   2880
gcggccgctt aagggcgaat tctgcagata tccatcacac tggcggccgc tcgagcatgc   2940
atctagaggg cccaattcgc cctatagtga gtcgtattac aattcactgg ccgtcgtttt   3000
```

```
acaacgtcgt gactgggaaa accctggcgt tacccaactt aatcgccttg cagcacatcc   3060
cccttcgcc  agctggcgta atagcgaaga ggcccgcacc gatcgccctt cccaacagtt   3120
gcgcagccta tacgtacggc agtttaaggt ttacacctat aaaagagaga gccgttatcg   3180
tctgtttgtg gatgtacaga gtgatattat tgacacgccg gggcgacgga tggtgatccc   3240
cctggccagt gcacgtctgc tgtcagataa agtctcccgt gaactttacc cggtggtgca   3300
tatcggggat gaaagctggc gcatgatgac caccgatatg gccagtgtgc cggtctccgt   3360
tatcggggaa gaagtggctg atctcagcca ccgcgaaaat gacatcaaaa acgccattaa   3420
cctgatgttc tggggaatat aaatgtcagg catgagatta tcaaaaagga tcttcaccta   3480
gatccttttc acgtagaaag ccagtccgca gaaacggtgc tgaccccgga tgaatgtcag   3540
ctactgggct atctgacaa  gggaaaacgc aagcgcaaag agaaagcagg tagcttgcag   3600
tgggcttaca tggcgatagc tagactgggc ggttttatgg acagcaagcg aaccggaatt   3660
gccagctggg gcgccctctg gtaaggttgg gaagccctgc aaagtaaact ggatggcttt   3720
ctcgccgcca aggatctgat ggcgcagggg atcaagctct gatcaagaga caggatgagg   3780
atcgtttcgc atgattgaac aagatggatt gcacgcaggt tctccggccg cttgggtgga   3840
gaggctattc ggctatgact gggcacaaca gacaatcggc tgctctgatg ccgccgtgtt   3900
ccggctgtca gcgcaggggc gcccggttct ttttgtcaag accgacctgt ccggtgccct   3960
gaatgaactg caagacgagg cagcgcggct atcgtggctg gccacgacgg gcgttccttg   4020
cgcagctgtg ctcgacgttg tcactgaagc gggaagggac tggctgctat tgggcgaagt   4080
gccggggcag gatctcctgt catctcacct tgctcctgcc gagaaagtat ccatcatggc   4140
tgatgcaatg cggcggctgc atacgcttga tccggctacc tgcccattcg accaccaagc   4200
gaaacatcgc atcgagcgag cacgtactcg gatggaagcc ggtcttgtcg atcaggatga   4260
tctggacgaa gagcatcagg ggctcgcgcc agccgaactg ttcgccaggc tcaaggcgag   4320
catgcccgac ggcgaggatc tcgtcgtgac ccatggcgat gcctgcttgc cgaatatcat   4380
ggtggaaaat ggccgctttt ctggattcat cgactgtggc cggctgggtg tggcggaccg   4440
ctatcaggac atagcgttgg ctacccgtga tattgctgaa gagcttggcg gcgaatgggc   4500
tgaccgcttc ctcgtgcttt acggtatcgc cgctcccgat tcgcagcgca tcgccttcta   4560
tcgccttctt gacgagttct tctgaattat taacgcttac aatttcctga tgcggtattt   4620
tctccttacg catctgtgcg gtatttcaca ccgcatacag gtggcacttt tcggggaaat   4680
gtgcgcggaa cccctatttg tttattttc  taaatacatt caaatatgta tccgctcatg   4740
agacaataac cctgataaat gcttcaataa tagcacgtga ggagggccac catggccaag   4800
ttgaccagtg ccgttccggt gctcaccgcg cgcgacgtcg ccggagcggt cgagttctgg   4860
accgaccggc tcgggttctc ccgggacttc gtggaggacg acttcgccgg tgtggtccgg   4920
gacgacgtga ccctgttcat cagcgcggtc caggaccagg tggtgccgga caacaccctg   4980
gcctgggtgt gggtgcgcgg cctggacgag ctgtacgccg agtggtcgga ggtcgtgtcc   5040
acgaacttcc gggacgcctc cgggccggcc atgaccgaga tcggcgagca gccgtggggg   5100
cgggagttcg ccctgcgcga cccggccggc aactgcgtgc acttcgtggc cgaggagcag   5160
gactgacacg tgctaaaact tcattttta  tttaaaagga tctaggtgaa gatcctttt    5220
gataatctca tgaccaaaat cccttaacgt gagttttcgt tccactgagc gtcagacccc   5280
gtagaaaaga tcaaaggatc ttcttgagat cctttttttc tgcgcgtaat ctgctgcttg   5340
caaacaaaaa aaccaccgct accagcggtg gtttgtttgc cggatcaaga gctaccaact   5400
```

```
cttttttccga aggtaactgg cttcagcaga gcgcagatac caaatactgt ccttctagtg    5460
tagccgtagt taggccacca cttcaagaac tctgtagcac cgcctacata cctcgctctg    5520
ctaatcctgt taccagtggc tgctgccagt ggcgataagt cgtgtcttac cgggttggac    5580
tcaagacgat agttaccgga taaggcgcag cggtcgggct gaacgggggg ttcgtgcaca    5640
cagcccagct tggagcgaac gacctacacc gaactgagat acctacagcg tgagctatga    5700
gaaagcgcca cgcttcccga agggagaaag gcggacaggt atccggtaag cggcagggtc    5760
ggaacaggag agcgcacgag ggagcttcca gggggaaacg cctggtatct ttatagtcct    5820
gtcgggtttc gccacctctg acttgagcgt cgatttttgt gatgctcgtc aggggggcgg    5880
agcctatgga aaaacgccag caacgcggcc ttttttacggt tcctgggctt ttgctggcct    5940
tttgctcaca tgttctttcc tgcgttatcc cctgattctg tggataaccg tattaccgcc    6000
tttgagtgag ctgataccgc tcgccgcagc cgaacgaccg agcgcagcga gtcagtgagc    6060
gaggaagcgg aag                                                        6073
```

<210> SEQ ID NO 35
<211> LENGTH: 6189
<212> TYPE: DNA
<213> ORGANISM: Artificial Sequence
<220> FEATURE:
<223> OTHER INFORMATION: pRN635; TOPO-BLUNT-HXT2::loxP-kanMX-loxP
<220> FEATURE:
<221> NAME/KEY: source
<222> LOCATION: (1)..(6189)
<223> OTHER INFORMATION: /organism="Artificial Sequence" /note="pRN635;
      TOPO-BLUNT-HXT2::loxP-kanMX-loxP" /mol_type="unassigned DNA"

<400> SEQUENCE: 35

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctat     240
ttaggtgaca ctatagaata ctcaagctat gcatcaagct tggtaccgag ctcggatcca     300
ctagtaacgg ccgccagtgt gctggaattc gcccttgact agtaccggtg ttttcaaaac     360
ctagcaaccc ccaccaaact tgtcatcgtt cccggattca caaatgatat aaaaagcgat     420
tacaattcta cattctaacc agatttgaga tttcctcttt ctcaattcct cttatattag     480
attataagaa caacaaatta aattacaaaa agacttataa agcaacataa tgtctgaatt     540
cgctactagc cgcgttgaaa gtggctctca acaaacttct atccactcta ctccgatagt     600
gcagaaatta gagacggatg aatctcctat tcaaaccaaa tctgaataca ctaacgctga     660
actcccagca aagccaatcg ccgcatattg gactgttatc tgtttatgtc taatgattgc     720
atttggtggg tttgtctttg gttgggatac tggtaccatc tctggttttg ttaatcaaac     780
cgatttcaaa agaagatttg gtcaaatgaa atctgatggt accttccgga agacgcgtac     840
gtataacttc gtatagcata cattatacga agttattcta gtaacggccg ccagtgtgct     900
ggaattcgcc cttaagcttg cctcgtcccc gccgggtcac ccggccagcg acatggaggc     960
ccagaatacc ctccttgaca gtcttgacgt gcgcagctca ggggcatgat gtgactgtcg    1020
cccgtacatt tagcccatac atccccatgt ataatcattt gcatccatac attttgatgg    1080
ccgcacggcg cgaagcaaaa attacggctc tcgctgcag acctgcgagc agggaaacgc    1140 tccccctcaca gacgcgttga attgtcccca cgccgcgccc ctgtagagaa atataaaagg    1200
```

```
ttaggatttg ccactgaggt tcttctttca tatacttcct tttaaaatct tgctaggata    1260
cagttctcac atcacatccg aacataaaca accatgggta aggaaaagac tcacgtttcg    1320
aggccgcgat taaattccaa catggatgct gatttatatg ggtataaatg ggctcgcgat    1380
aatgtcgggc aatcaggtgc gacaatctat cgattgtatg gaagcccga tgcgccagag    1440 ttgtttctga acatggcaa aggtagcgtt gccaatgatg ttacagatga gatggtcaga    1500
ctaaactggc tgacggaatt tatgcctctt ccgaccatca agcatttat ccgtactcct    1560 gatgatgcat ggttactcac cactgcgatc cccggcaaaa cagcattcca ggtattagaa    1620
gaatatcctg attcaggtga aaatattgtt gatgcgctgg cagtgttcct gcgccggttg    1680
cattcgattc ctgtttgtaa ttgtccttt aacagcgatc gcgtatttcg tctcgctcag    1740
gcgcaatcac gaatgaataa cggtttggtt gatgcgagtg attttgatga cgagcgtaat    1800
ggctggcctg ttgaacaagt ctggaaagaa atgcataagc ttttgccatt ctcaccggat    1860
tcagtcgtca ctcatggtga tttctcactt gataaccta ttttttgacga ggggaaatta    1920 ataggttgta ttgatgttgg acgagtcgga atcgcagacc gataccagga tcttgccatc    1980
ctatggaact gcctcggtga gttttctcct tcattacaga aacggctttt tcaaaaatat    2040
ggtattgata atcctgatat gaataaattg cagtttcatt tgatgctcga tgagttttc    2100 taatcagtac tgacaataaa aagattcttg ttttcaagaa cttgtcattt gtatagtttt    2160
tttatattgt agttgttcta ttttaatcaa atgttagcgt gatttatatt ttttttcgcc    2220
tcgacatcat ctgcccagat gcgaagttaa gtgcgcagaa agtaatatca tgcgtcaatc    2280
gtatgtgaat gctggtcgct atactgctgt cgattcgata ctaacgccgc catccagtgt    2340
cgacgatatc tagagcgcgc ataacttcgt ataatgtatg ctatacgaag ttataggcct    2400
cgagacgtcc tttgtctgtg aaaccaaggg cttaacatta gaggaagtta atgaaatgta    2460
tgttgaaggt gtcaaaccat ggaaatctgg tagctggatc tcaaaagaaa aaagagtttc    2520
cgaggaataa gagattatac ttaaactagc actgattttt ttaaggctaa tggctactaa    2580
tactttaata gatgatcttc atactttttt atttaacgat ttttaatgat gttttattt    2640 gtaccactca tttatctaga ttttttaat actgatcaaa tcttacggac tcgacgttaa    2700
aaagttccta catacgtctg gtacttgaaa cgctgcttcg aggtattgac actataagaa    2760
tacgatccaa atacttacac cgcatgtaaa aatatgccga caatatgaat acttgttgat    2820
gaatgatatt tgattttaat ccggcaattt acctccttta tataatccaa taattgttga    2880
taattagtgg ttaggttgca gtactaataa gaattaagac aaatattctt ctactatata    2940
aaaggtgcaa acaaaacaca cgccgatcgg ccatactaaa caagaccaac ataagggccc    3000
gtcgacaagg gcgaattctg cagatatcca tcacactggc ggccgctcga gcatgcatct    3060
agagggccca attcgcccta gtgagtcg tattacaatt cactggccgt cgttttacaa    3120
cgtcgtgact gggaaaaccc tggcgttacc caacttaatc gccttgcagc acatcccct    3180 ttcgccagct ggcgtaatag cgaagaggcc cgcaccgatc gcccttccca acagttgcgc    3240
agcctatacg tacggcagtt taaggtttac acctataaaa gagagagccg ttatcgtctg    3300
tttgtggatg tacagagtga tattattgac acgccggggc gacggatggt gatcccctg    3360 gccagtgcac gtctgctgtc agataaagtc tcccgtgaac tttacccggt ggtgcatatc    3420
ggggatgaaa gctggcgcat gatgaccacc gatatggcca gtgtgccggt ctccgttatc    3480
ggggaagaag tggctgatct cagccaccgc gaaaatgaca tcaaaaacgc cattaacctg    3540
```

```
atgttctggg gaatataaat gtcaggcatg agattatcaa aaaggatctt cacctagatc    3600
cttttcacgt agaaagccag tccgcagaaa cggtgctgac cccggatgaa tgtcagctac    3660
tgggctatct ggacaaggga aaacgcaagc gcaaagagaa agcaggtagc ttgcagtggg    3720
cttacatggc gatagctaga ctgggcggtt ttatggacag caagcgaacc ggaattgcca    3780
gctggggcgc cctctggtaa ggttgggaag ccctgcaaag taaactggat ggctttctcg    3840
ccgccaagga tctgatggcg caggggatca agctctgatc aagagacagg atgaggatcg    3900
tttcgcatga ttgaacaaga tggattgcac gcaggttctc cggccgcttg ggtggagagg    3960
ctattcggct atgactgggc acaacagaca atcggctgct ctgatgccgc cgtgttccgg    4020
ctgtcagcgc aggggcgccc ggttcttttt gtcaagaccg acctgtccgg tgccctgaat    4080
gaactgcaag acgaggcagc gcggctatcg tggctggcca cgacgggcgt tccttgcgca    4140
gctgtgctcg acgttgtcac tgaagcggga agggactggc tgctattggg cgaagtgccg    4200
gggcaggatc tcctgtcatc tcaccttgct cctgccgaga agtatccat catggctgat    4260
gcaatgcggc ggctgcatac gcttgatccg gctacctgcc cattcgacca ccaagcgaaa    4320
catcgcatcg agcgagcacg tactcggatg aagccggtc ttgtcgatca ggatgatctg    4380
gacgaagagc atcaggggct cgcgccagcc gaactgttcg ccaggctcaa ggcgagcatg    4440
cccgacggcg aggatctcgt cgtgacccat ggcgatgcct gcttgccgaa tatcatggtg    4500
gaaaatggcc gcttttctgg attcatcgac tgtggccggc tgggtgtggc ggaccgctat    4560
caggacatag cgttggctac ccgtgatatt gctgaagagc ttggcggcga atgggctgac    4620
cgcttcctcg tgctttacgg tatcgccgct cccgattcgc agcgcatcgc cttctatcgc    4680
cttcttgacg agttcttctg aattattaac gcttacaatt tcctgatgcg gtattttctc    4740
cttacgcatc tgtgcggtat ttcacaccgc atacaggtgg cactttcgg ggaaatgtgc    4800
gcggaacccc tatttgttta ttttctaaa tacattcaaa tatgtatccg ctcatgagac    4860
aataaccctg ataaatgctt caataatagc acgtgaggag gccaccatg gccaagttga    4920
ccagtgccgt tccggtgctc accgcgcgcg acgtcgccgg agcggtcgag ttctggaccg    4980
accggctcgg gttctcccgg gacttcgtgg aggacgactt cgccggtgtg gtccgggacg    5040
acgtgaccct gttcatcagc gcggtccagg accaggtggt gccggacaac accctggcct    5100
gggtgtgggt gcgcggcctg gacgagctgt acgccgagtg gtcggaggtc gtgtccacga    5160
acttccggga cgcctccggg ccggccatga ccgagatcgg cgagcagccg tggggcggg    5220
agttcgccct gcgcgacccg gccggcaact gcgtgcactt cgtggccgag gagcaggact    5280
gacacgtgct aaaacttcat ttttaattta aaaggatcta ggtgaagatc cttttgata    5340
atctcatgac caaaatccct taacgtgagt tttcgttcca ctgagcgtca gaccccgtag    5400
aaaagatcaa aggatcttct tgagatcctt tttttctgcg cgtaatctgc tgcttgcaaa    5460
caaaaaaacc accgctacca gcggtggttt gtttgccgga tcaagagcta ccaactcttt    5520
ttccgaaggt aactggcttc agcagagcgc agataccaaa tactgtcctt ctagtgtagc    5580
cgtagttagg ccaccacttc aagaactctg tagcaccgcc tacatacctc gctctgctaa    5640
tcctgttacc agtggctgct gccagtgcg ataagtcgtg tcttaccggg ttggactcaa    5700
gacgatagtt accggataag gcgcagcggt cgggctgaac ggggggttcg tgcacacagc    5760
ccagcttgga gcgaacgacc tacaccgaac tgagatacct acagcgtgag ctatgagaaa    5820
gcgccacgct tcccgaaggg agaaaggcgg acaggtatcc ggtaagcggc agggtcgaa    5880
caggagagcg cacgagggag cttccagggg gaaacgcctg gtatctttat agtcctgtcg    5940
```

```
ggtttcgcca cctctgactt gagcgtcgat ttttgtgatg ctcgtcaggg gggcggagcc    6000
tatggaaaaa cgccagcaac gcggccttt tacggttcct gggcttttgc tggccttttg    6060
ctcacatgtt ctttcctgcg ttatcccctg attctgtgga taaccgtatt accgcctttg    6120
agtgagctga taccgctcgc cgcagccgaa cgaccgagcg cagcgagtca gtgagcgagg    6180
aagcggaag                                                           6189
```

<210> SEQ ID NO 36
<211> LENGTH: 24
<212> TYPE: DNA
<213> ORGANISM: Artificial Sequence
<220> FEATURE:
<223> OTHER INFORMATION: primer 281-Hx3inr2
<220> FEATURE:
<221> NAME/KEY: source
<222> LOCATION: (1)..(24)
<223> OTHER INFORMATION: /organism="Artificial Sequence"
      /note="primer 281-Hx3inr2" /mol_type="unassigned DNA"

<400> SEQUENCE: 36
gctcttttca cggagaaatt cggg                                           24

<210> SEQ ID NO 37
<211> LENGTH: 22
<212> TYPE: DNA
<213> ORGANISM: Artificial Sequence
<220> FEATURE:
<223> OTHER INFORMATION: primer 323-Hx7inr1
<220> FEATURE:
<221> NAME/KEY: source
<222> LOCATION: (1)..(22)
<223> OTHER INFORMATION: /organism="Artificial Sequence"
      /note="primer 323-Hx7inr1" /mol_type="unassigned DNA"

<400> SEQUENCE: 37
gatgagaatc cttggcaacc gc                                             22

<210> SEQ ID NO 38
<211> LENGTH: 25
<212> TYPE: DNA
<213> ORGANISM: Artificial Sequence
<220> FEATURE:
<223> OTHER INFORMATION: primer Hx4inr2
<220> FEATURE:
<221> NAME/KEY: source
<222> LOCATION: (1)..(25)
<223> OTHER INFORMATION: /organism="Artificial Sequence"
      /note="primer Hx4inr2" /mol_type="unassigned DNA"

<400> SEQUENCE: 38
ccatactatt tgtcgactca agcgc                                          25

<210> SEQ ID NO 39
<211> LENGTH: 25
<212> TYPE: DNA
<213> ORGANISM: Artificial Sequence
<220> FEATURE:
<223> OTHER INFORMATION: primer Hx5inf
<220> FEATURE:
<221> NAME/KEY: source
<222> LOCATION: (1)..(25)
<223> OTHER INFORMATION: /organism="Artificial Sequence"
      /note="primer Hx5inf" /mol_type="unassigned DNA"

<400> SEQUENCE: 39
gggttaatta gttttagggg cacgg                                          25

```
<210> SEQ ID NO 40
<211> LENGTH: 24
<212> TYPE: DNA
<213> ORGANISM: Artificial Sequence
<220> FEATURE:
<223> OTHER INFORMATION: primer 324-Ga2inf1
<220> FEATURE:
<221> NAME/KEY: source
<222> LOCATION: (1)..(24)
<223> OTHER INFORMATION: /organism="Artificial Sequence"
      /note="primer 324-Ga2inf1" /mol_type="unassigned DNA"

<400> SEQUENCE: 40
tcaattcgga aagcttcctt ccgg                                           24

<210> SEQ ID NO 41
<211> LENGTH: 23
<212> TYPE: DNA
<213> ORGANISM: Artificial Sequence
<220> FEATURE:
<223> OTHER INFORMATION: primer 325-Ga2inr1
<220> FEATURE:
<221> NAME/KEY: source
<222> LOCATION: (1)..(23)
<223> OTHER INFORMATION: /organism="Artificial Sequence"
      /note="primer 325-Ga2inr1" /mol_type="unassigned DNA"

<400> SEQUENCE: 41
cagtgatagt ttggttcgag cgg                                            23

<210> SEQ ID NO 42
<211> LENGTH: 23
<212> TYPE: DNA
<213> ORGANISM: Artificial Sequence
<220> FEATURE:
<223> OTHER INFORMATION: primer 289-Hx2inf
<220> FEATURE:
<221> NAME/KEY: source
<222> LOCATION: (1)..(23)
<223> OTHER INFORMATION: /organism="Artificial Sequence"
      /note="primer 289-Hx2inf" /mol_type="unassigned DNA"

<400> SEQUENCE: 42
tcttcgggaa ctagataggt ggc                                            23

<210> SEQ ID NO 43
<211> LENGTH: 23
<212> TYPE: DNA
<213> ORGANISM: Artificial Sequence
<220> FEATURE:
<223> OTHER INFORMATION: primer 290-Hx2inr
<220> FEATURE:
<221> NAME/KEY: source
<222> LOCATION: (1)..(23)
<223> OTHER INFORMATION: /organism="Artificial Sequence"
      /note="primer 290-Hx2inr" /mol_type="unassigned DNA"

<400> SEQUENCE: 43
gaagtaatca gccacaatac gcc                                            23

<210> SEQ ID NO 44
<211> LENGTH: 73
<212> TYPE: DNA
<213> ORGANISM: Artificial Sequence
<220> FEATURE:
<223> OTHER INFORMATION: primer 838-Glk1-psuc227f
<220> FEATURE:
<221> NAME/KEY: source
<222> LOCATION: (1)..(73)
<223> OTHER INFORMATION: /organism="Artificial Sequence"
```

/note="primer 838-Glk1-psuc227f" /mol_type="unassigned DNA"

<400> SEQUENCE: 44
atgtcattcg acgacttaca caaagccact gagagagcgg tcatccaggc ccgtcgacct    60
cgagtaccgt tcg    73

<210> SEQ ID NO 45
<211> LENGTH: 73
<212> TYPE: DNA
<213> ORGANISM: Artificial Sequence
<220> FEATURE:
<223> OTHER INFORMATION: primer 834- Hxk2-psuc227f
<220> FEATURE:
<221> NAME/KEY: source
<222> LOCATION: (1)..(73)
<223> OTHER INFORMATION: /organism="Artificial Sequence" /note="primer
      834- Hxk2-psuc227f" /mol_type="unassigned DNA"

<400> SEQUENCE: 45
gccagaaagg gttccatggc cgatgtgcca aaggaattga tgcaacaaat ccgtcgacct    60
cgagtaccgt tcg    73

<210> SEQ ID NO 46
<211> LENGTH: 21
<212> TYPE: DNA
<213> ORGANISM: Artificial Sequence
<220> FEATURE:
<223> OTHER INFORMATION: primer 645-pSUC227r
<220> FEATURE:
<221> NAME/KEY: source
<222> LOCATION: (1)..(21)
<223> OTHER INFORMATION: /organism="Artificial Sequence"
      /note="primer 645-pSUC227r" /mol_type="unassigned DNA"

<400> SEQUENCE: 46
gcaatttcgg ctatacgtaa c    21

<210> SEQ ID NO 47
<211> LENGTH: 73
<212> TYPE: DNA
<213> ORGANISM: Artificial Sequence
<220> FEATURE:
<223> OTHER INFORMATION: primer 839-Glk1-psuc225r
<220> FEATURE:
<221> NAME/KEY: source
<222> LOCATION: (1)..(73)
<223> OTHER INFORMATION: /organism="Artificial Sequence"
      /note="primer 839-Glk1-psuc225r" /mol_type="unassigned DNA"

<400> SEQUENCE: 47
caatcttcaa gtgcaccttc ctctcaccct cggcacccaa gggtgacaag ccggatccta    60
ccgttcgtat agc    73

<210> SEQ ID NO 48
<211> LENGTH: 73
<212> TYPE: DNA
<213> ORGANISM: Artificial Sequence
<220> FEATURE:
<223> OTHER INFORMATION: primer 835-Hxk2-psuc225r
<220> FEATURE:
<221> NAME/KEY: source
<222> LOCATION: (1)..(73)
<223> OTHER INFORMATION: /organism="Artificial Sequence"
      /note="primer 835-Hxk2-psuc225r" /mol_type="unassigned DNA"

<400> SEQUENCE: 48
gccagaaagg gttccatggc cgatgtgcca aaggaattga tgcaacaaat ccgtcgacct    60
cgagtaccgt tcg                                                          73

<210> SEQ ID NO 49
<211> LENGTH: 21
<212> TYPE: DNA
<213> ORGANISM: Artificial Sequence
<220> FEATURE:
<223> OTHER INFORMATION: primer 646-pSUC225f
<220> FEATURE:
<221> NAME/KEY: source
<222> LOCATION: (1)..(21)
<223> OTHER INFORMATION: /organism="Artificial Sequence"
      /note="primer 646-pSUC225f" /mol_type="unassigned DNA"

<400> SEQUENCE: 49
cgttcactca tggaaaatag c                                                 21

<210> SEQ ID NO 50
<211> LENGTH: 72
<212> TYPE: DNA
<213> ORGANISM: Artificial Sequence
<220> FEATURE:
<223> OTHER INFORMATION: primer 846-Hxk1_loxP_f
<220> FEATURE:
<221> NAME/KEY: source
<222> LOCATION: (1)..(72)
<223> OTHER INFORMATION: /organism="Artificial Sequence"
      /note="primer 846-Hxk1_loxP_f" /mol_type="unassigned DNA"

<400> SEQUENCE: 50
atggttcatt taggtccaaa gaaaccacag gctagaaagg gttccatggc cggatccact        60
agcataactt cg                                                           72

<210> SEQ ID NO 51
<211> LENGTH: 72
<212> TYPE: DNA
<213> ORGANISM: Artificial Sequence
<220> FEATURE:
<223> OTHER INFORMATION: primer 847-Hxk1_loxP_r
<220> FEATURE:
<221> NAME/KEY: source
<222> LOCATION: (1)..(72)
<223> OTHER INFORMATION: /organism="Artificial Sequence"
      /note="primer 847-Hxk1_loxP_r" /mol_type="unassigned DNA"

<400> SEQUENCE: 51
atggttcatt taggtccaaa gaaaccacag gctagaaagg gttccatggc cggatccact        60
agcataactt cg                                                           72

<210> SEQ ID NO 52
<211> LENGTH: 72
<212> TYPE: DNA
<213> ORGANISM: Artificial Sequence
<220> FEATURE:
<223> OTHER INFORMATION: primer 848-Gal1_loxP_f
<220> FEATURE:
<221> NAME/KEY: source
<222> LOCATION: (1)..(72)
<223> OTHER INFORMATION: /organism="Artificial Sequence"
      /note="primer 848-Gal1_loxP_f" /mol_type="unassigned DNA"

<400> SEQUENCE: 52
atgactaaat ctcattcaga agaagtgatt gtacctgagt tcaattctag cggatccact        60
agcataactt cg                                                           72

<210> SEQ ID NO 53

```
<211> LENGTH: 70
<212> TYPE: DNA
<213> ORGANISM: Artificial Sequence
<220> FEATURE:
<223> OTHER INFORMATION: primer 849-Gal1_loxP_r
<220> FEATURE:
<221> NAME/KEY: source
<222> LOCATION: (1)..(70)
<223> OTHER INFORMATION: /organism="Artificial Sequence"
      /note="primer 849-Gal1_loxP_r" /mol_type="unassigned DNA"

<400> SEQUENCE: 53
ttataattca tatagacagc tgcccaatgc tggtttagag acgatgatag ttgggccgcc      60
agtgtgatgg                                                              70

<210> SEQ ID NO 54
<211> LENGTH: 5250
<212> TYPE: DNA
<213> ORGANISM: Artificial Sequence
<220> FEATURE:
<223> OTHER INFORMATION: pRN774; TOPO-BLUNT-loxP-hphMX-loxP (loxP sites
      in opposite orientation)
<220> FEATURE:
<221> NAME/KEY: source
<222> LOCATION: (1)..(5250)
<223> OTHER INFORMATION: /organism="Artificial Sequence" /note="pRN774;
      TOPO-BLUNT-loxP-hphMX-loxP (loxP sites in opposite orientation) "
      /mol_type="unassigned DNA"

<400> SEQUENCE: 54
gcttccggct cgtatgttgt gtggaattgt gagcggataa caatttcaca caggaaacag      60
ctatgaccat gattacgcca agctatttag gtgacactat agaatactca agctatgcat     120
caagcttggt accgagctcg gatccactag caacttcg tataatgtat gctatacgaa       180
gttattctag taacggccgc cagtgtgctg gaattcgccc ttaagctttg cctcgtcccc     240
gccgggtcac ccggccagcg acatggaggc ccagaatacc ctccttgaca gtcttgacgt     300
gcgcagctca ggggcatgat gtgactgtcg cccgtacatt tagcccatac atccccatgt     360
ataatcattt gcatccatac attttgatgg ccgcacggcg cgaagcaaaa attacggctc     420
ctcgctgcag acctgcgagc agggaaacgc tcccctcaca gacgcgtgaa ttgtccccac     480
gccgcgcccc tgtagagaaa tataaaaggt taggatttgc cactgaggtt cttctttcat     540
atacttcctt ttaaaatctt gctaggatac agttctcaca tcacatccga acataaacaa     600
ccatgggtaa aaagcctgaa ctcaccgcga cgtctgtcga agtttctg atcgaaaagt       660 tcgacagcgt ctccgacctg atgcagctct cggagggcga agaatctcgt gctttcagct     720
tcgatgtagg agggcgtgga tatgtcctgc gggtaaatag ctgcgccgat ggtttctaca     780
aagatcgtta tgtttatcgg cactttgcat cggccgcgct cccgattccg gaagtgcttg     840
acattgggga attcagcgag agcctgacct attgcatctc ccgccgtgca cagggtgtca     900
cgttgcaaga cctgcctgaa accgaactgc ccgctgttct gcagccggtc gcggaggcca     960
tggatgcgat cgctgcggcc gatcttagcc agacgagcgg gttcggccca ttcggaccgc    1020
aaggaatcgg tcaatacact acatggcgtg atttcatatg cgcgattgct gatccccatg    1080
tgtatcactg gcaaactgtg atggacgaca ccgtcagtgc gtccgtcgcg caggctctcg    1140
atgagctgat gctttgggcc gaggactgcc ccgaagtccg gcacctcgtg cacgcggatt    1200
tcggctccaa caatgtcctg acggacaatg gccgcataac agcggtcatt gactggagcg    1260
aggcgatgtt cggggattcc caatacgagg tcgccaacat cttcttctgg aggccgtggt    1320
tggcttgtat ggagcagcag acgcgctact tcgagcggag gcatccggag cttgcaggat    1380
```

```
cgccgcgggct  ccgggcgtat  atgctccgca  ttggtcttga  ccaactctat  cagagcttgg   1440
ttgacggcaa  tttcgatgat  gcagcttggg  cgcagggtcg  atgcgacgca  atcgtccgat   1500
ccggagccgg  gactgtcggg  cgtacacaaa  tcgcccgcag  aagcgcggcc  gtctggaccg   1560
atggctgtgt  agaagtactc  gccgatagtg  gaaaccgacg  ccccagcact  cgtccgaggg   1620
caaaggaata  atcagtactg  acaataaaaa  gattcttgtt  ttcaagaact  tgtcatttgt   1680 atagttttt   tatattgtag  ttgttctatt  ttaatcaaat  gttagcgtga  tttatatttt   1740
ttttcgcctc  gacatcatct  gcccagatgc  gaagttaagt  gcgcagaaag  taatatcatg   1800
cgtcaatcgt  atgtgaatgc  tggtcgctat  actgctgtcg  attcgatact  aacgccgcca   1860
tccagtgtcg  aaaacgagct  cgaattcatc  gatgatatcc  atcacactgg  cggccgctcg   1920
acgatatcta  gagcgcgcat  aacttcgtat  aatgtatgct  atacgaagtt  ataggatcca   1980
tcacactggc  ggcccaattc  gccctatagt  gagtcgtatt  acaattcact  ggccgtcgtt   2040
ttacaacgtc  gtgactggga  aaaccctggc  gttacccaac  ttaatcgcct  tgcagcacat   2100 cccccttttcg  ccagctggcg  taatagcgaa  gaggcccgca  ccgatcgccc  ttcccaacag   2160
ttgcgcagcc  tatacgtacg  gcagtttaag  gtttacacct  ataaaagaga  gagccgttat   2220
cgtctgtttg  tggatgtaca  gagtgatatt  attgacacgc  cggggcgacg  gatggtgatc   2280
cccctggcca  gtgcacgtct  gctgtcagat  aaagtctccc  gtgaacttta  cccggtggtg   2340
catatcgggg  atgaaagctg  gcgcatgatg  accaccgata  tggccagtgt  gccggtctcc   2400
gttatcgggg  aagaagtggc  tgatctcagc  caccgcgaaa  atgacatcaa  aaacgccatt   2460
aacctgatgt  tctggggaat  ataaatgtca  ggcatgagat  tatcaaaaag  gatcttcacc   2520
tagatccttt  tcacgtagaa  agccagtccg  cagaaacggt  gctgaccccg  gatgaatgtc   2580
agctactggg  ctatctggac  aagggaaaac  gcaagcgcaa  agagaaagca  ggtagcttgc   2640
agtgggctta  catggcgata  gctagactgg  gcggttttat  ggacagcaag  cgaaccggaa   2700
ttgccagctg  gggcgccctc  tggtaaggtt  gggaagccct  gcaaagtaaa  ctggatggct   2760
ttctcgccgc  caaggatctg  atggcgcagg  ggatcaagct  ctgatcaaga  gacaggatga   2820
ggatcgtttc  gcatgattga  acaagatgga  ttgcacgcag  gttctccggc  cgcttgggtg   2880
gagaggctat  tcggctatga  ctgggcacaa  cagacaatcg  gctgctctga  tgccgccgtg   2940
ttccggctgt  cagcgcaggg  gcgcccggtt  ctttttgtca  agaccgacct  gtccggtgcc   3000
ctgaatgaac  tgcaagacga  ggcagcgcgg  ctatcgtggc  tggccacgac  gggcgttcct   3060
tgcgcagctg  tgctcgacgt  tgtcactgaa  gcgggaaggg  actggctgct  attgggcgaa   3120
gtgccggggc  aggatctcct  gtcatctcac  cttgctcctg  ccgagaaagt  atccatcatg   3180
gctgatgcaa  tgcggcggct  gcatacgctt  gatccggcta  cctgcccatt  cgaccaccaa   3240
gcgaaacatc  gcatcgagcg  agcacgtact  cggatggaag  ccggtcttgt  cgatcaggat   3300
gatctggacg  aagagcatca  ggggctcgcg  ccagccgaac  tgttcgccag  gctcaaggcg   3360
agcatgcccg  acggcgagga  tctcgtcgtg  acccatggcg  atgcctgctt  gccgaatatc   3420
atggtggaaa  atggccgctt  ttctggattc  atcgactgtg  gccggctggg  tgtggcggac   3480
cgctatcagg  acatagcgtt  ggctacccgt  gatattgctg  aagagcttgg  cggcgaatgg   3540
gctgaccgct  tcctcgtgct  ttacggtatc  gccgctcccg  attcgcagcg  catcgccttc   3600
tatcgccttc  ttgacgagtt  cttctgaatt  attaacgctt  acaatttcct  gatgcggtat   3660
tttctcctta  cgcatctgtg  cggtatttca  caccgcatac  aggtggcact  tttcggggaa   3720
```

-continued

```
atgtgcgcgg aaccccuat tgtttattt tctaaataca ttcaaatatg tatccgctca    3780
tgagacaata accctgataa atgcttcaat aatagcacgt gaggagggcc accatggcca    3840
agttgaccag tgccgttccg gtgctcaccg cgcgcgacgt cgccggagcg gtcgagttct    3900
ggaccgaccg gctcgggttc tcccgggact tcgtggagga cgacttcgcc ggtgtggtcc    3960
gggacgacgt gaccctgttc atcagcgcgg tccaggacca ggtggtgccg gacaacaccc    4020
tggcctgggt gtgggtgcgc ggcctggacg agctgtacgc cgagtggtcg gaggtcgtgt    4080
ccacgaactt ccgggacgcc tccgggccgg ccatgaccga gatcggcgag cagccgtggg    4140
ggcgggagtt cgccctgcgc gacccggccg gcaactgcgt gcacttcgtg gccgaggagc    4200
aggactgaca cgtgctaaaa cttcattttt aatttaaaag gatctaggtg aagatccttt    4260
ttgataatct catgaccaaa atcccttaac gtgagttttc gttccactga gcgtcagacc    4320
ccgtagaaaa gatcaaagga tcttcttgag atcctttttt tctgcgcgta atctgctgct    4380
tgcaaacaaa aaaaccaccg ctaccagcgg tggtttgttt gccggatcaa gagctaccaa    4440
ctcttttcc gaaggtaact ggcttcagca gagcgcagat accaaatact gtccttctag    4500
tgtagccgta gttaggccac cacttcaaga actctgtagc accgcctaca tacctcgctc    4560
tgctaatcct gttaccagtg gctgctgcca gtggcgataa gtcgtgtctt accgggttgg    4620
actcaagacg atagttaccg gataaggcgc agcggtcggg ctgaacgggg gttcgtgca    4680
cacagcccag cttggagcga acgacctaca ccgaactgag atacctacag cgtgagctat    4740
gagaaagcgc cacgcttccc gaagggagaa aggcggacag gtatccggta agcggcaggg    4800
tcggaacagg agagcgcacg agggagcttc caggggaaa cgcctggtat ctttatagtc    4860
ctgtcgggtt tcgccaccct tgacttgagc gtcgatttt gtgatgctcg tcaggggggc    4920
ggagcctatg gaaaaacgcc agcaacgcgg ccttttacg gttcctgggc ttttgctggc    4980
cttttgctca catgttcttt cctgcgttat cccctgattc tgtggataac cgtattaccg    5040
cctttgagtg agctgatacc gctcgccgca gccgaacgac cgagcgcagc gagtcaagcg    5100
cccaatacgc aaaccgcctc tccccgcgcg ttggccgatt cattaatgca gctggcacga    5160
caggtttccc gactggaaag cgggcagtga gcgcaacgca attaatgtga gttagctcac    5220
tcattaggca ccccaggctt tacactttat                                     5250
```

<210> SEQ ID NO 55
<211> LENGTH: 4744
<212> TYPE: DNA
<213> ORGANISM: Artificial Sequence
<220> FEATURE:
<223> OTHER INFORMATION: pRN775; TOPO-BLUNT-loxP-natMX-loxP (loxP sites in opposite orientation)
<220> FEATURE:
<221> NAME/KEY: source
<222> LOCATION: (1)..(4744)
<223> OTHER INFORMATION: /organism="Artificial Sequence" /note="pRN775; TOPO-BLUNT-loxP-natMX-loxP (loxP sites in opposite orientation)" /mol_type="unassigned DNA"

<400> SEQUENCE: 55

```
gcttccggct cgtatgttgt gtggaattgt gagcggataa caatttcaca caggaaacag     60
ctatgaccat gattacgcca agctatttag gtgacactat agaatactca agctatgcat    120
caagcttggt accgagctcg gatccactag caacttcg tataatgtat gctatacgaa    180
gttattctag taacgccgc cagtgtgctg gaattcgccc ttaagcttgc ctcgtccccg    240
ccgggtcacc cggccagcga catggaggcc cagaataccc tccttgacag tcttgacgtg    300
```

```
cgcagctcag gggcatgatg tgactgtcgc ccgtacattt agcccataca tccccatgta    360
taatcatttg catccataca ttttgatggc cgcacggcgc gaagcaaaaa ttacggctcc    420
tcgctgcaga cctgcgagca gggaaacgct cccctcacag acgcgttgaa ttgtccccac    480
gccgcgcccc tgtagagaaa tataaaaggt taggatttgc cactgaggtt cttctttcat    540
atacttcctt ttaaaatctt gctaggatac agttctcaca tcacatccga acataaacaa    600
ccatgtaaaa tgaccactct tgacgacacg gcttaccggt accgcaccag tgtcccgggg    660
gacgccgagg ccatcgaggc actggatggg tccttcacca ccgacaccgt cttccgcgtc    720
accgccaccg gggacggctt caccctgcgg gaggtgccgg tggacccgcc cctgaccaag    780
gtgttccccg acgacgaatc ggacgacgaa tcggacgccg gggaggacgg cgacccggac    840
tcccggacgt tcgtcgcgta cggggacgac ggcgacctgg cgggcttcgt ggtcgtctcg    900
tactccggct ggaaccgccg gctgaccgtc gaggacatcg aggtcgcccc ggagcaccgg    960
gggcacgggg tcgggcgcgc gttgatgggg ctcgcgacgg agttcgcccg cgagcggggc   1020
gccgggcacc tctggctgga ggtcaccaac gtcaacgcac cggcgatcca cgcgtaccgg   1080
cggatggggt tcaccctctg cggcctggac accgccctgt acgacggcac cgcctcggac   1140
ggcgagcagg cgctctacat gagcatgccc tgccccagt actgacaata aaaagattct   1200
tgttttcaag aacttgtcat ttgtatagtt tttttatatt gtagttgttc tattttaatc   1260
aaatgttagc gtgatttata ttttttttcg cctcgacatc atctgcccag atgcgaagtt   1320
aagtgcgcag aaagtaatat catgcgtcaa tcgtatgtga atgctggtcg ctatactgct   1380
gtcgattcga tactaacgcc gccatccagt gtcgacgata tctagagcgc gcataacttc   1440
gtataatgta tgctatacga agttatagga tccatcacac tggcggccca attcgcccta   1500
tagtgagtcg tattacaatt cactggccgt cgttttacaa cgtcgtgact gggaaaaccc   1560
tggcgttacc caacttaatc gccttgcagc acatccccct ttcgccagct ggcgtaatag   1620
cgaagaggcc cgcaccgatc gcccttccca acagttgcgc agcctatacg tacggcagtt   1680
taaggtttac acctataaaa gagagagccg ttatcgtctg tttgtggatg tacagagtga   1740
tattattgac acgccgggc gacggatggt gatcccctg ccagtgcac gtctgctgtc   1800 agataaagtc tcccgtgaac tttacccggt ggtgcatatc ggggatgaaa gctggcgcat   1860
gatgaccacc gatatggcca gtgtgccggt ctccgttatc ggggaagaag tggctgatct   1920
cagccaccgc gaaaatgaca tcaaaaacgc cattaacctg atgttctggg aatataaat   1980 gtcaggcatg agattatcaa aaaggatctt caccctagatc cttttcacgt agaaagccag   2040
tccgcagaaa cggtgctgac cccggatgaa tgtcagctac tgggctatct ggacaaggga   2100
aaacgcaagc gcaaagagaa agcaggtagc ttgcagtggg cttacatggc gatagctaga   2160
ctgggcggtt ttatggacag caagcgaacc ggaattgcca gctgggcgc cctctggtaa   2220 ggttgggaag ccctgcaaag taaactggat ggctttctcg ccgccaagga tctgatggcg   2280 cagggatca agctctgatc aagagacagg atgaggatc tttcgcatga ttgaacaaga   2340
tggattgcac gcaggttctc cggccgcttg ggtggagagg ctattcggct atgactgggc   2400
acaacagaca atcggctgct ctgatgccgc cgtgttccgg ctgtcagcgc aggggcgccc   2460
ggttcttttt gtcaagaccg acctgtccgg tgccctgaat gaactgcaag acgaggcagc   2520
gcggctatcg tggctggcca cgacgggcgt tccttgcgca gctgtgctcg acgttgtcac   2580
tgaagcggga agggactggc tgctattggg cgaagtgccg gggcaggatc tcctgtcatc   2640
tcaccttgct cctgccgaga aagtatccat catggctgat gcaatgcggc ggctgcatac   2700
```

```
gcttgatccg gctacctgcc cattcgacca ccaagcgaaa catcgcatcg agcgagcacg    2760
tactcggatg gaagccggtc ttgtcgatca ggatgatctg gacgaagagc atcagggcgt    2820
cgcgccagcc gaactgttcg ccaggctcaa ggcgagcatg cccgacggcg aggatctcgt    2880
cgtgacccat ggcgatgcct gcttgccgaa tatcatggtg gaaaatggcc gcttttctgg    2940
attcatcgac tgtggccggc tgggtgtggc ggaccgctat caggacatag cgttggctac    3000
ccgtgatatt gctgaagagc ttggcggcga atgggctgac cgcttcctcg tgctttacgg    3060
tatcgccgct cccgattcgc agcgcatcgc cttctatcgc cttcttgacg agttcttctg    3120
aattattaac gcttacaatt tcctgatgcg gtatttctc cttacgcatc tgtgcggtat    3180
ttcacaccgc atacaggtgg cacttttcgg ggaaatgtgc gcggaacccc tatttgttta    3240
tttttctaaa tacattcaaa tatgtatccg ctcatgagac aataaccctg ataaatgctt    3300
caataatagc acgtgaggag ggccaccatg gccaagttga ccagtgccgt tccggtgctc    3360
accgcgcgcg acgtcgccgg agcggtcgag ttctggaccg accggctcgg gttctcccgg    3420
gacttcgtgg aggacgactt cgccggtgtg gtccgggacg acgtgaccct gttcatcagc    3480
gcggtccagg accaggtggt gccggacaac accctggcct gggtgtgggt gcgcggcctg    3540
gacgagctgt acgccgagtg gtcggaggtc gtgtccacga acttccggga cgcctccggg    3600
ccggccatga ccgagatcgg cgagcagccg tggggcggg agttcgccct gcgcgacccg    3660
gccggcaact gcgtgcactt cgtggccgag gagcaggact gacacgtgct aaaacttcat    3720
ttttaattta aaaggatcta ggtgaagatc ctttttgata atctcatgac caaaatccct    3780
taacgtgagt tttcgttcca ctgagcgtca gaccccgtag aaaagatcaa aggatcttct    3840
tgagatcctt ttttttctgcg cgtaatctgc tgcttgcaaa caaaaaaacc accgctacca    3900
gcggtggttt gtttgccgga tcaagagcta ccaactcttt ttccgaaggt aactggcttc    3960
agcagagcgc agataccaaa tactgtcctt ctagtgtagc cgtagttagg ccaccacttc    4020
aagaactctg tagcaccgcc tacatacctc gctctgctaa tcctgttacc agtggctgct    4080
gccagtggcg ataagtcgtg tcttaccggg ttggactcaa gacgatagtt accggataag    4140
gcgcagcggt cgggctgaac ggggggttcg tgcacacagc ccagcttgga gcgaacgacc    4200
tacaccgaac tgagatacct acagcgtgag ctatgagaaa gcgccacgct tcccgaaggg    4260
agaaaggcgg acaggtatcc ggtaagcggc agggtcggaa caggagagcg cacgagggag    4320
cttccagggg gaaacgcctg gtatctttat agtcctgtcg ggtttcgcca cctctgactt    4380
gagcgtcgat ttttgtgatg ctcgtcaggg ggcggagcc tatggaaaaa cgccagcaac    4440
gcggcctttt tacggttcct ggcttttgc tggccttttg ctcacatgtt ctttcctgcg    4500
ttatcccctg attctgtgga taaccgtatt accgcctttg agtgagctga taccgctcgc    4560
cgcagccgaa cgaccgagcg cagcgagtca gcgcccaat acgcaaaccg cctctccccg    4620
cgcgttggcc gattcattaa tgcagctggc acgacaggtt tcccgactgg aaagcgggca    4680
gtgagcgcaa cgcaattaat gtgagttagc tcactcatta ggcaccccag gctttacact    4740
ttat                                                                 4744
```

<210> SEQ ID NO 56
<211> LENGTH: 1725
<212> TYPE: DNA
<213> ORGANISM: Saccharomyces cerevisiae
<220> FEATURE:
<221> NAME/KEY: source
<222> LOCATION: (1)..(1725)

<223> OTHER INFORMATION: /organism="Saccharomyces cerevisiae"
     /note="WT-GAL2 DNA sequence " /mol_type="unassigned DNA"

<400> SEQUENCE: 56

```
atggcagttg aggagaacaa tatgcctgtt gtttcacagc aaccccaagc tggtgaagac      60
gtgatctctt cactcagtaa agattcccat ttaagcgcac aatctcaaaa gtattccaat     120
gatgaattga aagccggtga gtcagggcct gaaggctccc aaagtgttcc tatagagata     180
cccaagaagc ccatgtctga atatgttacc gtttccttgc tttgtttgtg tgttgccttc     240
ggcggcttca tgtttggctg ggataccggt actatttctg gtttgttgt ccaaacagac      300
tttttgagaa ggtttggtat gaaacataag gatggtaccc actatttgtc aaacgtcaga     360
acaggtttaa tcgtcgccat tttcaatatt ggctgtgcct ttggtggtat tatacttcc      420
aaaggtggag atatgtatgg ccgtaaaaag ggtctttcga ttgtcgtctc ggtttatata     480
gttggtatta tcattcaaat gcctctatc aacaagtggt accaatattt cattggtaga      540
atcatatctg gtttgggtgt cggcggcatc gccgtcttat gtcctatgtt gatctctgaa     600
attgctccaa agcacttgag aggcacacta gtttcttgtt atcagctgat gattactgca     660
ggtatctttt tgggctactg tactaattac ggtacaaaga gctattcgaa ctcagttcaa     720
tggagagttc cattagggct atgtttcgct tggtcattat ttatgattgg cgctttgacg     780
ttagttcctg aatccccacg ttatttatgt gaggtaataa aggtagaaga cgccaagctt     840
tccattgcta agtctaacaa ggtgtcacca gaggatcctg ccgtccaggc agagttagat     900
ctgatcatgg ccggtatagaa agctgaaaaa ctggctggca atgcgtcctg gggggaatta     960
ttttccacca agaccaaagt atttcaacgt ttgttgatgg gtgtatttgt tcaaatgttc    1020
caacaattaa ccgtaacaa ttattttttc tactacggta ccgttatttt caagtcagtt    1080
ggcctggatg attcctttga acatccatt gtcattggtg tagtcaactt tgcctccact    1140
ttctttagtt tgtggactgt cgaaaacttg gggcgtcgta aatgtttact tttgggcgct    1200
gccactatga tggcttgtat ggtcatctac gcctctgttg gtgttaccag attatatcct    1260
cacggtaaaa gccagccatc ttctaaaggt gccggtaact gtatgattgt ctttacctgt    1320
ttttatattt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttccacccca ttcatcacat ctgccattaa cttctactac    1500
ggttatgtct tcatgggctg tttggttgcc atgtttttt atgtctttt ctttgttcca    1560
gaaactaaag gccatcgtt agaagaaatt caagaattat gggaagaagg tgttttacct    1620
tggaaatctg aaggctggat tccttcatcc agaagaggta ataattacga tttagaggat    1680
ttacaacatg acgacaaacc gtggtacaag gccatgctag aataa              1725
```

<210> SEQ ID NO 57
<211> LENGTH: 7392
<212> TYPE: DNA
<213> ORGANISM: Artificial Sequence
<220> FEATURE:
<223> OTHER INFORMATION: pRN993
<220> FEATURE:
<221> NAME/KEY: source
<222> LOCATION: (1)..(7392)
<223> OTHER INFORMATION: /organism="Artificial Sequence" /note="pRN993 "
     /mol_type="unassigned DNA"

<400> SEQUENCE: 57

```
tcgcgcgttt cggtgatgac ggtgaaaacc tctgacacat gcagctcccg gagacggtca      60
```

-continued

```
cagcttgtct gtaagcggat gccgggagca gacaagcccg tcaggcgcg tcagcgggtg      120 ttggcgggtg tcgggctgg cttaactatg cggcatcaga gcagattgta ctgagagtgc      180
accataattc cgttttaaga gcttggtgag cgctaggagt cactgccagg tatcgtttga     240
acacggcatt agtcagggaa gtcataacac agtcctttcc cgcaatttc tttttctatt     300 actcttggcc tcctctagta cactctatat tttttatgc ctcggtaatg attttcattt     360
ttttttttcc acctagcgga tgactctttt tttttcttag cgattggcat tatcacataa    420
tgaattatac attatataaa gtaatgtgat ttcttcgaag aatatactaa aaaatgagca    480
ggcaagataa acgaaggcaa agatgacaga gcagaaagcc ctagtaaagc gtattacaaa    540
tgaaaccaag attcagattg cgatctcttt aaagggtggt cccctagcga tagagcactc    600
gatcttccca gaaaagagg cagaagcagt agcagaacag gccacacaat cgcaagtgat     660
taacgtccac acaggtatag ggtttctgga ccatatgata catgctctgg ccaagcattc    720
cggctggtcg ctaatcgttg agtgcattgg tgacttacac atagacgacc atcacaccac    780
tgaagactgc gggattgctc tcggtcaagc ttttaaagag gccctactgg cgcgtggagt    840
aaaaaggttt ggatcaggat ttgcgccttt ggatgaggca cttccagag cggtggtaga     900 tctttcgaac aggccgtacg cagttgtcga acttggtttg caaagggaga agtaggaga     960 tctctcttgc gagatgatcc cgcattttct tgaaagcttt gcagaggcta gcagaattac   1020
cctccacgtt gattgtctgc gaggcaagaa tgatcatcac cgtagtgaga gtgcgttcaa    1080
ggctcttgcg gttgccataa agaaagccac ctcgcccaat ggtaccaacg atgttccctc    1140
caccaaaggt gttcttatgt agtgacaccg attatttaaa gctgcagcat acgatatata    1200
tacatgtgta tatatgtata cctatgaatg tcagtaagta tgtatacgaa cagtatgata    1260
ctgaagatga caaggtaatg catcattcta tacgtgtcat tctgaacgag gcgcgatcgc    1320
gctttccttt tttcttttg cttttttctt tttttttctct tgaactcgac ggatcatatg     1380
cggtgtgaaa taccgcacag atgcgtaagg agaaaatacc gcatcaggaa attgtaaacg    1440
ttaatatttt gttaaaattc gcgttaaatt tttgttaaat cagctcattt tttaaccaat    1500
aggccgaaat cggcaaaatc ccttataaat caaaagaata gaccgagata gggttgagtg    1560
ttgttccagt ttggaacaag agtccactat taaagaacgt ggactccaac gtcaaagggc    1620
gaaaaaccgt ctatcagggc gatggcccac tacgtgaacc atcaccctaa tcaagttttt    1680
tggggtcgag gtgccgtaaa gcactaaatc ggaaccctaa agggagcccc cgatttagag    1740
cttgacgggg aaagccggcg aacgtggcga aaaggaagg gaagaaagcg aaggagcggg    1800
cgctagggcg ctggcaagtg tagcggtcac gctgcgcgta accaccacac ccgccgcgct    1860
taatgcgccg ctacagggcg cgtcgcgcca ttcgccattc aggctgcgca actgttggga   1920
agggcgatcg gtgcgggcct cttcgctatt acgccagctg gcgaagggg gatgtgctgc    1980 aaggcgatta agttgggtaa cgccagggtt ttcccagtca cgacgttgta aaacgacggc    2040
cagtgaattg taatacgact cactataggg cgaattggag ctccaccgcg gtggcggccg   2100
cggctacttc tcgtaggaac aatttcgggc ccctgcgtgt tcttctgagg ttcatctttt    2160
acatttgctt ctgctggata ttttcagag gcaacaagga aaaattagat ggcaaaaagt    2220
cgtctttcaa ggaaaaatcc ccaccatctt tcgagatccc ctgtaactta ttggcaactg    2280
aaagaatgaa aaggaggaaa atacaaaata tactagaact gaaaaaaaaa agtataaat    2340 agagacgata tatgccaata cttcacaatg ttcgaatcta ttcttcattt gcagctattg    2400
```

```
taaaataata aaacatcaag aacaaacaag ctcaacttgt cttttctaag aacaaagaat    2460
aaacacaaaa acaaaaagtt tttttaattc tgcagatctc tagaaaatgg cagttgagga    2520
gaacaatatg cctgttgttt cacagcaacc ccaagctggt gaagacgtga tctcttcact    2580
cagtaaagat tcccatttaa gcgcacaatc tcaaaagtat tctaatgatg aattgaaagc    2640
cggtgagtca gggtctgaag ctcccaaag tgttcctata gagataccca agaagcccat     2700
gtctgaatat gttaccgttt ccttgctttg tttgtgtgtt gccttcggcg gcttcatgtt    2760
tggctgggat accggtacta tttctgggtt tgttgtccaa acagactttt tgagaaggtt    2820
tggtatgaaa cataaggatg gtacccacta tttgtcaaac gtcagaacag gtttaatcgt    2880
cgccattttc aatattggct gtgcctttgg tggtattata ctttccaaag gtggagatat    2940
gtatggccgt aaaaagggtc tttcgattgt cgtctcggtt tatatagttg gtattatcat    3000
tcaaattgcc tctatcaaca agtggtacca atatttcatt ggtagaatca tatctggttt    3060
gggtgtcggc ggcatcgccg tcttatgtcc tatgttgatc tctgaaattg ctccaaagca    3120
cttgagaggc acactagttt cttgttatca gctgatgatt actgcaggta tctttttggg    3180
ctactgtact aattacggta caaagagcta ttcgaactca gttcaatgga gagttccatt    3240
agggctatgt ttcgcttggt cattatttat gattggcgct ttgacgttag ttcctgaatc    3300
cccacgttat ttatgtgagg tgaataaggt agaagacgcc aagcgttcca ttgctaagtc    3360
taacaaggtg tcaccagagg atcctgccgt ccaggcagag ttagatctga tcatggccgg    3420
tatagaagct gaaaaactgg ctggcaatgc gtcctggggg gaattatttt ccaccaagac    3480
caaagtattt caacgtttgt tgatgggtgt gtttgttcaa atgttccaac aattaaccgg    3540
taacaattat ttttctact acggtaccgt tattttcaag tcagttggcc tggatgattc     3600
ctttgaaaca tccattgtca ttggtgtagt caactttgcc tccactttct ttagtttgtg    3660
gactgtcgaa aacttgggac atcgtaaatg tttacttttg ggcgctgcca ctatgatggc    3720
ttgtatggtc atctacgcct ctgttggtgt tactagatta tatcctcacg gtaaaagcca    3780
gccatcttct aaaggtgccg gtaactgtat gattgtcttt acctgttttt atattttctg    3840
ttatgccaca acctgggcgc cagttgcctg ggtcatcaca gcagaatcat tcccactgag    3900
agtcaagtcg aaatgtatgg cgttggcctc tgcttccaat tgggtatggg ggttcttgat    3960
tgcatttttc accccattca tcacatctgc cattaacttc tactacggtt atgtcttcat    4020
gggctgtttg gttgccatgt tttttatgt ctttttcttt gttccagaaa ctaaaggcct     4080
atcgttagaa gaaattcaag aattatggga agaaggtgtt ttaccttgga atctgaagg     4140
ctggattcct tcatccagaa gaggtaataa ttacgattta gaggatttac aacatgacga    4200
caaaccgtgg tacaaggcca tgctagaata agcttgcgcg cgaatttctt atgatttatg    4260
attttattta ttaaataagt tataaaaaaa ataagtgtat acaaatttta aagtgactct    4320
taggttttaa aacgaaaatt cttattcttg agtaactctt tcctgtaggt caggttgctt    4380
tctcaggtat agcatgaggt cgctcttatt gaccacacct ctaccggcat gccgagcaaa    4440
tgcctgcaaa tcgctcccca tttcacccaa ttgtagatat gctaactcca gcaatgagtt    4500
gatgaatctc ggtgtgtatt ttatgtcctc agaggacaac acctgttgta atcgttcttc    4560
cacacgtacg aagcttatcg ataccgtcga ggggggcccc ggtacccagc ttttgttccc    4620
tttagtgagg gttaattccg agcttggcgt aatcatggtc atagctgttt cctgtgtgaa    4680
attgttatcc gctcacaatt ccacacaaca taggagccgg aagcataaag tgtaaagcct    4740
ggggtgccta atgagtgagg taactcacat taattgcgtt gcgctcactg cccgctttcc    4800
```

```
agtcgggaaa cctgtcgtgc cagctgcatt aatgaatcgg ccaacgcgcg gggagaggcg   4860
gtttgcgtat tgggcgctct tccgcttcct cgctcactga ctcgctgcgc tcggtcgttc   4920
ggctgcggcg agcggtatca gctcactcaa aggcggtaat acggttatcc acagaatcag   4980
gggataacgc aggaaagaac atgtgagcaa aaggccagca aaaggccagg aaccgtaaaa   5040
aggccgcgtt gctggcgttt ttccataggc tcggccccc tgacgagcat cacaaaaatc   5100
gacgctcaag tcagaggtgg cgaaacccga caggactata agataccag gcgttccccc   5160 ctggaagctc cctcgtgcgc tctcctgttc cgaccctgcc gcttaccgga tacctgtccg   5220
cctttctccc ttcgggaagc gtggcgcttt ctcaatgctc acgctgtagg tatctcagtt   5280
cggtgtaggt cgttcgctcc aagctgggct gtgtgcacga accccccgtt cagcccgacc   5340
gctgcgcctt atccggtaac tatcgtcttg agtccaaccc ggtaagacac gacttatcgc   5400
cactggcagc agccactggt aacaggatta gcagagcgag gtatgtaggc ggtgctacag   5460
agttcttgaa gtggtggcct aactacggct acactagaag gacagtattt ggtatctgcg   5520
ctctgctgaa gccagttacc ttcggaaaaa gagttggtag ctcttgatcc ggcaaacaaa   5580
ccaccgctgg tagcggtggt ttttttgttt gcaagcagca gattacgcgc agaaaaaaag   5640
gatctcaaga agatcctttg atcttttcta cggggtctga cgctcagtgg aacgaaaact   5700
cacgttaagg gattttggtc atgagattat caaaaaggat cttcacctag atcctttaa    5760 attaaaaatg aagttttaaa tcaatctaaa gtatatatga gtaaacttgg tctgacagtt   5820
accaatgctt aatcagtgag gcacctatct cagcgatctg tctatttcgt tcatccatag   5880
ttgcctgact gcccgtcgtg tagataacta cgatacggga gggcttacca tctggcccca   5940
gtgctgcaat gataccgcga gacccacgct caccggctcc agatttatca gcaataaacc   6000
agccagccgg aagggccgag cgcagaagtg gtcctgcaac tttatccgcc tccatccagt   6060
ctattaattg ttgccgggaa gctagagtaa gtagttcgcc agttaatagt ttgcgcaacg   6120
ttgttgccat tgctacaggc atcgtggtgt cacgctcgtc gtttggtatg gcttcattca   6180
gctccggttc ccaacgatca aggcgagtta catgatcccc catgttgtga aaaaaagcgg   6240
ttagctcctt cggtcctccg atcgttgtca gaagtaagtt ggccgcagtg ttatcactca   6300
tggttatggc agcactgcat aattctctta ctgtcatgcc atccgtaaga tgcttttctg   6360
tgactggtga gtactcaacc aagtcattct gagaatagtg tatgcggcga ccgagttgct   6420
cttgcccggc gtcaatacgg gataataccg cgccacatag cagaacttta aaagtgctca   6480
tcattggaaa acgttcttcg gggcgaaaac tctcaaggat cttaccgctg ttgagatcca   6540
gttcgatgta acccactcgt gcacccaact gatcttcagc atcttttact ttcaccacgt   6600
ttctgggtga gcaaaaacag gaaggcaaaa tgccgcaaaa aagggaataa gggcgacacg   6660
gaaatgttga atactcatac tcttcctttt tcaatattat tgaagcattt atcagggtta   6720
ttgtctcatg agcggataca tatttgaatg tatttagaaa aataaacaaa taggggttcc   6780
gcgcacattt ccccgaaaag tgccacctgg gtccttttca tcacgtgcta taaaaataat   6840
tataatttaa atttttttaat ataaatatat aaattaaaaa tagaaagtaa aaaagaaat   6900 taaagaaaaa atagtttttg ttttccgaag atgtaaaaga ctctaggggg atcgccaaca   6960
aatactacct tttatcttgc tcttcctgct ctcaggtatt aatgccgaat tgtttcatct   7020
tgtctgtgta aagaccaca cacgaaaatc ctgtgatttt acattttact tatcgttaat   7080
cgaatgtata tctatttaat ctgcttttct tgtctaataa atatatatgt aaagtacgct   7140
```

```
tttttgttgaa attttttaaa cctttgttta tttttttttc ttcattccgt aactcttcta    7200
ccttctttat ttactttcta aaatccaaat acaaaacata aaaataaata aacacagagt    7260
aaattcccaa attattccat cattaaaaga tacgaggcgc gtgtaagtta caggcaagcg    7320
atccgtccta agaaaccatt attatcatga cattaaccta taaaaatagg cgtatcacga    7380 ggcccttctcg tc                                                       7392

<210> SEQ ID NO 58
<211> LENGTH: 7389
<212> TYPE: DNA
<213> ORGANISM: Artificial Sequence
<220> FEATURE:
<223> OTHER INFORMATION: pDB1250; WT-GAL2 expression vector for
      screening
<220> FEATURE:
<221> NAME/KEY: source
<222> LOCATION: (1)..(7389)
<223> OTHER INFORMATION: /organism="Artificial Sequence"
      /note="pDB1250; WT-GAL2 expression vector for screening"
      /mol_type="unassigned DNA"

<400> SEQUENCE: 58
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataattc cgttttaaga gcttggtgag cgctaggagt cactgccagg tatcgtttga    240
acacggcatt agtcagggaa gtcataacac agtcctttcc cgcaattttc tttttctatt    300
actcttggcc tcctctagta cactctatat tttttatgc ctcggtaatg atttcatt     360 ttttttttcc acctagcgga tgactctttt tttttcttag cgattggcat tatcacataa    420
tgaattatac attatataaa gtaatgtgat ttcttcgaag aatatactaa aaaatgagca    480
ggcaagataa acgaaggcaa agatgacaga gcagaaagcc ctagtaaagc gtattacaaa    540
tgaaaccaag attcagattg cgatctcttt aaagggtggt cccctagcga tagagcactc    600
gatcttccca gaaaaagagg cagaagcagt agcagaacag gccacacaat cgcaagtgat    660
taacgtccac acaggtatag ggtttctgga ccatatgata catgctctgg ccaagcattc    720
cggctggtcg ctaatcgttg agtgcattgg tgacttacac atagacgacc atcacaccac    780
tgaagactgc gggattgctc tcggtcaagc ttttaaagag gccctactgg cgcgtggagt    840
aaaaaggttt ggatcaggat ttgcgccttt ggatgaggca ctttccagag cggtggtaga    900
tctttcgaac aggccgtacg cagttgtcga acttggtttg caagggaga agtaggaga    960 tctctcttgc gagatgatcc cgcattttct tgaaagcttt gcagaggcta gcagaattac    1020
cctccacgtt gattgtctgc gaggcaagaa tgatcatcac cgtagtgaga gtgcgttcaa    1080
ggctcttgcg gttgccataa gagaagccac ctcgcccaat ggtaccaacg atgttccctc    1140
caccaaaggt gttcttatgt agtgacaccg attatttaaa gctgcagcat acgatatata    1200
tacatgtgta tatatgtata cctatgaatg tcagtaagta tgtatacgaa cagtatgata    1260
ctgaagatga caaggtaatg catcattcta tacgtgtcat tctgaacgag gcgcgatcgc    1320
gctttccttt tttctttttg cttttctttt tttttctct tgaactcgac ggatcatatg    1380
cggtgtgaaa taccgcacag atgcgtaagg agaaaatacc gcatcaggaa attgtaaacg    1440
ttaatatttt gttaaaattc gcgttaaatt tttgttaaat cagctcattt tttaaccaat    1500
aggccgaaat cggcaaaatc ccttataaat caaaagaata gaccgagata gggttgagtg    1560
```

```
ttgttccagt ttggaacaag agtccactat taaagaacgt ggactccaac gtcaaagggc    1620
gaaaaaccgt ctatcagggc gatggcccac tacgtgaacc atcaccctaa tcaagttttt    1680
tggggtcgag gtgccgtaaa gcactaaatc ggaaccctaa agggagcccc cgatttagag    1740
cttgacgggg aaagccggcg aacgtggcga gaaaggaagg gaagaaagcg aaggagcggg    1800
cgctagggcg ctggcaagtg tagcggtcac gctgcgcgta accaccacac ccgccgcgct    1860
taatgcgccg ctacagggcg cgtcgcgcca ttcgccattc aggctgcgca actgttggga    1920
agggcgatcg gtgcgggcct cttcgctatt acgccagctg gcgaaggggg gatgtgctgc    1980
aaggcgatta agttgggtaa cgccagggtt ttcccagtca cgacgttgta aaacgacggc    2040
cagtgaattg taatacgact cactataggg cgaattggag ctccaccgcg gtggcggccg    2100
cggctacttc tcgtaggaac aatttcgggc ccctgcgtgt tcttctgagg ttcatctttt    2160
acatttgctt ctgctggata ttttcagag gcaacaagga aaaattagat ggcaaaaagt    2220 cgtcttcaa ggaaaaatcc ccaccatctt tcgagatccc ctgtaactta ttggcaactg    2280
aaagaatgaa aaggaggaaa atacaaaata tactagaact gaaaaaaaaa aagtataaat    2340
agagacgata tatgccaata cttcacaatg ttcgaatcta ttcttcattt gcagctattg    2400
taaaataata aaacatcaag aacaaacaag ctcaacttgt cttttctaag aacaaagaat    2460
aaacacaaaa acaaaaagtt tttttaattc tgcagatctc tagaaaaatg gcagttgagg    2520
agaacaatat gcctgttgtt tcacagcaac cccaagctgg tgaagacgtg atctcttcac    2580
tcagtaaaga ttcccattta agcgcacaat ctcaaaagta ttccaatgat gaattgaaag    2640
ccggtgagtc agggcctgaa ggctcccaaa gtgttcctat agagataccc aagaagccca    2700
tgtctgaata tgttaccgtt tccttgcttt gtttgtgtgt tgccttcggc ggcttcatgt    2760
ttggctggga taccggtact atttctgggt tgttgtcca acagactttt ttgagaaggt    2820
ttggtatgaa acataaggat ggtacccact atttgtcaaa cgtcagaaca ggtttaatcg    2880
tcgccatttt caatattggc tgtgcctttg gtggtattat actttccaaa ggtggagata    2940
tgtatggccg taaaagggt ctttcgattg tcgtctcggt ttatatagtt ggtattatca    3000
ttcaaattgc ctctatcaac aagtggtacc aatatttcat tggtagaatc atatctggtt    3060
tgggtgtcgg cggcatcgcc gtcttatgtc ctatgttgat ctctgaaatt gctccaaagc    3120
acttgagagg cacactagtt tcttgttatc agctgtgat tactgcaggt atcttttgg    3180 gctactgtac taattacggt acaaagagct attcgaactc agttcaatgg agagttccat    3240
tagggctatg tttcgcttgg tcattattta tgattggcgc tttgacgtta gttcctgaat    3300
ccccacgtta tttatgtgag gtgaataagg tagaagacgc caagctttcc attgctaagt    3360
ctaacaaggt gtcaccagag gatcctgccg tccaggcaga gttagatctg atcatggccg    3420
gtatagaagc tgaaaaactg gctggcaatg cgtcctgggg ggaattattt tccaccaaga    3480
ccaaagtatt tcaacgtttg ttgatgggtg tatttgttca aatgttccaa caattaaccg    3540
gtaacaatta ttttttctac tacgtaccg ttattttcaa gtcagttggc ctggatgatt    3600
cctttgaaac atccattgtc attggtgtag tcaactttgc ctccactttc tttagtttgt    3660
ggactgtcga aaactgggg cgtcgtaaat gtttactttt gggcgctgcc actatgatgg    3720
cttgtatggt catctacgcc tctgttggtg ttaccagatt atatcctcac ggtaaaagcc    3780
agccatcttc taaggtgcc ggtaactgta tgattgtctt tacctgtttt tatatttct    3840 gttatgccac aacctgggcg ccagttgcct gggtcatcac agcagaatca ttcccactga    3900
gagtcaagtc gaaatgtatg gcgttggcct ctgcttccaa ttgggtatgg gggttcttga    3960
```

-continued

```
ttgcattttt cacccattc atcacatctg ccattaactt ctactacggt tatgtcttca    4020
tgggctgttt ggttgccatg ttttttatg tcttttctt tgttccagaa actaaaggcc     4080
tatcgttaga agaaattcaa gaattatggg aagaaggtgt tttaccttgg aaatctgaag   4140
gctggattcc ttcatccaga agaggtaata attacgattt agaggattta caacatgacg   4200
acaaaccgtg gtacaaggcc atgctagaat aagcgcgcga atttcttatg atttatgatt  4260
tttattatta aataagttat aaaaaaaata agtgtataca aattttaaag tgactcttag   4320
gttttaaaac gaaaattctt attcttgagt aactctttcc tgtaggtcag gttgctttct   4380
caggtatagc atgaggtcgc tcttattgac cacacctcta ccggcatgcc gagcaaatgc   4440
ctgcaaatcg ctccccattt cacccaattg tagatatgct aactccagca atgagttgat   4500
gaatctcggt gtgtatttta tgtcctcaga ggacaacacc tgttgtaatc gttcttccac   4560
acgtacgaag cttatcgata ccgtcgaggg ggggcccggt acccagcttt tgttcccttt   4620
agtgagggtt aattccgagc ttggcgtaat catggtcata gctgtttcct gtgtgaaatt   4680
gttatccgct cacaattcca cacaacatag gagccggaag cataaagtgt aaagcctggg   4740
gtgcctaatg agtgaggtaa ctcacattaa ttgcgttgcg ctcactgccc gctttccagt   4800
cgggaaacct gtcgtgccag ctgcattaat gaatcggcca acgcgcgggg agaggcggtt   4860
tgcgtattgg gcgctcttcc gcttcctcgc tcactgactc gctgcgctcg tcgttcggc    4920 tgcggcgagc ggtatcagct cactcaaagg cggtaatacg ttatccaca gaatcagggg    4980 ataacgcagg aaagaacatg tgagcaaaag gccagcaaaa ggccaggaac cgtaaaaagg   5040
ccgcgttgct ggcgtttttc cataggctcg gcccccctga cgagcatcac aaaaatcgac   5100
gctcaagtca gaggtggcga aacccgacag gactataaag ataccaggcg ttcccccctg   5160
gaagctccct cgtgcgctct cctgttccga ccctgccgct taccggatac ctgtccgcct   5220
ttctcccttc gggaagcgtg gcgctttctc aatgctcacg ctgtaggtat ctcagttcgg   5280
tgtaggtcgt tcgctccaag ctgggctgtg tgcacgaacc ccccgttcag cccgaccgct   5340
gcgccttatc cggtaactat cgtcttgagt ccaacccggt aagacacgac ttatcgccac   5400
tggcagcagc cactggtaac aggattagca gagcgaggta tgtaggcggt gctacagagt   5460
tcttgaagtg gtggcctaac tacggctaca ctagaaggac agtatttggt atctgcgctc   5520
tgctgaagcc agttaccttc ggaaaaagag ttggtagctc ttgatccggc aaacaaacca   5580
ccgctggtag cggtggtttt tttgtttgca agcagcagat tacgcgcaga aaaaaaggat   5640
ctcaagaaga tccttttgatc ttttctacgg ggtctgacgc tcagtggaac gaaaactcac   5700
gttaagggat tttggtcatg agattatcaa aaaggatctt cacctagatc cttttaaatt   5760
aaaaatgaag ttttaaatca atctaaagta tatatgagta aacttggtct gacagttacc   5820
aatgcttaat cagtgaggca cctatctcag cgatctgtct atttcgttca tccatagttg   5880
cctgactgcc cgtcgtgtag ataactacga tacggggggg cttaccatct ggccccagtg   5940
ctgcaatgat accgcgagac ccacgctcac cggctccaga tttatcagca ataaaccagc   6000
cagccggaag ggccgagcgc agaagtggtc ctgcaacttt atccgcctcc atccagtcta   6060
ttaattgttg ccgggaagct agagtaagta gttcgccagt taatagtttg cgcaacgttg   6120
ttgccattgc tacaggcatc gtggtgtcac gctcgtcgtt tggtatggct tcattcagct   6180
ccggttccca acgatcaagg cgagttacat gatcccccat gttgtgaaaa aaagcggtta   6240
gctccttcgg tcctccgatc gttgtcagaa gtaagttggc cgcagtgtta tcactcatgg   6300
```

-continued

```
ttatggcagc actgcataat tctcttactg tcatgccatc cgtaagatgc tttttctgtga   6360 ctggtgagta ctcaaccaag tcattctgag aatagtgtat gcggcgaccg agttgctctt   6420
gcccggcgtc aatacgggat aataccgcgc cacatagcag aactttaaaa gtgctcatca   6480
ttggaaaacg ttcttcgggg cgaaaactct caaggatctt accgctgttg agatccagtt   6540
cgatgtaacc cactcgtgca cccaactgat cttcagcatc ttttactttc accacgtttc   6600
tgggtgagca aaaacaggaa ggcaaaatgc cgcaaaaaag ggaataaggg cgacacggaa   6660
atgttgaata ctcatactct ccttttttca atattattga agcatttatc agggttattg   6720
tctcatgagc ggatacatat ttgaatgtat ttagaaaaat aaacaaatag gggttccgcg   6780
cacatttccc cgaaaagtgc cacctgggtc cttttcatca cgtgctataa aaataattat   6840
aatttaaatt ttttaatata aatatataaa ttaaaaatag aaagtaaaaa aagaaattaa   6900
agaaaaaata gttttgtttt tccgaagatg taaaagactc taggggggatc gccaacaaat   6960 actaccttt atcttgctct tcctgctctc aggtattaat gccgaattgt ttcatcttgt   7020
ctgtgtagaa gaccacacac gaaaatcctg tgattttaca tttttacttat cgttaatcga   7080 atgtatatct atttaatctg cttttcttgt ctaataaata tatatgtaaa gtacgctttt   7140
tgttgaaatt ttttaaacct ttgtttattt ttttttcttc attccgtaac tcttctacct   7200
tctttattta ctttctaaaa tccaaataca aaacataaaa ataaataaac acagagtaaa   7260
ttcccaaatt attccatcat taaaagatac gaggcgcgtg taagttacag gcaagcgatc   7320
cgtcctaaga aaccattatt atcatgacat taacctataa aaataggcgt atcacgaggc   7380
cctttcgtc                                                          7389
```

<210> SEQ ID NO 59
<211> LENGTH: 574
<212> TYPE: PRT
<213> ORGANISM: Saccharomyces cerevisiae
<220> FEATURE:
<221> NAME/KEY: MISC_FEATURE
<222> LOCATION: (1)..(574)
<223> OTHER INFORMATION: WT Gal2p amino acid sequence

<400> SEQUENCE: 59

```
Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Pro Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
    130                 135                 140

Met Tyr Gly Arg Lys Lys Gly Leu Ser Ile Val Val Ser Val Tyr Ile
145                 150                 155                 160
```

```
Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
                180                 185                 190

Leu Cys Pro Met Leu Ile Ser Glu Ile Ala Pro Lys His Leu Arg Gly
                195                 200                 205

Thr Leu Val Ser Cys Tyr Gln Leu Met Ile Thr Ala Gly Ile Phe Leu
            210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
                260                 265                 270

Asn Lys Val Glu Asp Ala Lys Leu Ser Ile Ala Lys Ser Asn Lys Val
            275                 280                 285

Ser Pro Glu Asp Pro Ala Val Gln Ala Glu Leu Asp Leu Ile Met Ala
            290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
                340                 345                 350

Gly Thr Val Ile Phe Lys Ser Val Gly Leu Asp Asp Ser Phe Glu Thr
            355                 360                 365

Ser Ile Val Ile Gly Val Val Asn Phe Ala Ser Thr Phe Phe Ser Leu
            370                 375                 380

Trp Thr Val Glu Asn Leu Gly Arg Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
                420                 425                 430

Asn Cys Met Ile Val Phe Thr Cys Phe Tyr Ile Phe Cys Tyr Ala Thr
            435                 440                 445

Thr Trp Ala Pro Val Ala Trp Val Ile Thr Ala Glu Ser Phe Pro Leu
            450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
                500                 505                 510

Phe Tyr Val Phe Phe Phe Val Pro Glu Thr Lys Gly Leu Ser Leu Glu
            515                 520                 525

Glu Ile Gln Glu Leu Trp Glu Glu Gly Val Leu Pro Trp Lys Ser Glu
530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570
```

-continued

```
<210> SEQ ID NO 60
<211> LENGTH: 9400
<212> TYPE: DNA
<213> ORGANISM: Artificial Sequence
<220> FEATURE:
<223> OTHER INFORMATION: pRN187 (pSH65-derived CRE recombinase
      expressing vector)
<220> FEATURE:
<221> NAME/KEY: source
<222> LOCATION: (1)..(9400)
<223> OTHER INFORMATION: /organism="Artificial Sequence" /note="pRN187
      (pSH65-derived CRE recombinase expressing vector)"
      /mol_type="unassigned DNA"

<400> SEQUENCE: 60
cctctagagt cgacctgcag cttctcaatg atattcgaat acgctttgag gagatacagc      60
ctaatatccg acaaactgtt ttacagattt acgatcgtac ttgttaccca tcattgaatt     120
ttgaacatcc gaacctggga gttttccctg aaacagatag tatatttgaa cctgtataat     180
aatatatagt ctagcgcttt acggaagaca atgtatgtat ttcggttcct ggagaaacta     240
ttgcatctat tgcataggta atcttgcacg tcgcatcccc ggttcatttt ctgcgtttcc     300
atcttgcact tcaatagcat atctttgtta acgaagcatc tgtgcttcat tttgtagaac     360
aaaaatgcaa cgcgagagcg ctaattttc aaacaaagaa tctgagctgc attttacag      420 aacagaaatg caacgcgaaa gcgctatttt accaacgaag aatctgtgct tcattttgt      480 aaaacaaaaa tgcaacgcga gagcgctaat ttttcaaaca agaatctga gctgcattttt    540 tacagaacag aaatgcaacg cgagagcgct attttaccaa caagaatct atacttcttt    600 tttgttctac aaaaatgcat cccgagagcg ctattttct aacaaagcat cttagattac    660 ttttttctc ctttgtgcgc tctataatgc agtctcttga taactttttg cactgtaggt    720
ccgttaaggt tagaagaagg ctactttggt gtctatttct cttccataa aaaagcctg      780 actccacttc ccgcgtttac tgattactag cgaagctgcg ggtgcatttt ttcaagataa    840
aggcatcccc gattatattc tataccgatg tggattgcgc atactttgtg aacagaaagt    900
gatagcgttg atgattcttc attggtcaga aaattatgaa cggtttcttc tattttgtct    960
ctatatacta cgtataggaa atgtttacat tttcgtattg tttttcgattc actctatgaa    1020 tagttcttac tacaattttt ttgtctaaag agtaatacta gagataaaca taaaaaatgt   1080
agaggtcgag tttagatgca agttcaagga gcgaaaggtg gatgggtagg ttatataggg   1140
atatagcaca gagatatata gcaaagagat acttttgagc aatgtttgtg gaagcggtat    1200
tcgcaatatt ttagtagctc gttacagtcc ggtgcgtttt tggttttttg aaagtgcgtc    1260
ttcagagcgc ttttggtttt caaaagcgct ctgaagttcc tatactttct agagaatagg    1320
aacttcggaa taggaacttc aaagcgtttc cgaaaacgag cgcttccgaa aatgcaacgc    1380
gagctgcgca catacagctc actgttcacg tcgcacctat atctgcgtgt tgcctgtata    1440
tatatataca tgagaagaac ggcatagtgc gtgtttatgc ttaaatgcgt acttatatgc    1500
gtctatttat gtaggatgaa aggtagtcta gtacctcctg tgatattatc ccattccatg    1560
cggggtatcg tatgcttcct tcagcactac cctttagctg ttctatatgc tgccactcct    1620
caattggatt agtctcatcc ttcaatgcta tcatttcctt tgatattgga tcatatgcat    1680
agtaccgaga aactagtgcg aagtagtgat caggtattgc tgttatctga tgagtatacg    1740
ttgtcctggc cacggcagaa gcacgcttat cgctccaatt tcccacaaca ttagtcaact    1800
ccgttaggcc cttcattgaa agaaatgagg tcatcaaatg tcttccaatg tgagattttg    1860
```

```
ggccattttt tatagcaaag attgaataag gcgcattttt cttcaaagct ttattgtacg      1920
atctgactaa gttatctttt aataattggt attcctgttt attgcttgaa gaattgccgg      1980
tcctatttac tcgttttagg actggttcag aattcttgaa gacgaaaggg cctcgtgata      2040
cgcctatttt tataggttaa tgtcatgata taatggtttt cttagacgtc aggtggcact      2100
tttcggggaa atgtgcgcgg aacccctatt tgtttatttt tctaaataca ttcaaatatg      2160
tatccgctca tgagacaata accctgataa atgcttcaat aatattgaaa aggaagagt       2220 atgagtattc aacatttccg tgtcgccctt attcccttttt tgcggcatt  ttgccttcct     2280 gttttttgctc acccagaaac gctggtgaaa gtaaaagatg ctgaagatca gttgggtgca     2340
cgagtgggtt acatcgaact ggatctcaac agcggtaaga tccttgagag ttttcgcccc      2400
gaagaacgtt ttccaatgat gagcactttt aaagttctgc tatgtggcgc ggtattatcc      2460
cgtgttgacg ccgggcaaga gcaactcggt cgccgcatac actattctca gaatgacttg      2520
gttgagtact caccagtcac agaaaagcat cttacggatg gcatgacagt aagagaatta      2580
tgcagtgctg ccataaccat gagtgataac actgcggcca acttacttct gacaacgatc      2640
ggaggaccga aggagctaac cgcttttttg cacaacatgg gggatcatgt aactcgcctt      2700
gatcgttggg aaccggagct gaatgaagcc ataccaaacg acgagcgtga caccacgatg      2760
cctgtagcaa tggcaacaac gttgcgcaaa ctattaactg gcgaactact tactctagct      2820
tcccggcaac aattaataga ctggatggag gcggataaag ttgcaggacc acttctgcgc      2880
tcggcccttc cggctggctg gtttattgct gataaatctg gagccggtga gcgtgggtct      2940
cgcggtatca ttgcagcact ggggccagat ggtaagccct cccgtatcgt agttatctac      3000
acgacgggga gtcaggcaac tatggatgaa cgaaatagac agatcgctga gataggtgcc      3060
tcactgatta agcattggta actgtcagac caagtttact catatatact ttagattgat      3120
ttaaaacttc attttaatt taaaaggatc taggtgaaga tcctttttga taatctcatg      3180
accaaaatcc cttaacgtga gttttcgttc cactgagcgt cagaccccgt agaaaagatc      3240
aaaggatctt cttgagatcc tttttttctg cgcgtaatct gctgcttgca acaaaaaaa      3300 ccaccgctac cagcggtggt ttgtttgccg gatcaagagc taccaactct ttttccgaag      3360
gtaactggct tcagcagagc gcagatacca atactgtcc ttctagtgta gccgtagtta      3420
ggccaccact tcaagaactc tgtagcaccg cctacatacc tcgctctgct aatcctgtta      3480
ccagtggctg ctgccagtgg cgataagtcg tgtcttaccg ggttggactc aagacgatag      3540
ttaccggata aggcgcagcg gtcgggctga acggggggtt cgtgcacaca gcccagcttg      3600
gagcgaacga cctacaccga actgagatac ctacagcgtg agctatgaga aagcgccacg      3660
cttcccgaag ggagaaaggc ggacaggtat ccggtaagcg gcagggtcgg aacaggagag      3720
cgcacgaggg agcttccagg gggaaacgcc tggtatcttt atagtcctgt cgggtttcgc      3780
cacctctgac ttgagcgtcg attttttgtga tgctcgtcag ggggggcgag cctatggaaa      3840
aacgccagca acgcggcctt tttacggttc ctggcctttt gctggccttt tgctcacatg      3900
ttctttcctg cgttatcccc tgattctgtg ataaccgta ttaccgcctt tgagtgagct       3960
gataccgctc gccgcagccg aacgaccgag cgcagcgagt cagtgagcga ggaagcggaa      4020
gagcgcccaa tacgcaaacc gcctctcccc gcgcgttggc cgattcatta atgcagctgg      4080
cacgacaggt ttcccgactg gaaagcgggc agtgagcgca acgcaattaa tgtgagttac      4140
ctcactcatt aggcacccca ggctttacac tttatgcttc cggctcctat gttgtgtgga      4200
attgtgagcg gataacaatt tcacacagga aacagctatg accatgatta cgccaagcgc      4260
```

```
gcaattaacc ctcactaaag ggaacaaaag ctggagctct agtacggatt agaagccgcc    4320
gagcgggtga cagccctccg aaggaagact ctcctccgtg cgtcctcgtc ttcaccggtc    4380
gcgttcctga acgcagatg tgcctcgcgc cgcactgctc cgaacaataa agattctaca    4440
atactagctt ttatggttat gaagaggaaa aattggcagt aacctggccc cacaaacctt    4500
caaatgaacg aatcaaatta acaaccatag gatgataatg cgattagttt tttagcctta    4560
tttctggggt aattaatcag cgaagcgatg attttttgatc tattaacaga tatataaatg    4620
caaaaactgc ataaccactt taactaatac tttcaacatt ttcggtttgt attacttctt    4680
attcaaatgt aataaaagta tcaacaaaaa attgttaata tacctctata ctttaacgtc    4740
aaggagaaaa aaccccggat tctagaacta gtggatcccc cgggctgcag gaattcgata    4800
tcaagcttat cgataccgtc gaggggcaga gccgatcctg tacactttac ttaaaaccat    4860
tatctgagtg ttaaatgtcc aatttactga ccgtacacca aaatttgcct gcattaccgg    4920
tcgatgcaac gagtgatgag gttcgcaaga acctgatgga catgttcagg gatcgccagg    4980
cgttttctga gcatacctgg aaaatgcttc tgtccgtttg ccggtcgtgg cggcatggt     5040 gcaagttgaa taaccggaaa tggtttcccg cagaacctga agatgttcgc gattatcttc    5100
tatatcttca ggcgcgcggt ctggcagtaa aaactatcca gcaacatttg ggccagctaa    5160
acatgcttca tcgtcggtcc gggctgccac gaccaagtga cagcaatgct gtttcactgg    5220
ttatgcggcg gatccgaaaa gaaaacgttg atgccggtga acgtgcaaaa caggctctag    5280
cgttcgaacg cactgatttc gaccaggttc gttcactcat ggaaaatagc gatcgctgcc    5340
aggatatacg taatctggca tttctgggga ttgcttataa caccctgtta cgtatagccg    5400
aaattgccag gatcagggtt aaagatatct cacgtactga cggtgggaga atgttaatcc    5460
atattggcag aacgaaaacg ctggttagca ccgcaggtgt agagaaggca cttagcctgg    5520
gggtaactaa actggtcgag cgatggattt ccgtctctgg tgtagctgat gatccgaata    5580
actacctgtt tgccgggtc agaaaaaatg gtgttgccgc gccatctgcc accagccagc    5640
tatcaactcg cgccctggaa gggatttttg aagcaactca tcgattgatt tacggcgcta    5700
aggatgactc tggtcagaga tacctggcct ggtctggaca cagtgcccgt gtcggagccg    5760
cgcgagatat ggcccgcgct ggagtttcaa taccggagat catgcaagct ggtggctgga    5820
ccaatgtaaa tattgtcatg aactatatcc gtaccctgga tagtgaaaca ggggcaatgg    5880
tgcgcctgct ggaagatggc gattagccat taacgcgtaa atgattgcta taattatttg    5940
atatttatgg tgacatatga gaaaggattt caacatcgac ggaaaatatg tagtgctgtc    6000
tgtaagcact aatattcagt cgccagccgt cattgtcact gtaaagctga gcgatagaat    6060
gcctgatatt gactcaatat ccgttgcgtt tcctgtcaaa agtatgcgta gtgctgaaca    6120
tttcgtgatg aatgccaccg aggaagaagc acggcgcggt tttgcaaagt gatgtctgag    6180
tttggcgaac tcttgggtaa ggttggaatt gtcgacctcg agtcatgtaa ttagttatgt    6240
cacgcttaca ttcacgccct ccccccacat ccgctctaac cgaaaggaa ggagttagac     6300 aacctgaagt ctaggtccct atttattttt ttatagttat gttagtatta agaacgttat    6360
ttatatttca aattttcttt tttttctgt acagacgcgt gtacgcatgt aacattatac    6420
tgaaaacctt gcttgagaag gttttgggac gctcgaaggc tttaatttgc ggccggtacc    6480
taggaccggt ttatcattat caatactgcc atttcaaaga atacgtaaat aattaatagt    6540
agtgattttc ctaactttat ttagtcaaaa aattagcctt taattctgc tgtaacccgt     6600
```

```
acatgcccaa aatagggggc gggttacaca gaatatataa catcgtaggt gtctgggtga      6660
acagtttatt cctggcatcc actaaatata atggagcccg ctttttaagc tggcatccag      6720
aaaaaaaaag aatcccagca ccaaaatatt gttttcttca ccaaccatca gttcataggt      6780
ccattctctt agcgcaacta cagagaacag gggcacaaac aggcaaaaaa cgggcacaac      6840
ctcaatggag tgatgcaacc tgcctggagt aaatgatgac acaaggcaat tgacccacgc      6900
atgtatctat ctcattttct tacaccttct attaccttct gctctctctg atttggaaaa      6960
agctgaaaaa aaaggttgaa accagttccc tgaaattatt cccctacttg actaataagt      7020
atataaagac ggtaggtatt gattgtaatt ctgtaaatct atttcttaaa cttcttaaat      7080 tctacttttta tagttagtct ttttttttagt tttaaaacac caagaactta gtttcgaata      7140
aacacacata aagaattcaa aatggtttca aaggtgaag aagataatat ggctattatt      7200
aaagaattta tgagatttaa agttcatatg gaaggttcag ttaatggtca tgaatttgaa      7260
attgaaggtg aaggtgaagg tagaccatat gaaggtactc aaactgctaa attgaaagtt      7320
actaaaggtg gtccattacc atttgcttgg gatatttgt caccacaatt tatgtatggt      7380
tcaaaagctt atgttaaaca tccagctgat attccagatt attttaaaatt gtcatttcca      7440 gaaggtttta aatgggaaag agttatgaat tttgaagatg gtggtgttgt tactgttact      7500
caagattcat cattacaaga tggtgaattt atttataaag ttaaattgag aggtactaat      7560
tttccatcag atggtccagt tatgcaaaaa aaaactatgg gttgggaagc ttcatcagaa      7620
agaatgtatc cagaagatgg tgctttaaaa ggtgaaatta acaaagatt gaaattaaaa      7680 gatggtggtc attatgatgc tgaagttaaa actacttata aagctaaaaa accagttcaa      7740
ttaccaggtg cttataatgt taatattaaa ttggatatta cttcacataa tgaagattat      7800
actattgttg aacaatatga aagagctgaa ggtagacatt caactggtgg tatggatgaa      7860
ttatataaat aatctagaca aatcgctctt aaatatatac ctaaagaaca ttaaagctat      7920
attataagca aagatacgta aattttgctt atattattat acacatatca tatttctata      7980
tttttaagat ttggttatat aatgtacgta atgcaaagga aataaatttttt atacattatt      8040 gaacagcgtc caagtaacta cattatgtgc actaatagtt tagcgtcgtg aagactttat      8100
tgtgtcgcga aaagtaaaaa ttttaaaaat tagagcacct tgaacttgcg aaaaaggttc      8160
tcatcaactg ttttaaaagat ctgagctcgc ggccgcgata tcgctagctc gagcccacac      8220
accatagctt caaaatgttt ctactccttt tttactcttc cagattttct cggactccgc      8280
gcatcgccgt accacttcaa aacacccaag cacagcatac taaattttcc ctctttcttc      8340
ctctagggtg tcgttaatta cccgtactaa aggtttggaa aagaaaaaag agaccgcctc      8400
gtttcttttt cttcgtcgaa aaaggcaata aaaattttta tcacgtttct ttttcttgaa      8460 atttttttttt ttagtttttt tctctttcag tgacctccat tgatatttaa gttaataaac      8520
ggtcttcaat ttctcaagtt tcagtttcat ttttcttgtt ctattacaac ttttttttact      8580 tcttgttcat tagaaagaaa gcatagcaat ctaatctaag gggcggtgtt gacaattaat      8640
catcggcata gtatatcggc atagtataat acgacaaggt gaggaactaa accatggcca      8700
agttgaccag tgccgttccg gtgctcaccg cgcgcgacgt cgccggagcg gtcgagttct      8760
ggaccgaccg gctcgggttc tcccgggact tcgtggagga cgacttcgcc ggtgtggtcc      8820
gggacgacgt gaccctgttc atcagcgcgc tccaggacca ggtggtgccg gacaacaccc      8880
tggcctgggt gtgggcgcgc ggcctggacg agctgtacgc cgagtggtcg gaggtcgtgt      8940
ccacgaactt ccgggacgcc tccgggccgg ccatgaccga gatcggcgag cagccgtggg      9000
```

```
ggcgggagtt cgccctgcgc gacccggccg gcaactgcgt gcacttcgtg gccgaggagc      9060
aggactgaca cgtccgacgg cggcccacgg gtcccaggcc tcggagatcc gtcccccttt      9120
tcctttgtcg atatcatgta attagttatg tcacgcttac attcacgccc tccccccaca      9180
tccgctctaa ccgaaaagga aggagttaga caacctgaag tctaggtccc tatttatttt      9240
tttatagtta tgttagtatt aagaacgtta tttatatttc aaattttttct ttttttttctg     9300 tacagacgcg tgtacgcatg taacattata ctgaaaacct tgcttgagaa ggttttggga      9360
cgctcgaagg ctttaatttg caagctgaat tcccggggat                             9400

<210> SEQ ID NO 61
<211> LENGTH: 5763
<212> TYPE: DNA
<213> ORGANISM: Artificial Sequence
<220> FEATURE:
<223> OTHER INFORMATION: pRN486 (TOPO-BLUNT-his3::loxP-natMX-loxP)
<220> FEATURE:
<221> NAME/KEY: source
<222> LOCATION: (1)..(5763)
<223> OTHER INFORMATION: /organism="Artificial Sequence" /note="pRN486
      (TOPO-BLUNT-his3::loxP-natMX-loxP)" /mol_type="unassigned DNA"

<400> SEQUENCE: 61
acttcgtata atgtatgcta tacgaagtta tacgtacgca gttgtcgaac ttggtttgca        60
aagggagaaa gtaggagatc tctcttgcga gatgatcccg cattttcttg aaagctttgc       120
agaggctagc agaattaccc tccacgttga ttgtctgcga ggcaagaatg atcatcaccg       180
tagtgagagt gcgttcaagg ctcttgcggt tgccataaga gaagccacct cgcccaatgg       240
taccaacgat gttccctcca ccaaaggtgt tcttatgtag tgacaccgat tatttaaagc       300
tgcagcatac gatatatata catgtgtata tatgtatacc tatgaatgtc agtaagtatg       360
tatacgaaca gtatgatact gaagatgaca aggtaatgca tcattctata cgtgtcattc       420
tgaacgaggc gcgcttttcct ttttctttt tgcttttttct ttttttttct cttgaactcg       480
acggatcata tgcggtgtga aatactcgag atcttgctga aaaactcgag ccatccggaa       540
gatctggctt aagggcgaat tctgagatat ccatcacact ggcggccgct cgagcatgca       600
tctagagggc ccaattcgcc ctatagtgag tcgtattaca attcactggc cgtcgtttta       660
caacgtcgtg actgggaaaa ccctggcgtt acccaactta atcgccttgc agcacatccc       720
cctttcgcca gctggcgtaa tagcgaagag gcccgcaccg atcgcccttc ccaacagttg       780
cgcagcctat acgtacggca gtttaaggtt tacacctata aaagagagag ccgttatcgt       840
ctgtttgtgg atgtacagag tgatattatt gacacgccgg ggcgacggat ggtgatcccc       900
ctggccagtg cacgtctgct gtcagataaa gtctcccgtg aactttaccc ggtggtgcat       960
atcggggatg aaagctggcg catgatgacc accgatatgg ccagtgtgcc ggtctccgtt      1020
atcggggaag aagtggctga tctcagccac cgcgaaaatg acatcaaaaa cgccattaac      1080
ctgatgttct ggggaatata atgtcaggc atgagattat caaaaaggat cttcacctag       1140
atccttttca cgtagaaagc cagtccgcag aaacggtgct gaccccggat gaatgtcagc      1200
tactgggcta tctggacaag ggaaaacgca agcgcaaaga gaaagcaggt agcttgcagt      1260
gggcttacat ggcgatagct agactgggcg gttttatgga cagcaagcga accggaattg      1320
ccagctgggg cgccctctgg taaggttggg aagccctgca agtaaactg gatggctttc      1380 tcgccgccaa ggatcgatg gcgcagggga tcaagctctg atcaagagac aggatgagga      1440
tcgtttcgca tgattgaaca agatggattg cacgcaggtt ctccggccgc ttgggtggag      1500
```

```
aggctattcg gctatgactg ggcacaacag acaatcggct gctctgatgc cgccgtgttc    1560
cggctgtcag cgcaggggcg cccggttctt tttgtcaaga ccgacctgtc cggtgccctg    1620
aatgaactgc aagacgaggc agcgcggcta tcgtggctgg ccacgacggg cgttccttgc    1680
gcagctgtgc tcgacgttgt cactgaagcg ggaagggact ggctgctatt gggcgaagtg    1740
ccggggcagg atctcctgtc atctcacctt gctcctgccg agaaagtatc catcatggct    1800
gatgcaatgc ggcggctgca tacgcttgat ccggctacct gcccattcga ccaccaagcg    1860
aaacatcgca tcgagcgagc acgtactcgg atggaagccg gtcttgtcga tcaggatgat    1920
ctggacgaag agcatcaggg gctcgcgcca gccgaactgt tcgccaggct caaggcgagc    1980
atgcccgacg gcgaggatct cgtcgtgacc catggcgatg cctgcttgcc gaatatcatg    2040
gtggaaaatg gccgcttttc tggattcatc gactgtggcc ggctgggtgt ggcggaccgc    2100
tatcaggaca tagcgttggc tacccgtgat attgctgaag agcttggcgg cgaatgggct    2160
gaccgcttcc tcgtgcttta cggtatcgcc gctcccgatt cgcagcgcat cgccttctat    2220
cgccttcttg acgagttctt ctgaattatt aacgcttaca atttcctgat gcggtatttt    2280
ctccttacgc atctgtgcgg tatttcacac cgcatacagg tggcactttt cggggaaatg    2340
tgcgcggaac ccctatttgt ttatttttct aaatacattc aaatatgtat ccgctcatga    2400
gacaataacc ctgataaatg cttcaataat agcacgtgag gagggccacc atggccaagt    2460
tgaccagtgc cgttccggtg ctcaccgcgc gcgacgtcgc cggagcggtc gagttctgga    2520
ccgaccggct cgggttctcc cgggacttcg tggaggacga cttcgccggt gtggtccggg    2580
acgacgtgac cctgttcatc agcgcggtcc aggaccaggt ggtgccggac aacaccctgg    2640
cctgggtgtg ggtgcgcggc ctggacgagc tgtacgccga gtggtcggag gtcgtgtcca    2700
cgaacttccg ggacgcctcc gggccggcca tgaccgagat cggcgagcag ccgtgggggc    2760
gggagttcgc cctgcgcgac ccggccggca actgcgtgca cttcgtggcc gaggagcagg    2820
actgacacgt gctaaaactt catttttaat ttaaaaggat ctaggtgaag atccttttg     2880 ataatctcat gaccaaaatc ccttaacgtg agttttcgtt ccactgagcg tcagaccccg    2940
tagaaaagat caaaggatct tcttgagatc ctttttttct gcgcgtaatc tgctgcttgc    3000
aaacaaaaaa accaccgcta ccagcggtgg tttgtttgcc ggatcaagag ctaccaactc    3060
tttttccgaa ggtaactggc ttcagcagag cgcagatacc aaatactgtc cttctagtgt    3120
agccgtagtt aggccaccac ttcaagaact ctgtagcacc gcctacatac ctcgctctgc    3180
taatcctgtt accagtggct gctgccagtg gcgataagtc gtgtcttacc gggttggact    3240
caagacgata gttaccggat aaggcgcagc ggtcgggctg aacggggggt tcgtgcacac    3300
agcccagctt ggagcgaacg acctacaccg aactgagata cctacagcgt gagctatgag    3360
aaagcgccac gcttcccgaa gggagaaagg cggacaggta tccggtaagc ggcagggtcg    3420
gaacaggaga gcgcacgagg gagcttccag ggggaaacgc ctggtatctt tatagtcctg    3480
tcgggtttcg ccacctctga cttgagcgtc gatttttgtg atgctcgtca ggggggcgga    3540
gcctatggaa aaacgccagc aacgcggcct ttttacggtt cctgggcttt tgctggcctt    3600
ttgctcacat gttctttcct gcgttatccc ctgattctgt ggataaccgt attaccgcct    3660
ttgagtgagc tgataccgct cgccgcagcc gaacgaccga gcgcagcgag tcaagcgccc    3720
aatacgcaaa ccgcctctcc ccgcgcgttg gccgattcat taatgcagct ggcacgacag    3780
gtttcccgac tggaaagcgg gcagtgagcg caacgcaatt aatgtgagtt agctcactca    3840
```

```
ttaggcaccc caggctttac actttatgct tccggctcgt atgttgtgtg gaattgtgag    3900
cggataacaa tttcacacag gaaacagcta tgaccatgat tacgccaagc tatttaggtg    3960
acactataga atactcaagc tatgcatcaa gcttggtacc gagctcggat ccactagtaa    4020
cggccgccag tgtgctggaa ttcgccccat ggcagctgag aatattgtag gagatcttct    4080
agaaagattg tacatccgga attctagatt ggtgagcgct aggagtcact gccaggtatc    4140
gtttgaacac ggcattagtc agggaagtca taacacagtc cttccccgca attttctttt    4200
tctattactc ttggcctcct ctagtacact ctatattttt ttatgcctcg gtaatgattt    4260 tcatttttt ttttccacct agcggatgac tcttttttt tcttagcgat tggcattatc    4320
acataatgaa ttatacatta tataaagtaa tgtgatttct tcgaagaata tactaaaaaa    4380
tgagcaggca agataaacga aggcaaagat gacagagcag aaagccctag taaagcgtat    4440
tacaaatgaa accaagattc agattgcgat ctctttccta taacttcgta tagcatacat    4500
tatacgaagt tatgcgcgct ctagatatcg tcgacactgg atggcggcgt tagtatcgaa    4560
tcgacagcag tatagcgacc agcattcaca tacgattgac gcatgatatt actttctgcg    4620 cacttaacttt cgcatctggg cagatgatgt cgaggcgaaa aaaatataa atcacgctaa    4680 catttgatta aaatagaaca actacaatat aaaaaaacta tacaaatgac aagttcttga    4740
aaacaagaat cttttattg tcagtactag gggcagggca tgctcatgta gagcgcctgc    4800
tcgccgtccg aggcggtgcc gtcgtacagg gcggtgtcca ggccgcagag ggtgaacccc    4860
atccgccggt acgcgtggat cgccggtgcg ttgacgttgg tgacctccag ccagaggtgc    4920
ccggcgcccc gctcgcgggc gaactccgtc gcgagcccca tcaacgcgcg cccgaccccg    4980 tgccccggt gctccggggc gacctcgatg tcctcgacgg tcagccggcg gttccagccg    5040
gagtacgaga cgaccacgaa gcccgccagg tcgccgtcgt ccccgtacgc gacgaacgtc    5100
cgggagtccg ggtcgccgtc ctccccggcg tccgattcgt cgtccgattc gtcgtcgggg    5160
aacaccttgg tcaggggcgg gtccaccggc acctcccgca gggtgaagcc gtccccggtg    5220
gcggtgacgc ggaagacggt gtcggtggtg aaggacccat ccagtgcctc gatggcctcg    5280
gcgtcccccg ggacactggt gcggtaccgg taagccgtgt cgtcaagagt ggtcatttta    5340
catggttgtt tatgttcgga tgtgatgtga aactgtatc ctagcaagat tttaaagga    5400 agtatatgaa agaagaacct cagtggcaaa tcctaacctt ttatatttct ctacaggggc    5460
gcggcgtggg gacaattcaa cgcgtctgtg aggggagcgt ttccctgctc gcaggtctgc    5520
agcgaggagc cgtaattttt gcttcgcgcc gtgcggccat caaaatgtat ggatgcaaat    5580
gattatacat ggggatgtat gggctaaatg tacgggcgac agtcacatca tgcccctgag    5640
ctgcgcacgt caagactgtc aaggagggta ttctgggcct ccatgtcgct ggccgggtga    5700
cccggcgggg acgaggcaag cttaagggcg aattccagca cactggcggc cgttactaga    5760
ata                                                                  5763
```

<210> SEQ ID NO 62
<211> LENGTH: 23
<212> TYPE: DNA
<213> ORGANISM: Artificial Sequence
<220> FEATURE:
<223> OTHER INFORMATION: Primer ActinF (Real time PCR)
<220> FEATURE:
<221> NAME/KEY: source
<222> LOCATION: (1)..(23)
<223> OTHER INFORMATION: /organism="Artificial Sequence" /note="Primer ActinF (Real time PCR)" /mol_type="unassigned DNA"

<400> SEQUENCE: 62
ggattctgag gttgctgctt tgg                                             23

<210> SEQ ID NO 63
<211> LENGTH: 23
<212> TYPE: DNA
<213> ORGANISM: Artificial Sequence
<220> FEATURE:
<223> OTHER INFORMATION: Primer ActinR (Real time PCR)
<220> FEATURE:
<221> NAME/KEY: source
<222> LOCATION: (1)..(23)
<223> OTHER INFORMATION: /organism="Artificial Sequence" /note="Primer
      ActinR (Real time PCR)" /mol_type="unassigned DNA"

<400> SEQUENCE: 63
gagcttcatc accaacgtag gag                                             23

<210> SEQ ID NO 64
<211> LENGTH: 23
<212> TYPE: DNA
<213> ORGANISM: Artificial Sequence
<220> FEATURE:
<223> OTHER INFORMATION: Primer HXT1F (Real time PCR)
<220> FEATURE:
<221> NAME/KEY: source
<222> LOCATION: (1)..(23)
<223> OTHER INFORMATION: /organism="Artificial Sequence" /note="Primer
      HXT1F (Real time PCR)" /mol_type="unassigned DNA"

<400> SEQUENCE: 64
tgttctctgt acaccgttga ccg                                             23

<210> SEQ ID NO 65
<211> LENGTH: 23
<212> TYPE: DNA
<213> ORGANISM: Artificial Sequence
<220> FEATURE:
<223> OTHER INFORMATION: Primer HXT1R (Real time PCR)
<220> FEATURE:
<221> NAME/KEY: source
<222> LOCATION: (1)..(23)
<223> OTHER INFORMATION: /organism="Artificial Sequence" /note="Primer
      HXT1R (Real time PCR)" /mol_type="unassigned DNA"

<400> SEQUENCE: 65
agatcataca gttaccagca ccc                                             23

<210> SEQ ID NO 66
<211> LENGTH: 19
<212> TYPE: DNA
<213> ORGANISM: Artificial Sequence
<220> FEATURE:
<223> OTHER INFORMATION: Primer HXT2F (Real time PCR)
<220> FEATURE:
<221> NAME/KEY: source
<222> LOCATION: (1)..(19)
<223> OTHER INFORMATION: /organism="Artificial Sequence" /note=" Primer
      HXT2F (Real time PCR)" /mol_type="unassigned DNA"

<400> SEQUENCE: 66
cttcgcatcc actttcgtg                                                  19

<210> SEQ ID NO 67
<211> LENGTH: 22
<212> TYPE: DNA
<213> ORGANISM: Artificial Sequence
<220> FEATURE:
<223> OTHER INFORMATION: Primer HXT2R (Real time PCR)

-continued

```
<220> FEATURE:
<221> NAME/KEY: source
<222> LOCATION: (1)..(22)
<223> OTHER INFORMATION: /organism="Artificial Sequence" /note="Primer
      HXT2R (Real time PCR)" /mol_type="unassigned DNA"

<400> SEQUENCE: 67
aatcatgacg ttaccggcag cc                                           22

<210> SEQ ID NO 68
<211> LENGTH: 23
<212> TYPE: DNA
<213> ORGANISM: Artificial Sequence
<220> FEATURE:
<223> OTHER INFORMATION: Primer HXT3F (Real time PCR)
<220> FEATURE:
<221> NAME/KEY: source
<222> LOCATION: (1)..(23)
<223> OTHER INFORMATION: /organism="Artificial Sequence" /note="Primer
      HXT3F (Real time PCR)" /mol_type="unassigned DNA"

<400> SEQUENCE: 68
gaagctagag ctgctggttc agc                                          23

<210> SEQ ID NO 69
<211> LENGTH: 24
<212> TYPE: DNA
<213> ORGANISM: Artificial Sequence
<220> FEATURE:
<223> OTHER INFORMATION: Primer HXT3R (Real time PCR)
<220> FEATURE:
<221> NAME/KEY: source
<222> LOCATION: (1)..(24)
<223> OTHER INFORMATION: /organism="Artificial Sequence" /note="Primer
      HXT3R (Real time PCR)" /mol_type="unassigned DNA"

<400> SEQUENCE: 69
acaacgacat aaggaattgg agcc                                         24

<210> SEQ ID NO 70
<211> LENGTH: 24
<212> TYPE: DNA
<213> ORGANISM: Artificial Sequence
<220> FEATURE:
<223> OTHER INFORMATION: Primer HXT4F (Real time PCR)
<220> FEATURE:
<221> NAME/KEY: source
<222> LOCATION: (1)..(24)
<223> OTHER INFORMATION: /organism="Artificial Sequence" /note="Primer
      HXT4F (Real time PCR)" /mol_type="unassigned DNA"

<400> SEQUENCE: 70
atggagagtt ccattaggtc tagg                                         24

<210> SEQ ID NO 71
<211> LENGTH: 24
<212> TYPE: DNA
<213> ORGANISM: Artificial Sequence
<220> FEATURE:
<223> OTHER INFORMATION: Primer HXT4R (Real time PCR)
<220> FEATURE:
<221> NAME/KEY: source
<222> LOCATION: (1)..(24)
<223> OTHER INFORMATION: /organism="Artificial Sequence" /note="Primer
      HXT4R (Real time PCR)" /mol_type="unassigned DNA"

<400> SEQUENCE: 71
atggagagtt ccattaggtc tagg                                         24
```

```
<210> SEQ ID NO 72
<211> LENGTH: 23
<212> TYPE: DNA
<213> ORGANISM: Artificial Sequence
<220> FEATURE:
<223> OTHER INFORMATION: Primer HXT5F (Real time PCR)
<220> FEATURE:
<221> NAME/KEY: source
<222> LOCATION: (1)..(23)
<223> OTHER INFORMATION: /organism="Artificial Sequence" /note="Primer
      HXT5F (Real time PCR)" /mol_type="unassigned DNA"

<400> SEQUENCE: 72
ttgctatgtc gtctatgcct ctg                                            23

<210> SEQ ID NO 73
<211> LENGTH: 22
<212> TYPE: DNA
<213> ORGANISM: Artificial Sequence
<220> FEATURE:
<223> OTHER INFORMATION: Primer HXT5R (Real time PCR)
<220> FEATURE:
<221> NAME/KEY: source
<222> LOCATION: (1)..(22)
<223> OTHER INFORMATION: /organism="Artificial Sequence" /note="Primer
      HXT5R (Real time PCR)" /mol_type="unassigned DNA"

<400> SEQUENCE: 73
agataaggac ataggcaacg gg                                             22

<210> SEQ ID NO 74
<211> LENGTH: 21
<212> TYPE: DNA
<213> ORGANISM: Artificial Sequence
<220> FEATURE:
<223> OTHER INFORMATION: Primer HXT7F (Real time PCR)
<220> FEATURE:
<221> NAME/KEY: source
<222> LOCATION: (1)..(21)
<223> OTHER INFORMATION: /organism="Artificial Sequence" /note="Primer
      HXT7F (Real time PCR)" /mol_type="unassigned DNA"

<400> SEQUENCE: 74
gggtgctgca tccatgactg c                                              21

<210> SEQ ID NO 75
<211> LENGTH: 24
<212> TYPE: DNA
<213> ORGANISM: Artificial Sequence
<220> FEATURE:
<223> OTHER INFORMATION: Primer HXT7R (Real time PCR)
<220> FEATURE:
<221> NAME/KEY: source
<222> LOCATION: (1)..(24)
<223> OTHER INFORMATION: /organism="Artificial Sequence" /note="Primer
      HXT7R (Real time PCR)" /mol_type="unassigned DNA"

<400> SEQUENCE: 75
acaacgacat aaggaattgg agcc                                           24

<210> SEQ ID NO 76
<211> LENGTH: 25
<212> TYPE: DNA
<213> ORGANISM: Artificial Sequence
<220> FEATURE:
<223> OTHER INFORMATION: Primer HXT8F ( (Real time PCR)
<220> FEATURE:
<221> NAME/KEY: source
<222> LOCATION: (1)..(25)
<223> OTHER INFORMATION: /organism="Artificial Sequence"
      /note="Primer HXT8F ( (Real time PCR)" /mol_type="unassigned DNA"
```

<400> SEQUENCE: 76
gtactactat cttcaaatct gtcgg                                              25

<210> SEQ ID NO 77
<211> LENGTH: 21
<212> TYPE: DNA
<213> ORGANISM: Artificial Sequence
<220> FEATURE:
<223> OTHER INFORMATION: Primer HXT8R (Real time PCR)
<220> FEATURE:
<221> NAME/KEY: source
<222> LOCATION: (1)..(21)
<223> OTHER INFORMATION: /organism="Artificial Sequence" /note="Primer
      HXT8R (Real time PCR)" /mol_type="unassigned DNA"

<400> SEQUENCE: 77
cttgtgacgc aacggaggc g                                                   21

<210> SEQ ID NO 78
<211> LENGTH: 22
<212> TYPE: DNA
<213> ORGANISM: Artificial Sequence
<220> FEATURE:
<223> OTHER INFORMATION: Primer HXT9F (Real time PCR)
<220> FEATURE:
<221> NAME/KEY: source
<222> LOCATION: (1)..(22)
<223> OTHER INFORMATION: /organism="Artificial Sequence" /note="Primer
      HXT9F (Real time PCR)" /mol_type="unassigned DNA"

<400> SEQUENCE: 78
ccattgagag gtttggacgc cg                                                 22

<210> SEQ ID NO 79
<211> LENGTH: 23
<212> TYPE: DNA
<213> ORGANISM: Artificial Sequence
<220> FEATURE:
<223> OTHER INFORMATION: Primer HXT9R (Real time PCR)
<220> FEATURE:
<221> NAME/KEY: source
<222> LOCATION: (1)..(23)
<223> OTHER INFORMATION: /organism="Artificial Sequence" /note="Primer
      HXT9R (Real time PCR)" /mol_type="unassigned DNA"

<400> SEQUENCE: 79
acacaatcat acagttaccg gcg                                                23

<210> SEQ ID NO 80
<211> LENGTH: 23
<212> TYPE: DNA
<213> ORGANISM: Artificial Sequence
<220> FEATURE:
<223> OTHER INFORMATION: Primer HXT10F (Real time PCR)
<220> FEATURE:
<221> NAME/KEY: source
<222> LOCATION: (1)..(23)
<223> OTHER INFORMATION: /organism="Artificial Sequence" /note="Primer
      HXT10F (Real time PCR)" /mol_type="unassigned DNA"

<400> SEQUENCE: 80
ggaatgcaag actctttcga gac                                                23

<210> SEQ ID NO 81
<211> LENGTH: 21
<212> TYPE: DNA
<213> ORGANISM: Artificial Sequence
<220> FEATURE:

```
<223> OTHER INFORMATION: Primer HXT10R (Real time PCR)
<220> FEATURE:
<221> NAME/KEY: source
<222> LOCATION: (1)..(21)
<223> OTHER INFORMATION: /organism="Artificial Sequence" /note="Primer
      HXT10R (Real time PCR)" /mol_type="unassigned DNA"

<400> SEQUENCE: 81
ctagtgacgc aacggtggc g                                              21

<210> SEQ ID NO 82
<211> LENGTH: 21
<212> TYPE: DNA
<213> ORGANISM: Artificial Sequence
<220> FEATURE:
<223> OTHER INFORMATION: Primer HXT11F (Real time PCR)
<220> FEATURE:
<221> NAME/KEY: source
<222> LOCATION: (1)..(21)
<223> OTHER INFORMATION: /organism="Artificial Sequence" /note="Primer
      HXT11F (Real time PCR)" /mol_type="unassigned DNA"

<400> SEQUENCE: 82
gccactcaat ggagagtcgg c                                             21

<210> SEQ ID NO 83
<211> LENGTH: 22
<212> TYPE: DNA
<213> ORGANISM: Artificial Sequence
<220> FEATURE:
<223> OTHER INFORMATION: Primer HXT11R (Real time PCR)
<220> FEATURE:
<221> NAME/KEY: source
<222> LOCATION: (1)..(22)
<223> OTHER INFORMATION: /organism="Artificial Sequence" /note="Primer
      HXT11R (Real time PCR)" /mol_type="unassigned DNA"

<400> SEQUENCE: 83
caactagcaa ggctggatcg tc                                            22

<210> SEQ ID NO 84
<211> LENGTH: 23
<212> TYPE: DNA
<213> ORGANISM: Artificial Sequence
<220> FEATURE:
<223> OTHER INFORMATION: Primer HXT12F (Real time PCR)
<220> FEATURE:
<221> NAME/KEY: source
<222> LOCATION: (1)..(23)
<223> OTHER INFORMATION: /organism="Artificial Sequence" /note="Primer
      HXT12F (Real time PCR)" /mol_type="unassigned DNA"

<400> SEQUENCE: 84
caccatcttc aaatctgtcg gtc                                           23

<210> SEQ ID NO 85
<211> LENGTH: 23
<212> TYPE: DNA
<213> ORGANISM: Artificial Sequence
<220> FEATURE:
<223> OTHER INFORMATION: Primer HXT12R (Real time PCR)
<220> FEATURE:
<221> NAME/KEY: source
<222> LOCATION: (1)..(23)
<223> OTHER INFORMATION: /organism="Artificial Sequence" /note="Primer
      HXT12R (Real time PCR)" /mol_type="unassigned DNA"

<400> SEQUENCE: 85
caatcataca gttaccggca ccc                                           23
```

```
<210> SEQ ID NO 86
<211> LENGTH: 20
<212> TYPE: DNA
<213> ORGANISM: Artificial Sequence
<220> FEATURE:
<223> OTHER INFORMATION: Primer HXT13F (Real time PCR)
<220> FEATURE:
<221> NAME/KEY: source
<222> LOCATION: (1)..(20)
<223> OTHER INFORMATION: /organism="Artificial Sequence" /note="Primer
      HXT13F (Real time PCR)" /mol_type="unassigned DNA"

<400> SEQUENCE: 86
ccctcatggc caggacggtc                                                  20

<210> SEQ ID NO 87
<211> LENGTH: 23
<212> TYPE: DNA
<213> ORGANISM: Artificial Sequence
<220> FEATURE:
<223> OTHER INFORMATION: Primer HXT13R (Real time PCR)
<220> FEATURE:
<221> NAME/KEY: source
<222> LOCATION: (1)..(23)
<223> OTHER INFORMATION: /organism="Artificial Sequence" /note="Primer
      HXT13R (Real time PCR)" /mol_type="unassigned DNA"

<400> SEQUENCE: 87
ttgccataac cagttgcatg cag                                              23

<210> SEQ ID NO 88
<211> LENGTH: 24
<212> TYPE: DNA
<213> ORGANISM: Artificial Sequence
<220> FEATURE:
<223> OTHER INFORMATION: Primer HXT14F (Real time PCR)
<220> FEATURE:
<221> NAME/KEY: source
<222> LOCATION: (1)..(24)
<223> OTHER INFORMATION: /organism="Artificial Sequence" /note="Primer
      HXT14F (Real time PCR)" /mol_type="unassigned DNA"

<400> SEQUENCE: 88
gccttagtag tgtactgcat cggt                                             24

<210> SEQ ID NO 89
<211> LENGTH: 23
<212> TYPE: DNA
<213> ORGANISM: Artificial Sequence
<220> FEATURE:
<223> OTHER INFORMATION: Primer HXT14R (Real time PCR)
<220> FEATURE:
<221> NAME/KEY: source
<222> LOCATION: (1)..(23)
<223> OTHER INFORMATION: /organism="Artificial Sequence" /note="Primer
      HXT14R (Real time PCR)" /mol_type="unassigned DNA"

<400> SEQUENCE: 89
tgatacgtag ataccatgga gcc                                              23

<210> SEQ ID NO 90
<211> LENGTH: 21
<212> TYPE: DNA
<213> ORGANISM: Artificial Sequence
<220> FEATURE:
<223> OTHER INFORMATION: Primer HXT15F (Real time PCR)
<220> FEATURE:
<221> NAME/KEY: source
<222> LOCATION: (1)..(21)
<223> OTHER INFORMATION: /organism="Artificial Sequence" /note="Primer
```

-continued

HXT15F (Real time PCR)" /mol_type="unassigned DNA"

<400> SEQUENCE: 90
gaggcctgtg tctccatcgc c                                            21

<210> SEQ ID NO 91
<211> LENGTH: 24
<212> TYPE: DNA
<213> ORGANISM: Artificial Sequence
<220> FEATURE:
<223> OTHER INFORMATION: Primer HXT15R (Real time PCR)
<220> FEATURE:
<221> NAME/KEY: source
<222> LOCATION: (1)..(24)
<223> OTHER INFORMATION: /organism="Artificial Sequence" /note="Primer
      HXT15R (Real time PCR)" /mol_type="unassigned DNA"

<400> SEQUENCE: 91
cacaagaata cctgtgatca aacg                                         24

<210> SEQ ID NO 92
<211> LENGTH: 24
<212> TYPE: DNA
<213> ORGANISM: Artificial Sequence
<220> FEATURE:
<223> OTHER INFORMATION: Primer HXT16F (Real time PCR)
<220> FEATURE:
<221> NAME/KEY: source
<222> LOCATION: (1)..(24)
<223> OTHER INFORMATION: /organism="Artificial Sequence" /note="Primer
      HXT16F (Real time PCR)" /mol_type="unassigned DNA"

<400> SEQUENCE: 92
caaggaagta tagtaatact gcgc                                         24

<210> SEQ ID NO 93
<211> LENGTH: 21
<212> TYPE: DNA
<213> ORGANISM: Artificial Sequence
<220> FEATURE:
<223> OTHER INFORMATION: Primer HXT16R (Real time PCR)
<220> FEATURE:
<221> NAME/KEY: source
<222> LOCATION: (1)..(21)
<223> OTHER INFORMATION: /organism="Artificial Sequence" /note="Primer
      HXT16R (Real time PCR)" /mol_type="unassigned DNA"

<400> SEQUENCE: 93
ttggcgatgg agacacaggc c                                            21

<210> SEQ ID NO 94
<211> LENGTH: 23
<212> TYPE: DNA
<213> ORGANISM: Artificial Sequence
<220> FEATURE:
<223> OTHER INFORMATION: Primer HXT17F (Real time PCR)
<220> FEATURE:
<221> NAME/KEY: source
<222> LOCATION: (1)..(23)
<223> OTHER INFORMATION: /organism="Artificial Sequence" /note="Primer
      HXT17F (Real time PCR)" /mol_type="unassigned DNA"

<400> SEQUENCE: 94
taacactgca caatggagag tcc                                          23

<210> SEQ ID NO 95
<211> LENGTH: 22
<212> TYPE: DNA
<213> ORGANISM: Artificial Sequence -continued

```
<220> FEATURE:
<223> OTHER INFORMATION: Primer HXT17R (Real time PCR)
<220> FEATURE:
<221> NAME/KEY: source
<222> LOCATION: (1)..(22)
<223> OTHER INFORMATION: /organism="Artificial Sequence" /note="Primer
      HXT17R (Real time PCR)" /mol_type="unassigned DNA"

<400> SEQUENCE: 95
tgagtaccca tggatcctct gg                                            22

<210> SEQ ID NO 96
<211> LENGTH: 23
<212> TYPE: DNA
<213> ORGANISM: Artificial Sequence
<220> FEATURE:
<223> OTHER INFORMATION: Primer GAL2F (Real time PCR)
<220> FEATURE:
<221> NAME/KEY: source
<222> LOCATION: (1)..(23)
<223> OTHER INFORMATION: /organism="Artificial Sequence" /note="Primer
      GAL2F (Real time PCR)" /mol_type="unassigned DNA"

<400> SEQUENCE: 96
tcaatggaga gttccattag ggc                                           23

<210> SEQ ID NO 97
<211> LENGTH: 21
<212> TYPE: DNA
<213> ORGANISM: Artificial Sequence
<220> FEATURE:
<223> OTHER INFORMATION: Primer GAL2R (Real time PCR)
<220> FEATURE:
<221> NAME/KEY: source
<222> LOCATION: (1)..(21)
<223> OTHER INFORMATION: /organism="Artificial Sequence" /note="Primer
      GAL2R (Real time PCR)" /mol_type="unassigned DNA"

<400> SEQUENCE: 97
ctggacggca ggatcctctg g                                             21

<210> SEQ ID NO 98
<211> LENGTH: 82
<212> TYPE: DNA
<213> ORGANISM: Artificial Sequence
<220> FEATURE:
<223> OTHER INFORMATION: Primer KOP11* for KO HXT11
<220> FEATURE:
<221> NAME/KEY: source
<222> LOCATION: (1)..(82)
<223> OTHER INFORMATION: /organism="Artificial Sequence" /note="Primer
      KOP11* for KO HXT11" /mol_type="unassigned DNA"

<400> SEQUENCE: 98
aataatcatt gcacaattta gttctaaacg cttttgttat tactcaatat ccgttttaag   60
agcttggtga gcgctaggag tc                                            82

<210> SEQ ID NO 99
<211> LENGTH: 101
<212> TYPE: DNA
<213> ORGANISM: Artificial Sequence
<220> FEATURE:
<223> OTHER INFORMATION: Primer KOT11* for KO HXT11
<220> FEATURE:
<221> NAME/KEY: source
<222> LOCATION: (1)..(101)
<223> OTHER INFORMATION: /organism="Artificial Sequence" /note="Primer
      KOT11* for KO HXT11" /mol_type="unassigned DNA"

<400> SEQUENCE: 99
```
tcgtcaattt ttttttttgc ttttttacca atttaccgaa aactagaaga gagttcaaga    60
gaaaaaaaaa gaaaaagcaa aaagaaaaaa ggaaagcgcg c    101

<210> SEQ ID NO 100
<211> LENGTH: 39
<212> TYPE: DNA
<213> ORGANISM: Artificial Sequence
<220> FEATURE:
<223> OTHER INFORMATION: Primer iHXT11F (Inverse HXT11)
<220> FEATURE:
<221> NAME/KEY: source
<222> LOCATION: (1)..(39)
<223> OTHER INFORMATION: /organism="Artificial Sequence"
      /note="Primer iHXT11F (Inverse HXT11)" /mol_type="unassigned DNA"

<400> SEQUENCE: 100
ggcctctaga tcagctggaa aagaacctct tgtaaattg    39

<210> SEQ ID NO 101
<211> LENGTH: 41
<212> TYPE: DNA
<213> ORGANISM: Artificial Sequence
<220> FEATURE:
<223> OTHER INFORMATION: Primer iHXT11R (Inverse HXT11)
<220> FEATURE:
<221> NAME/KEY: source
<222> LOCATION: (1)..(41)
<223> OTHER INFORMATION: /organism="Artificial Sequence"
      /note="Primer iHXT11R (Inverse HXT11)" /mol_type="unassigned DNA"

<400> SEQUENCE: 101
gctaggatcc atgtcaggtg ttaataatac atccgcaaat g    41

<210> SEQ ID NO 102
<211> LENGTH: 36
<212> TYPE: DNA
<213> ORGANISM: Artificial Sequence
<220> FEATURE:
<223> OTHER INFORMATION: Primer HXT11F (Cloning)
<220> FEATURE:
<221> NAME/KEY: source
<222> LOCATION: (1)..(36)
<223> OTHER INFORMATION: /organism="Artificial Sequence"
      /note="Primer HXT11F (Cloning)" /mol_type="unassigned DNA"

<400> SEQUENCE: 102
ggcctctaga atgtcaggtg ttaataatac atccgc    36

<210> SEQ ID NO 103
<211> LENGTH: 37
<212> TYPE: DNA
<213> ORGANISM: Artificial Sequence
<220> FEATURE:
<223> OTHER INFORMATION: Primer HXT12F (Cloning)
<220> FEATURE:
<221> NAME/KEY: source
<222> LOCATION: (1)..(37)
<223> OTHER INFORMATION: /organism="Artificial Sequence"
      /note="Primer HXT12F (Cloning)" /mol_type="unassigned DNA"

<400> SEQUENCE: 103
ggcctctaga atgggtttga ttgtctcaat attcaac    37

<210> SEQ ID NO 104
<211> LENGTH: 39
<212> TYPE: DNA
<213> ORGANISM: Artificial Sequence
<220> FEATURE:

```
<223> OTHER INFORMATION: Primer HXT11/12R (Cloning)
<220> FEATURE:
<221> NAME/KEY: source
<222> LOCATION: (1)..(39)
<223> OTHER INFORMATION: /organism="Artificial Sequence" /note="Primer
      HXT11/12R (Cloning)" /mol_type="unassigned DNA"

<400> SEQUENCE: 104
cgatggatcc tcagctggaa aagaacctct tgtaaattg                                39

<210> SEQ ID NO 105
<211> LENGTH: 36
<212> TYPE: DNA
<213> ORGANISM: Artificial Sequence
<220> FEATURE:
<223> OTHER INFORMATION: Primer HXT1 Xbal (Cloning)
<220> FEATURE:
<221> NAME/KEY: source
<222> LOCATION: (1)..(36)
<223> OTHER INFORMATION: /organism="Artificial Sequence"
      /note="Primer HXT1 Xbal (Cloning)" /mol_type="unassigned DNA"

<400> SEQUENCE: 105
gcattctaga atgaattcaa ctcccgatct aatatc                                   36

<210> SEQ ID NO 106
<211> LENGTH: 38
<212> TYPE: DNA
<213> ORGANISM: Artificial Sequence
<220> FEATURE:
<223> OTHER INFORMATION: Primer R HXT1 Cfr9i (Cloning)
<220> FEATURE:
<221> NAME/KEY: source
<222> LOCATION: (1)..(38)
<223> OTHER INFORMATION: /organism="Artificial Sequence" /note="Primer
      R HXT1 Cfr9i (Cloning)" /mol_type="unassigned DNA"

<400> SEQUENCE: 106
tgcatcccgg gttatttcct gctaaacaaa ctcttgta                                 38

<210> SEQ ID NO 107
<211> LENGTH: 33
<212> TYPE: DNA
<213> ORGANISM: Artificial Sequence
<220> FEATURE:
<223> OTHER INFORMATION: Primer F HXT2 Xbai (Cloning)
<220> FEATURE:
<221> NAME/KEY: source
<222> LOCATION: (1)..(33)
<223> OTHER INFORMATION: /organism="Artificial Sequence" /note="Primer
      F HXT2 Xbai (Cloning)" /mol_type="unassigned DNA"

<400> SEQUENCE: 107
gtcctctaga atgtctgaat tcgctactag ccg                                      33

<210> SEQ ID NO 108
<211> LENGTH: 40
<212> TYPE: DNA
<213> ORGANISM: Artificial Sequence
<220> FEATURE:
<223> OTHER INFORMATION: Primer R HXT2 Cfr9i (Cloning)
<220> FEATURE:
<221> NAME/KEY: source
<222> LOCATION: (1)..(40)
<223> OTHER INFORMATION: /organism="Artificial Sequence" /note="Primer
      R HXT2 Cfr9i (Cloning)" /mol_type="unassigned DNA"

<400> SEQUENCE: 108
catcgcccgg gttattcctc ggaaactctt ttttcttttg                               40
```

```
<210> SEQ ID NO 109
<211> LENGTH: 38
<212> TYPE: DNA
<213> ORGANISM: Artificial Sequence
<220> FEATURE:
<223> OTHER INFORMATION: Primer F HXT3 XbaI (Cloning)
<220> FEATURE:
<221> NAME/KEY: source
<222> LOCATION: (1)..(38)
<223> OTHER INFORMATION: /organism="Artificial Sequence" /note="Primer
      F HXT3 XbaI (Cloning)" /mol_type="unassigned DNA"

<400> SEQUENCE: 109
gcattctaga atgaattcaa ctccagattt aatatctc                              38

<210> SEQ ID NO 110
<211> LENGTH: 36
<212> TYPE: DNA
<213> ORGANISM: Artificial Sequence
<220> FEATURE:
<223> OTHER INFORMATION: Primer R HXT6 Cfr9i (Cloning)
<220> FEATURE:
<221> NAME/KEY: source
<222> LOCATION: (1)..(36)
<223> OTHER INFORMATION: /organism="Artificial Sequence" /note="Primer
      R HXT6 Cfr9i (Cloning)" /mol_type="unassigned DNA"

<400> SEQUENCE: 110
catcgcccgg gttatttggt gctgaacatt ctcttg                                36

<210> SEQ ID NO 111
<211> LENGTH: 35
<212> TYPE: DNA
<213> ORGANISM: Artificial Sequence
<220> FEATURE:
<223> OTHER INFORMATION: Primer F HXT4 XbaI (Cloning)
<220> FEATURE:
<221> NAME/KEY: source
<222> LOCATION: (1)..(35)
<223> OTHER INFORMATION: /organism="Artificial Sequence" /note="Primer
      F HXT4 XbaI (Cloning)" /mol_type="unassigned DNA"

<400> SEQUENCE: 111
gtcctctaga atgtctgaag aagctgccta tcaag                                 35

<210> SEQ ID NO 112
<211> LENGTH: 38
<212> TYPE: DNA
<213> ORGANISM: Artificial Sequence
<220> FEATURE:
<223> OTHER INFORMATION: Primer R HXT4RN Cfr9l (Cloning)
<220> FEATURE:
<221> NAME/KEY: source
<222> LOCATION: (1)..(38)
<223> OTHER INFORMATION: /organism="Artificial Sequence" /note="Primer
      R HXT4RN Cfr9l (Cloning)" /mol_type="unassigned DNA"

<400> SEQUENCE: 112
tatcgcccgg gttaattaac tgacctactt ttttccga                              38

<210> SEQ ID NO 113
<211> LENGTH: 35
<212> TYPE: DNA
<213> ORGANISM: Artificial Sequence
<220> FEATURE:
<223> OTHER INFORMATION: Primer F HXT5 XbaI (Cloning)
<220> FEATURE:
<221> NAME/KEY: source
<222> LOCATION: (1)..(35)
<223> OTHER INFORMATION: /organism="Artificial Sequence" /note="Primer
```

F HXT5 XbaI (Cloning)" /mol_type="unassigned DNA"

<400> SEQUENCE: 113
gtcctctaga atgtcggaac ttgaaaacgc tcatc                35

<210> SEQ ID NO 114
<211> LENGTH: 40
<212> TYPE: DNA
<213> ORGANISM: Artificial Sequence
<220> FEATURE:
<223> OTHER INFORMATION: Primer R HXT5 Cfr9i (Cloning)
<220> FEATURE:
<221> NAME/KEY: source
<222> LOCATION: (1)..(40)
<223> OTHER INFORMATION: /organism="Artificial Sequence" /note="Primer
    R HXT5 Cfr9i (Cloning)" /mol_type="unassigned DNA"

<400> SEQUENCE: 114
gcatcccggg ttatttttct ttagtgaaca tccttttata                40

<210> SEQ ID NO 115
<211> LENGTH: 34
<212> TYPE: DNA
<213> ORGANISM: Artificial Sequence
<220> FEATURE:
<223> OTHER INFORMATION: Primer F HXT7 XbaI (Cloning)
<220> FEATURE:
<221> NAME/KEY: source
<222> LOCATION: (1)..(34)
<223> OTHER INFORMATION: /organism="Artificial Sequence" /note="Primer
    F HXT7 XbaI (Cloning)" /mol_type="unassigned DNA"

<400> SEQUENCE: 115
gtcctctaga atgtcacaag acgctgctat tgca                34

<210> SEQ ID NO 116
<211> LENGTH: 36
<212> TYPE: DNA
<213> ORGANISM: Artificial Sequence
<220> FEATURE:
<223> OTHER INFORMATION: Primer R HXT7 Cfr9l (Cloning)
<220> FEATURE:
<221> NAME/KEY: source
<222> LOCATION: (1)..(36)
<223> OTHER INFORMATION: /organism="Artificial Sequence" /note="Primer
    R HXT7 Cfr9l (Cloning)" /mol_type="unassigned DNA"

<400> SEQUENCE: 116
catcgcccgg gttatttggt gctgaacatt ctcttg                36

<210> SEQ ID NO 117
<211> LENGTH: 6338
<212> TYPE: DNA
<213> ORGANISM: Artificial Sequence
<220> FEATURE:
<223> OTHER INFORMATION: Plasmid pRS313-P7T7
<220> FEATURE:
<221> NAME/KEY: source
<222> LOCATION: (1)..(6338)
<223> OTHER INFORMATION: /organism="Artificial Sequence" /note="Plasmid
    pRS313-P7T7" /mol_type="unassigned DNA"

<400> SEQUENCE: 117
tcgcgcgttt cggtgatgac ggtgaaaacc tctgacacat gcagctcccg gagacggtca        60
cagcttgtct gtaagcggat gccgggagca gacaagcccg tcaggcgcg tcagcgggtg       120 ttggcgggtg tcggggctgg cttaactatg cggcatcaga gcagattgta ctgagagtgc       180
accataattc cgttttaaga gcttggtgag cgctaggagt cactgccagg tatcgtttga       240

```
acacggcatt agtcagggaa gtcataacac agtcctttcc cgcaattttc ttttttctatt    300 actcttggcc tcctctagta cactctatat tttttatgc ctcggtaatg attttcattt      360
ttttttttcc acctagcgga tgactctttt tttttcttag cgattggcat tatcacataa    420
tgaattatac attatataaa gtaatgtgat ttcttcgaag aatatactaa aaaatgagca    480
ggcaagataa acgaaggcaa agatgacaga gcagaaagcc ctagtaaagc gtattacaaa    540
tgaaaccaag attcagattg cgatctcttt aaagggtggt cccctagcga tagagcactc    600
gatcttccca gaaaagagg cagaagcagt agcagaacag gccacacaat cgcaagtgat     660
taacgtccac acaggtatag ggtttctgga ccatatgata catgctctgg ccaagcattc    720
cggctggtcg ctaatcgttg agtgcattgg tgacttacac atagacgacc atcacaccac    780
tgaagactgc gggattgctc tcggtcaagc ttttaaagag gccctactgg cgcgtggagt    840
aaaaaggttt ggatcaggat ttgcgccttt ggatgaggca ctttccagag cggtggtaga    900
tctttcgaac aggccgtacg cagttgtcga acttggtttg caaagggaga agtaggaga     960 tctctcttgc gagatgatcc cgcatttttct tgaaagcttt gcagaggcta gcagaattac   1020
cctccacgtt gattgtctgc gaggcaagaa tgatcatcac cgtagtgaga gtgcgttcaa    1080
ggctcttgcg gttgccataa gagaagccac ctcgcccaat ggtaccaacg atgttccctc    1140
caccaaaggt gttcttatgt agtgacaccg attatttaaa gctgcagcat acgatatata    1200
tacatgtgta tatatgtata cctatgaatg tcagtaagta tgtatacgaa cagtatgata    1260
ctgaagatga caaggtaatg catcattcta acgtgtcat tctgaacgag gcgcgctttc     1320
cttttttctt tttgcttttt ctttttttt ctcttgaact cgacggatca tatgcggtgt      1380
gaaataccgc acagatgcgt aaggagaaaa taccgcatca ggaaattgta aacgttaata    1440
ttttgttaaa attcgcgtta aattttttgtt aaatcagctc atttttttaac caataggccg   1500 aaatcggcaa aatccccttat aaatcaaaag aatagaccga gatagggttg agtgttgttc    1560
cagtttggaa caagagtcca ctattaaaga acgtggactc caacgtcaaa gggcgaaaaa     1620
ccgtctatca gggcgatggc ccactacgtg aaccatcacc ctaatcaagt ttttgggt      1680 cgaggtgccg taaagcacta atcggaacc ctaaagggag cccccgattt agagcttgac    1740
ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa ggggggatgt gctgcaaggc    1980
gattaagttg ggtaacgcca gggttttccc agtcacgacg ttgtaaaacg acggccagtg    2040
aattgtaata cgactcacta tagggcgaat tggagctctc tcgtaggaac aatttcgggc    2100
ccctgcgtgt tcttctgagg ttcatctttt acatttgctt ctgctggata attttcagag    2160
gcaacaagga aaaattagat ggcaaaaagt cgtctttcaa ggaaaaatcc ccaccatctt    2220
tcgagatccc ctgtaactta ttggcaactg aaagaatgaa aaggaggaaa atacaaaata    2280
tactagaact gaaaaaaaaa aagtataaat agagacgata tatgccaata cttcacaatg    2340
ttcgaatcta ttcttcattt gcagctattg taaaataata aaacatcaag aacaaacaag    2400
ctcaacttgt ctttttctaag aacaaagaat aaacacaaaa acaaaaagtt tttttaattt   2460
taatcaaaaa tctagaacta gtggatcccc cgggctgcag gaattcgata tcaagcttat    2520
cgattttgcg aacacttttta ttaattcatg atcacgctct aatttgtgca tttgaaatgt   2580
```

```
actctaattc taattttata tttttaatga tatcttgaaa agtaaatacg tttttaatat    2640
atacaaaata atacagttta attttcaagt ttttgatcat ttgttctcag aaagttgagt    2700
gggacggaga caaagaaact ttaaagagaa atgcaaagtg ggaagaagtc agttgtttac    2760
cgaccgcact gttattcaca aatattccaa ttttgcctgc agacccacgt ctacaaattt    2820
tggttagttt ggtaaatggt aaggatatag tagagccttt ttgaaatggg aaatatcttc    2880
tttttctgta tcccgcttca aaagtgtct aatgagtcag ttatttcttt cttactcatc    2940
gcccgtcact aaaagaaga aaaattactt tcatgatgcg aagcgaaaaa aattttagc     3000
ttcaatttc acaatgcatc tatggagagg atattataag gttacgaaat aaattcttga    3060
gtgttgtaaa ttctgttaat caaagaaaaa gcaatagctc gttttctac agaatggcta    3120
gcacagcaaa tatgatttct caactaaaga aactatctat cgcggaacct gcggttgcca    3180
aggattctca tcctgatgta aatatcgtgg atttgatgag aaattacatt tcacaagaat    3240
taagcaagat ttccggcgta gactcgtctc ttattttcc agcattagaa tggacaaata    3300
ctatggagag aggcgatttg ttgattccta tcccaagatt gagaatcaaa ggtgccaatc    3360
caaaggattt ggcagtccaa tgggctgaaa aatttccatg tggagatttc ttggagaaag    3420
ttgaagcgaa tggcccgttc atccagtttt tcttcaaccc tcaattttta gcaaaacttg    3480
tcatcccaga tatcttaacc agaaaggagg attatggttc ttgcgtcgac ctcgagggg    3540
ggcccggtac ccagcttttg ttccctttag tgagggttaa ttccgagctt ggcgtaatca    3600
tggtcatagc tgtttcctgt gtgaaattgt tatccgctca caattccaca acacatagga    3660
gccgaagca taaagtgtaa agcctggggt gcctaatgag tgaggtaact cacattaatt    3720
gcgttgcgct cactgcccgc tttccagtcg ggaaacctgt cgtgccagct gcattaatga    3780
atcggccaac gcgcgggag aggcggtttg cgtattgggc gctcttccgc ttcctcgctc    3840
actgactcgc tgcgctcggt cgttcggctg cggcgagcgg tatcagctca ctcaaaggcg    3900
gtaatacggt tatccacaga atcaggggat aacgcaggaa agaacatgtg agcaaaaggc    3960
cagcaaaagg ccaggaaccg taaaaaggcc gcgttgctgg cgtttttcca taggctcggc    4020
cccctgacg agcatcacaa aaatcgacgc tcaagtcaga ggtggcgaaa cccgacagga    4080
ctataaagat accaggcgtt ccccctgga agctccctcg tgcgctctcc tgttccgacc    4140
ctgccgctta ccggatacct gtccgccttt ctcccttcgg gaagcgtggc gctttctcaa    4200
tgctcacgct gtaggtatct cagttcggtg taggtcgttc gctccaagct gggctgtgtg    4260
cacgaacccc ccgttcagcc cgaccgctgc gccttatccg gtaactatcg tcttgagtcc    4320
aacccggtaa gacacgactt atcgccactg gcagcagcca ctggtaacag gattagcaga    4380
gcgaggtatg taggcggtgc tacagagttc ttgaagtggt ggcctaacta cggctacact    4440
agaaggacag tatttggtat ctgcgctctg ctgaagccag ttaccttcgg aaaaagagtt    4500
ggtagctctt gatccggcaa acaaaccacc gctggtagcg gtggttttt tgtttgcaag    4560
cagcagatta cgcgcagaaa aaaaggatct caagaagatc ctttgatctt ttctacgggg    4620
tctgacgctc agtggaacga aaactcacgt taagggattt tggtcatgag attatcaaaa    4680
aggatcttca cctagatcct tttaaattaa aaatgaagtt ttaaatcaat ctaaagtata    4740
tatgagtaaa cttggtctga cagttaccaa tgcttaatca gtgaggcacc tatctcagcg    4800
atctgtctat ttcgttcatc catagttgcc tgactgcccg tcgtgtagat aactacgata    4860
cgggagggct taccatctgg ccccagtgct gcaatgatac cgcgagaccc acgctcaccg    4920
gctccagatt tatcagcaat aaaccagcca gccggaaggg ccgagcgcag aagtggtcct    4980
```

```
gcaactttat ccgcctccat ccagtctatt aattgttgcc gggaagctag agtaagtagt    5040
tcgccagtta atagtttgcg caacgttgtt gccattgcta caggcatcgt ggtgtcacgc    5100
tcgtcgtttg gtatggcttc attcagctcc ggttcccaac gatcaaggcg agttacatga    5160
tcccccatgt tgtgaaaaaa agcggttagc tccttcggtc ctccgatcgt tgtcagaagt    5220
aagttggccg cagtgttatc actcatggtt atggcagcac tgcataattc tcttactgtc    5280
atgccatccg taagatgctt ttctgtgact ggtgagtact caaccaagtc attctgagaa    5340
tagtgtatgc ggcgaccgag ttgctcttgc ccggcgtcaa tacgggataa taccgcgcca    5400
catagcagaa ctttaaaagt gctcatcatt ggaaaacgtt cttcggggcg aaaactctca    5460
aggatcttac cgctgttgag atccagttcg atgtaaccca ctcgtgcacc caactgatct    5520
tcagcatctt ttactttcac cagcgtttct gggtgagcaa aaacaggaag gcaaaatgcc    5580
gcaaaaaagg gaataagggc gacacggaaa tgttgaatac tcatactctt cctttttcaa    5640
tattattgaa gcatttatca gggttattgt ctcatgagcg gatacatatt tgaatgtatt    5700
tagaaaaata aacaaatagg ggttccgcgc acatttcccc gaaaagtgcc acctgggtcc    5760
ttttcatcac gtgctataaa aataattata atttaaattt tttaatataa atatataaat    5820
taaaaataga agtaaaaaa agaaattaaa gaaaaaatag ttttgtttt ccgaagatgt    5880 aaaagactct aggggatcg ccaacaaata ctacctttta tcttgctctt cctgctctca    5940
ggtattaatg ccgaattgtt tcatcttgtc tgtgtagaag accacacacg aaaatcctgt    6000 gatttttacat tttacttatc gttaatcgaa tgtatatcta tttaatctgc ttttcttgtc    6060
taataaatat atatgtaaag tacgcttttt gttgaaattt tttaaaccttt tgtttatttt    6120 tttttcttca ttccgtaact cttctacctt ctttatttac tttctaaaat ccaaatacaa    6180
aacataaaaa taaataaaca cagagtaaat tcccaaatta ttccatcatt aaaagatacg    6240
aggcgcgtgt aagttacagg caagcgatcc gtcctaagaa accattatta tcatgacatt    6300
aacctataaa aataggcgta tcacgaggcc ctttcgtc                            6338
```

<210> SEQ ID NO 118
<211> LENGTH: 8726
<212> TYPE: DNA
<213> ORGANISM: Artificial Sequence
<220> FEATURE:
<223> OTHER INFORMATION: Plasmid pRS313-P7t7-HXT11+GFP
<220> FEATURE:
<221> NAME/KEY: source
<222> LOCATION: (1)..(8726)
<223> OTHER INFORMATION: /organism="Artificial Sequence" /note="Plasmid pRS313-P7t7-HXT11+GFP" /mol_type="unassigned DNA"

<400> SEQUENCE: 118

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accataattc cgttttaaga gcttggtgag cgctaggagt cactgccagg tatcgtttga    240
acacggcatt agtcagggaa gtcataacac agtcctttcc cgcaatttc ttttctatt     300 actcttggcc tcctctagta cactctatat tttttatgc ctcggtaatg attttcattt    360 tttttttcc acctagcgga tgactctttt ttttcttag cgattggcat tatcacataa    420
tgaattatac attatataaa gtaatgtgat ttcttcgaag aatatactaa aaaatgagca    480
ggcaagataa acgaaggcaa agatgacaga gcagaaagcc ctagtaaagc gtattacaaa    540
```

```
tgaaaccaag attcagattg cgatctcttt aaagggtggt cccctagcga tagagcactc    600
gatcttccca gaaaagagg cagaagcagt agcagaacag gccacacaat cgcaagtgat    660
taacgtccac acaggtatag ggtttctgga ccatatgata catgctctgg ccaagcattc    720
cggctggtcg ctaatcgttg agtgcattgg tgacttacac atagacgacc atcacaccac    780
tgaagactgc gggattgctc tcggtcaagc ttttaaagag ccctactgg cgcgtggagt    840 aaaaaggttt ggatcaggat ttgcgccttt ggatgaggca cttccagag cggtggtaga    900 tctttcgaac aggccgtacg cagttgtcga acttggtttg caaagggaga agtaggaga    960 tctctcttgc gagatgatcc cgcatttct tgaaagcttt gcagaggcta gcagaattac    1020
cctccacgtt gattgtctgc gaggcaagaa tgatcatcac cgtagtgaga gtgcgttcaa    1080
ggctcttgcg gttgccataa gagaagccac ctcgcccaat ggtaccaacg atgttccctc    1140 caccaaggt gttcttatgt agtgacaccg attatttaaa gctgcagcat acgatatata    1200
tacatgtgta tatatgtata cctatgaatg tcagtaagta tgtatacgaa cagtatgata    1260
ctgaagatga caaggtaatg catcattcta tacgtgtcat tctgaacgag gcgcgctttc    1320 ctttttttctt tttgcttttt ctttttttt ctcttgaact cgacggatca tatgcggtgt    1380
gaaataccgc acagatgcgt aaggagaaaa taccgcatca ggaaattgta aacgttaata    1440
ttttgttaaa attcgcgtta aattttttgtt aaatcagctc attttttaac caataggccg    1500
aaatcggcaa aatcccttat aaatcaaaag aatagaccga gataggggttg agtgttgttc    1560 cagtttggaa caagagtcca ctattaaaga acgtggactc caacgtcaaa gggcgaaaaa    1620
ccgtctatca gggcgatggc ccactacgtg aaccatcacc ctaatcaagt ttttggggt    1680 cgaggtgccg taaagcacta atcggaacc ctaaagggag cccccgattt agagcttgac    1740
ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa gggggatgt gctgcaaggc    1980 gattaagttg ggtaacgcca gggttttccc agtcacgacg ttgtaaaacg acggccagtg    2040
aattgtaata cgactcacta tagggcgaat tggagctctc tcgtaggaac aatttcgggc    2100
ccctgcgtgt tcttctgagg ttcatctttt acatttgctt ctgctggata attttcagag    2160
gcaacaagga aaattagat ggcaaaaagt cgtctttcaa ggaaaatcc ccaccatctt    2220 tcgagatccc ctgtaactta ttggcaactg aagaatgaa aaggaggaaa atacaaaata    2280
tactagaact gaaaaaaaa aagtataaat agagacgata tatgccaata cttcacaatg    2340
ttcgaatcta ttcttcattt gcagctattg taaaataata aaacatcaag aacaaacaag    2400
ctcaacttgt ctttttctaag aacaaagaat aaacacaaaa acaaaagtt ttttttaattt    2460 taatcaaaaa tctagaatgt caggtgttaa taatacatcc gcaatgagt tatctactac    2520 catgtctaac tctaactcag cagtaggcgc tccctctgtt aagactgaac acggtgactc    2580
taaaaattcc cttaacctag atgccaatga gccacctatt gacttacctc aaaaaccct    2640 ctctgcgtat accaccgtcg caatcctgtg tttgatgatt gcatttggcg gcttcatctt    2700
tggttgggat accggtacca tttctggttt tgttaacctt tctgatttca tcagaaggtt    2760
cggtcaaaaa aatgacaagg gaacctacta cttatcgaaa gtaagaatgg gtttgatcgt    2820
ctcaatattc aacattggct gcgccatagg cggaattgtc ttgtcaaaag tcggtgatat    2880
```

-continued

```
atatggtcgt cgtattggat tgattacagt tactgccatt tacgttgtag gcatcctaat    2940
ccaaataact tccataaaca agtggtacca atacttcatt ggaagaatta tttctggcct    3000
aggagtggga ggcattgctg tcctttcccc aatgttgata tctgaagttg ctcccaaaca    3060
tatcagagga actctggtcc aattgtacca gctgatgggt acgatgggta ttttctagg    3120
atactgtacc aattacggta ccaagaacta tcacaacgcc actcaatgga gagtcggcct    3180
tggtctttgc tttgcctggg ctacattcat ggttagtgga atgatgtttg taccagaatc    3240
accacgttac ctgattgagg ttggtaaaga tgaggaagcg aaacgttcac tatcgaaatc    3300
caacaaagtc tcagttgacg atccagcctt gctagttgaa tatgacacta taaaggcagg    3360
aattgaactt gaaaagctgg caggtaacgc atcatggtct gaactactct ccactaaaac    3420
aaaggtcttt cagcgtgttc tcatgggagt gatgatccaa tcgctgcagc aattaaccgg    3480
tgacaactac ttcttttact acggtaccac catcttcaaa tctgtcggtc taaaggactc    3540
ctttcagact tcgatcatta tcggtgtggt taatttttc tcttcattca tagcggtata    3600
caccattgag aggtttggac gccgtacgtg tctattgtgg ggtgctgctt ctatgctatg    3660
ctgctttgct gtgtttgcct ccgtcggtgt gacaaagttg tggcctcaag aagcagtca    3720
ccaagacatt acttctcagg gcgccggtaa ctgtatgatt gtgtttacta tgttcttcat    3780
tttttcgttc gccaccactt gggcaggcgg ctgttacgtt attgtctcag agacgtttcc    3840
tcttagggtc aaatcaagag gaatggcaat cgcaacagct gcaaactgga tgtgggttt    3900
cctgattagt ttcttttaccc cattcattac cggggcaatc aacttttact acggttacgt    3960
attcttaggc tgtctggttt ttgcatactt ttatgtcttt ttctttgtcc cagaaacaaa    4020
aggcctgaca ctggaggagg tgaatactat gtggctggaa ggtgtgccag catggaaatc    4080
ggcctcatgg gtgccaccgg agagaagaac cgcagattac gatgctgatg caatagatca    4140
tgacaataga ccaatttaca agaggttctt ttccagctga cccgggatgg tgagcaaggg    4200
cgaggagctg ttcaccgggg tggtgcccat cctggtcgag ctggacgcg acgtaaacgg    4260
ccacaagttc agcgtgtccg gcgagggcga gggcgatgcc acctacggca agctgaccct    4320
gaagttcatc tgcaccaccg gcaagctgcc cgtgccctgg cccaccctcg tgaccaccct    4380
gacctacggc gtgcagtgct tcagccgcta ccccgaccac atgaagcagc acgacttctt    4440
caagtccgcc atgcccgaag gctacgtcca ggagcgcacc atcttcttca aggacgacgg    4500
caactacaag acccgcgccg aggtgaagtt cgagggcgac accctggtga accgcatcga    4560
gctgaagggc atcgacttca aggaggacgg caacatcctg ggcacaagc tggagtacaa    4620
ctacaacagc cacaacgtct atatcatggc cgacaagcag aagaacggca tcaaggtgaa    4680
cttcaagatc cgccacaaca tcgaggacgg cagcgtgcag ctcgccgacc actaccagca    4740
gaacaccccc atcggcgacg gccccgtgct gctgcccgac aaccactacc tgagcaccca    4800
gtccgccctg agcaaagatc ccaacgagaa gcgcgatcac atggtcctgc tggagttcgt    4860
gaccgccgcc gggatcactc tcggcatgga cgagctgtac aagtaaatcg attttgcgaa    4920
cactttatt aattcatgat cacgctctaa tttgtgcatt tgaaatgtac tctaattcta    4980
attttatatt tttaatgata tcttgaaaag taaatacgtt tttaatatat acaaaataat    5040
acagtttaat tttcaagttt ttgatcattt gttctcagaa agttgagtgg gacggagaca    5100
aagaaacttt aaagagaaat gcaaagtggg aagaagtcag ttgtttaccg accgcactgt    5160
tattcacaaa tattccaatt ttgcctgcag acccacgtct acaaattttg gttagtttgg    5220
taaatggtaa ggatatagta gagccttttt gaaatgggaa atatcttctt tttctgtatc    5280
```

```
ccgcttcaaa aagtgtctaa tgagtcagtt atttctttct tactcatcgc ccgtcactta    5340
aaagaagaaa aattactttc atgatgcgaa gcgaaaaaaa tttttagctt caattttcac    5400
aatgcatcta tggagaggat attataaggt tacgaaataa attcttgagt gttgtaaatt    5460
ctgttaatca agaaaaagc aatagctcgt ttttctacag aatggctagc acagcaaata    5520
tgatttctca actaaagaaa ctatctatcg cggaacctgc ggttgccaag gattctcatc    5580
ctgatgtaaa tatcgtggat ttgatgagaa attacatttc acaagaatta agcaagattt    5640
ccggcgtaga ctcgtctctt attttccag cattagaatg acaaatact atggagagag     5700 gcgatttgtt gattcctatc ccaagattga gaatcaaagg tgccaatcca aaggatttgg    5760
cagtccaatg ggctgaaaaa tttccatgtg gagatttctt ggagaaagtt gaagcgaatg    5820
gcccgttcat ccagtttttc ttcaaccctc aattttagc aaaacttgtc atcccagata    5880
tcttaaccag aaaggaggat tatggttctt gcgtcgacct cgagggggg cccggtaccc     5940 agcttttgtt ccctttagtg agggttaatt ccgagcttgg cgtaatcatg gtcatagctg    6000
tttcctgtgt gaaattgtta tccgctcaca attccacaca ataggagc cggaagcata      6060 aagtgtaaag cctggggtgc ctaatgagtg aggtaactca cattaattgc gttgcgctca    6120
ctgcccgctt tccagtcggg aaacctgtcg tgccagctgc attaatgaat cggccaacgc    6180
gcggggagag gcggtttgcg tattgggcgc tcttccgctt cctcgctcac tgactcgctg    6240
cgctcggtcg ttcggctgcg gcgagcggta tcagctcact caaaggcggt aatacggtta    6300
tccacagaat caggggataa cgcaggaaag aacatgtgag caaaaggcca gcaaaaggcc    6360
aggaaccgta aaaaggccgc gttgctggcg ttttccata ggctcggccc ccctgacgag     6420
catcacaaaa atcgacgctc aagtcagagg tggcgaaacc cgacaggact ataaagatac    6480
caggcgttcc ccctggaag ctccctcgtg cgctctcctg ttccgaccct gccgcttacc     6540
ggatacctgt ccgcctttct cccttcggga agcgtggcgc tttctcaatg ctcacgctgt    6600
aggtatctca gttcggtgta ggtcgttcgc tccaagctgg gctgtgtgca cgaaccccc     6660 gttcagcccg accgctgcgc cttatccggt aactatcgtc ttgagtccaa cccggtaaga    6720
cacgacttat cgccactggc agcagccact ggtaacagga ttagcagagc gaggtatgta    6780
ggcggtgcta cagagttctt gaagtggtgg cctaactacg gctacactag aaggacagta    6840
tttggtatct gcgctctgct gaagccagtt accttcggaa aaagagttgg tagctcttga    6900
tccggcaaac aaaccaccgc tggtagcggt ggtttttttg tttgcaagca gcagattacg    6960
cgcagaaaaa aaggatctca agaagatcct ttgatctttt ctacgggtc tgacgctcag     7020 tggaacgaaa actcacgtta agggattttg gtcatgagat tatcaaaaag gatcttcacc    7080
tagatccttt taaattaaaa atgaagtttt aaatcaatct aaagtatata tgagtaaact    7140
tggtctgaca gttaccaatg cttaatcagt gaggcaccta tctcagcgat ctgtctattt    7200
cgttcatcca tagttgcctg actgcccgtc gtgtagataa ctacgatacg ggagggctta    7260
ccatctggcc ccagtgctgc aatgataccg cgagacccac gctcaccggc tccagattta    7320
tcagcaataa accagccagc cggaagggcc gagcgcagaa gtggtcctgc aactttatcc    7380
gcctccatcc agtctattaa ttgttgccgg gaagctagag taagtagttc gccagttaat    7440
agtttgcgca acgttgttgc cattgctaca ggcatcgtgg tgtcacgctc gtcgtttggt    7500
atggcttcat tcagctccgg ttcccaacga tcaaggcgag ttacatgatc ccccatgttg    7560
tgaaaaaaag cggttagctc cttcggtcct ccgatcgttg tcagaagtaa gttggccgca    7620
```

-continued

| | |
|---|---|
| gtgttatcac tcatggttat ggcagcactg cataattctc ttactgtcat gccatccgta | 7680 |
| agatgctttt ctgtgactgg tgagtactca accaagtcat tctgagaata gtgtatgcgg | 7740 |
| cgaccgagtt gctcttgccc ggcgtcaata cgggataata ccgcgccaca tagcagaact | 7800 |
| ttaaaagtgc tcatcattgg aaaacgttct tcggggcgaa aactctcaag gatcttaccg | 7860 |
| ctgttgagat ccagttcgat gtaacccact cgtgcaccca actgatcttc agcatctttt | 7920 |
| actttcacca gcgtttctgg gtgagcaaaa acaggaaggc aaaatgccgc aaaaaaggga | 7980 |
| ataagggcga cacggaaatg ttgaatactc atactcttcc ttttcaata ttattgaagc | 8040 |
| atttatcagg gttattgtct catgagcgga tacatatttg aatgtattta gaaaaataaa | 8100 |
| caaatagggg ttccgcgcac atttccccga aaagtgccac ctgggtcctt ttcatcacgt | 8160 |
| gctataaaaa taattataat ttaaattttt taatataaat atataaatta aaaatagaaa | 8220 |
| gtaaaaaaag aaattaaaga aaaaatagtt tttgttttcc gaagatgtaa aagactctag | 8280 |
| ggggatcgcc aacaaatact acctttatc ttgctcttcc tgctctcagg tattaatgcc | 8340 |
| gaattgtttc atcttgtctg tgtagaagac cacacacgaa aatcctgtga ttttacattt | 8400 |
| tacttatcgt taatcgaatg tatatctatt taatctgctt ttcttgtcta ataaatatat | 8460 |
| atgtaaagta cgcttttgt tgaaattttt taaacctttg tttatttttt tttcttcatt | 8520 |
| ccgtaactct tctaccttct ttatttactt tctaaaatcc aaatacaaaa cataaaaata | 8580 |
| aataaacaca gagtaaattc ccaaattatt ccatcattaa aagatacgag gcgcgtgtaa | 8640 |
| gttacaggca agcgatccgt cctaagaaac cattattatc atgacattaa cctataaaaa | 8700 |
| taggcgtatc acgaggccct ttcgtc | 8726 |

<210> SEQ ID NO 119
<211> LENGTH: 1704
<212> TYPE: DNA
<213> ORGANISM: Saccharomyces cerevisiae
<220> FEATURE:
<221> NAME/KEY: source
<222> LOCATION: (1)..(1704)
<223> OTHER INFORMATION: /organism="Saccharomyces cerevisiae"
      /note="HXT11 ORF RN1053" /mol_type="unassigned DNA"

<400> SEQUENCE: 119

| | |
|---|---|
| atgtcaggtg ttaataatac atccgcaaat gagttatcta ctaccatgtc taactctaac | 60 |
| tcagcagtag gcgctcccctc tgttaagact gaacacggtg actctaaaaa ttcccttaac | 120 |
| ctagatgcca atgagccacc tattgactta cctcaaaaac ccctctctgc gtataccacc | 180 |
| gtcgcaatcc tgtgtttgat gattgcattt ggcggcttca tctttggttg ggataccggt | 240 |
| accatttctg gttttgttaa cctttctgat ttcatcagaa ggttcggtca aaaaaatgac | 300 |
| aagggaacct actacttatc gaaagtaaga atgggtttga tcgtctcaat attcaacatt | 360 |
| ggctgcgcca taggcggaat tgtcttgtca aaagtcggtg atatatatgg tcgtcgtatt | 420 |
| ggattgatta cagttactgc catttacgtt gtaggcatcc taatccaaat aacttccata | 480 |
| aacaagtggt accaatactt cattggaaga attatttctg gcctaggagt gggaggcatt | 540 |
| gctgtccttt ccccaatgtt gatatctgaa gttgctccca acatatcag aggaactctg | 600 |
| gtccaattgt accagctgat gggtacgatg gtatttttc taggatactg taccaattac | 660 |
| ggtaccaaga actatcacaa cgccactcaa tggagagtcg gccttggtct ttgctttgcc | 720 |
| tgggctacat tcatggttag tggaatgatg ttgtaccag aatcaccacg ttacctgatt | 780 |
| gaggttggta agatgaggaa agcgaaacgt tcactatcga aatccaacaa agtctcagtt | 840 |

```
gacgatccag ccttgctagt tgaatatgac actataaagg caggaattga acttgaaaag    900
ctggcaggta acgcatcatg gtctgaacta ctctccacta aaacaaaggt ctttcagcgt    960
gttctcatgg gagtgatgat ccaatcgctg cagcaattaa ccggtgacaa ctacttcttt   1020
tactacggta ccaccatctt caaatctgtc ggtctaaagg actcctttca gacttcgatc   1080
attatcggtg tggttaattt tttctcttca ttcatagcgg tatacaccat tgagaggttt   1140
ggacgccgta cgtgtctatt gtggggtgct gcttctatgc tatgctgctt tgctgtgttt   1200
gcctccgtcg gtgtgacaaa gttgtggcct caaggaagca gtcaccaaga cattacttct   1260
cagggcgccg gtaactgtat gattgtgttt actatgttct tcattttttc gttcgccacc   1320
acttgggcag gcggctgtta cgttattgtc tcagagacgt ttcctcttag ggtcaaatca   1380
agaggaatgg caatcgcaac agctgcaaac tggatgtggg gtttcctgat tagtttcttt   1440
accccattca ttaccggggc aatcaacttt tactacggtt acgtattctt aggctgtctg   1500 gttttttgcat acttttatgt cttttttcttt gtcccagaaa caaaaggcct gacactggag   1560
gaggtgaata ctatgtggct ggaaggtgtg ccagcatgga aatcggcctc atgggtgcca   1620
ccggagagaa gaaccgcaga ttacgatgct gatgcaatag atcatgacaa tagaccaatt   1680
tacaagaggt tcttttccag ctga                                           1704

<210> SEQ ID NO 120
<211> LENGTH: 1626
<212> TYPE: DNA
<213> ORGANISM: Saccharomyces cerevisiae
<220> FEATURE:
<221> NAME/KEY: source
<222> LOCATION: (1)..(1626)
<223> OTHER INFORMATION: /organism="Saccharomyces
      cerevisiae" /note="HXT2 ORF" /mol_type="unassigned DNA"

<400> SEQUENCE: 120
atgtctgaat tcgctactag ccgcgttgaa agtggctctc aacaaacttc tatccactct     60
actccgatag tgcagaaatt agagacggat gaatctccta ttcaaaccaa atctgaatac    120
actaacgctg aactcccagc aaagccaatc gccgcatatt ggactgttat ctgtttatgt    180
ctaatgattg catttggtgg gtttgtcttt ggttgggata ctggtaccat ctctggtttt    240
gttaatcaaa ccgatttcaa agaagattt ggtcaaatga atctgatgg tacctattat    300 ctttcggacg tccggactgg tttgatcgtt ggtatcttca atattggttg tgcctttggt    360
gggttaacct taggacgtct gggtgatatg tatggacgta gaattggttt gatgtgcgtc    420
gttctggtat acatcgttgg tattgtgatt caaattgctt ctagtgacaa atggtaccaa    480
tatttcattg gtagaattat ctctggtatg ggtgtcggtg gtattgctgt cctatctcca    540
actttgattt ccgaaacagc accaaaaacac attagaggta cctgtgtttc tttctatcag    600
ttaatgatca ctctaggtat tttcttaggt tactgtacca actatggtac taaagactac    660
tccaattcag ttcaatggag agtgcctttg ggtttgaact ttgccttcgc tattttcatg    720
atcgctggta tgctaatggt tccagaatct ccaagattct tagtcgaaaa aggcagatac    780
gaagacgcta acgttctttt ggcaaaatct aacaaagtca ccattgaaga tccaagtatt    840
gttgctgaaa tggatacaat tatggccaac gttgaaacta aagattagc cggtaacgct    900 tcttggggtg agttattctc caacaaaggt gctattttac ctcgtgtgat tatgggtatt    960
atgattcaat ccttacaaca attaactggt aacaattact tcttctatta tggtactact   1020
attttcaacg ccgtcggtat gaagattct ttccaaactc ccatcgtttt aggtatagtc   1080
```

-continued

| | |
|---|---|
| aacttcgcat ccactttcgt ggccttatac actgttgata aatttggtcg tcgtaagtgt | 1140 |
| ctattgggtg gttctgcttc catggccatt tgttttgtta tcttctctac tgtcggtgtc | 1200 |
| acaagcttat atccaaatgg taaagatcaa ccatcttcca aggctgccgg taacgtcatg | 1260 |
| attgtcttta cctgtttatt cattttcttc ttcgctatta gttgggcccc aattgcctac | 1320 |
| gttattgttg ccgaatccta tccttttgcgt gtcaaaaatc gtgctatggc tattgctgtt | 1380 |
| ggtgccaact ggatttgggg tttcttgatt ggtttcttca ctcccttcat tacaagtgca | 1440 |
| attggatttt catacgggta tgtcttcatg ggctgtttgg tattttcatt cttctacgtg | 1500 |
| tttttctttg tctgtgaaac caagggctta acattagagg aagttaatga aatgtatgtt | 1560 |
| gaaggtgtca aaccatggaa atctggtagc tggatctcaa aagaaaaaag agtttccgag | 1620 |
| gaataa | 1626 |

<210> SEQ ID NO 121
<211> LENGTH: 1725
<212> TYPE: DNA
<213> ORGANISM: Saccharomyces cerevisiae
<220> FEATURE:
<221> NAME/KEY: source
<222> LOCATION: (1)..(1725)
<223> OTHER INFORMATION: /organism="Saccharomyces
    cerevisiae" /note="GAL2 ORF" /mol_type="unassigned DNA"

<400> SEQUENCE: 121

| | |
|---|---|
| atggcagttg aggagaacaa tatgcctgtt gtttcacagc aaccccaagc tggtgaagac | 60 |
| gtgatctctt cactcagtaa agattcccat ttaagcgcac aatctcaaaa gtattccaat | 120 |
| gatgaattga agccggtga gtcagggcct gaaggctccc aaagtgttcc tatagagata | 180 |
| cccaagaagc ccatgtctga atatgttacc gtttccttgc tttgtttgtg tgttgccttc | 240 |
| ggcggcttca tgtttggctg ggataccggt actatttctg ggtttgttgt ccaaacagac | 300 |
| tttttgagaa ggtttggtat gaaacataag gatggtaccc actatttgtc aaacgtcaga | 360 |
| acaggtttaa tcgtcgccat tttcaatatt ggctgtgcct tggtggtat tatactttcc | 420 |
| aaaggtggag atatgtatgg ccgtaaaaag ggtctttcga ttgtcgtctc ggtttatata | 480 |
| gttggtatta tcattcaaat tgcctctatc aacaagtgg accaatattt cattggtaga | 540 |
| atcatatctg gtttgggtgt cggcggcatc gccgtcttat gtcctatgtt gatctctgaa | 600 |
| attgctccaa agcacttgag aggcacacta gtttcttgtt atcagctgat gattactgca | 660 |
| ggtatctttt gggctactg tactaattac ggtacaaaga gctattcgaa ctcagttcaa | 720 |
| tggagagttc cattagggct atgtttcgct tggtcattat ttatgattgg cgcttttgacg | 780 |
| ttagttcctg aatccccacg ttatttatgt gaggtgaata aggtagaaga cgccaagctt | 840 |
| tccattgcta agtctaacaa ggtgtcacca gaggatcctg ccgtccaggc agagttagat | 900 |
| ctgatcatgg ccggtataga agctgaaaaa ctggctggca atgcgtcctg ggggaatta | 960 |
| ttttccacca gaccaaagt atttcaacgt tgttgatgg gtgtatttgt tcaaatgttc | 1020 |
| caacaattaa ccggtaacaa ttatttttc tactacggta ccgttatttt caagtcagtt | 1080 |
| ggcctggatg attcctttga acatccatt gtcattggtg tagtcaactt tgcctccact | 1140 |
| ttctttagtt tgtggactgt cgaaaacttg ggcgtcgta aatgtttact tttgggcgct | 1200 |
| gccactatga tggcttgtat ggtcatctac gcctctgttg gtgttaccag attatatcct | 1260 |
| cacggtaaaa gccagccatc ttctaaaggt gccggtaact gtatgattgt ctttacctgt | 1320 |
| ttttatattt tctgttatgc cacaacctgg gcgccagttg cctgggtcat cacagcagaa | 1380 |

| | |
|---|---|
| tcattcccac tgagagtcaa gtcgaaatgt atggcgttgg cctctgcttc caattgggta | 1440 |
| tgggggttct tgattgcatt tttcacccca ttcatcacat ctgccattaa cttctactac | 1500 |
| ggttatgtct tcatgggctg tttggttgcc atgttttttt atgtcttttt ctttgttcca | 1560 |
| gaaactaaag gcctatcgtt agaagaaatt caagaattat gggaagaagg tgttttacct | 1620 |
| tggaaatctg aaggctggat tccttcatcc agaagaggta ataattacga tttagaggat | 1680 |
| ttacaacatg acgacaaacc gtggtacaag gccatgctag aataa | 1725 |

```
<210> SEQ ID NO 122
<211> LENGTH: 1704
<212> TYPE: DNA
<213> ORGANISM: Saccharomyces cerevisiae
<220> FEATURE:
<221> NAME/KEY: source
<222> LOCATION: (1)..(1704)
<223> OTHER INFORMATION: /organism="Saccharomyces
      cerevisiae" /note="HXT3-6 ORF" /mol_type="unassigned DNA"

<400> SEQUENCE: 122
```

| | |
|---|---|
| atgaattcaa ctccagattt aatatctcca caaaagtcaa gtgagaattc gaatgctgac | 60 |
| ctgccttcga atagctctca ggtaatgaac atgcctgaag aaaaaggtgt tcaagatgat | 120 |
| ttccaagctg aggccgacca agtacttacc aacccaaata caggtaaagg tgcatatgtc | 180 |
| actgtgtcta tctgttgtgt tatggttgcc ttcggtggtt tcgttttcgg ttgggatact | 240 |
| ggtaccattt ctggtttcgt cgcccaaact gatttcttga agattcgg tatgaagcat | 300 |
| aaagatggta gttattattt gtctaaggtt agaactggtt taattgtctc cattttcaac | 360 |
| attggttgtg ccattggtgg tattattttg gctaaattgg gtgatatgta cggtcgtaaa | 420 |
| atgggtttga ttgtcgttgt tgttatctac atcatcggta ttattattca aattgcatcc | 480 |
| atcaacaaat ggtaccaata tttcatcggt agaattattt ccggtttggg tgttggtggt | 540 |
| attgccgttt tatctcctat gttgatttct gaagtcgctc taaggaaat gagaggtact | 600 |
| ttagtctcct gttaccaact gatgattacc ttgggtattt tcttgggtta ctgtaccaac | 660 |
| ttcggtacta gaactactc caactctgtg caatggagag ttccattagg tttgtgtttt | 720 |
| gcctgggctt tgtttatgat cggtggtatg actttcgttc cagaatcccc acgttatttg | 780 |
| gttgaagctg gtcaaattga cgaagcaaga gcatctcttt ccaaagttaa caaggttgcc | 840 |
| ccagaccatc cattcattca acaagagttg gaagttattg aagctagtgt tgaagaagct | 900 |
| agagctgctg gttcagcatc atggggtgag ttgttcactg gtaagccggc catgtttaag | 960 |
| cgtactatga tgggtatcat gatccaatct ctacaacaat tgactggtga taactatttc | 1020 |
| ttctactatg gtactaccgt tttaacgct gttggtatga gtgattcttt cgaaacttct | 1080 |
| attgttttcg gtgtcgtcaa cttcttctct acttgttgtt ctttgtacac tgtcgatcgt | 1140 |
| tttggacgtc gtaactgttt gttatatggt gccattggta tggtctgctg ttatgtagtt | 1200 |
| tacgcttctg ttggtgtcac cagactatgg ccaaatggtg aaggtaatgg ttcatccaag | 1260 |
| ggtgctggta actgtatgat tgtctttgcc tgtttctata ttttctgttt tgctactaca | 1320 |
| tgggctccaa ttccttatgt cgttgttcct gaaactttcc cattgagagt caagtctaag | 1380 |
| gctatgtcta ttgctacagc tgctaattgg ttgtggggtt tcttgattgg tttcttcact | 1440 |
| ccatttatta ctggtgctat taacttctac tacggttacg ttttcatggg ctgtttggtc | 1500 |
| ttcatgttct tctatgtttt gttagttgtt ccagaaacta agggtttgac tttgaagaa | 1560 |
| gtcaacacca tgtgggaaga aggtgttcta ccatggaagt ctgcctcatg ggttccacca | 1620 |

```
tctagaagag gtgccaacta cgacgctgaa gaaatggctc acgatgataa gccattgtac    1680
aagagaatgt tcagcaccaa ataa                                           1704
```

<210> SEQ ID NO 123
<211> LENGTH: 567
<212> TYPE: PRT
<213> ORGANISM: Saccharomyces cerevisiae
<220> FEATURE:
<221> NAME/KEY: MISC_FEATURE
<222> LOCATION: (1)..(567)
<223> OTHER INFORMATION: Hxt11p

<400> SEQUENCE: 123

```
Met Ser Gly Val Asn Asn Thr Ser Ala Asn Glu Leu Ser Thr Thr Met
1               5                   10                  15

Ser Asn Ser Asn Ser Ala Val Gly Ala Pro Ser Val Lys Thr Glu His
            20                  25                  30

Gly Asp Ser Lys Asn Ser Leu Asn Leu Asp Ala Asn Glu Pro Pro Ile
        35                  40                  45

Asp Leu Pro Gln Lys Pro Leu Ser Ala Tyr Thr Thr Val Ala Ile Leu
    50                  55                  60

Cys Leu Met Ile Ala Phe Gly Gly Phe Ile Phe Gly Trp Asp Thr Gly
65                  70                  75                  80

Thr Ile Ser Gly Phe Val Asn Leu Ser Asp Phe Ile Arg Arg Phe Gly
                85                  90                  95

Gln Lys Asn Asp Lys Gly Thr Tyr Tyr Leu Ser Lys Val Arg Met Gly
            100                 105                 110

Leu Ile Val Ser Ile Phe Asn Ile Gly Cys Ala Ile Gly Gly Ile Val
        115                 120                 125

Leu Ser Lys Val Gly Asp Ile Tyr Gly Arg Arg Ile Gly Leu Ile Thr
    130                 135                 140

Val Thr Ala Ile Tyr Val Val Gly Ile Leu Gln Ile Thr Ser Ile
145                 150                 155                 160

Asn Lys Trp Tyr Gln Tyr Phe Ile Gly Arg Ile Ile Ser Gly Leu Gly
                165                 170                 175

Val Gly Gly Ile Ala Val Leu Ser Pro Met Leu Ile Ser Glu Val Ala
            180                 185                 190

Pro Lys His Ile Arg Gly Thr Leu Val Gln Leu Tyr Gln Leu Met Gly
        195                 200                 205

Thr Met Gly Ile Phe Leu Gly Tyr Cys Thr Asn Tyr Gly Thr Lys Asn
    210                 215                 220

Tyr His Asn Ala Thr Gln Trp Arg Val Gly Leu Gly Leu Cys Phe Ala
225                 230                 235                 240

Trp Ala Thr Phe Met Val Ser Gly Met Met Phe Val Pro Glu Ser Pro
                245                 250                 255

Arg Tyr Leu Ile Glu Val Gly Lys Asp Glu Glu Ala Lys Arg Ser Leu
            260                 265                 270

Ser Lys Ser Asn Lys Val Ser Val Asp Asp Pro Ala Leu Leu Val Glu
        275                 280                 285

Tyr Asp Thr Ile Lys Ala Gly Ile Glu Leu Lys Leu Ala Gly Asn
    290                 295                 300

Ala Ser Trp Ser Glu Leu Leu Ser Thr Lys Thr Lys Val Phe Gln Arg
305                 310                 315                 320

Val Leu Met Gly Val Met Ile Gln Ser Leu Gln Gln Leu Thr Gly Asp
                325                 330                 335
```

```
Asn Tyr Phe Phe Tyr Tyr Gly Thr Thr Ile Phe Lys Ser Val Gly Leu
            340                 345                 350

Lys Asp Ser Phe Gln Thr Ser Ile Ile Ile Gly Val Val Asn Phe Phe
        355                 360                 365

Ser Ser Phe Ile Ala Val Tyr Thr Ile Glu Arg Phe Gly Arg Arg Thr
    370                 375                 380

Cys Leu Leu Trp Gly Ala Ala Ser Met Leu Cys Cys Phe Ala Val Phe
385                 390                 395                 400

Ala Ser Val Gly Val Thr Lys Leu Trp Pro Gln Gly Ser Ser His Gln
                405                 410                 415

Asp Ile Thr Ser Gln Gly Ala Gly Asn Cys Met Ile Val Phe Thr Met
            420                 425                 430

Phe Phe Ile Phe Ser Phe Ala Thr Thr Trp Ala Gly Gly Cys Tyr Val
        435                 440                 445

Ile Val Ser Glu Thr Phe Pro Leu Arg Val Lys Ser Arg Gly Met Ala
    450                 455                 460

Ile Ala Thr Ala Ala Asn Trp Met Trp Gly Phe Leu Ile Ser Phe Phe
465                 470                 475                 480

Thr Pro Phe Ile Thr Gly Ala Ile Asn Phe Tyr Tyr Gly Tyr Val Phe
                485                 490                 495

Leu Gly Cys Leu Val Phe Ala Tyr Phe Tyr Val Phe Phe Val Pro
            500                 505                 510

Glu Thr Lys Gly Leu Thr Leu Glu Glu Val Asn Thr Met Trp Leu Glu
        515                 520                 525

Gly Val Pro Ala Trp Lys Ser Ala Ser Trp Val Pro Pro Glu Arg Arg
    530                 535                 540

Thr Ala Asp Tyr Asp Ala Asp Ala Ile Asp His Asp Asn Arg Pro Ile
545                 550                 555                 560

Tyr Lys Arg Phe Phe Ser Ser
                565

<210> SEQ ID NO 124
<211> LENGTH: 541
<212> TYPE: PRT
<213> ORGANISM: Saccharomyces cerevisiae
<220> FEATURE:
<221> NAME/KEY: MISC_FEATURE
<222> LOCATION: (1)..(541)
<223> OTHER INFORMATION: Hxt2p

<400> SEQUENCE: 124

Met Ser Glu Phe Ala Thr Ser Arg Val Glu Ser Gly Ser Gln Gln Thr
1               5                   10                  15

Ser Ile His Ser Thr Pro Ile Val Gln Lys Leu Glu Thr Asp Glu Ser
            20                  25                  30

Pro Ile Gln Thr Lys Ser Glu Tyr Thr Asn Ala Glu Leu Pro Ala Lys
        35                  40                  45

Pro Ile Ala Ala Tyr Trp Thr Val Ile Cys Leu Cys Leu Met Ile Ala
    50                  55                  60

Phe Gly Gly Phe Val Phe Gly Trp Asp Thr Gly Thr Ile Ser Gly Phe
65                  70                  75                  80

Val Asn Gln Thr Asp Phe Lys Arg Arg Phe Gly Gln Met Lys Ser Asp
                85                  90                  95

Gly Thr Tyr Tyr Leu Ser Asp Val Arg Thr Gly Leu Ile Val Gly Ile
            100                 105                 110

Phe Asn Ile Gly Cys Ala Phe Gly Gly Leu Thr Leu Gly Arg Leu Gly
```

-continued

```
            115                 120                 125
Asp Met Tyr Gly Arg Arg Ile Gly Leu Met Cys Val Leu Val Tyr
    130                 135                 140
Ile Val Gly Ile Val Ile Gln Ile Ala Ser Ser Asp Lys Trp Tyr Gln
145                 150                 155                 160
Tyr Phe Ile Gly Arg Ile Ile Ser Gly Met Gly Val Gly Gly Ile Ala
                165                 170                 175
Val Leu Ser Pro Thr Leu Ile Ser Glu Thr Ala Pro Lys His Ile Arg
            180                 185                 190
Gly Thr Cys Val Ser Phe Tyr Gln Leu Met Ile Thr Leu Gly Ile Phe
            195                 200                 205
Leu Gly Tyr Cys Thr Asn Tyr Gly Thr Lys Asp Tyr Ser Asn Ser Val
        210                 215                 220
Gln Trp Arg Val Pro Leu Gly Leu Asn Phe Ala Phe Ala Ile Phe Met
225                 230                 235                 240
Ile Ala Gly Met Leu Met Val Pro Glu Ser Pro Arg Phe Leu Val Glu
                245                 250                 255
Lys Gly Arg Tyr Glu Asp Ala Lys Arg Ser Leu Ala Lys Ser Asn Lys
            260                 265                 270
Val Thr Ile Glu Asp Pro Ser Ile Val Ala Glu Met Asp Thr Ile Met
            275                 280                 285
Ala Asn Val Glu Thr Glu Arg Leu Ala Gly Asn Ala Ser Trp Gly Glu
        290                 295                 300
Leu Phe Ser Asn Lys Gly Ala Ile Leu Pro Arg Val Ile Met Gly Ile
305                 310                 315                 320
Met Ile Gln Ser Leu Gln Gln Leu Thr Gly Asn Asn Tyr Phe Phe Tyr
                325                 330                 335
Tyr Gly Thr Thr Ile Phe Asn Ala Val Gly Met Lys Asp Ser Phe Gln
            340                 345                 350
Thr Ser Ile Val Leu Gly Ile Val Asn Phe Ala Ser Thr Phe Val Ala
            355                 360                 365
Leu Tyr Thr Val Asp Lys Phe Gly Arg Arg Lys Cys Leu Leu Gly Gly
        370                 375                 380
Ser Ala Ser Met Ala Ile Cys Phe Val Ile Phe Ser Thr Val Gly Val
385                 390                 395                 400
Thr Ser Leu Tyr Pro Asn Gly Lys Asp Gln Pro Ser Ser Lys Ala Ala
                405                 410                 415
Gly Asn Val Met Ile Val Phe Thr Cys Leu Phe Ile Phe Phe Phe Ala
            420                 425                 430
Ile Ser Trp Ala Pro Ile Ala Tyr Val Ile Val Ala Glu Ser Tyr Pro
            435                 440                 445
Leu Arg Val Lys Asn Arg Ala Met Ala Ile Ala Val Gly Ala Asn Trp
        450                 455                 460
Ile Trp Gly Phe Leu Ile Gly Phe Phe Thr Pro Phe Ile Thr Ser Ala
465                 470                 475                 480
Ile Gly Phe Ser Tyr Gly Tyr Val Phe Met Gly Cys Leu Val Phe Ser
                485                 490                 495
Phe Phe Tyr Val Phe Phe Val Cys Glu Thr Lys Gly Leu Thr Leu
            500                 505                 510
Glu Glu Val Asn Glu Met Tyr Val Glu Gly Val Lys Pro Trp Lys Ser
            515                 520                 525
Gly Ser Trp Ile Ser Lys Glu Lys Arg Val Ser Glu Glu
        530                 535                 540
```

<210> SEQ ID NO 125
<211> LENGTH: 574
<212> TYPE: PRT
<213> ORGANISM: Saccharomyces cerevisiae
<220> FEATURE:
<221> NAME/KEY: misc_feature
<222> LOCATION: (1)..(574)
<223> OTHER INFORMATION: Gal2p

<400> SEQUENCE: 125

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Ser Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
    130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
    210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
            260                 265                 270

Asn Lys Val Glu Asp Ala Lys Arg Ser Ile Ala Lys Ser Asn Lys Val
        275                 280                 285

Ser Pro Glu Asp Pro Ala Val Gln Ala Glu Leu Asp Leu Ile Met Ala
    290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
            340                 345                 350

```
Gly Thr Val Ile Phe Lys Ser Val Gly Leu Asp Asp Ser Phe Glu Thr
            355                 360                 365

Ser Ile Val Ile Gly Val Val Asn Phe Ala Ser Thr Phe Phe Ser Leu
370                 375                 380

Trp Thr Val Glu Asn Leu Gly His Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Lys Gly Ala Gly
            420                 425                 430

Asn Cys Met Ile Val Phe Thr Cys Phe Tyr Ile Phe Cys Tyr Ala Thr
            435                 440                 445

Thr Trp Ala Pro Val Ala Trp Val Ile Thr Ala Glu Ser Phe Pro Leu
        450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
            500                 505                 510

Phe Tyr Val Phe Phe Val Pro Glu Thr Lys Gly Leu Ser Leu Glu
        515                 520                 525

Glu Ile Gln Glu Leu Trp Glu Glu Gly Val Leu Pro Trp Lys Ser Glu
530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
            565                 570

<210> SEQ ID NO 126
<211> LENGTH: 508
<212> TYPE: PRT
<213> ORGANISM: Saccharomyces cerevisiae
<220> FEATURE:
<221> NAME/KEY: MISC_FEATURE
<222> LOCATION: (1)..(508)
<223> OTHER INFORMATION: Hxt3-6p

<400> SEQUENCE: 126

Met Asn Ser Thr Pro Asp Leu Ile Ser Pro Gln Lys Ser Ser Glu Asn
1               5                   10                  15

Ser Asn Ala Asp Leu Pro Ser Asn Ser Ser Gln Val Met Asn Met Pro
            20                  25                  30

Glu Glu Lys Gly Val Gln Asp Asp Phe Gln Ala Glu Ala Asp Gln Val
        35                  40                  45

Leu Thr Asn Pro Asn Thr Gly Lys Gly Ala Tyr Val Thr Val Ser Ile
    50                  55                  60

Cys Cys Val Met Val Ala Phe Gly Gly Phe Val Phe Gly Trp Asp Thr
65                  70                  75                  80

Gly Thr Ile Ser Gly Phe Val Ala Gln Thr Asp Phe Leu Arg Arg Phe
                85                  90                  95

Gly Met Lys His Lys Asp Gly Ser Tyr Tyr Leu Ser Lys Val Arg Thr
            100                 105                 110

Gly Leu Ile Val Ser Ile Ile Asn Ile Gly Cys Ala Ile Gly Gly Ile
        115                 120                 125

Ile Leu Ala Lys Leu Gly Asp Met Tyr Gly Arg Lys Met Gly Leu Ile
```

```
            130                 135                 140
Val Val Val Ile Tyr Ile Gly Ile Ile Gln Ile Ala Ser
145                 150                 155                 160

Ile Asn Lys Trp Tyr Gln Tyr Phe Ile Gly Arg Ile Ile Ser Gly Leu
                165                 170                 175

Gly Val Gly Gly Ile Ala Val Leu Ser Pro Met Leu Ile Ser Glu Val
                180                 185                 190

Ala Pro Lys Glu Met Arg Gly Thr Leu Val Ser Cys Tyr Gln Leu Met
                195                 200                 205

Ile Thr Leu Gly Ile Phe Leu Gly Tyr Cys Thr Asn Phe Gly Thr Lys
                210                 215                 220

Asn Tyr Ser Asn Ser Val Gln Trp Arg Val Pro Leu Gly Leu Cys Phe
225                 230                 235                 240

Ala Trp Ala Leu Phe Met Ile Gly Gly Met Thr Phe Val Pro Glu Ser
                245                 250                 255

Pro Arg Tyr Leu Val Glu Ala Gly Gln Ile Asp Glu Ala Arg Ala Ser
                260                 265                 270

Leu Ser Lys Val Asn Lys Val Ala Pro Asp His Pro Phe Ile Gln Gln
                275                 280                 285

Glu Leu Glu Val Ile Glu Ala Ser Val Glu Glu Ala Arg Ala Ala Gly
                290                 295                 300

Ser Ala Ser Trp Gly Glu Leu Phe Thr Gly Lys Pro Ala Met Phe Lys
305                 310                 315                 320

Arg Thr Met Met Gly Ile Met Ile Gln Ser Leu Gln Gln Leu Thr Gly
                325                 330                 335

Asp Asn Tyr Phe Phe Tyr Tyr Gly Thr Thr Val Phe Asn Ala Val Gly
                340                 345                 350

Met Ser Asp Ser Phe Glu Thr Ser Ile Val Phe Gly Val Val Asn Phe
                355                 360                 365

Phe Ser Thr Cys Cys Ser Leu Tyr Thr Val Asp Arg Phe Gly Arg Arg
                370                 375                 380

Asn Cys Leu Leu Tyr Gly Ala Ile Gly Met Val Cys Cys Tyr Val Val
385                 390                 395                 400

Tyr Ala Ser Val Gly Val Thr Arg Leu Trp Pro Asn Gly Glu Gly Asn
                405                 410                 415

Gly Ser Ser Lys Gly Ala Gly Asn Cys Met Ile Cys Phe Ala Cys Phe
                420                 425                 430

Tyr Ile Phe Cys Phe Ala Thr Thr Trp Ala Pro Ile Ala Tyr Val Val
                435                 440                 445

Ile Ser Glu Thr Phe Pro Leu Arg Val Lys Ser Lys Ala Met Ser Ile
                450                 455                 460

Ala Thr Ala Ala Asn Trp Leu Trp Gly Phe Leu Ile Gly Phe Phe Thr
465                 470                 475                 480

Pro Phe Ile Thr Gly Ala Ile Asn Phe Tyr Tyr Gly Tyr Val Phe Met
                485                 490                 495

Gly Cys Gln Glu Gln Thr Ser Ser Thr Cys Leu Phe
                500                 505

<210> SEQ ID NO 127
<211> LENGTH: 38
<212> TYPE: DNA
<213> ORGANISM: Artificial Sequence
<220> FEATURE:
<223> OTHER INFORMATION: primer F HXT36 Bcui
<220> FEATURE:
```

```
<221> NAME/KEY: source
<222> LOCATION: (1)..(38)
<223> OTHER INFORMATION: /organism="Artificial Sequence" /note="primer
      F HXT36 Bcui" /mol_type="unassigned DNA"

<400> SEQUENCE: 127
gcatactagt atgaattcaa ctccagattt aatatctc                           38

<210> SEQ ID NO 128
<211> LENGTH: 30
<212> TYPE: DNA
<213> ORGANISM: Artificial Sequence
<220> FEATURE:
<223> OTHER INFORMATION: primer R HXT36 367NNN
<220> FEATURE:
<221> NAME/KEY: source
<222> LOCATION: (1)..(30)
<223> OTHER INFORMATION: /organism="Artificial Sequence" /note="primer
      R HXT36 367NNN" /mol_type="unassigned DNA"
<220> FEATURE:
<221> NAME/KEY: misc_feature
<222> LOCATION: (18)..(20)
<223> OTHER INFORMATION: n is a, c, g, or t

<400> SEQUENCE: 128
caacaagtag agaagaannn gacgacaccg                                    30

<210> SEQ ID NO 129
<211> LENGTH: 30
<212> TYPE: DNA
<213> ORGANISM: Artificial Sequence
<220> FEATURE:
<223> OTHER INFORMATION: primer F HXT36 367NNN
<220> FEATURE:
<221> NAME/KEY: source
<222> LOCATION: (1)..(30)
<223> OTHER INFORMATION: /organism="Artificial Sequence" /note="primer
      F HXT36 367NNN" /mol_type="unassigned DNA"
<220> FEATURE:
<221> NAME/KEY: misc_feature
<222> LOCATION: (11)..(13)
<223> OTHER INFORMATION: n is a, c, g, or t

<400> SEQUENCE: 129
cggtgtcgtc nnnttcttct ctacttgttg                                    30

<210> SEQ ID NO 130
<211> LENGTH: 36
<212> TYPE: DNA
<213> ORGANISM: Artificial Sequence
<220> FEATURE:
<223> OTHER INFORMATION: primer R HXT36 BamHi
<220> FEATURE:
<221> NAME/KEY: source
<222> LOCATION: (1)..(36)
<223> OTHER INFORMATION: /organism="Artificial Sequence" /note="primer
      R HXT36 BamHi" /mol_type="unassigned DNA"

<400> SEQUENCE: 130
acgtggatcc ttatttggtg ctgaacattc tcttgt                             36

<210> SEQ ID NO 131
<211> LENGTH: 35
<212> TYPE: DNA
<213> ORGANISM: Artificial Sequence
<220> FEATURE:
<223> OTHER INFORMATION: primer R HXT36 BamHI-stop
<220> FEATURE:
<221> NAME/KEY: source
<222> LOCATION: (1)..(35)
<223> OTHER INFORMATION: /organism="Artificial Sequence" /note="primer
```

R HXT36 BamHI-stop" /mol_type="unassigned DNA"

<400> SEQUENCE: 131
ccatggatcc tttggtgctg aacattctct tgtac                              35

<210> SEQ ID NO 132
<211> LENGTH: 31
<212> TYPE: DNA
<213> ORGANISM: Artificial Sequence
<220> FEATURE:
<223> OTHER INFORMATION: primer F GFP BamHI
<220> FEATURE:
<221> NAME/KEY: source
<222> LOCATION: (1)..(31)
<223> OTHER INFORMATION: /organism="Artificial Sequence" /note="primer
    F GFP BamHI" /mol_type="unassigned DNA"

<400> SEQUENCE: 132
aaaggatcca tggtgagcaa gggcgaggag c                                  31

<210> SEQ ID NO 133
<211> LENGTH: 28
<212> TYPE: DNA
<213> ORGANISM: Artificial Sequence
<220> FEATURE:
<223> OTHER INFORMATION: primer R GFP ClaI
<220> FEATURE:
<221> NAME/KEY: source
<222> LOCATION: (1)..(28)
<223> OTHER INFORMATION: /organism="Artificial Sequence" /note="primer
    R GFP ClaI" /mol_type="unassigned DNA"

<400> SEQUENCE: 133
aaaatcgatt tacttgtaca gctcgtcc                                      28

<210> SEQ ID NO 134
<211> LENGTH: 36
<212> TYPE: DNA
<213> ORGANISM: Artificial Sequence
<220> FEATURE:
<223> OTHER INFORMATION: F HXT11 XbaI
<220> FEATURE:
<221> NAME/KEY: source
<222> LOCATION: (1)..(36)
<223> OTHER INFORMATION: /organism="Artificial Sequence"
    /note="F HXT11 XbaI" /mol_type="unassigned DNA"

<400> SEQUENCE: 134
ggcctctaga atgtcaggtg ttaataatac atccgc                             36

<210> SEQ ID NO 135
<211> LENGTH: 39
<212> TYPE: DNA
<213> ORGANISM: Artificial Sequence
<220> FEATURE:
<223> OTHER INFORMATION: R HXT11 BamHI
<220> FEATURE:
<221> NAME/KEY: source
<222> LOCATION: (1)..(39)
<223> OTHER INFORMATION: /organism="Artificial Sequence"
    /note="R HXT11 BamHI" /mol_type="unassigned DNA"

<400> SEQUENCE: 135
cgatggatcc tcagctggaa aagaacctct tgtaaattg                          39

<210> SEQ ID NO 136
<211> LENGTH: 28
<212> TYPE: DNA
<213> ORGANISM: Artificial Sequence

```
<220> FEATURE:
<223> OTHER INFORMATION: F HXT11 366NNN
<220> FEATURE:
<221> NAME/KEY: source
<222> LOCATION: (1)..(28)
<223> OTHER INFORMATION: /organism="Artificial Sequence"
      /note="F HXT11 366NNN" /mol_type="unassigned DNA"
<220> FEATURE:
<221> NAME/KEY: misc_feature
<222> LOCATION: (11)..(13)
<223> OTHER INFORMATION: n is a, c, g, or t

<400> SEQUENCE: 136
cggtgtggtt nnntttttct cttcattc                                    28

<210> SEQ ID NO 137
<211> LENGTH: 28
<212> TYPE: DNA
<213> ORGANISM: Artificial Sequence
<220> FEATURE:
<223> OTHER INFORMATION: R HXT11 366NNN
<220> FEATURE:
<221> NAME/KEY: source
<222> LOCATION: (1)..(28)
<223> OTHER INFORMATION: /organism="Artificial Sequence"
      /note="R HXT11 366NNN" /mol_type="unassigned DNA"
<220> FEATURE:
<221> NAME/KEY: misc_feature
<222> LOCATION: (16)..(18)
<223> OTHER INFORMATION: n is a, c, g, or t

<400> SEQUENCE: 137
gaatgaagag aaaaannnaa ccacaccg                                    28

<210> SEQ ID NO 138
<211> LENGTH: 28
<212> TYPE: DNA
<213> ORGANISM: Artificial Sequence
<220> FEATURE:
<223> OTHER INFORMATION: F HXT11 N366F
<220> FEATURE:
<221> NAME/KEY: source
<222> LOCATION: (1)..(28)
<223> OTHER INFORMATION: /organism="Artificial Sequence"
      /note="F HXT11 N366F" /mol_type="unassigned DNA"

<400> SEQUENCE: 138
cggtgtggtt ttttttttct cttcattc                                    28

<210> SEQ ID NO 139
<211> LENGTH: 28
<212> TYPE: DNA
<213> ORGANISM: Artificial Sequence
<220> FEATURE:
<223> OTHER INFORMATION: R HXT11 N366F
<220> FEATURE:
<221> NAME/KEY: source
<222> LOCATION: (1)..(28)
<223> OTHER INFORMATION: /organism="Artificial Sequence"
      /note="R HXT11 N366F" /mol_type="unassigned DNA"

<400> SEQUENCE: 139
gaatgaagag aaaaaaaaaa ccacaccg                                    28

<210> SEQ ID NO 140
<211> LENGTH: 28
<212> TYPE: DNA
<213> ORGANISM: Artificial Sequence
<220> FEATURE:
<223> OTHER INFORMATION: F HXT11 N366E
<220> FEATURE:
```

```
<221> NAME/KEY: source
<222> LOCATION: (1)..(28)
<223> OTHER INFORMATION: /organism="Artificial Sequence"
      /note="F HXT11 N366E" /mol_type="unassigned DNA"

<400> SEQUENCE: 140
cggtgtggtt gagtttttct cttcattc                                              28

<210> SEQ ID NO 141
<211> LENGTH: 28
<212> TYPE: DNA
<213> ORGANISM: Artificial Sequence
<220> FEATURE:
<223> OTHER INFORMATION: R HXT11 N366E
<220> FEATURE:
<221> NAME/KEY: source
<222> LOCATION: (1)..(28)
<223> OTHER INFORMATION: /organism="Artificial Sequence"
      /note="R HXT11 N366E" /mol_type="unassigned DNA"

<400> SEQUENCE: 141
gaatgaagag aaaaactcaa ccacaccg                                              28

<210> SEQ ID NO 142
<211> LENGTH: 28
<212> TYPE: DNA
<213> ORGANISM: Artificial Sequence
<220> FEATURE:
<223> OTHER INFORMATION: F HXT11 N366K
<220> FEATURE:
<221> NAME/KEY: source
<222> LOCATION: (1)..(28)
<223> OTHER INFORMATION: /organism="Artificial Sequence"
      /note="F HXT11 N366K" /mol_type="unassigned DNA"

<400> SEQUENCE: 142
cggtgtggtt aaattttcct cttcattc                                              28

<210> SEQ ID NO 143
<211> LENGTH: 28
<212> TYPE: DNA
<213> ORGANISM: Artificial Sequence
<220> FEATURE:
<223> OTHER INFORMATION: R HXT11 N366K
<220> FEATURE:
<221> NAME/KEY: source
<222> LOCATION: (1)..(28)
<223> OTHER INFORMATION: /organism="Artificial Sequence" /note="R
      HXT11 N366K " /mol_type="unassigned DNA"

<400> SEQUENCE: 143
gaatgaagag aaaaatttaa ccacaccg                                              28

<210> SEQ ID NO 144
<211> LENGTH: 28
<212> TYPE: DNA
<213> ORGANISM: Artificial Sequence
<220> FEATURE:
<223> OTHER INFORMATION: F HXT11 N366M
<220> FEATURE:
<221> NAME/KEY: source
<222> LOCATION: (1)..(28)
<223> OTHER INFORMATION: /organism="Artificial Sequence"
      /note="F HXT11 N366M" /mol_type="unassigned DNA"

<400> SEQUENCE: 144
cggtgtggtt atgtttttct cttcattc                                              28

<210> SEQ ID NO 145
```

```
<211> LENGTH: 28
<212> TYPE: DNA
<213> ORGANISM: Artificial Sequence
<220> FEATURE:
<223> OTHER INFORMATION: R HXT11 N366M
<220> FEATURE:
<221> NAME/KEY: source
<222> LOCATION: (1)..(28)
<223> OTHER INFORMATION: /organism="Artificial Sequence"
      /note="R HXT11 N366M" /mol_type="unassigned DNA"

<400> SEQUENCE: 145
gaatgaagag aaaaacataa ccacaccg                                    28

<210> SEQ ID NO 146
<211> LENGTH: 28
<212> TYPE: DNA
<213> ORGANISM: Artificial Sequence
<220> FEATURE:
<223> OTHER INFORMATION: F HXT11 N366W
<220> FEATURE:
<221> NAME/KEY: source
<222> LOCATION: (1)..(28)
<223> OTHER INFORMATION: /organism="Artificial Sequence"
      /note="F HXT11 N366W" /mol_type="unassigned DNA"

<400> SEQUENCE: 146
cggtgtggtt tggttttact cttcattc                                    28

<210> SEQ ID NO 147
<211> LENGTH: 28
<212> TYPE: DNA
<213> ORGANISM: Artificial Sequence
<220> FEATURE:
<223> OTHER INFORMATION: R HXT11 N366W
<220> FEATURE:
<221> NAME/KEY: source
<222> LOCATION: (1)..(28)
<223> OTHER INFORMATION: /organism="Artificial Sequence"
      /note="R HXT11 N366W" /mol_type="unassigned DNA"

<400> SEQUENCE: 147
gaatgaagag aaaaaccaaa ccacaccg                                    28

<210> SEQ ID NO 148
<211> LENGTH: 28
<212> TYPE: DNA
<213> ORGANISM: Artificial Sequence
<220> FEATURE:
<223> OTHER INFORMATION: F HXT11 N366Y
<220> FEATURE:
<221> NAME/KEY: source
<222> LOCATION: (1)..(28)
<223> OTHER INFORMATION: /organism="Artificial Sequence"
      /note="F HXT11 N366Y" /mol_type="unassigned DNA"

<400> SEQUENCE: 148
cggtgtggtt tatttttct cttcattc                                     28

<210> SEQ ID NO 149
<211> LENGTH: 28
<212> TYPE: DNA
<213> ORGANISM: Artificial Sequence
<220> FEATURE:
<223> OTHER INFORMATION: R HXT11 N366Y
<220> FEATURE:
<221> NAME/KEY: source
<222> LOCATION: (1)..(28)
<223> OTHER INFORMATION: /organism="Artificial Sequence"
      /note="R HXT11 N366Y" /mol_type="unassigned DNA"
```

```
<400> SEQUENCE: 149
gaatgaagag aaaaaataaa ccacaccg                                              28

Figure 10A:
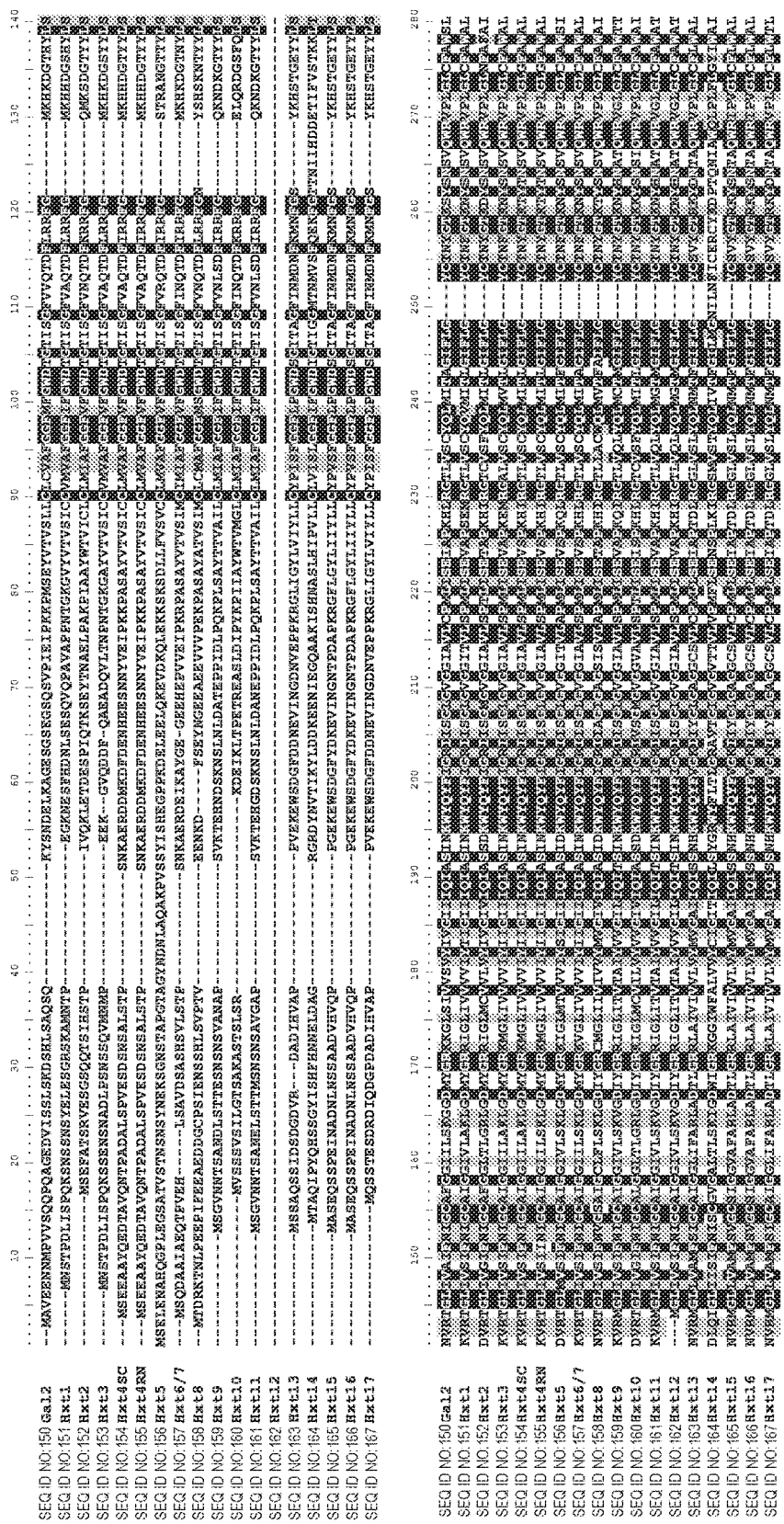
FIG. 10 shows an alignment of permease protein sequences.

<210> SEQ ID NO 150
<211> LENGTH: 574
<212> TYPE: PRT
<213> ORGANISM: Saccharomyces cerevisiae
<220> FEATURE:
<221> NAME/KEY: MISC_FEATURE
<222> LOCATION: (1)..(574)
<223> OTHER INFORMATION: Gal2 (Fig. 10)

<400> SEQUENCE: 150
```

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Ser Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
    130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
    210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
            260                 265                 270

Asn Lys Val Glu Asp Ala Lys Arg Ser Ile Ala Lys Ser Asn Lys Val
        275                 280                 285

Ser Pro Glu Asp Pro Ala Val Gln Ala Glu Leu Asp Leu Ile Met Ala
    290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

```
Val Gln Met Phe Gln Gln Leu Thr Gly Asn Asn Tyr Phe Phe Tyr Tyr
                340                 345                 350

Gly Thr Val Ile Phe Lys Ser Val Gly Leu Asp Asp Ser Phe Glu Thr
            355                 360                 365

Ser Ile Val Ile Gly Val Val Asn Phe Ala Ser Thr Phe Phe Ser Leu
        370                 375                 380

Trp Thr Val Glu Asn Leu Gly His Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
                420                 425                 430

Asn Cys Met Ile Val Phe Thr Cys Phe Tyr Ile Phe Cys Tyr Ala Thr
                435                 440                 445

Thr Trp Ala Pro Val Ala Trp Val Ile Thr Ala Glu Ser Phe Pro Leu
            450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
                500                 505                 510

Phe Tyr Val Phe Phe Phe Val Pro Glu Thr Lys Gly Leu Ser Leu Glu
                515                 520                 525

Glu Ile Gln Glu Leu Trp Glu Glu Gly Val Leu Pro Trp Lys Ser Glu
            530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570

<210> SEQ ID NO 151
<211> LENGTH: 570
<212> TYPE: PRT
<213> ORGANISM: Saccharomyces cerevisiae
<220> FEATURE:
<221> NAME/KEY: MISC_FEATURE
<222> LOCATION: (1)..(570)
<223> OTHER INFORMATION: Hxt1 (Fig. 10)

<400> SEQUENCE: 151

Met Asn Ser Thr Pro Asp Leu Ile Ser Pro Gln Lys Ser Asn Ser Ser
1               5                   10                  15

Asn Ser Tyr Glu Leu Glu Ser Gly Arg Ser Lys Ala Met Asn Thr Pro
            20                  25                  30

Glu Gly Lys Asn Glu Ser Phe His Asp Asn Leu Ser Glu Ser Gln Val
        35                  40                  45

Gln Pro Ala Val Ala Pro Asn Thr Gly Lys Gly Val Tyr Val Thr
    50                  55                  60

Val Ser Ile Cys Cys Val Met Val Ala Phe Gly Gly Phe Ile Phe Gly
65                  70                  75                  80

Trp Asp Thr Gly Thr Ile Ser Gly Phe Val Ala Gln Thr Asp Phe Leu
                85                  90                  95

Arg Arg Phe Gly Met Lys His His Asp Gly Ser His Tyr Leu Ser Lys
                100                 105                 110

Val Arg Thr Gly Leu Ile Val Ser Ile Phe Asn Ile Gly Cys Ala Ile
```

```
            115                 120                 125
Gly Gly Ile Val Leu Ala Lys Leu Gly Asp Met Tyr Gly Arg Arg Ile
            130                 135                 140
Gly Leu Ile Val Val Val Ile Tyr Thr Ile Gly Ile Ile Ile Gln
145                 150                 155                 160
Ile Ala Ser Ile Asn Lys Trp Tyr Gln Tyr Phe Ile Gly Arg Ile Ile
                165                 170                 175
Ser Gly Leu Gly Val Gly Gly Ile Thr Val Leu Ser Pro Met Leu Ile
                180                 185                 190
Ser Glu Val Ala Pro Ser Glu Met Arg Gly Thr Leu Val Ser Cys Tyr
                195                 200                 205
Gln Val Met Ile Thr Leu Gly Ile Phe Leu Gly Tyr Cys Thr Asn Phe
            210                 215                 220
Gly Thr Lys Asn Tyr Ser Asn Ser Val Gln Trp Arg Val Pro Leu Gly
225                 230                 235                 240
Leu Cys Phe Ala Trp Ala Leu Phe Met Ile Gly Gly Met Met Phe Val
                245                 250                 255
Pro Glu Ser Pro Arg Tyr Leu Val Glu Ala Gly Arg Ile Asp Glu Ala
                260                 265                 270
Arg Ala Ser Leu Ala Lys Val Asn Lys Cys Pro Pro Asp His Pro Tyr
            275                 280                 285
Ile Gln Tyr Glu Leu Glu Thr Ile Glu Ala Gly Val Glu Glu Met Arg
290                 295                 300
Ala Ala Gly Thr Ala Ser Trp Gly Glu Leu Phe Thr Gly Lys Pro Ala
305                 310                 315                 320
Met Phe Gln Arg Thr Met Met Gly Ile Met Ile Gln Ser Leu Gln Gln
                325                 330                 335
Leu Thr Gly Asp Asn Tyr Phe Phe Tyr Tyr Gly Thr Ile Val Phe Gln
            340                 345                 350
Ala Val Gly Leu Ser Asp Ser Phe Glu Thr Ser Ile Val Phe Gly Val
            355                 360                 365
Val Asn Phe Phe Ser Thr Cys Cys Ser Leu Tyr Thr Val Asp Arg Phe
370                 375                 380
Gly Arg Arg Asn Cys Leu Met Trp Gly Ala Val Gly Met Val Cys Cys
385                 390                 395                 400
Tyr Val Val Tyr Ala Ser Val Gly Val Thr Arg Leu Trp Pro Asn Gly
                405                 410                 415
Gln Asn Asn Gly Ser Ser Lys Gly Ala Gly Asn Cys Met Ile Cys Phe
                420                 425                 430
Ala Cys Phe Tyr Ile Phe Cys Phe Ala Thr Thr Trp Ala Pro Ile Ala
            435                 440                 445
Tyr Val Val Ile Ser Glu Cys Phe Pro Leu Arg Val Lys Ser Lys Cys
            450                 455                 460
Met Ser Ile Ala Ser Ala Ala Asn Trp Ile Trp Gly Phe Leu Ile Ser
465                 470                 475                 480
Phe Phe Thr Pro Phe Ile Thr Gly Ala Ile Asn Phe Tyr Gly Tyr
                485                 490                 495
Val Phe Met Gly Cys Met Val Phe Ala Tyr Phe Tyr Val Phe Phe Phe
                500                 505                 510
Val Pro Glu Thr Lys Gly Leu Ser Leu Glu Glu Val Asn Asp Met Tyr
            515                 520                 525
Ala Glu Gly Val Leu Pro Trp Lys Ser Ala Ser Trp Val Pro Val Ser
            530                 535                 540
```

```
Lys Arg Gly Ala Asp Tyr Asn Ala Asp Asp Leu Met His Asp Asp Gln
545                 550                 555                 560

Pro Phe Tyr Lys Ser Leu Phe Ser Arg Lys
                565                 570

<210> SEQ ID NO 152
<211> LENGTH: 541
<212> TYPE: PRT
<213> ORGANISM: Saccharomyces cerevisiae
<220> FEATURE:
<221> NAME/KEY: MISC_FEATURE
<222> LOCATION: (1)..(541)
<223> OTHER INFORMATION: Hxt2 (Fig. 10)

<400> SEQUENCE: 152

Met Ser Glu Phe Ala Thr Ser Arg Val Glu Ser Gly Ser Gln Gln Thr
1               5                   10                  15

Ser Ile His Ser Thr Pro Ile Val Gln Lys Leu Glu Thr Asp Glu Ser
            20                  25                  30

Pro Ile Gln Thr Lys Ser Glu Tyr Thr Asn Ala Glu Leu Pro Ala Lys
        35                  40                  45

Pro Ile Ala Ala Tyr Trp Thr Val Ile Cys Leu Cys Leu Met Ile Ala
    50                  55                  60

Phe Gly Gly Phe Val Phe Gly Trp Asp Thr Gly Thr Ile Ser Gly Phe
65                  70                  75                  80

Val Asn Gln Thr Asp Phe Lys Arg Arg Phe Gly Gln Met Lys Ser Asp
                85                  90                  95

Gly Thr Tyr Tyr Leu Ser Asp Val Arg Thr Gly Leu Ile Val Gly Ile
            100                 105                 110

Phe Asn Ile Gly Cys Ala Phe Gly Gly Leu Thr Leu Gly Arg Leu Gly
        115                 120                 125

Asp Met Tyr Gly Arg Arg Ile Gly Leu Met Cys Val Val Leu Val Tyr
130                 135                 140

Ile Val Gly Ile Val Ile Gln Ile Ala Ser Ser Asp Lys Trp Tyr Gln
145                 150                 155                 160

Tyr Phe Ile Gly Arg Ile Ile Ser Gly Met Gly Val Gly Gly Ile Ala
                165                 170                 175

Val Leu Ser Pro Thr Leu Ile Ser Glu Thr Ala Pro Lys His Ile Arg
            180                 185                 190

Gly Thr Cys Val Ser Phe Tyr Gln Leu Met Ile Thr Leu Gly Ile Phe
        195                 200                 205

Leu Gly Tyr Cys Thr Asn Tyr Gly Thr Lys Asp Tyr Ser Asn Ser Val
    210                 215                 220

Gln Trp Arg Val Pro Leu Gly Leu Asn Phe Ala Phe Ala Ile Phe Met
225                 230                 235                 240

Ile Ala Gly Met Leu Met Val Pro Glu Ser Pro Arg Phe Leu Val Glu
                245                 250                 255

Lys Gly Arg Tyr Glu Asp Ala Lys Arg Ser Leu Ala Lys Ser Asn Lys
            260                 265                 270

Val Thr Ile Glu Asp Pro Ser Ile Val Ala Glu Met Asp Thr Ile Met
        275                 280                 285

Ala Asn Val Glu Thr Glu Arg Leu Ala Gly Asn Ala Ser Trp Gly Glu
    290                 295                 300

Leu Phe Ser Asn Lys Gly Ala Ile Leu Pro Arg Val Ile Met Gly Ile
305                 310                 315                 320
```

Met Ile Gln Ser Leu Gln Gln Leu Thr Gly Asn Asn Tyr Phe Phe Tyr
                325                 330                 335

Tyr Gly Thr Thr Ile Phe Asn Ala Val Gly Met Lys Asp Ser Phe Gln
            340                 345                 350

Thr Ser Ile Val Leu Gly Ile Val Asn Phe Ala Ser Thr Phe Val Ala
        355                 360                 365

Leu Tyr Thr Val Asp Lys Phe Gly Arg Arg Lys Cys Leu Leu Gly Gly
    370                 375                 380

Ser Ala Ser Met Ala Ile Cys Phe Val Ile Phe Ser Thr Val Gly Val
385                 390                 395                 400

Thr Ser Leu Tyr Pro Asn Gly Lys Asp Gln Pro Ser Ser Lys Ala Ala
            405                 410                 415

Gly Asn Val Met Ile Val Phe Thr Cys Leu Phe Ile Phe Phe Phe Ala
            420                 425                 430

Ile Ser Trp Ala Pro Ile Ala Tyr Val Ile Val Ala Glu Ser Tyr Pro
        435                 440                 445

Leu Arg Val Lys Asn Arg Ala Met Ala Ile Ala Val Gly Ala Asn Trp
    450                 455                 460

Ile Trp Gly Phe Leu Ile Gly Phe Phe Thr Pro Phe Ile Thr Ser Ala
465                 470                 475                 480

Ile Gly Phe Ser Tyr Gly Tyr Val Phe Met Gly Cys Leu Val Phe Ser
            485                 490                 495

Phe Phe Tyr Val Phe Phe Phe Val Cys Glu Thr Lys Gly Leu Thr Leu
            500                 505                 510

Glu Glu Val Asn Glu Met Tyr Val Gly Val Lys Pro Trp Lys Ser
            515                 520                 525

Gly Ser Trp Ile Ser Lys Glu Lys Arg Val Ser Glu Glu
    530                 535                 540

<210> SEQ ID NO 153
<211> LENGTH: 567
<212> TYPE: PRT
<213> ORGANISM: Saccharomyces cerevisiae
<220> FEATURE:
<221> NAME/KEY: MISC_FEATURE
<222> LOCATION: (1)..(567)
<223> OTHER INFORMATION: Hxt3 (Fig. 10)

<400> SEQUENCE: 153

Met Asn Ser Thr Pro Asp Leu Ile Ser Pro Gln Lys Ser Ser Glu Asn
1               5                   10                  15

Ser Asn Ala Asp Leu Pro Ser Asn Ser Ser Gln Val Met Asn Met Pro
            20                  25                  30

Glu Glu Lys Gly Val Gln Asp Asp Phe Gln Ala Glu Ala Asp Gln Val
        35                  40                  45

Leu Thr Asn Pro Asn Thr Gly Lys Gly Ala Tyr Val Thr Val Ser Ile
    50                  55                  60

Cys Cys Val Met Val Ala Phe Gly Gly Phe Val Phe Gly Trp Asp Thr
65                  70                  75                  80

Gly Thr Ile Ser Gly Phe Val Ala Gln Thr Asp Phe Leu Arg Arg Phe
            85                  90                  95

Gly Met Lys His Lys Asp Gly Ser Tyr Tyr Leu Ser Lys Val Arg Thr
            100                 105                 110

Gly Leu Ile Val Ser Ile Phe Asn Ile Gly Cys Ala Ile Gly Gly Ile
        115                 120                 125

Ile Leu Ala Lys Leu Gly Asp Met Tyr Gly Arg Lys Met Gly Leu Ile

```
            130             135             140
Val Val Val Ile Tyr Ile Gly Ile Ile Gln Ile Ala Ser
145                 150             155             160

Ile Asn Lys Trp Tyr Gln Tyr Phe Ile Gly Arg Ile Ser Gly Leu
                165             170             175

Gly Val Gly Gly Ile Ala Val Leu Ser Pro Met Leu Ile Ser Glu Val
            180             185             190

Ala Pro Lys Glu Met Arg Gly Ala Leu Val Ser Cys Tyr Gln Leu Met
        195             200             205

Val Thr Leu Gly Ile Phe Leu Gly Tyr Cys Thr Asn Phe Gly Thr Lys
        210             215             220

Asn Tyr Ser Asn Ser Val Gln Trp Arg Val Pro Leu Gly Leu Cys Phe
225             230             235             240

Ala Trp Ala Leu Phe Met Ile Gly Gly Met Thr Phe Val Pro Glu Ser
                245             250             255

Pro Arg Tyr Leu Val Glu Ala Gly Gln Ile Asp Glu Ala Arg Ala Ser
            260             265             270

Leu Ser Lys Val Asn Lys Val Ala Pro Asp His Pro Phe Ile Gln Gln
        275             280             285

Glu Leu Glu Val Ile Glu Ala Ser Val Glu Glu Ala Arg Ala Ala Gly
        290             295             300

Ser Ala Ser Trp Gly Glu Leu Phe Thr Gly Lys Pro Ala Met Phe Lys
305             310             315             320

Arg Thr Met Ile Gly Ile Met Ile Gln Ser Leu Gln Gln Leu Thr Gly
                325             330             335

Asp Asn Tyr Phe Phe Tyr Tyr Gly Thr Thr Val Phe Asn Ala Val Gly
            340             345             350

Met Ser Asp Ser Phe Glu Thr Ser Ile Val Phe Gly Val Val Asn Phe
        355             360             365

Phe Ser Thr Cys Cys Ser Leu Tyr Thr Val Asp Arg Phe Gly Arg Arg
        370             375             380

Asn Cys Leu Met Trp Gly Ala Val Gly Met Val Cys Cys Tyr Val Val
385             390             395             400

Tyr Ala Ser Val Gly Val Thr Arg Leu Trp Pro Asn Gly Glu Gly Asn
                405             410             415

Gly Ser Ser Lys Gly Ala Gly Asn Cys Met Ile Val Phe Ala Cys Phe
            420             425             430

Tyr Ile Phe Cys Phe Ala Thr Thr Trp Ala Pro Ile Ala Tyr Val Val
        435             440             445

Ile Ser Glu Thr Phe Pro Leu Arg Val Lys Ser Lys Ala Met Ser Ile
        450             455             460

Ala Thr Ala Ala Asn Trp Leu Trp Gly Phe Leu Ile Gly Phe Phe Thr
465             470             475             480

Pro Phe Ile Thr Gly Ala Ile Asn Phe Tyr Tyr Gly Tyr Val Phe Met
                485             490             495

Gly Cys Met Val Phe Ala Tyr Phe Tyr Val Phe Phe Val Pro Glu
            500             505             510

Thr Lys Gly Leu Thr Leu Glu Glu Val Asn Asp Met Tyr Ala Glu Gly
        515             520             525

Val Leu Pro Trp Lys Ser Ala Ser Trp Val Pro Thr Ser Gln Arg Gly
        530             535             540

Ala Asn Tyr Asp Ala Asp Ala Leu Met His Asp Asp Gln Pro Phe Tyr
545             550             555             560
```

```
Lys Lys Met Phe Gly Lys Lys
                565

<210> SEQ ID NO 154
<211> LENGTH: 560
<212> TYPE: PRT
<213> ORGANISM: Saccharomyces cerevisiae
<220> FEATURE:
<221> NAME/KEY: MISC_FEATURE
<222> LOCATION: (1)..(560)
<223> OTHER INFORMATION: Hxt4SC (Fig. 10)

<400> SEQUENCE: 154

Met Ser Glu Glu Ala Ala Tyr Gln Glu Asp Thr Ala Val Gln Asn Thr
1               5                   10                  15

Pro Ala Asp Ala Leu Ser Pro Val Glu Ser Asp Ser Asn Ser Ala Leu
            20                  25                  30

Ser Thr Pro Ser Asn Lys Ala Glu Arg Asp Asp Met Lys Asp Phe Asp
        35                  40                  45

Glu Asn His Glu Glu Ser Asn Asn Tyr Val Glu Ile Pro Lys Lys Pro
    50                  55                  60

Ala Ser Ala Tyr Val Thr Val Ser Ile Cys Cys Leu Met Val Ala Phe
65                  70                  75                  80

Gly Gly Phe Val Phe Gly Trp Asp Thr Gly Thr Ile Ser Gly Phe Val
                85                  90                  95

Ala Gln Thr Asp Phe Ile Arg Arg Phe Gly Met Lys His His Asp Gly
            100                 105                 110

Thr Tyr Tyr Leu Ser Lys Val Arg Thr Gly Leu Ile Val Ser Ile Phe
        115                 120                 125

Asn Ile Gly Cys Ala Ile Gly Gly Ile Ile Leu Ala Lys Leu Gly Asp
    130                 135                 140

Met Tyr Gly Arg Lys Met Gly Leu Ile Val Val Val Ile Tyr Ile
145                 150                 155                 160

Ile Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Ser Pro Met Leu Ile Ser Glu Val Ser Pro Lys His Ile Arg Gly
        195                 200                 205

Thr Leu Val Ser Cys Tyr Gln Leu Met Ile Thr Leu Gly Ile Phe Leu
    210                 215                 220

Gly Tyr Cys Thr Asn Tyr Gly Thr Lys Thr Tyr Thr Asn Ser Val Gln
225                 230                 235                 240

Trp Arg Val Pro Leu Gly Leu Gly Phe Ala Trp Ala Leu Phe Met Ile
                245                 250                 255

Gly Gly Met Thr Phe Val Pro Glu Ser Pro Arg Tyr Leu Val Glu Val
            260                 265                 270

Gly Lys Ile Glu Glu Ala Lys Arg Ser Ile Ala Leu Ser Asn Lys Val
        275                 280                 285

Ser Ala Asp Asp Pro Ala Val Met Ala Glu Val Glu Val Val Gln Ala
    290                 295                 300

Thr Val Glu Ala Glu Lys Leu Ala Gly Asn Ala Ser Trp Gly Glu Ile
305                 310                 315                 320

Phe Ser Thr Lys Thr Lys Val Phe Gln Arg Leu Ile Met Gly Ala Met
                325                 330                 335
```

-continued

```
Ile Gln Ser Leu Gln Gln Leu Thr Gly Asp Asn Tyr Phe Phe Tyr Tyr
            340                 345                 350

Gly Thr Thr Val Phe Thr Ala Val Gly Leu Glu Asp Ser Phe Glu Thr
            355                 360                 365

Ser Ile Val Leu Gly Ile Val Asn Phe Ala Ser Thr Phe Val Gly Ile
            370                 375                 380

Phe Leu Val Glu Arg Tyr Gly Arg Arg Arg Cys Leu Leu Trp Gly Ala
385                 390                 395                 400

Ala Ser Met Thr Ala Cys Met Val Val Phe Ala Ser Val Gly Val Thr
            405                 410                 415

Arg Leu Trp Pro Asn Gly Lys Lys Asn Gly Ser Ser Lys Gly Ala Gly
            420                 425                 430

Asn Cys Met Ile Val Phe Thr Cys Phe Tyr Leu Phe Cys Phe Ala Thr
            435                 440                 445

Thr Trp Ala Pro Ile Pro Phe Val Val Asn Ser Glu Thr Phe Pro Leu
            450                 455                 460

Arg Val Lys Ser Lys Cys Met Ala Ile Ala Gln Ala Cys Asn Trp Ile
465                 470                 475                 480

Trp Gly Phe Leu Ile Gly Phe Thr Pro Phe Ile Ser Gly Ala Ile
            485                 490                 495

Asp Phe Tyr Tyr Gly Tyr Val Phe Met Gly Cys Leu Val Phe Ser Tyr
            500                 505                 510

Phe Tyr Val Phe Phe Val Pro Glu Thr Lys Gly Leu Thr Leu Glu
            515                 520                 525

Glu Val Asn Thr Leu Trp Glu Glu Gly Val Leu Pro Trp Lys Ser Pro
            530                 535                 540

Ser Trp Phe His Gln Thr Arg Glu Val Leu Thr Thr Thr Leu Met Ile
545                 550                 555                 560

<210> SEQ ID NO 155
<211> LENGTH: 581
<212> TYPE: PRT
<213> ORGANISM: Saccharomyces cerevisiae
<220> FEATURE:
<221> NAME/KEY: MISC_FEATURE
<222> LOCATION: (1)..(581)
<223> OTHER INFORMATION: Hxt4RN (Fig. 10)

<400> SEQUENCE: 155

Met Ser Glu Glu Ala Ala Tyr Gln Glu Asp Thr Ala Val Gln Asn Thr
1               5                   10                  15

Pro Ala Asp Ala Leu Ser Pro Val Glu Ser Asp Ser Asn Ser Ala Leu
            20                  25                  30

Ser Thr Pro Ser Asn Lys Ala Glu Arg Asp Asp Met Lys Asp Phe Asp
            35                  40                  45

Glu Asn His Glu Glu Ser Asn Asn Tyr Val Glu Ile Pro Lys Lys Pro
    50                  55                  60

Ala Ser Ala Tyr Val Thr Val Ser Ile Cys Cys Leu Met Val Ala Phe
65              70                  75                  80

Gly Gly Phe Val Phe Gly Trp Asp Thr Gly Thr Ile Ser Gly Phe Val
            85                  90                  95

Ala Gln Thr Asp Phe Ile Arg Arg Phe Gly Met Lys His His Asp Gly
            100                 105                 110

Thr Tyr Tyr Leu Ser Lys Val Arg Thr Gly Leu Ile Val Ser Ile Ile
            115                 120                 125

Asn Ile Gly Cys Ala Ile Gly Gly Ile Ile Leu Ser Lys Leu Gly Asp
```

```
                130                 135                 140
Met Tyr Gly Arg Lys Met Gly Leu Ile Val Val Val Ile Tyr Ile
145                 150                 155                 160

Ile Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
                180                 185                 190

Leu Ser Pro Met Leu Ile Ser Glu Val Ser Pro Lys His Ile Arg Gly
                195                 200                 205

Thr Leu Val Ser Cys Tyr Gln Leu Met Ile Thr Leu Gly Ile Phe Leu
                210                 215                 220

Gly Tyr Cys Thr Asn Tyr Gly Thr Lys Thr Tyr Thr Asn Ser Val Gln
225                 230                 235                 240

Trp Arg Val Pro Leu Gly Leu Gly Phe Ala Trp Ala Leu Phe Met Ile
                245                 250                 255

Gly Gly Met Thr Leu Val Pro Glu Ser Pro Arg Tyr Leu Val Glu Val
                260                 265                 270

Gly Lys Ile Glu Glu Ala Lys Arg Ser Ile Ala Leu Ser Asn Lys Val
                275                 280                 285

Asn Ala Asp Asp Pro Ala Val Met Ala Glu Val Val Gln Ala
290                 295                 300

Thr Val Glu Ala Glu Lys Leu Ala Gly Asn Ala Ser Trp Gly Glu Ile
305                 310                 315                 320

Phe Ser Thr Lys Thr Lys Val Phe Gln Arg Leu Ile Met Gly Ala Met
                325                 330                 335

Ile Gln Ser Leu Gln Gln Leu Thr Gly Asp Asn Tyr Phe Phe Tyr Tyr
                340                 345                 350

Gly Thr Thr Val Phe Thr Ala Val Gly Leu Glu Asp Ser Phe Glu Thr
                355                 360                 365

Ser Ile Val Leu Gly Ile Val Asn Phe Ala Ser Thr Phe Val Gly Ile
                370                 375                 380

Phe Leu Val Glu Arg Tyr Gly Arg Arg Arg Cys Leu Leu Trp Gly Ala
385                 390                 395                 400

Ala Ser Met Thr Ala Cys Met Val Val Phe Ala Ser Val Gly Val Thr
                405                 410                 415

Arg Leu Trp Pro Asn Gly Lys Lys Asn Gly Ser Ser Lys Gly Ala Gly
                420                 425                 430

Asn Cys Met Ile Val Phe Thr Cys Phe Tyr Leu Phe Cys Phe Ala Thr
                435                 440                 445

Thr Trp Ala Pro Ile Pro Phe Val Val Asn Ser Glu Thr Phe Pro Leu
                450                 455                 460

Arg Val Lys Ser Lys Cys Met Ala Ile Ala Gln Ala Cys Asn Trp Ile
465                 470                 475                 480

Trp Gly Phe Leu Ile Gly Phe Phe Thr Pro Phe Ile Ser Gly Ala Ile
                485                 490                 495

Asp Phe Tyr Tyr Gly Tyr Val Phe Met Gly Cys Leu Val Phe Ser Tyr
                500                 505                 510

Phe Tyr Val Phe Phe Val Pro Glu Thr Lys Gly Leu Thr Leu Glu
                515                 520                 525

Glu Val Asn Thr Leu Trp Glu Glu Gly Val Leu Pro Trp Lys Ser Pro
530                 535                 540

Ser Trp Val Pro Pro Asn Lys Arg Gly Thr Asp Tyr Asn Ala Asp Asp
545                 550                 555                 560
```

```
Leu Met His Asp Gly Ser Thr His Phe Thr Arg Arg Cys Ser Glu Lys
            565                 570                 575
Ser Arg Ser Val Asn
            580

<210> SEQ ID NO 156
<211> LENGTH: 592
<212> TYPE: PRT
<213> ORGANISM: Saccharomyces cerevisiae
<220> FEATURE:
<221> NAME/KEY: MISC_FEATURE
<222> LOCATION: (1)..(592)
<223> OTHER INFORMATION: Hxt5 (Fig. 10)

<400> SEQUENCE: 156

Met Ser Glu Leu Glu Asn Ala His Gln Gly Pro Leu Glu Gly Ser Ala
1               5                   10                  15

Thr Val Ser Thr Asn Ser Asn Ser Tyr Asn Glu Lys Ser Gly Asn Ser
            20                  25                  30

Thr Ala Pro Gly Thr Ala Gly Tyr Asn Asp Asn Leu Ala Gln Ala Lys
        35                  40                  45

Pro Val Ser Ser Tyr Ile Ser His Glu Gly Pro Pro Lys Asp Glu Leu
    50                  55                  60

Glu Glu Leu Gln Lys Glu Val Asp Lys Gln Leu Glu Lys Lys Ser Lys
65                  70                  75                  80

Ser Asp Leu Leu Phe Val Ser Val Cys Cys Leu Met Val Ala Phe Gly
                85                  90                  95

Gly Phe Val Phe Gly Trp Asp Thr Gly Thr Ile Ser Gly Phe Val Arg
            100                 105                 110

Gln Thr Asp Phe Ile Arg Arg Phe Gly Ser Thr Arg Ala Asn Gly Thr
        115                 120                 125

Thr Tyr Leu Ser Asp Val Arg Thr Gly Leu Met Val Ser Ile Phe Asn
130                 135                 140

Ile Gly Cys Ala Ile Gly Gly Ile Val Leu Ser Lys Leu Gly Asp Met
145                 150                 155                 160

Tyr Gly Arg Lys Ile Gly Leu Met Thr Val Val Ile Tyr Ser Ile
                165                 170                 175

Gly Ile Ile Ile Gln Ile Ala Ser Ile Asp Lys Trp Tyr Gln Tyr Phe
            180                 185                 190

Ile Gly Arg Ile Ile Ser Gly Leu Gly Val Gly Gly Ile Thr Val Leu
        195                 200                 205

Ala Pro Met Leu Ile Ser Glu Val Ser Pro Lys Gln Leu Arg Gly Thr
    210                 215                 220

Leu Val Ser Cys Tyr Gln Leu Met Ile Thr Phe Gly Ile Phe Leu Gly
225                 230                 235                 240

Tyr Cys Thr Asn Phe Gly Thr Lys Asn Tyr Ser Asn Ser Val Gln Trp
                245                 250                 255

Arg Val Pro Leu Gly Leu Cys Phe Ala Trp Ser Ile Phe Met Ile Val
            260                 265                 270

Gly Met Thr Phe Val Pro Glu Ser Pro Arg Tyr Leu Val Glu Val Gly
        275                 280                 285

Lys Ile Glu Glu Ala Lys Arg Ser Leu Ala Arg Ala Asn Lys Thr Thr
    290                 295                 300

Glu Asp Ser Pro Leu Val Thr Leu Glu Met Glu Asn Tyr Gln Ser Ser
305                 310                 315                 320
```

```
Ile Glu Ala Glu Arg Leu Ala Gly Ser Ala Ser Trp Gly Glu Leu Val
                325                 330                 335

Thr Gly Lys Pro Gln Met Phe Arg Thr Leu Met Gly Met Met Ile
            340                 345                 350

Gln Ser Leu Gln Gln Leu Thr Gly Asp Asn Tyr Phe Tyr Tyr Gly
            355                 360                 365

Thr Thr Ile Phe Gln Ala Val Gly Leu Glu Asp Ser Phe Glu Thr Ala
    370                 375                 380

Ile Val Leu Gly Val Val Asn Phe Val Ser Thr Phe Phe Ser Leu Tyr
385                 390                 395                 400

Thr Val Asp Arg Phe Gly Arg Arg Asn Cys Leu Leu Trp Gly Cys Val
                405                 410                 415

Gly Met Ile Cys Cys Tyr Val Val Tyr Ala Ser Val Gly Val Thr Arg
                420                 425                 430

Leu Trp Pro Asn Gly Gln Asp Gln Pro Ser Ser Lys Gly Ala Gly Asn
            435                 440                 445

Cys Met Ile Val Phe Ala Cys Phe Tyr Ile Phe Cys Phe Ala Thr Thr
    450                 455                 460

Trp Ala Pro Val Ala Tyr Val Leu Ile Ser Glu Ser Tyr Pro Leu Arg
465                 470                 475                 480

Val Arg Gly Lys Ala Met Ser Ile Ala Ser Ala Cys Asn Trp Ile Trp
                485                 490                 495

Gly Phe Leu Ile Ser Phe Phe Thr Pro Phe Ile Thr Ser Ala Ile Asn
            500                 505                 510

Phe Tyr Tyr Gly Tyr Val Phe Met Gly Cys Met Val Phe Ala Tyr Phe
            515                 520                 525

Tyr Val Phe Phe Phe Val Pro Glu Thr Lys Gly Leu Thr Leu Glu Glu
    530                 535                 540

Val Asn Glu Met Tyr Glu Glu Asn Val Leu Pro Trp Lys Ser Thr Lys
545                 550                 555                 560

Trp Ile Pro Pro Ser Arg Arg Thr Thr Asp Tyr Asp Leu Asp Ala Thr
                565                 570                 575

Arg Asn Asp Pro Arg Pro Phe Tyr Lys Arg Met Phe Thr Lys Glu Lys
                580                 585                 590

<210> SEQ ID NO 157
<211> LENGTH: 570
<212> TYPE: PRT
<213> ORGANISM: Saccharomyces cerevisiae
<220> FEATURE:
<221> NAME/KEY: MISC_FEATURE
<222> LOCATION: (1)..(570)
<223> OTHER INFORMATION: Hxt6/7 (Fig. 10)

<400> SEQUENCE: 157

Met Ser Gln Asp Ala Ala Ile Ala Glu Gln Thr Pro Val Glu His Leu
1               5                   10                  15

Ser Ala Val Asp Ser Ala Ser His Ser Val Leu Ser Thr Pro Ser Asn
                20                  25                  30

Lys Ala Glu Arg Asp Glu Ile Lys Ala Tyr Gly Glu Gly Glu Glu His
            35                  40                  45

Glu Pro Val Val Glu Ile Pro Lys Arg Pro Ala Ser Ala Tyr Val Thr
        50                  55                  60

Val Ser Ile Met Cys Ile Met Ile Ala Phe Gly Gly Phe Val Phe Gly
65                  70                  75                  80

Trp Asp Thr Gly Thr Ile Ser Gly Phe Ile Asn Gln Thr Asp Phe Ile
```

```
                85                  90                  95
Arg Arg Phe Gly Met Lys His Lys Asp Gly Thr Asn Tyr Leu Ser Lys
            100                 105                 110
Val Arg Thr Gly Leu Ile Val Ser Ile Phe Asn Ile Gly Cys Ala Ile
            115                 120                 125
Gly Gly Ile Ile Leu Ser Lys Leu Gly Asp Met Tyr Gly Arg Lys Val
130                 135                 140
Gly Leu Ile Val Val Val Ile Tyr Ile Ile Gly Ile Ile Ile Gln
145                 150                 155                 160
Ile Ala Ser Ile Asn Lys Trp Tyr Gln Tyr Phe Ile Gly Arg Ile Ile
            165                 170                 175
Ser Gly Leu Gly Val Gly Ile Ala Val Leu Ser Pro Met Leu Ile
            180                 185                 190
Ser Glu Val Ser Pro Lys His Leu Arg Gly Thr Leu Val Ser Cys Tyr
            195                 200                 205
Gln Leu Met Ile Thr Ala Gly Ile Phe Leu Gly Tyr Cys Thr Asn Phe
            210                 215                 220
Gly Thr Lys Asn Tyr Ser Asn Ser Val Gln Trp Arg Val Pro Leu Gly
225                 230                 235                 240
Leu Cys Phe Ala Trp Ala Leu Phe Met Ile Gly Met Thr Phe Val
            245                 250                 255
Pro Glu Ser Pro Arg Tyr Leu Ala Glu Val Gly Lys Ile Glu Glu Ala
            260                 265                 270
Lys Arg Ser Ile Ala Val Ser Asn Lys Val Ala Val Asp Asp Pro Ser
            275                 280                 285
Val Leu Ala Glu Val Glu Ala Val Leu Ala Gly Val Glu Ala Glu Lys
            290                 295                 300
Leu Ala Gly Asn Ala Ser Trp Gly Glu Leu Phe Ser Ser Lys Thr Lys
305                 310                 315                 320
Val Leu Gln Arg Leu Ile Met Gly Ala Met Ile Gln Ser Leu Gln Gln
            325                 330                 335
Leu Thr Gly Asp Asn Tyr Phe Phe Tyr Tyr Gly Thr Thr Ile Phe Lys
            340                 345                 350
Ala Val Gly Leu Ser Asp Ser Phe Glu Thr Ser Ile Val Leu Gly Ile
            355                 360                 365
Val Asn Phe Ala Ser Thr Phe Val Gly Ile Tyr Val Val Glu Arg Tyr
            370                 375                 380
Gly Arg Arg Thr Cys Leu Leu Trp Gly Ala Ala Ser Met Thr Ala Cys
385                 390                 395                 400
Met Val Val Tyr Ala Ser Val Gly Val Thr Arg Leu Trp Pro Asn Gly
            405                 410                 415
Gln Asp Gln Pro Ser Ser Lys Gly Ala Gly Asn Cys Met Ile Val Phe
            420                 425                 430
Ala Cys Phe Tyr Ile Phe Cys Phe Ala Thr Thr Trp Ala Pro Ile Pro
            435                 440                 445
Tyr Val Val Ser Glu Thr Phe Pro Leu Arg Val Lys Ser Lys Ala
            450                 455                 460
Met Ser Ile Ala Thr Ala Ala Asn Trp Leu Trp Gly Phe Leu Ile Gly
465                 470                 475                 480
Phe Phe Thr Pro Phe Ile Thr Gly Ala Ile Asn Phe Tyr Tyr Gly Tyr
            485                 490                 495
Val Phe Met Gly Cys Leu Val Phe Met Phe Phe Tyr Val Leu Leu Val
            500                 505                 510
```

```
Val Pro Glu Thr Lys Gly Leu Thr Leu Glu Glu Val Asn Thr Met Trp
            515                 520                 525
Glu Glu Gly Val Leu Pro Trp Lys Ser Ala Ser Trp Val Pro Pro Ser
            530                 535                 540
Arg Arg Gly Ala Asn Tyr Asp Ala Glu Glu Met Thr His Asp Asp Lys
545                 550                 555                 560
Pro Leu Tyr Lys Arg Met Phe Ser Thr Lys
            565                 570

<210> SEQ ID NO 158
<211> LENGTH: 569
<212> TYPE: PRT
<213> ORGANISM: Saccharomyces cerevisiae
<220> FEATURE:
<221> NAME/KEY: MISC_FEATURE
<222> LOCATION: (1)..(569)
<223> OTHER INFORMATION: Hxt8 (Fig. 10)

<400> SEQUENCE: 158

Met Thr Asp Arg Lys Thr Asn Leu Pro Glu Glu Pro Ile Phe Glu Glu
1               5                   10                  15
Ala Glu Asp Asp Gly Cys Pro Ser Ile Glu Asn Ser Ser His Leu Ser
            20                  25                  30
Val Pro Thr Val Glu Glu Asn Lys Asp Phe Ser Glu Tyr Asn Gly Glu
            35                  40                  45
Glu Ala Glu Glu Val Val Pro Glu Lys Pro Ala Ser Ala Tyr Ala
            50                  55                  60
Thr Val Ser Ile Met Cys Leu Cys Met Ala Phe Gly Gly Phe Met Ser
65                  70                  75                  80
Gly Trp Asp Thr Gly Thr Ile Ser Gly Phe Val Asn Gln Thr Asp Phe
            85                  90                  95
Leu Arg Arg Phe Gly Asn Tyr Ser His Ser Lys Asn Thr Tyr Tyr Leu
            100                 105                 110
Ser Asn Val Arg Thr Gly Leu Ile Val Ser Ile Phe Asn Val Gly Ser
            115                 120                 125
Ala Ile Gly Cys Leu Phe Leu Ser Lys Leu Gly Asp Ile Tyr Gly Arg
            130                 135                 140
Cys Met Gly Leu Ile Ile Val Ile Val Val Tyr Met Val Gly Ile Val
145                 150                 155                 160
Ile Gln Ile Ala Ser Ile Asp Lys Trp Tyr Gln Tyr Phe Ile Gly Arg
            165                 170                 175
Ile Ile Ala Gly Ile Gly Ala Gly Ser Ile Ser Val Leu Ala Pro Met
            180                 185                 190
Leu Ile Ser Glu Thr Ala Pro Lys His Ile Arg Gly Thr Leu Leu Ala
            195                 200                 205
Cys Trp Gln Leu Met Val Thr Phe Ala Ile Phe Leu Gly Tyr Cys Thr
            210                 215                 220
Asn Tyr Gly Thr Lys Thr Tyr Ser Asn Ser Val Gln Trp Arg Val Pro
225                 230                 235                 240
Leu Gly Leu Cys Phe Ala Trp Ala Ile Ile Met Ile Gly Gly Met Thr
            245                 250                 255
Phe Val Pro Glu Ser Pro Arg Phe Leu Val Gln Val Gly Lys Ile Glu
            260                 265                 270
Gln Ala Lys Ala Ser Phe Ala Lys Ser Asn Lys Leu Ser Val Asp Asp
            275                 280                 285
```

```
Pro Ala Val Val Ala Glu Ile Asp Leu Leu Val Ala Gly Val Glu Ala
290                 295                 300

Glu Glu Ala Met Gly Thr Ala Ser Trp Lys Glu Leu Phe Ser Arg Lys
305                 310                 315                 320

Thr Lys Val Phe Gln Arg Leu Thr Met Thr Val Met Ile Asn Ser Leu
            325                 330                 335

Gln Gln Leu Thr Gly Asp Asn Tyr Phe Tyr Tyr Gly Thr Thr Ile
            340                 345                 350

Phe Lys Ser Val Gly Met Asn Asp Ser Phe Glu Thr Ser Ile Val Leu
            355                 360                 365

Gly Ile Val Asn Phe Ala Ser Cys Phe Phe Ser Leu Tyr Ser Val Asp
370                 375                 380

Lys Leu Gly Arg Arg Cys Leu Leu Leu Gly Ala Ala Thr Met Thr
385                 390                 395                 400

Ala Cys Met Val Ile Tyr Ala Ser Val Gly Val Thr Arg Leu Tyr Pro
                405                 410                 415

Asn Gly Lys Ser Glu Pro Ser Ser Lys Gly Ala Gly Asn Cys Thr Ile
            420                 425                 430

Val Phe Thr Cys Phe Tyr Ile Phe Cys Phe Ser Cys Thr Trp Gly Pro
            435                 440                 445

Val Cys Tyr Val Ile Ile Ser Glu Thr Phe Pro Leu Arg Val Arg Ser
450                 455                 460

Lys Cys Met Ser Val Ala Thr Ala Ala Asn Leu Leu Trp Gly Phe Leu
465                 470                 475                 480

Ile Gly Phe Phe Thr Pro Phe Ile Thr Ser Ala Ile Asn Phe Tyr Tyr
                485                 490                 495

Gly Tyr Val Phe Met Gly Cys Leu Ala Phe Ser Tyr Phe Tyr Val Phe
            500                 505                 510

Phe Phe Val Pro Glu Thr Lys Gly Leu Thr Leu Glu Glu Val Asp Glu
            515                 520                 525

Met Trp Met Asp Gly Val Leu Pro Trp Lys Ser Glu Ser Trp Val Pro
530                 535                 540

Ala Ser Arg Arg Asp Gly Asp Tyr Asp Asn Glu Lys Leu Gln His Asp
545                 550                 555                 560

Glu Lys Pro Phe Tyr Lys Arg Met Phe
                565
```

<210> SEQ ID NO 159
<211> LENGTH: 567
<212> TYPE: PRT
<213> ORGANISM: Saccharomyces cerevisiae
<220> FEATURE:
<221> NAME/KEY: MISC_FEATURE
<222> LOCATION: (1)..(567)
<223> OTHER INFORMATION: Hxt9 (Fig. 10)

<400> SEQUENCE: 159

```
Met Ser Gly Val Asn Asn Thr Ser Ala Asn Asp Leu Ser Thr Thr Glu
1               5                   10                  15

Ser Asn Ser Asn Ser Val Ala Asn Ala Pro Ser Val Lys Thr Glu His
                20                  25                  30

Asn Asp Ser Lys Asn Ser Leu Asn Leu Asp Ala Thr Glu Pro Pro Ile
            35                  40                  45

Asp Leu Pro Gln Lys Pro Leu Ser Ala Tyr Thr Thr Val Ala Ile Leu
        50                  55                  60

Cys Leu Met Ile Ala Phe Gly Gly Phe Ile Phe Gly Trp Asp Thr Gly
```

```
                 65                  70                  75                  80
        Thr Ile Ser Gly Phe Val Asn Leu Ser Asp Phe Ile Arg Arg Phe Gly
                             85                  90                  95

Gln Lys Asn Asp Lys Gly Thr Tyr Tyr Leu Ser Lys Val Arg Met Gly
                            100                 105                 110

Leu Ile Val Ser Ile Phe Asn Ile Gly Cys Ala Ile Gly Gly Ile Val
                            115                 120                 125

Leu Ser Lys Val Gly Asp Ile Tyr Gly Arg Arg Ile Gly Leu Ile Thr
                            130                 135                 140

Val Thr Ala Ile Tyr Val Val Gly Ile Leu Ile Gln Ile Thr Ser Ile
        145                 150                 155                 160

Asn Lys Trp Tyr Gln Tyr Phe Ile Gly Arg Ile Ile Ser Gly Leu Gly
                            165                 170                 175

Val Gly Gly Ile Ala Val Leu Ser Pro Met Leu Ile Ser Glu Val Ala
                            180                 185                 190

Pro Lys Gln Ile Arg Gly Thr Leu Val Gln Leu Tyr Gln Leu Met Cys
                            195                 200                 205

Thr Met Gly Ile Phe Leu Gly Tyr Cys Thr Asn Tyr Gly Thr Lys Asn
                            210                 215                 220

Tyr His Asn Ala Thr Gln Trp Arg Val Gly Leu Gly Leu Cys Phe Ala
        225                 230                 235                 240

Trp Thr Thr Phe Met Val Ser Gly Met Met Phe Val Pro Glu Ser Pro
                            245                 250                 255

Arg Tyr Leu Ile Glu Val Gly Lys Asp Glu Glu Ala Lys Arg Ser Leu
                            260                 265                 270

Ser Lys Ser Asn Lys Val Ser Val Asp Asp Pro Ala Leu Leu Ala Glu
                            275                 280                 285

Tyr Asp Thr Ile Lys Ala Gly Ile Glu Leu Glu Lys Leu Ala Gly Asn
                            290                 295                 300

Ala Ser Trp Ser Glu Leu Leu Ser Thr Lys Thr Lys Val Phe Gln Arg
        305                 310                 315                 320

Val Leu Met Gly Val Met Ile Gln Ser Leu Gln Gln Leu Thr Gly Asp
                            325                 330                 335

Asn Tyr Phe Phe Tyr Tyr Gly Thr Thr Ile Phe Lys Ser Val Gly Leu
                            340                 345                 350

Lys Asp Ser Phe Gln Thr Ser Ile Ile Ile Gly Val Val Asn Phe Phe
                            355                 360                 365

Ser Ser Phe Ile Ala Val Tyr Thr Ile Glu Arg Phe Gly Arg Arg Thr
                            370                 375                 380

Cys Leu Leu Trp Gly Ala Ala Ser Met Leu Cys Cys Phe Ala Val Phe
        385                 390                 395                 400

Ala Ser Val Gly Val Thr Lys Leu Trp Pro Gln Gly Ser Ser His Gln
                            405                 410                 415

Asp Ile Thr Ser Gln Gly Ala Gly Asn Cys Met Ile Val Phe Thr Met
                            420                 425                 430

Phe Phe Ile Phe Ser Phe Ala Thr Thr Trp Ala Gly Gly Cys Tyr Val
                            435                 440                 445

Ile Val Ser Glu Thr Phe Pro Leu Arg Val Lys Ser Arg Gly Met Ala
                            450                 455                 460

Ile Ala Thr Ala Ala Asn Trp Met Trp Gly Phe Leu Ile Ser Phe Phe
        465                 470                 475                 480

Thr Pro Phe Ile Thr Gly Ala Ile Asn Phe Tyr Tyr Gly Tyr Val Phe
                            485                 490                 495
```

```
Leu Gly Cys Leu Val Phe Ala Tyr Phe Tyr Val Phe Phe Val Pro
            500                 505                 510

Glu Thr Lys Gly Leu Thr Leu Glu Glu Val Asn Thr Met Trp Leu Glu
            515                 520                 525

Gly Val Pro Ala Trp Lys Ser Ala Ser Trp Val Pro Pro Glu Arg Arg
530                 535                 540

Thr Ala Asp Tyr Asp Ala Asp Ala Ile Asp His Asp Asp Arg Pro Ile
545                 550                 555                 560

Tyr Lys Arg Phe Phe Ser Ser
                565

<210> SEQ ID NO 160
<211> LENGTH: 546
<212> TYPE: PRT
<213> ORGANISM: Saccharomyces cerevisiae
<220> FEATURE:
<221> NAME/KEY: MISC_FEATURE
<222> LOCATION: (1)..(546)
<223> OTHER INFORMATION: Hxt10 (Fig. 10)

<400> SEQUENCE: 160

Met Val Ser Ser Val Ser Ile Leu Gly Thr Ser Ala Lys Ala Ser
1               5                   10                  15

Thr Ser Leu Ser Arg Lys Asp Glu Ile Lys Leu Thr Pro Glu Thr Arg
            20                  25                  30

Glu Ala Ser Leu Asp Ile Pro Tyr Lys Pro Ile Ile Ala Tyr Trp Thr
            35                  40                  45

Val Met Gly Leu Cys Leu Met Ile Ala Phe Gly Gly Phe Ile Phe Gly
50                  55                  60

Trp Asp Thr Gly Thr Ile Ser Gly Phe Ile Asn Gln Thr Asp Phe Lys
65                  70                  75                  80

Arg Arg Phe Gly Glu Leu Gln Arg Asp Gly Ser Phe Gln Leu Ser Asp
            85                  90                  95

Val Arg Thr Gly Leu Ile Val Gly Ile Phe Asn Ile Gly Cys Ala Leu
            100                 105                 110

Gly Gly Leu Thr Leu Gly Arg Leu Gly Asp Ile Tyr Gly Arg Lys Ile
            115                 120                 125

Gly Leu Met Cys Val Ile Leu Val Tyr Val Val Gly Ile Val Ile Gln
130                 135                 140

Ile Ala Ser Ser Asp Lys Trp Tyr Gln Tyr Phe Ile Gly Arg Ile Val
145                 150                 155                 160

Ser Gly Met Gly Val Gly Gly Val Ala Val Leu Ser Pro Thr Leu Ile
            165                 170                 175

Ser Glu Ile Ser Pro Lys His Leu Arg Gly Thr Cys Val Ser Phe Tyr
            180                 185                 190

Gln Leu Met Ile Thr Leu Gly Ile Phe Leu Gly Tyr Cys Thr Asn Tyr
            195                 200                 205

Gly Thr Lys Lys Tyr Ser Asn Ser Ile Gln Trp Arg Val Pro Leu Gly
            210                 215                 220

Leu Cys Phe Ala Trp Ala Ile Phe Met Val Ile Gly Met Val Met Val
225                 230                 235                 240

Pro Glu Ser Pro Arg Tyr Leu Val Glu Lys Gly Lys Tyr Glu Glu Ala
            245                 250                 255

Arg Arg Ser Leu Ala Lys Ser Asn Lys Val Thr Val Thr Asp Pro Gly
            260                 265                 270
```

Val Val Phe Glu Phe Asp Thr Ile Val Ala Asn Met Glu Leu Glu Arg
                275                 280                 285

Ala Val Gly Asn Ala Ser Trp His Glu Leu Phe Ser Asn Lys Gly Ala
        290                 295                 300

Ile Leu Pro Arg Val Ile Met Gly Ile Val Gln Ser Leu Gln Gln
305                 310                 315                 320

Leu Thr Gly Cys Asn Tyr Phe Phe Tyr Tyr Gly Thr Thr Ile Phe Asn
                325                 330                 335

Ala Val Gly Met Gln Asp Ser Phe Glu Thr Ser Ile Val Leu Gly Ala
                340                 345                 350

Val Asn Phe Ala Ser Thr Phe Val Ala Leu Tyr Ile Val Asp Lys Phe
                355                 360                 365

Gly Arg Arg Lys Cys Leu Leu Trp Gly Ser Ala Ser Met Ala Ile Cys
                370                 375                 380

Phe Val Ile Phe Ala Thr Val Gly Val Thr Arg Leu Trp Pro Gln Gly
385                 390                 395                 400

Lys Asp Gln Pro Ser Ser Gln Ser Ala Gly Asn Val Met Ile Val Phe
                405                 410                 415

Thr Cys Phe Phe Ile Phe Ser Phe Ala Ile Thr Trp Ala Pro Ile Ala
                420                 425                 430

Tyr Val Ile Val Ala Glu Thr Tyr Pro Leu Arg Val Lys Asn Arg Ala
                435                 440                 445

Met Ala Ile Ala Val Gly Ala Asn Trp Met Trp Gly Phe Leu Ile Gly
                450                 455                 460

Phe Phe Thr Pro Phe Ile Thr Arg Ser Ile Gly Phe Ser Tyr Gly Tyr
465                 470                 475                 480

Val Phe Met Gly Cys Leu Ile Phe Ser Tyr Phe Tyr Val Phe Phe Phe
                485                 490                 495

Val Cys Glu Thr Lys Gly Leu Thr Leu Glu Glu Val Asn Glu Met Tyr
                500                 505                 510

Glu Glu Arg Ile Lys Pro Trp Lys Ser Gly Gly Trp Ile Pro Ser Ser
                515                 520                 525

Arg Arg Thr Pro Gln Pro Thr Ser Ser Thr Pro Leu Val Ile Val Asp
                530                 535                 540

Ser Lys
545

<210> SEQ ID NO 161
<211> LENGTH: 567
<212> TYPE: PRT
<213> ORGANISM: Saccharomyces cerevisiae
<220> FEATURE:
<221> NAME/KEY: MISC_FEATURE
<222> LOCATION: (1)..(567)
<223> OTHER INFORMATION: Hxt11 (Fig. 10)

<400> SEQUENCE: 161

Met Ser Gly Val Asn Asn Thr Ser Ala Asn Glu Leu Ser Thr Thr Met
1               5                   10                  15

Ser Asn Ser Asn Ser Ala Val Gly Ala Pro Ser Val Lys Thr Glu His
                20                  25                  30

Gly Asp Ser Lys Asn Ser Leu Asn Leu Asp Ala Asn Glu Pro Pro Ile
            35                  40                  45

Asp Leu Pro Gln Lys Pro Leu Ser Ala Tyr Thr Thr Val Ala Ile Leu
        50                  55                  60

Cys Leu Met Ile Ala Phe Gly Gly Phe Ile Phe Gly Trp Asp Thr Gly

-continued

```
        65                  70                  75                  80
Thr Ile Ser Gly Phe Val Asn Leu Ser Asp Phe Ile Arg Arg Phe Gly
                85                  90                  95
Gln Lys Asn Asp Lys Gly Thr Tyr Tyr Leu Ser Lys Val Arg Met Gly
               100                 105                 110
Leu Ile Val Ser Ile Phe Asn Ile Gly Cys Ala Ile Gly Gly Ile Val
               115                 120                 125
Leu Ser Lys Val Gly Asp Ile Tyr Gly Arg Arg Ile Gly Leu Ile Thr
               130                 135                 140
Val Thr Ala Ile Tyr Val Val Gly Ile Leu Ile Gln Ile Thr Ser Ile
145                 150                 155                 160
Asn Lys Trp Tyr Gln Tyr Phe Ile Gly Arg Ile Ile Ser Gly Leu Gly
               165                 170                 175
Val Gly Gly Ile Ala Val Leu Ser Pro Met Leu Ile Ser Glu Val Ala
               180                 185                 190
Pro Lys His Ile Arg Gly Thr Leu Val Gln Leu Tyr Gln Leu Met Gly
               195                 200                 205
Thr Met Gly Ile Phe Leu Gly Tyr Cys Thr Asn Tyr Gly Thr Lys Asn
               210                 215                 220
Tyr His Asn Ala Thr Gln Trp Arg Val Gly Leu Gly Leu Cys Phe Ala
225                 230                 235                 240
Trp Ala Thr Phe Met Val Ser Gly Met Met Phe Val Pro Glu Ser Pro
               245                 250                 255
Arg Tyr Leu Ile Glu Val Gly Lys Asp Glu Glu Ala Lys Arg Ser Leu
               260                 265                 270
Ser Lys Ser Asn Lys Val Ser Val Asp Asp Pro Ala Leu Leu Val Glu
               275                 280                 285
Tyr Asp Thr Ile Lys Ala Gly Ile Glu Leu Glu Lys Leu Ala Gly Asn
               290                 295                 300
Ala Ser Trp Ser Glu Leu Leu Ser Thr Lys Thr Lys Val Phe Gln Arg
305                 310                 315                 320
Val Leu Met Gly Val Met Ile Gln Ser Leu Gln Gln Leu Thr Gly Asp
               325                 330                 335
Asn Tyr Phe Phe Tyr Tyr Gly Thr Thr Ile Phe Lys Ser Val Gly Leu
               340                 345                 350
Lys Asp Ser Phe Gln Thr Ser Ile Ile Ile Gly Val Val Asn Phe Phe
               355                 360                 365
Ser Ser Phe Ile Ala Val Tyr Thr Ile Glu Arg Phe Gly Arg Arg Thr
               370                 375                 380
Cys Leu Leu Trp Gly Ala Ala Ser Met Leu Cys Cys Phe Ala Val Phe
385                 390                 395                 400
Ala Ser Val Gly Val Thr Lys Leu Trp Pro Gln Gly Ser Ser His Gln
               405                 410                 415
Asp Ile Thr Ser Gln Gly Ala Gly Asn Cys Met Ile Val Phe Thr Met
               420                 425                 430
Phe Phe Ile Phe Ser Phe Ala Thr Thr Trp Ala Gly Gly Cys Tyr Val
               435                 440                 445
Ile Val Ser Glu Thr Phe Pro Leu Arg Val Lys Ser Arg Gly Met Ala
               450                 455                 460
Ile Ala Thr Ala Ala Asn Trp Met Trp Gly Phe Leu Ile Ser Phe Phe
465                 470                 475                 480
Thr Pro Phe Ile Thr Gly Ala Ile Asn Phe Tyr Tyr Gly Tyr Val Phe
               485                 490                 495
```

```
Leu Gly Cys Leu Val Phe Ala Tyr Phe Tyr Val Phe Phe Val Pro
            500                 505                 510

Glu Thr Lys Gly Leu Thr Leu Glu Glu Val Asn Thr Met Trp Leu Glu
            515                 520                 525

Gly Val Pro Ala Trp Lys Ser Ala Ser Trp Val Pro Pro Glu Arg Arg
            530                 535                 540

Thr Ala Asp Tyr Asp Ala Asp Ala Ile Asp His Asp Asn Arg Pro Ile
545                 550                 555                 560

Tyr Lys Arg Phe Phe Ser Ser
                565

<210> SEQ ID NO 162
<211> LENGTH: 457
<212> TYPE: PRT
<213> ORGANISM: Saccharomyces cerevisiae
<220> FEATURE:
<221> NAME/KEY: MISC_FEATURE
<222> LOCATION: (1)..(457)
<223> OTHER INFORMATION: Hxt12 (Fig. 10)

<400> SEQUENCE: 162

Met Gly Leu Ile Val Ser Ile Phe Asn Ile Gly Cys Ala Ile Gly Gly
1               5                   10                  15

Ile Val Leu Ser Lys Val Gly Asp Ile Tyr Gly Arg Arg Ile Gly Leu
            20                  25                  30

Ile Thr Val Thr Ala Ile Tyr Val Val Gly Ile Leu Ile Gln Ile Thr
            35                  40                  45

Ser Ile Asn Lys Trp Tyr Gln Tyr Phe Ile Gly Arg Ile Ile Ser Gly
    50                  55                  60

Ile Gly Val Gly Gly Ile Ala Val Leu Ser Pro Met Leu Ile Ser Glu
65              70                  75                  80

Val Ala Pro Lys His Ile Arg Gly Thr Leu Val Gln Leu Tyr Gln Leu
                85                  90                  95

Met Gly Thr Met Gly Ile Phe Leu Gly Tyr Cys Thr Asn Tyr Gly Thr
            100                 105                 110

Lys Asn Tyr His Asn Ala Thr Gln Trp Arg Val Gly Leu Gly Leu Cys
        115                 120                 125

Phe Ala Trp Ala Thr Phe Met Val Ser Gly Met Met Phe Val Pro Glu
    130                 135                 140

Ser Pro Arg Tyr Leu Ile Glu Val Gly Lys Asp Glu Glu Ala Lys His
145                 150                 155                 160

Ser Leu Ser Lys Ser Asn Lys Val Ser Val Asp Asp Pro Ala Leu Leu
                165                 170                 175

Ala Glu Tyr Asp Thr Ile Lys Ala Gly Ile Glu Ile Glu Lys Leu Ala
            180                 185                 190

Gly Asn Ala Ser Trp Ser Glu Leu Leu Ser Thr Lys Thr Lys Val Phe
        195                 200                 205

Gln Arg Val Leu Met Gly Val Ile Ile Gln Ser Leu Gln Gln Leu Thr
    210                 215                 220

Gly Asp Asn Tyr Phe Phe Tyr Tyr Gly Thr Thr Ile Phe Lys Ser Val
225                 230                 235                 240

Gly Leu Lys Asp Ser Phe Gln Thr Ser Ile Ile Ile Gly Val Val Asn
                245                 250                 255

Phe Phe Ser Ser Phe Ile Ala Val Tyr Thr Ile Glu Arg Phe Gly Arg
            260                 265                 270
```

```
Arg Thr Cys Leu Leu Trp Gly Ala Ala Ser Met Leu Cys Cys Phe Ala
            275                 280                 285

Val Phe Ala Ser Val Gly Val Thr Lys Leu Trp Pro Gln Gly Ser Ser
290                 295                 300

His Gln Asp Ile Thr Ser Gln Gly Ala Gly Asn Cys Met Ile Val Phe
305                 310                 315                 320

Thr Met Phe Phe Ile Phe Ser Phe Ala Thr Thr Trp Ala Gly Gly Cys
                325                 330                 335

Phe Val Ile Val Ser Glu Thr Phe Pro Leu Arg Ala Lys Ser Arg Gly
                340                 345                 350

Met Ala Ile Ala Thr Ala Ala Asn Trp Met Trp Gly Phe Leu Ile Ser
            355                 360                 365

Phe Phe Thr Pro Phe Ile Thr Gly Ala Ile Asn Phe Tyr Tyr Gly Tyr
            370                 375                 380

Val Phe Leu Gly Cys Leu Val Phe Ala Tyr Phe Tyr Val Phe Phe Phe
385                 390                 395                 400

Val Pro Glu Thr Lys Gly Leu Thr Leu Glu Glu Val Asn Thr Met Trp
                405                 410                 415

Leu Glu Gly Val Pro Ala Trp Lys Ser Ala Ser Trp Val Pro Pro Glu
            420                 425                 430

Arg Arg Thr Ala Asp Tyr Asp Ala Asp Ala Ile Asp His Asp Asn Arg
            435                 440                 445

Pro Ile Tyr Lys Arg Phe Phe Ser Ser
        450                 455

<210> SEQ ID NO 163
<211> LENGTH: 564
<212> TYPE: PRT
<213> ORGANISM: Saccharomyces cerevisiae
<220> FEATURE:
<221> NAME/KEY: MISC_FEATURE
<222> LOCATION: (1)..(564)
<223> OTHER INFORMATION: Hxt13 (Fig. 10)

<400> SEQUENCE: 163

Met Ser Ser Ala Gln Ser Ser Ile Asp Ser Asp Gly Asp Val Arg Asp
1               5                   10                  15

Ala Asp Ile His Val Ala Pro Pro Val Glu Lys Glu Trp Ser Asp Gly
            20                  25                  30

Phe Asp Asp Asn Glu Val Ile Asn Gly Asp Asn Val Glu Pro Pro Lys
        35                  40                  45

Arg Gly Leu Ile Gly Tyr Leu Val Ile Tyr Leu Leu Cys Tyr Pro Ile
50                  55                  60

Ser Phe Gly Gly Phe Leu Pro Gly Trp Asp Ser Gly Ile Thr Ala Gly
65                  70                  75                  80

Phe Ile Asn Met Asp Asn Phe Lys Met Asn Phe Gly Ser Tyr Lys His
                85                  90                  95

Ser Thr Gly Glu Tyr Tyr Leu Ser Asn Val Arg Met Gly Leu Leu Val
            100                 105                 110

Ala Met Phe Ser Ile Gly Cys Ala Ile Gly Gly Leu Ile Phe Ala Arg
        115                 120                 125

Leu Ala Asp Thr Leu Gly Arg Arg Leu Ala Ile Val Ile Val Val Leu
    130                 135                 140

Val Tyr Met Val Gly Ala Ile Ile Gln Ile Ser Ser Asn His Lys Trp
145                 150                 155                 160

Tyr Gln Tyr Phe Val Gly Lys Ile Ile Tyr Gly Leu Gly Ala Gly Gly
```

```
              165                 170                 175
Cys Ser Val Leu Cys Pro Met Leu Leu Ser Glu Ile Ala Pro Thr Asp
            180                 185                 190

Leu Arg Gly Gly Leu Val Ser Leu Tyr Gln Leu Asn Met Thr Phe Gly
            195                 200                 205

Ile Phe Leu Gly Tyr Cys Ser Val Tyr Gly Thr Arg Lys Tyr Asp Asn
210                 215                 220

Thr Ala Gln Trp Arg Val Pro Leu Gly Leu Cys Phe Leu Trp Ala Leu
225                 230                 235                 240

Ile Ile Ile Ile Gly Met Leu Leu Val Pro Glu Ser Pro Arg Tyr Leu
                245                 250                 255

Ile Glu Cys Glu Arg His Glu Glu Ala Arg Ala Ser Ile Ala Lys Ile
                260                 265                 270

Asn Lys Val Ser Pro Glu Asp Pro Trp Val Leu Lys Gln Ala Asp Glu
            275                 280                 285

Ile Asn Ala Gly Val Leu Ala Gln Arg Glu Leu Gly Glu Ala Ser Trp
290                 295                 300

Lys Glu Leu Phe Ser Val Lys Thr Lys Val Leu Gln Arg Leu Ile Thr
305                 310                 315                 320

Gly Ile Leu Val Gln Thr Phe Leu Gln Leu Thr Gly Glu Asn Tyr Phe
                325                 330                 335

Phe Phe Tyr Gly Thr Thr Ile Phe Lys Ser Val Gly Leu Thr Asp Gly
                340                 345                 350

Phe Glu Thr Ser Ile Val Leu Gly Thr Val Asn Phe Phe Ser Thr Ile
            355                 360                 365

Ile Ala Val Met Val Val Asp Lys Ile Gly Arg Arg Lys Cys Leu Leu
370                 375                 380

Phe Gly Ala Ala Gly Met Met Ala Cys Met Val Ile Phe Ala Ser Ile
385                 390                 395                 400

Gly Val Lys Cys Leu Tyr Pro His Gly Gln Asp Gly Pro Ser Ser Lys
                405                 410                 415

Gly Ala Gly Asn Ala Met Ile Val Phe Thr Cys Phe Tyr Ile Phe Cys
                420                 425                 430

Phe Ala Thr Thr Trp Ala Pro Val Ala Tyr Ile Val Val Ala Glu Ser
            435                 440                 445

Phe Pro Ser Lys Val Lys Ser Arg Ala Met Ser Ile Ser Thr Ala Cys
450                 455                 460

Asn Trp Leu Trp Gln Phe Leu Ile Gly Phe Phe Thr Pro Phe Ile Thr
465                 470                 475                 480

Gly Ser Ile His Phe Tyr Tyr Gly Tyr Val Phe Val Gly Cys Leu Val
                485                 490                 495

Ala Met Phe Leu Tyr Val Phe Phe Leu Pro Glu Thr Ile Gly Leu
                500                 505                 510

Ser Leu Glu Glu Ile Gln Leu Leu Tyr Glu Glu Gly Ile Lys Pro Trp
            515                 520                 525

Lys Ser Ala Ser Trp Val Pro Pro Ser Arg Arg Gly Ile Ser Ser Glu
530                 535                 540

Glu Ser Lys Thr Glu Lys Lys Asp Trp Lys Lys Phe Leu Lys Phe Ser
545                 550                 555                 560

Lys Asn Ser Asp

<210> SEQ ID NO 164
<211> LENGTH: 540
```

<212> TYPE: PRT
<213> ORGANISM: Saccharomyces cerevisiae
<220> FEATURE:
<221> NAME/KEY: MISC_FEATURE
<222> LOCATION: (1)..(540)
<223> OTHER INFORMATION: Hxt14 (Fig. 10)

<400> SEQUENCE: 164

```
Met Thr Ala Gln Ile Pro Tyr Gln His Ser Ser Gly Tyr Ile Ser His
1               5                   10                  15

Phe His Asn Asn Glu Leu Asp Ala Gly Arg Gly Arg Asp Tyr Asn Val
            20                  25                  30

Thr Ile Lys Tyr Leu Asp Asp Lys Glu Glu Asn Ile Glu Gly Gln Ala
        35                  40                  45

Ala Lys Ile Ser His Asn Ala Ser Leu His Ile Pro Val Leu Leu Cys
    50                  55                  60

Leu Val Ile Ser Leu Gly Gly Phe Ile Phe Gly Trp Asp Ile Gly Thr
65                  70                  75                  80

Ile Gly Gly Met Thr Asn Met Val Ser Phe Gln Glu Lys Phe Gly Thr
                85                  90                  95

Thr Asn Ile Ile His Asp Asp Glu Thr Ile Phe Val Ser Thr Lys Lys
            100                 105                 110

Leu Thr Asp Leu Gln Ile Gly Leu Ile Ile Ser Ile Phe Asn Ile Ser
        115                 120                 125

Cys Gly Val Gly Ala Leu Thr Leu Ser Lys Ile Gly Asp Trp Ile Gly
    130                 135                 140

Arg Lys Gly Gly Ile Trp Phe Ala Leu Val Val Tyr Cys Ile Gly Ile
145                 150                 155                 160

Thr Ile Gln Ile Leu Ser Tyr Gly Arg Trp Tyr Phe Leu Thr Leu Gly
                165                 170                 175

Arg Ala Val Thr Gly Ile Gly Val Gly Val Thr Thr Val Leu Val Pro
            180                 185                 190

Met Phe Leu Ser Glu Asn Ser Pro Leu Lys Ile Arg Gly Ser Met Val
        195                 200                 205

Ser Thr Tyr Gln Leu Ile Val Thr Phe Gly Ile Leu Met Gly Asn Ile
    210                 215                 220

Leu Asn Phe Ile Cys Glu Arg Cys Tyr Lys Asp Pro Thr Gln Asn Ile
225                 230                 235                 240

Ala Trp Gln Leu Pro Leu Phe Leu Gly Tyr Ile Trp Ala Ile Ile Ile
                245                 250                 255

Gly Met Ser Leu Val Tyr Val Pro Glu Ser Pro Gln Tyr Leu Ala Lys
            260                 265                 270

Ile Lys Asn Asp Val Pro Ser Ala Lys Tyr Ser Phe Ala Arg Met Asn
        275                 280                 285

Gly Ile Pro Ala Thr Asp Ser Met Val Ile Glu Phe Ile Asp Asp Leu
    290                 295                 300

Leu Glu Asn Asn Tyr Asn Asn Glu Glu Thr Asn Asn Glu Ser Lys Lys
305                 310                 315                 320

Gln Ser Leu Val Lys Arg Asn Thr Phe Glu Phe Ile Met Gly Lys Pro
                325                 330                 335

Lys Leu Trp Leu Arg Leu Ile Ile Gly Met Met Ile Met Ala Phe Gln
            340                 345                 350

Gln Leu Ser Gly Ile Asn Tyr Phe Phe Tyr Tyr Gly Thr Ser Val Phe
        355                 360                 365

Lys Gly Val Gly Ile Lys Asp Pro Tyr Ile Thr Ser Ile Ile Leu Ser
```

```
            370                 375                 380
Ser Val Asn Phe Leu Ser Thr Ile Leu Gly Ile Tyr Tyr Val Glu Lys
385                 390                 395                 400

Trp Gly His Lys Thr Cys Leu Leu Tyr Gly Ser Thr Asn Leu Leu Phe
                405                 410                 415

Tyr Met Met Thr Tyr Ala Thr Val Gly Thr Phe Gly Arg Glu Thr Asp
                420                 425                 430

Phe Ser Asn Ile Val Leu Ile Ile Val Thr Cys Cys Phe Ile Phe Trp
                435                 440                 445

Phe Ala Ile Thr Leu Gly Pro Val Thr Phe Val Leu Val Ser Glu Leu
450                 455                 460

Phe Pro Leu Arg Thr Arg Ala Ile Ser Met Ala Ile Cys Thr Phe Ile
465                 470                 475                 480

Asn Trp Met Phe Asn Phe Leu Ile Ser Leu Leu Thr Pro Met Ile Val
                485                 490                 495

Ser Lys Ile Asp Phe Lys Leu Gly Tyr Ile Phe Ala Ala Cys Leu Leu
                500                 505                 510

Ala Leu Ile Ile Phe Ser Trp Ile Leu Val Pro Glu Thr Arg Lys Lys
                515                 520                 525

Asn Glu Gln Glu Ile Asn Lys Ile Phe Glu Pro Glu
                530                 535                 540

<210> SEQ ID NO 165
<211> LENGTH: 567
<212> TYPE: PRT
<213> ORGANISM: Saccharomyces cerevisiae
<220> FEATURE:
<221> NAME/KEY: MISC_FEATURE
<222> LOCATION: (1)..(567)
<223> OTHER INFORMATION: Hxt15 (Fig. 10)

<400> SEQUENCE: 165

Met Ala Ser Glu Gln Ser Ser Pro Glu Ile Asn Ala Asp Asn Leu Asn
1               5                   10                  15

Ser Ser Ala Ala Asp Val His Val Gln Pro Pro Gly Glu Lys Glu Trp
                20                  25                  30

Ser Asp Gly Phe Tyr Asp Lys Glu Val Ile Asn Gly Asn Thr Pro Asp
                35                  40                  45

Ala Pro Lys Arg Gly Phe Leu Gly Tyr Leu Ile Ile Tyr Leu Leu Cys
50                  55                  60

Tyr Pro Val Ser Phe Gly Gly Phe Leu Pro Gly Trp Asp Ser Gly Ile
65                  70                  75                  80

Thr Ala Gly Phe Ile Asn Met Asp Asn Phe Lys Met Asn Phe Gly Ser
                85                  90                  95

Tyr Lys His Ser Thr Gly Glu Tyr Tyr Leu Ser Asn Val Arg Met Gly
                100                 105                 110

Leu Leu Val Ala Met Phe Ser Val Gly Cys Ser Ile Gly Gly Val Ala
                115                 120                 125

Phe Ala Arg Leu Ala Asp Thr Leu Gly Arg Arg Leu Ala Ile Val Ile
                130                 135                 140

Val Val Leu Val Tyr Met Val Gly Ala Ile Ile Gln Ile Ser Ser Asn
145                 150                 155                 160

His Lys Trp Tyr Gln Tyr Phe Val Gly Lys Ile Ile Tyr Gly Leu Gly
                165                 170                 175

Ala Gly Gly Cys Ser Val Leu Cys Pro Met Leu Leu Ser Glu Ile Ala
                180                 185                 190
```

```
Pro Thr Asp Leu Arg Gly Gly Leu Val Ser Leu Tyr Gln Leu Asn Met
    195                 200                 205

Thr Phe Gly Ile Phe Leu Gly Tyr Cys Ser Val Tyr Gly Thr Arg Lys
210                 215                 220

Tyr Ser Asn Thr Ala Gln Trp Arg Ile Pro Val Gly Leu Cys Phe Leu
225                 230                 235                 240

Trp Ala Leu Ile Ile Ile Val Gly Met Leu Leu Val Pro Glu Ser Pro
                245                 250                 255

Arg Tyr Leu Ile Glu Cys Glu Arg His Glu Glu Ala Cys Val Ser Ile
                260                 265                 270

Ala Lys Ile Asn Lys Val Ser Pro Glu Asp Pro Trp Val Leu Lys Gln
            275                 280                 285

Ala Asp Glu Ile Asn Ala Gly Val Leu Ala Gln Arg Glu Leu Gly Glu
        290                 295                 300

Ala Ser Trp Lys Glu Leu Phe Ser Val Lys Thr Lys Val Leu Gln Arg
305                 310                 315                 320

Leu Ile Thr Gly Ile Leu Val Gln Thr Phe Leu Gln Leu Thr Gly Glu
                325                 330                 335

Asn Tyr Phe Phe Phe Tyr Gly Thr Thr Ile Phe Lys Ser Val Gly Leu
                340                 345                 350

Thr Asp Gly Phe Glu Thr Ser Ile Val Leu Gly Thr Val Asn Phe Phe
            355                 360                 365

Ser Thr Ile Ile Ala Val Met Val Val Asp Lys Ile Gly Arg Arg Lys
370                 375                 380

Cys Leu Leu Phe Gly Ala Ala Ser Met Met Ala Cys Met Val Ile Phe
385                 390                 395                 400

Ala Ser Ile Gly Val Lys Cys Leu Tyr Pro His Gly Gln Asp Gly Pro
                405                 410                 415

Ser Ser Lys Gly Ala Gly Asn Ala Met Ile Val Phe Thr Cys Phe Tyr
            420                 425                 430

Ile Phe Cys Phe Ala Thr Thr Trp Ala Pro Val Ala Tyr Ile Val Val
        435                 440                 445

Ala Glu Ser Phe Pro Ser Lys Val Lys Ser Lys Ala Met Ser Ile Ser
    450                 455                 460

Thr Ala Phe Asn Trp Leu Trp Gln Phe Leu Ile Gly Phe Phe Thr Pro
465                 470                 475                 480

Phe Ile Thr Gly Ser Ile His Phe Tyr Tyr Gly Tyr Val Phe Val Gly
                485                 490                 495

Cys Leu Val Ala Met Phe Leu Tyr Val Phe Phe Leu Pro Glu Thr
            500                 505                 510

Ile Gly Leu Ser Leu Glu Glu Ile Gln Leu Leu Tyr Glu Glu Gly Ile
        515                 520                 525

Lys Pro Trp Lys Ser Ala Ser Trp Val Pro Pro Ser Arg Arg Gly Ala
    530                 535                 540

Ser Ser Arg Glu Thr Glu Ala Lys Lys Lys Ser Trp Lys Glu Val Leu
545                 550                 555                 560

Lys Phe Pro Lys Ser Phe Asn
                565

<210> SEQ ID NO 166
<211> LENGTH: 567
<212> TYPE: PRT
<213> ORGANISM: Saccharomyces cerevisiae
<220> FEATURE:
```

```
<221> NAME/KEY: MISC_FEATURE
<222> LOCATION: (1)..(567)
<223> OTHER INFORMATION: Hxt16 (Fig. 10)

<400> SEQUENCE: 166
```

| | | | | | | | | | | | | | | | |
|---|---|---|---|---|---|---|---|---|---|---|---|---|---|---|---|
| Met | Ala | Ser | Glu | Gln | Ser | Ser | Pro | Glu | Ile | Asn | Ala | Asp | Asn | Leu | Asn |
| 1 | | | | 5 | | | | | 10 | | | | | 15 | |
| Ser | Ser | Ala | Ala | Asp | Val | His | Val | Gln | Pro | Pro | Gly | Glu | Lys | Glu | Trp |
| | | | 20 | | | | | 25 | | | | | 30 | | |
| Ser | Asp | Gly | Phe | Tyr | Asp | Lys | Glu | Val | Ile | Asn | Gly | Asn | Thr | Pro | Asp |
| | | 35 | | | | | 40 | | | | | 45 | | | |
| Ala | Pro | Lys | Arg | Gly | Phe | Leu | Gly | Tyr | Leu | Ile | Ile | Tyr | Leu | Leu | Cys |
| 50 | | | | | 55 | | | | | 60 | | | | | |
| Tyr | Pro | Val | Ser | Phe | Gly | Gly | Phe | Leu | Pro | Gly | Trp | Asp | Ser | Gly | Ile |
| 65 | | | | | 70 | | | | | 75 | | | | | 80 |
| Thr | Ala | Gly | Phe | Ile | Asn | Met | Asp | Asn | Phe | Lys | Met | Asn | Phe | Gly | Ser |
| | | | | 85 | | | | | 90 | | | | | 95 | |
| Tyr | Lys | His | Ser | Thr | Gly | Glu | Tyr | Tyr | Leu | Ser | Asn | Val | Arg | Met | Gly |
| | | | | 100 | | | | | 105 | | | | | 110 | |
| Leu | Leu | Val | Ala | Met | Phe | Ser | Val | Gly | Cys | Ser | Ile | Gly | Gly | Val | Ala |
| | | | 115 | | | | | 120 | | | | | 125 | | |
| Phe | Ala | Arg | Leu | Ala | Asp | Thr | Leu | Gly | Arg | Arg | Leu | Ala | Ile | Val | Ile |
| | | 130 | | | | | 135 | | | | | 140 | | | |
| Val | Val | Leu | Val | Tyr | Met | Val | Gly | Ala | Ile | Ile | Gln | Ile | Ser | Ser | Asn |
| 145 | | | | | 150 | | | | | 155 | | | | | 160 |
| His | Lys | Trp | Tyr | Gln | Tyr | Phe | Val | Gly | Lys | Ile | Ile | Tyr | Gly | Leu | Gly |
| | | | | 165 | | | | | 170 | | | | | 175 | |
| Ala | Gly | Gly | Cys | Ser | Val | Leu | Cys | Pro | Met | Leu | Leu | Ser | Glu | Ile | Ala |
| | | | | 180 | | | | | 185 | | | | | 190 | |
| Pro | Thr | Asp | Leu | Arg | Gly | Gly | Leu | Val | Ser | Leu | Tyr | Gln | Leu | Asn | Met |
| | | | 195 | | | | | 200 | | | | | 205 | | |
| Thr | Phe | Gly | Ile | Phe | Leu | Gly | Tyr | Cys | Ser | Val | Tyr | Gly | Thr | Arg | Lys |
| | | 210 | | | | | 215 | | | | | 220 | | | |
| Tyr | Ser | Asn | Thr | Ala | Gln | Trp | Arg | Ile | Pro | Val | Gly | Leu | Cys | Phe | Leu |
| 225 | | | | | 230 | | | | | 235 | | | | | 240 |
| Trp | Ala | Leu | Ile | Ile | Ile | Val | Gly | Met | Leu | Leu | Val | Pro | Glu | Ser | Pro |
| | | | | 245 | | | | | 250 | | | | | 255 | |
| Arg | Tyr | Leu | Ile | Glu | Cys | Glu | Arg | His | Glu | Glu | Ala | Cys | Val | Ser | Ile |
| | | | | 260 | | | | | 265 | | | | | 270 | |
| Ala | Lys | Ile | Asp | Lys | Val | Ser | Pro | Glu | Asp | Pro | Trp | Val | Leu | Lys | Gln |
| | | | 275 | | | | | 280 | | | | | 285 | | |
| Ala | Asp | Glu | Ile | Asn | Ala | Gly | Val | Leu | Ala | Gln | Arg | Glu | Leu | Gly | Glu |
| | | 290 | | | | | 295 | | | | | 300 | | | |
| Ala | Ser | Trp | Lys | Glu | Leu | Phe | Ser | Val | Lys | Thr | Lys | Val | Leu | Gln | Arg |
| 305 | | | | | 310 | | | | | 315 | | | | | 320 |
| Leu | Ile | Thr | Gly | Ile | Leu | Val | Gln | Thr | Phe | Leu | Gln | Leu | Thr | Gly | Glu |
| | | | | 325 | | | | | 330 | | | | | 335 | |
| Asn | Tyr | Phe | Phe | Phe | Tyr | Gly | Thr | Thr | Ile | Phe | Lys | Ser | Val | Gly | Leu |
| | | | | 340 | | | | | 345 | | | | | 350 | |
| Thr | Asp | Gly | Phe | Glu | Thr | Ser | Ile | Val | Leu | Gly | Thr | Val | Asn | Phe | Phe |
| | | | 355 | | | | | 360 | | | | | 365 | | |
| Ser | Thr | Ile | Ile | Ala | Val | Met | Val | Val | Asp | Lys | Ile | Gly | Arg | Arg | Lys |
| | | 370 | | | | | 375 | | | | | 380 | | | |
| Cys | Leu | Leu | Phe | Gly | Ala | Ala | Ser | Met | Met | Ala | Cys | Met | Val | Ile | Phe |

-continued

```
                385                 390                 395                 400
Ala Ser Ile Gly Val Lys Cys Leu Tyr Pro His Gly Gln Asp Gly Pro
                    405                 410                 415

Ser Ser Lys Gly Ala Gly Asn Ala Met Ile Val Phe Thr Cys Phe Tyr
                420                 425                 430

Ile Phe Cys Phe Ala Thr Thr Trp Ala Pro Val Ala Tyr Ile Val Val
            435                 440                 445

Ala Glu Ser Phe Pro Ser Lys Val Lys Ser Lys Ala Met Ser Ile Ser
        450                 455                 460

Thr Ala Phe Asn Trp Leu Trp Gln Phe Leu Ile Gly Phe Phe Thr Pro
465                 470                 475                 480

Phe Ile Thr Gly Ser Ile His Phe Tyr Tyr Gly Tyr Val Phe Val Gly
                    485                 490                 495

Cys Leu Val Ala Met Phe Leu Tyr Val Phe Phe Phe Leu Pro Glu Thr
                500                 505                 510

Ile Gly Leu Ser Leu Glu Glu Thr Gln Leu Leu Tyr Glu Glu Gly Ile
            515                 520                 525

Lys Pro Trp Lys Ser Ala Ser Trp Val Pro Pro Ser Arg Arg Gly Ala
        530                 535                 540

Ser Ser Arg Glu Thr Glu Ala Lys Lys Lys Ser Trp Lys Glu Val Leu
545                 550                 555                 560

Lys Phe Pro Lys Ser Phe Asn
                    565

<210> SEQ ID NO 167
<211> LENGTH: 564
<212> TYPE: PRT
<213> ORGANISM: Saccharomyces cerevisiae
<220> FEATURE:
<221> NAME/KEY: MISC_FEATURE
<222> LOCATION: (1)..(564)
<223> OTHER INFORMATION: Hxt17 (Fig. 10)

<400> SEQUENCE: 167

Met Gln Ser Ser Thr Glu Ser Asp Arg Asp Ile Gln Asp Gly Pro Asp
1               5                   10                  15

Ala Asp Ile His Val Ala Pro Pro Val Glu Lys Glu Trp Ser Asp Gly
                20                  25                  30

Phe Asp Asp Asn Glu Val Ile Asn Gly Asp Asn Val Glu Pro Pro Lys
            35                  40                  45

Arg Gly Leu Ile Gly Tyr Leu Val Ile Tyr Leu Leu Cys Tyr Pro Ile
        50                  55                  60

Ser Phe Gly Gly Phe Leu Pro Gly Trp Asp Ser Gly Ile Thr Ala Gly
65                  70                  75                  80

Phe Ile Asn Met Asp Asn Phe Lys Met Asn Phe Gly Ser Tyr Lys His
                85                  90                  95

Ser Thr Gly Glu Tyr Tyr Leu Ser Asn Val Arg Met Gly Leu Leu Val
                    100                 105                 110

Ala Met Phe Ser Ile Gly Cys Ala Ile Gly Gly Leu Ile Phe Ala Arg
            115                 120                 125

Leu Ala Asp Thr Leu Gly Arg Arg Leu Ala Ile Val Ile Val Val Leu
        130                 135                 140

Val Tyr Met Val Gly Ala Ile Ile Gln Ile Ser Ser Asn His Lys Trp
145                 150                 155                 160

Tyr Gln Tyr Phe Val Gly Lys Ile Ile Tyr Gly Leu Gly Ala Gly Gly
                    165                 170                 175
```

```
Cys Ser Val Leu Cys Pro Met Leu Leu Ser Glu Ile Ala Pro Thr Asp
            180                 185                 190

Leu Arg Gly Gly Leu Val Ser Leu Tyr Gln Leu Asn Met Thr Phe Gly
        195                 200                 205

Ile Phe Leu Gly Tyr Cys Ser Val Tyr Gly Thr Arg Lys Tyr Asp Asn
        210                 215                 220

Thr Ala Gln Trp Arg Val Pro Leu Gly Leu Cys Phe Leu Trp Thr Leu
225                 230                 235                 240

Ile Ile Ile Ile Gly Met Leu Leu Val Pro Glu Ser Pro Arg Tyr Leu
            245                 250                 255

Ile Glu Cys Glu Arg His Glu Glu Ala Arg Ala Ser Ile Ala Lys Ile
            260                 265                 270

Asn Lys Val Ser Pro Glu Asp Pro Trp Val Leu Lys Gln Ala Asp Glu
        275                 280                 285

Ile Asn Ala Gly Val Leu Ala Gln Arg Glu Leu Gly Glu Ala Ser Trp
        290                 295                 300

Lys Glu Leu Phe Ser Val Lys Thr Lys Val Leu Gln Arg Leu Ile Thr
305                 310                 315                 320

Gly Ile Leu Val Gln Thr Phe Leu Gln Leu Thr Gly Glu Asn Tyr Phe
            325                 330                 335

Phe Phe Tyr Gly Thr Thr Ile Phe Lys Ser Val Gly Leu Thr Asp Gly
            340                 345                 350

Phe Glu Thr Ser Ile Val Leu Gly Thr Val Asn Phe Phe Ser Thr Ile
        355                 360                 365

Ile Ala Val Met Val Val Asp Lys Ile Gly Arg Arg Lys Cys Leu Leu
        370                 375                 380

Phe Gly Ala Ala Gly Met Met Ala Cys Met Val Ile Phe Ala Ser Ile
385                 390                 395                 400

Gly Val Lys Cys Leu Tyr Pro His Gly Gln Asp Gly Pro Ser Ser Lys
            405                 410                 415

Gly Ala Gly Asn Ala Met Ile Val Phe Thr Cys Phe Tyr Ile Phe Cys
            420                 425                 430

Phe Ala Thr Thr Trp Ala Pro Val Ala Tyr Ile Val Val Ala Glu Ser
        435                 440                 445

Phe Pro Ser Lys Val Lys Ser Arg Ala Met Ser Ile Ser Thr Ala Cys
        450                 455                 460

Asn Trp Leu Trp Gln Phe Leu Ile Gly Phe Phe Thr Pro Phe Ile Thr
465                 470                 475                 480

Gly Ser Ile His Phe Tyr Tyr Gly Tyr Val Phe Val Gly Cys Leu Val
            485                 490                 495

Ala Met Phe Leu Tyr Val Phe Phe Leu Pro Glu Thr Ile Gly Leu
            500                 505                 510

Ser Leu Glu Glu Ile Gln Leu Leu Tyr Glu Glu Gly Ile Lys Pro Trp
        515                 520                 525

Lys Ser Ala Ser Trp Val Pro Pro Ser Arg Arg Gly Ile Pro Ser Glu
        530                 535                 540

Glu Ser Lys Thr Glu Lys Lys Asp Trp Lys Lys Phe Leu Lys Phe Ser
545                 550                 555                 560

Lys Gly Ser Asp
```